United States Patent
Castro et al.

(10) Patent No.: US 11,878,958 B2
(45) Date of Patent: Jan. 23, 2024

(54) MEK INHIBITORS AND USES THEREOF

(71) Applicant: Ikena Oncology, Inc., Boston, MA (US)

(72) Inventors: Alfredo C. Castro, Somerville, MA (US); Michael J. Burke, Melrose, MA (US); Thomas A. Wynn, Lexington, MA (US); Sabine K. Ruppel, Cambridge, MA (US); Sergio L. Santillana Soto, Lexington, MA (US); Eric Haines, Andover, MA (US); Lan Xu, Wellesley, MA (US); Oksana Zavidij, Westminster, MA (US)

(73) Assignee: Ikena Oncology, Inc., Boston, MA (US)

( * ) Notice: Subject to any disclaimer, the term of this patent is extended or adjusted under 35 U.S.C. 154(b) by 0 days.

(21) Appl. No.: 18/323,700

(22) Filed: May 25, 2023

(65) Prior Publication Data

US 2023/0382863 A1    Nov. 30, 2023

Related U.S. Application Data

(60) Provisional application No. 63/488,807, filed on Mar. 7, 2023, provisional application No. 63/479,131, filed on Jan. 9, 2023, provisional application No. 63/375,875, filed on Sep. 16, 2022, provisional application No. 63/345,698, filed on May 25, 2022.

(51) Int. Cl.
*C07D 213/64* (2006.01)
*A61P 35/00* (2006.01)

(52) U.S. Cl.
CPC .......... *C07D 213/64* (2013.01); *A61P 35/00* (2018.01)

(58) Field of Classification Search
CPC .............................. C07D 213/64; A61P 35/00
See application file for complete search history.

(56) References Cited

U.S. PATENT DOCUMENTS

| 8,889,638 B2 | 11/2014 | Cohen et al. |
| 2008/0263785 A1 | 10/2008 | David et al. |
| 2012/0238599 A1 | 9/2012 | Lee et al. |

FOREIGN PATENT DOCUMENTS

| CN | 113979995 A | 1/2022 |
|---|---|---|
| EP | 1243581 A1 | 9/2002 |
| EP | 1304101 A1 | 4/2003 |
| EP | 3061747 A1 | 8/2016 |
| EP | 3275866 A1 | 1/2018 |
| HU | 0101304 A2 | 12/2002 |
| JP | 2001140075 A | 5/2001 |
| JP | 2003005355 A | 1/2003 |
| JP | 2003063139 A | 3/2003 |
| JP | 2004339159 A | 12/2004 |
| JP | 4359237 B2 | 11/2009 |
| JP | 2019064403 A | 4/2019 |
| JP | 2019064404 A | 4/2019 |
| JP | 2019065135 A | 4/2019 |
| JP | 2019065136 A | 4/2019 |
| JP | 2019065137 A | 4/2019 |
| JP | 2019065138 A | 4/2019 |
| JP | 2021181432 A | 11/2021 |
| WO | WO-199844925 A1 | 10/1998 |
| WO | WO-2001025208 A1 | 4/2001 |
| WO | WO-2001096308 A1 | 12/2001 |
| WO | WO-2002024650 A2 | 3/2002 |
| WO | WO-2002053543 A1 | 7/2002 |
| WO | WO-2003031449 A2 | 4/2003 |
| WO | WO-2003043992 A1 | 5/2003 |
| WO | WO-2003047577 A2 | 6/2003 |
| WO | WO-2003070277 A1 | 8/2003 |
| WO | WO-2003099858 A1 | 12/2003 |
| WO | WO-2005051300 A2 | 6/2005 |
| WO | WO-2005051301 A2 | 6/2005 |
| WO | WO-2005051302 A2 | 6/2005 |
| WO | WO-2005051906 A2 | 6/2005 |
| WO | WO-2005054198 A2 | 6/2005 |
| WO | WO-2005085207 A2 | 9/2005 |
| WO | WO-2005118571 A1 | 12/2005 |
| WO | WO-2005121142 A1 | 12/2005 |
| WO | WO-2006002983 A1 | 1/2006 |
| WO | WO-2006039721 A2 | 4/2006 |
| WO | WO-2006107859 A2 | 10/2006 |
| WO | WO-2006107860 A2 | 10/2006 |
| WO | WO-2006109876 A1 | 10/2006 |
| WO | WO-2007024021 A1 | 3/2007 |
| WO | WO-2007044084 A2 | 4/2007 |
| WO | WO-2007109585 A2 | 9/2007 |
| WO | WO-2007132179 A2 | 11/2007 |
| WO | 2008012555 A2 | 1/2008 |
| WO | WO-2008005457 A2 | 1/2008 |
| WO | WO-2008103277 A2 | 8/2008 |
| WO | WO-2008128056 A1 | 10/2008 |
| WO | 2009001097 A2 | 12/2008 |
| WO | WO-2008154221 A2 | 12/2008 |
| WO | WO-2009011410 A1 | 1/2009 |
| WO | WO-2009011411 A1 | 1/2009 |
| WO | WO-2009011412 A2 | 1/2009 |
| WO | WO-2009046840 A1 | 4/2009 |
| WO | WO-2009054543 A1 | 4/2009 |
| WO | WO-2009054544 A1 | 4/2009 |
| WO | WO-2009082038 A2 | 7/2009 |
| WO | WO-2009082039 A1 | 7/2009 |
| WO | WO-2009093264 A2 | 7/2009 |
| WO | WO-2010072696 A2 | 7/2010 |
| WO | WO-2011140817 A1 | 11/2011 |
| WO | WO-2012163490 A1 | 12/2012 |
| WO | WO-2013016668 A2 | 1/2013 |
| WO | WO-2013070659 A1 | 5/2013 |

(Continued)

OTHER PUBLICATIONS

Abe et. al., "Discovery of a Highly Potent and Selective MEK Inhibitor: GSK1120212 (JTP-74057 DMSO Solvate)," ACS Med. Chem. Lett. 2011;2(4):320-324.

(Continued)

*Primary Examiner* — Erich A Leeser
(74) *Attorney, Agent, or Firm* — Dechert LLP; Andrea L. C. Reid; Gang Wang

(57) ABSTRACT

The present disclosure provides MEK inhibitors, compositions thereof, and methods of using the same.

22 Claims, No Drawings

(56) References Cited

FOREIGN PATENT DOCUMENTS

| | | |
|---|---|---|
| WO | WO-2014150427 A2 | 9/2014 |
| WO | WO-2014155301 A1 | 10/2014 |
| WO | WO-2014169843 A1 | 10/2014 |
| WO | WO-2014177982 A1 | 11/2014 |
| WO | WO-2014207100 A1 | 12/2014 |
| WO | WO-2015058589 A1 | 4/2015 |
| WO | WO-2015196072 A2 | 12/2015 |
| WO | WO-2016009306 A1 | 1/2016 |
| WO | WO-2016035008 A1 | 3/2016 |
| WO | 2016155473 A1 | 10/2016 |
| WO | WO-2017117687 A1 | 7/2017 |
| WO | WO-2018013789 A1 | 1/2018 |
| WO | WO-2018151830 A1 | 8/2018 |
| WO | WO-2019018119 A1 | 1/2019 |
| WO | WO-2019066069 A1 | 4/2019 |
| WO | WO-2019066070 A1 | 4/2019 |
| WO | WO-2020125747 A1 | 6/2020 |
| WO | WO-2020156162 A1 | 8/2020 |
| WO | 2021018112 A1 | 2/2021 |
| WO | WO-2021085636 A1 | 5/2021 |
| WO | WO-2021142144 A1 | 7/2021 |
| WO | WO-2021142345 A1 | 7/2021 |
| WO | WO-2021234003 A1 | 11/2021 |
| WO | 2021047573 A1 | 9/2022 |
| WO | 2022221866 A1 | 10/2022 |

OTHER PUBLICATIONS

Ishii et. al., "Enhanced inhibition of ERK signaling by a novel allosteric MEK inhibitor, CH5126766, that suppresses feedback reactivation of RAF activity," Cancer Res. 2013;1(73):4050-4060.

Khan et. al., "Structural basis for the action of the drug trametinib at KSR-bound MEK," Nature. 2020;588:509-514.

PCT International Search Report and Written Opinion from PCT/US2023/023482, dated Jul. 31, 2023.

MEK INHIBITORS AND USES THEREOF

CROSS-REFERENCE TO RELATED APPLICATIONS

This application claims the benefit of U.S. Provisional Application No. 63/488,807, filed on Mar. 7, 2023, U.S. Provisional Application No. 63/479,131, filed on Jan. 9, 2023, U.S. Provisional Application No. 63/375,875, filed on Sep. 16, 2022, and U.S. Provisional Application No. 63/345,698, filed on May 25, 2022, the entirety of each of which is hereby incorporated by reference.

TECHNICAL FIELD

The present disclosure relates to compounds and methods useful for inhibiting mitogen-activated protein kinase/extracellular signal-regulated kinase kinase (MEK). The disclosure also provides pharmaceutically acceptable compositions comprising compounds of the present disclosure and methods of using said compositions in the treatment of proliferative disorders, such as cancers.

BACKGROUND

Activation of the p42/44 MAPK signaling pathway comprising mitogen-activated protein kinase/extracellular signal-regulated kinase (ERK) kinase (MEK)-ERK has been implicated in the pathogenesis and progression of various cancers. The MEK-ERK pathway is often activated by mutation of upstream factors, BRAF or Ras, or by the signals of constitutively activated cell-surface receptors. Inhibition of MEK can be a promising strategy for controlling the growth of rumors, for example, the tumors associated with MEK pathway signaling.

SUMMARY

It has now been found that compounds of the present disclosure, and pharmaceutically acceptable compositions thereof, are effective as MEK inhibitors.

In one aspect, the instant disclosure provides a compound of Formula (I):

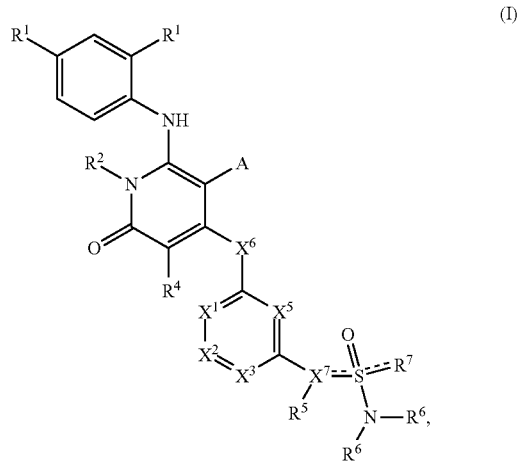

(I)

or a pharmaceutically acceptable salt thereof, wherein each variable is as defined and described herein.

In another aspect, the instant disclosure provides a compound of Formula (II):

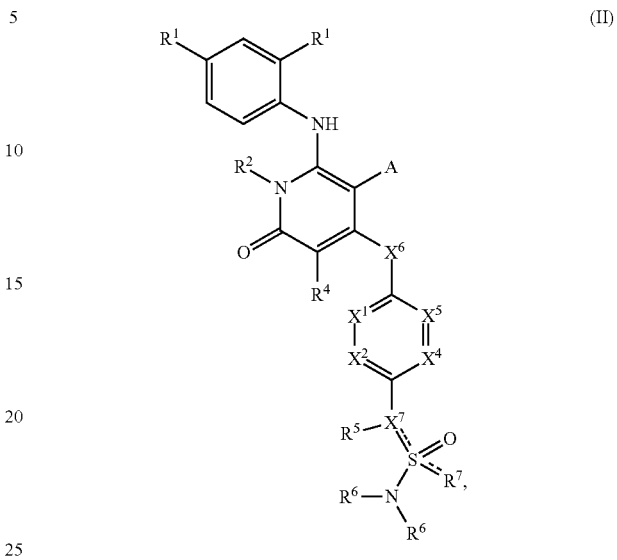

(II)

or a pharmaceutically acceptable salt thereof, wherein each variable is as defined and described herein.

Another aspect of the disclosure provides a method of treating a disorder mediated by MEK in a subject. The method comprises administering a therapeutically effective amount of a compound described herein to a subject in need thereof to treat the disorder mediated by MEK, as further described in the detailed description.

Another aspect of the disclosure provides a method of inhibiting MEK activity. The method comprises contacting MEK or a KSR-MEK complex or a RAF-MEK complex with an effective amount of a compound described herein, as further described in the detailed description.

In some aspects, compounds of the present disclosure, and pharmaceutically acceptable compositions thereof, are useful for treating proliferative disorders, such as the cancers as described herein.

DETAILED DESCRIPTION

Compounds of the present disclosure, and pharmaceutical compositions thereof, are useful as MEK inhibitors. Without wishing to be bound by any particular theory, it is believed that the compounds of the present disclosure may directly engage kinase suppressor of Ras (KSR) at the MEK interface, and that KSR may remodel the prototypical allosteric pocket of the MEK inhibitor in the KSR-MEK complex. Without wishing to be bound by any particular theory, it is believed that the compounds of the present disclosure may bind the KSR-MEK complex and may disrupt the related RAF-MEK complex.

I. Definitions

When introducing elements of the different aspects as described herein, the articles "a," "an," "the," and "said" are intended to mean that there are one or more of the elements. The terms "comprising," "including," and "having" are intended to be inclusive and mean that there may be additional elements other than the listed elements.

Compounds of the present disclosure include those described generally herein, and are further illustrated by the classes, subclasses, and species disclosed herein. As used herein, the following definitions shall apply unless otherwise indicated. For purposes of this disclosure, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic," or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl, or (cycloalkyl)alkenyl.

As used herein, the term "bicyclic ring" or "bicyclic ring system" refers to any bicyclic ring system, i.e., carbocyclic or heterocyclic, saturated or having one or more units of unsaturation, having one or more atoms in common between the two rings of the ring system. Thus, the term includes any permissible ring fusion, such as ortho-fused or spirocyclic. As used herein, the term "heterobicyclic" is a subset of "bicyclic" that requires that one or more heteroatoms are present in one or both rings of the bicycle. Such heteroatoms may be present at ring junctions and are optionally substituted, and may be selected from nitrogen (including N-oxides), oxygen, sulfur (including oxidized forms such as sulfones and sulfonates), phosphorus (including oxidized forms such as phosphates), boron, etc. In some embodiments, a bicyclic group has 7-12 ring members and 0-4 heteroatoms independently selected from nitrogen, oxygen, or sulfur. As used herein, the term "bridged bicyclic" refers to any bicyclic ring system, i.e., carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bicyclic rings include:

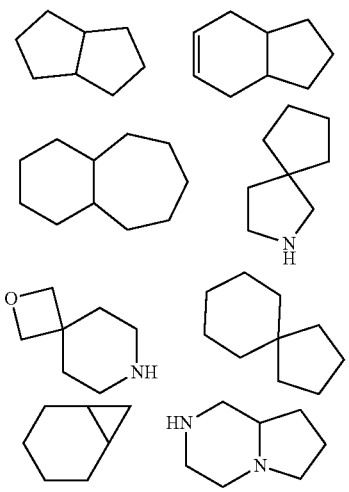

Exemplary bridged bicyclics include:

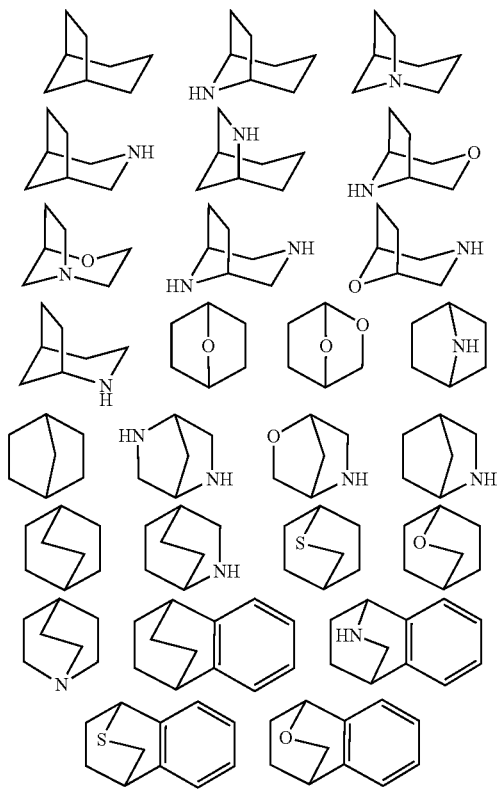

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$(as in N-substituted pyrrolidinyl)).

The term "unsaturated", as used herein, means that a moiety has one or more units of unsaturation.

As used herein, the term "bivalent $C_1$-$C_8$ (or $C_1$-$C_6$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

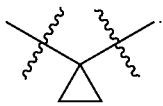 [SMILES: *C1(*)CC1]

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present disclosure, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the present disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Each optional substituent on a substitutable carbon is a monovalent substituent independently selected from halogen; —$(CH_2)_{0-4}R^°$; —$(CH_2)_{0-4}OR^°$; —$O(CH_2)_{0-4}R^°$, —$O$—$(CH_2)_{0-4}C(O)OR^°$; —$(CH_2)_{0-4}CH(OR^°)_2$; —$(CH_2)_{0-4}SR^°$; —$(CH_2)_{0-4}Ph$, which may be substituted with $R^°$; —$(CH_2)_{0-4}O(CH_2)_{0-1}Ph$ which may be substituted with $R^°$; —CH=CHPh, which may be substituted with $R^°$; —$(CH_2)_{0-4}O(CH_2)_{0-1}$-pyridyl which may be substituted with $R^°$; —$NO_2$; —CN; —$N_3$; —$(CH_2)_{0-4}N(R^°)_2$; —$(CH_2)_{0-4}N(R^°)C(O)R^°$; —$N(R^°)C(S)R^°$; —$(CH_2)_{0-4}N(R^°)C(O)NR^°_2$; —$N(R^°)C(S)NR^°_2$; —$(CH_2)_{0-4}N(R^°)C(O)OR^°$; —$N(R^°)N(R^°)C(O)R^°$; —$N(R^°)N(R^°)C(O)NR^°_2$; —$N(R^°)N(R^°)C(O)OR^°$; —$(CH_2)_{0-4}C(O)R^°$; —$C(S)R^°$; —$(CH_2)_{0-4}C(O)OR^°$; —$(CH_2)_{0-4}C(O)SR^°$; —$(CH_2)_{0-4}C(O)OSiR^°_3$; —$(CH_2)_{0-4}OC(O)R^°$; —$OC(O)(CH_2)_{0-4}SR$—, $SC(S)SR^°$; —$(CH_2)_{0-4}SC(O)R^°$; —$(CH_2)_{0-4}C(O)NR^{°2}$; —$C(S)NR^°_2$; —$C(S)SR^°$; —$SC(S)SR^°$, —$(CH_2)_{0-40}C(O)NR^{°2}$; —$C(O)N(OR^°)R^°$; —$C(O)C(O)R^°$; —$C(O)CH_2C(O)R^°$; —$C(NOR^°)R^°$; —$(CH_2)_{0-4}SSR^°$; —$(CH_2)_{0-4}S(O)_2R^°$; —$(CH_2)_{0-4}S(O)_2OR^°$; —$(CH_2)_{0-4}OS(O)_2R^°$; —$S(O)_2NR^{°2}$; —$S(O)(NR^°)R^°$; —$S(O)_2N=C(NR^°_2)_2$; —$(CH_2)_{0-4}S(O)R^°$; —$N(R^°)S(O)_2NR^°_2$; —$N(R^°)S(O)_2R^°$; —$N(OR^°)R^°$; —$C(NH)NR^°_2$; —$P(O)_2R^°$; —$P(O)R^°_2$; —$OP(O)R^°_2$; —$OP(O)(OR^°)_2$; $SiR^°_3$; —$(C_{1-4}$ straight or branched alkylene)O—$N(R^°)_2$; or —$(C_{1-4}$ straight or branched alkylene)C(O)O—$N(R^°)_2$.

Each $R^°$ is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^°$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted by a divalent substituent on a saturated carbon atom of $R^°$ selected from =O and =S; or each $R^°$ is optionally substituted with a monovalent substituent independently selected from halogen, —$(CH_2)_{0-2}R^•$, -(halo$R^•$), —$(CH_2)_{0-2}OH$, —$(CH_2)_{0-2}OR^•$, —$(CH_2)_{0-2}CH(OR^•)_2$; —O(halo$R^•$), —CN, —$N_3$, —$(CH_2)_{0-2}C(O)R^•$, —$(CH_2)_{0-2}C(O)OH$, —$(CH_2)_{0-2}C(O)OR^•$, —$(CH_2)_{0-2}SR^•$, —$(CH_2)_{0-2}SH$, —$(CH_2)_{0-2}NH_2$, —$(CH_2)_{0-2}NHR^•$, —$(CH_2)_{0-2}NR^•_2$, —$NO_2$, —$SiR^•_3$, —$OSiR^•_3$, —$C(O)SR^•$, —$(C_{1-4}$ straight or branched alkylene)C(O)O$R^•$, or —$SSR^•$.

Each $R^•$ is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, and wherein each $R^•$ is unsubstituted or where preceded by halo is substituted only with one or more halogens; or wherein an optional substituent on a saturated carbon is a divalent substituent independently selected from =O, =S, =NNR*_2, =NNHC(O)R*, =NNHC(O)OR*, =NNHS(O)_2R*, =NR*, =NOR*, —O(C(R*_2))_{2-3}O—, or —S(C(R*_2))_{2-3}S—, or a divalent substituent bound to vicinal substitutable carbons of an "optionally substituted" group is —O(CR*_2)_{2-3}O—, wherein each independent occurrence of R* is selected from hydrogen, $C_{1-6}$ aliphatic or an unsubstituted 5-6-membered saturated, partially unsaturated, or aryl ring having 0-4 heteroatoms independently selected from nitrogen, oxygen, or sulfur.

When R* is $C_{1-6}$ aliphatic, R* is optionally substituted with halogen, —$R^•$, -(halo$R^•$), —OH, —$OR^•$, —O(halo$R^•$), —CN, —C(O)OH, —C(O)O$R^•$, —$NH_2$, —NH$R^•$, —N$R^•_2$, or —$NO_2$, wherein each $R^•$ is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, and wherein each $R^•$ is unsubstituted or where preceded by halo is substituted only with one or more halogens.

An optional substituent on a substitutable nitrogen is independently —$R^†$, —$NR^†_2$, —$C(O)R^†$, —$C(O)OR^†$, —$C(O)C(O)R^†$, —$C(O)CH_2C(O)R^†$, —$S(O)_2R^†$, —$S(O)_2NR^†_2$, —$C(S)NR^†_2$, —$C(NH)NR^†_2$, or —$N(R^†)S(O)_2R^†$; wherein each $R^†$ is independently hydrogen, $C_1$-$C_6$ aliphatic, unsubstituted —OPh, or an unsubstituted 5-6-membered saturated, partially unsaturated, or aryl ring having 0-4 heteroatoms independently selected from nitrogen, oxygen, or sulfur, or, two independent occurrences of R, taken together with their intervening atom(s) form an unsubstituted 3-12-membered saturated, partially unsaturated, or aryl mono- or bicyclic ring having 0-4 heteroatoms independently selected from nitrogen, oxygen, or sulfur; wherein when $R^†$ is $C_1$-$C_6$ aliphatic, $R^†$ is optionally substituted with halogen, —$R^•$, -(halo$R^•$), —OH, —$OR^•$, —O(halo$R^•$), —CN, —C(O)OH, —C(O)O$R^•$, —$NH_2$, —NH$R^•$, —N$R^•_2$, or —$NO_2$, wherein each $R^•$ is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, and wherein each $R^•$ is unsubstituted or where preceded by halo is substituted only with one or more halogens.

In some embodiments, "alkyl" as used alone or as part of a group, refers to saturated monovalent hydrocarbon radicals having straight or branched hydrocarbon chains or, in the event that at least 3 carbon atoms are present, cyclic hydrocarbons or combinations thereof and contains 1 to 20 carbon atoms ($C_1$-$C_{20}$ alkyl), 1 to 10 carbon atoms ($C_1$-$C_{10}$ alkyl), 1 to 8 carbon atoms ($C_1$-$C_8$ alkyl), 1 to 6 carbon atoms ($C_1$-$C_4$ alkyl), or 1 to 4 carbon atoms ($C_1$-$C_4$ alkyl). In some embodiments, alkyl radicals include methyl, ethyl, propyl, isopropyl, n-butyl, isobutyl, sec-butyl, tert-butyl, pentyl, isoamyl, hexyl, cyclopropyl, cyclobutyl, cyclopentyl, cyclohexyl and the like.

In some embodiments, "alkoxy" refers to —O-(alkyl), wherein "alkyl" is as defined above.

In some embodiments, "cycloalkyl" as used alone or in combination, means a saturated or partially saturated monocyclic, bicyclic or tricyclic alkyl radical wherein each cyclic moiety contains from 3 to 8 carbon atoms, or from 3 to 6 carbon atoms. In some embodiments, cycloalkyl radicals include cyclopropyl, cyclobutyl, cyclopentyl, cyclohexyl and the like.

In some embodiments, halogen or halo is F, Cl, Br, or I.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_1-C_4alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the disclosure. Unless otherwise stated, all tautomeric forms of the compounds of the disclosure are within the scope of the disclosure. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this disclosure. Such compounds are useful, for example, as analytical tools, as probes in biological assays, or as therapeutic agents in accordance with the present disclosure.

As used herein, the term "provided compound" refers to any MEK inhibitor genus, subgenus, and/or species set forth herein.

As used herein, the terms "inhibitor" or "MEK inhibitor" or "MEK antagonist" are defined as a compound that binds to and/or inhibits MEK with measurable affinity. In some embodiments, inhibition in the presence of a MEK inhibitor or a MEK antagonist is observed in a dose-dependent manner. In some embodiments, the measured signal (e.g., signaling activity or biological activity) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or at least about 100% lower than the signal measured with a negative control under comparable conditions. The potency of an inhibitor is usually defined by its $IC_{50}$ value (half maximal inhibitory concentration or concentration required to inhibit 50% of the agonist response). The lower the $IC_{50}$ value the greater the potency of the antagonist and the lower the concentration that is required to inhibit the maximum biological response. In certain embodiments, an inhibitor has an $IC_{50}$ and/or binding constant of less than about 100 μM, less than about 50 μM, less than about 1 μM, less than about 500 nM, less than about 100 nM, less than about 10 nM, or less than about 1 nM.

The terms "measurable affinity" and "measurably inhibit," as used herein, means a measurable change or inhibition in MEK activity between a sample comprising a compound of the present disclosure, or composition thereof, and MEK, and an equivalent sample comprising MEK, in the absence of said compound, or composition thereof.

As used herein, the term "effective amount" refers to the amount of a compound sufficient to effect beneficial or desired results (e.g., a therapeutic, ameliorative, inhibitory, or preventative result). An effective amount can be administered in one or more administrations, applications, or dosages and is not intended to be limited to a particular formulation or administration route.

As used herein, the term "treating" includes any effect, e.g., lessening, reducing, modulating, ameliorating or eliminating, that results in the improvement of the condition, disease, disorder, and the like, or ameliorating a symptom thereof. In some embodiments, treatment can be administered after one or more symptoms have developed. In other embodiments, treatment can be administered in the absence of symptoms. For example, treatment can be administered to a susceptible individual prior to the onset of symptoms (e.g., in light of a history of symptoms and/or in light of genetic or other susceptibility factors). Treatment can also be continued after symptoms have resolved, for example, to prevent or delay their recurrence.

The phrases "disorder mediated by MEK" or "disease mediated by MEK" or "MEK-associated disease or disorder," as used herein, refer to diseases or disorders associated with, or mediated by MEK or MEK activity. A non-limiting example of a MEK-associated disease or disorder is a MEK-associated cancer.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, PA [1975].

As used herein, a "non-ATP competitive" or "ATP non-competitive" MEK inhibitor refers to an inhibitor of IEK that does not bind in the ATP pocket of IEK, or does not displace ATP from the MEK active site, and can form direct contacts when co-bound to the MEK-ATP complex. Non-ATP competitive inhibition by a compound of the present disclosure can be confirmed by art-recognized methods such as enzymology studies, competition assays, biophysical methods, including X-ray co-crystallography. An exemplary non-ATP competitive inhibitor of the present disclosure inhibits recombinant MEK1 or MEK2 with an $IC_{50}$ of from about 1 nM to about 50 µM. In some embodiments, an exemplary non-ATP competitive inhibitor of the present disclosure inhibits recombinant MEK1 or MEK2 with an $IC_{50}$ of about 1 nM to about 1000 nM, about 1 µM to about 50 µM, about 1 µM to about 25 µM, about 1 µM to about 10 µM, about 500 nM to about 5 µM, or about 10 nM to about 500 nM.

An "inhibitor pocket", as used herein, refers to a structure formed at the interface of the interaction between MEK and KSR or BRAF or CRAF with which an inhibitor of the present disclosure is engaged.

As used herein, a compound of the disclosure "allosterically binds an inhibitor pocket" when a compound binds outside the active site, including, for example, outside or adjacent to the ATP-binding site of a kinase.

As used herein, an "inhibitor-inhibitor pocket complex" describes a species in which an inhibitor of the present disclosure allosterically binds an inhibitor pocket formed at an interaction interface between human MEK (MEK1 or MEK2) and human Kinase Suppressor of Ras (KSR1, KSR2, or the KSR homolog BRAF or CRAF) adjacent to ATP in a physiological complex between MEK and KSR.

The term "trapping," as used herein, refers to when an inhibitor of the present disclosure binds to and stabilizes the CRAF-MEK complex in an inactive conformation.

As used herein, when a moiety on an inhibitor "engages" an amino acid residue of MEK1 and/or KSR and/or BRAF or CRAF in an inhibitor pocket, this interaction is detectable by X-ray crystallography, or similar structural methods, such as cryo-electron microscopy, NMR, or in silico docking, including fragment binding and computational simulations, which demonstrates that the interaction defining the engagement is a separation between the inhibitor moiety and the amino acid residue of not more than about 8 Å, including, for example, from about 2 A to about 5 Å, or from 5 Å to about 8 Å. The distances provided herein allow for the implicit inclusion of hydrogen atoms; however, hydrogen atoms were not included in the present crystallographic models, which is appropriate unless crystals diffract to very high resolutions (i.e., better than 1.5 Angstroms). Literature surveys of drug-receptor atom pairs across all structures in the protein data bank have used 4-5 Angstrom distance cutoffs (PMID 29308120, 26517868, 19221587) to evaluate reasonable small molecule hydrophobic bonding interactions and have found that intermolecular carbon-carbon interactions similar to the trametinib-KSR contacts are among the most highly represented drug-receptor atom pairs within the protein data bank. With respect to the interactions between the inhibitors of the present disclosure and the MEK-KSR and/o BRAF or CRAF complex, a 4 Angstrom contact is reasonable based on the nature of the trametinib-KSR interaction and precedence of known drug-receptor complexes. This contact is within the range of known contacts as defined by several independent groups (PMID 29308120, 26517868, 19221587).

II. Description of Compounds

In one aspect, the present disclosure provides a compound of Formula (I):

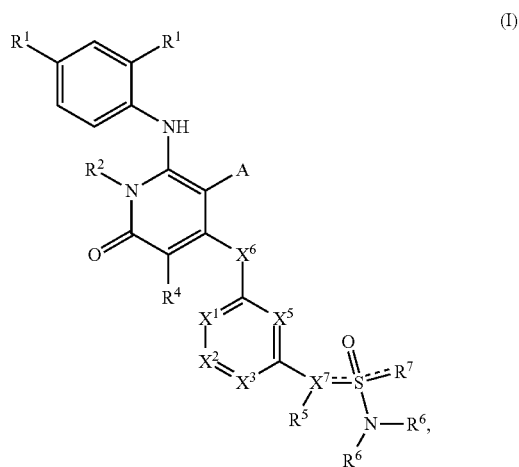

or a pharmaceutically acceptable salt thereof, wherein:
each

is independently a single or double bond;
each A is independently

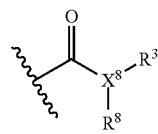

or optionally substituted 5-6 membered heteroaryl;
$X^1$, $X^2$, $X^3$, and $X^5$ are independently $CR^1$ or N;
$X^6$ is C(O), O or NH;
$X^7$ is CH or N;
$X^8$ is N or O;
each $R^1$ is independently hydrogen, halo, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, or optionally substituted $C_6$-$C_{10}$ aryl;
$R^2$, $R^3$, $R^4$, and $R^5$ are independently hydrogen, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, or optionally substituted $C_6$-$C_{10}$ aryl;
each $R^6$ is independently hydrogen, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, optionally substituted $C_6$-$C_{10}$ aryl, or both $R^6$ taken together with the atom to which they attach form an optionally substituted 3-7 membered hetercycloalkyl ring, or
$R^5$ and $R^6$ taken together with the atoms to which they attach form a 5-6 membered heterocycloalkyl ring; or
$R^5$ and $X^5$ or $X^3$ taken together with the atoms to which they attach form a 5-6 membered fused heterocycloalkyl ring;
$R^6$ and $X^5$ or $X^3$ taken together with the atoms to which they attach form a 5-6 membered fused heterocycloalkyl ring; and $R^7$ is O or optionally substituted $C_1$-$C_6$ aliphatic; and
$R^8$ is absent, hydrogen, or optionally substituted $C_1$-$C_6$ aliphatic.

In some aspects, the present disclosure provides a compound of Formula (I):

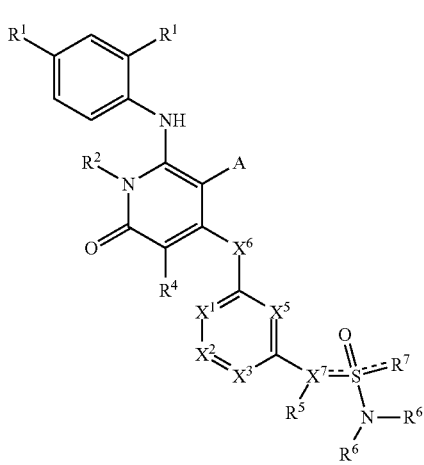

or a pharmaceutically acceptable salt thereof, wherein:
each

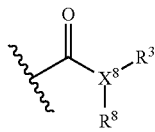

is independently a single or double bond;
each A is independently

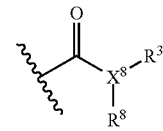

or optionally substituted 5-6 membered heteroaryl;
$X^1$, $X^2$, $X^3$, and $X^5$ are independently $CR^1$ or N;
$X^6$ is C(O), O or NH;
$X^7$ is CH or N;
$X^8$ is N or O;
each $R^1$ is independently hydrogen, deuterium, halo, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, or optionally substituted $C_6$-$C_{10}$ aryl;
$R^2$, $R^3$, $R^4$, and $R^5$ are independently hydrogen, $C(^2D)_3$, $OC(^2D)_3$, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, or optionally substituted $C_6$-$C_{10}$ aryl;
each $R^6$ is independently hydrogen, deuterium, $C(^2D)_3$, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, or optionally substituted $C_6$-$C_{10}$ aryl, or both $R^6$ taken together with the atom to which they attach form an optionally substituted 3-7 membered hetercycloalkyl ring, or $R^5$ and $R^6$ taken together with the atoms to which they attach form a 5-6 membered heterocycloalkyl ring; or
$R^5$ and $X^5$ or $X^3$ taken together with the atoms to which they attach form a 5-6 membered fused heterocycloalkyl ring;
$R^6$ and $X^5$ or $X^3$ taken together with the atoms to which they attach form a 5-6 membered fused heterocycloalkyl ring; and
$R^7$ is O or optionally substituted $C_1$-$C_6$ aliphatic; and
$R^8$ is absent, hydrogen, deuterium, or optionally substituted $C_1$-$C_6$ aliphatic.

As defined generally above, $X^1$, $X^2$, $X^3$, and $X^5$ are independently $CR^1$ or N. In some embodiments, $X^1$, $X^2$, $X^3$, and $X^5$ are $CR^1$. In some embodiments, $X^1$, $X^3$, and $X^5$ are $CR^1$ and $X^2$ is N. As defined generally above, $R^1$ is independently hydrogen, halo, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, and optionally substituted $C_6$-$C_{10}$ aryl. In some embodiments, $R^1$ is hydrogen, halo, or optionally substituted $C_1$-$C_6$ alkoxy. In some embodiments, $R^1$ is hydrogen, chloro, fluoro, methoxy, ethoxy, propoxy, ethoxy, or hexyloxy. In some embodiments, $R^1$ is hydrogen, fluoro, chloro, or methoxy.

As defined generally above, each

is independently a single or double bond.

As defined generally above, each A is independently

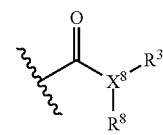

or optionally substituted 5-6 membered heteroaryl. In some embodiments, each A is independently

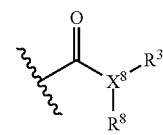

As defined generally above, $X^8$ is N or O. In some embodiments, $X^8$ is N. In some embodiments, $X^8$ is O. In some embodiments, $X^8$ is N; and $R^3$ and $R^8$, taken together with the N atom to which they attach, form an optionally substituted 3-7 membered hetercycloalkyl ring. As defined generally above, $R^8$ is hydrogen, halo, or optionally substituted $C_1$-$C_6$ aliphatic. In some embodiments, $R^8$ is hydrogen or methyl.

In some embodiments, each A is independently optionally substituted 5-6 membered heteroaryl. In some embodiments, each A is independently optionally substituted 5- or 6-membered heteroaryl. In some embodiments, each A is independently optionally substituted 5-membered heteroaryl. In some embodiments, each A is optionally substituted imidazole. In some embodiments, each A is

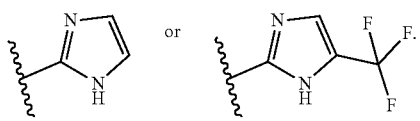 [SMILES: *c1ncc[nH]1 ; "or" ; *c1ncc(C(F)(F)F)[nH]1]

As defined generally above, $X^6$ is O or NH. In some embodiments, $X^6$ is O. In some embodiments, $X^6$ is NH. In some embodiments, $X^6$ is C(O).

As defined generally above, $X^7$ is CH or N. In some embodiments, $X^7$ is CH. In some embodiments, $X^7$ is N.

As defined generally above, each $R^1$ is independently hydrogen, halo, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, and optionally substituted $C_6$-$C_{10}$ aryl. In some embodiments, $R^1$ is halo. In some embodiments, $R^1$ is fluoro, chloro, iodo, —$OCF_3$, cyclopropyl, —$CF_3$, or ethyne. In some embodiments, $R^1$ is fluoro or iodo. In some embodiments, $R^1$ is —CN.

As defined generally above, each $R^1$ is independently hydrogen, deuterium, halo, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, and optionally substituted $C_6$-$C_{10}$ aryl. In some embodiments, $R^1$ is halo. In some embodiments, $R^1$ is fluoro, chloro, iodo, —$OCF_3$, cyclopropyl, —$CF_3$, or ethyne. In some embodiments, $R^1$ is fluoro or iodo. In some embodiments, $R^1$ is —CN.

As defined generally above, $R^2$ is hydrogen, halo, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, or optionally substituted $C_6$-$C_{10}$ aryl. In some embodiments, $R^2$ is optionally substituted $C_1$-$C_6$ aliphatic. In some embodiments, $R^2$ is methyl, ethyl, propyl, pentyl, butyl, or hexyl. In some embodiments, $R^2$ is methyl.

As defined generally above, $R^2$ is hydrogen, $C(^2D)_3$, $OC(^2D)_3$, halo, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, or optionally substituted $C_6$-$C_{10}$ aryl. In some embodiments, $R^8$ is optionally substituted $C_1$-$C_6$ aliphatic. In some embodiments, $R^8$ is methyl, ethyl, propyl, pentyl, butyl, or hexyl. In some embodiments, $R^2$ is methyl.

As defined generally above, $R^3$ is hydrogen, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, and optionally substituted $C_6$-$C_{10}$ aryl. In some embodiments, $R^3$ is optionally substituted $C_3$-$C_{10}$ cycloalkyl. In some embodiments, $R^3$ is optionally substituted $C_3$-$C_8$ cycloalkyl. In some embodiments, $R^3$ is optionally substituted $C_3$-$C_6$ cycloalkyl. In some embodiments, $R^3$ is cyclopropyl, cyclopentyl, cyclobutyl, or cyclohexyl. In some embodiments, $R^3$ is cyclopropyl or optionally substituted cyclopropyl. In some embodiments, $R^3$ is cyclopropyl. In some embodiments, $R^3$ is —$(C_3H_3)F_2$.

As defined generally above, $R^4$ is hydrogen, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, and optionally substituted $C_6$-$C_{10}$ aryl. In some embodiments, $R^4$ is optionally substituted $C_1$-$C_6$ aliphatic. In some embodiments, $R^4$ is methyl, ethyl, propyl, pentyl, butyl, or hexyl. In some embodiments, $R^4$ is methyl. In some embodiments, $R^4$ is $CF_3$.

As defined generally above, $R^4$ is hydrogen, $C(^2D)_3$, $OC(^2D)_3$, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, and optionally substituted $C_6$-$C_{10}$ aryl. In some embodiments, $R^4$ is optionally substituted $C_1$-$C_6$ aliphatic. In some embodiments, $R^4$ is methyl, ethyl, propyl, pentyl, butyl, or hexyl. In some embodiments, $R^4$ is methyl. In some embodiments, $R^4$ is $CF_3$.

As defined generally above, $R^5$ is hydrogen, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, and optionally substituted $C_6$-$C_{10}$ aryl. In some embodiments, $R^5$ is hydrogen, optionally substituted $C_1$-$C_6$ aliphatic, or optionally substituted $C_1$-$C_6$ alkoxy. In some embodiments, $R^5$ is hydrogen. In some embodiments, $R^5$ is absent when $X^7$ is N forming a double bond with the sulfur atom.

As defined generally above, each $R^6$ is independently hydrogen, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, optionally substituted $C_6$-$C_{10}$ aryl, or both $R^6$ taken together with the atom to which they attach form a 3-7 membered hetercycloalkyl ring, or $R^5$ and $R^6$ taken together with the atoms to which they attach form a 5-6 membered heterocycloalkyl ring.

In some embodiments, each $R^6$ is independently hydrogen or optionally substituted $C_1$-$C_6$ aliphatic. In some embodiments, each $R^6$ is independently hydrogen, methyl, or —$(CH_2)_2N(CH_3)_2$.

In some embodiments, both $R^6$ taken together with the atom to which they attach form a 3-7 membered hetercycloalkyl ring. In some embodiments, both $R^6$ taken together with the atom to which they attach form a 3-, 4-, 5-, 6-, or 7-membered hetercycloalkyl ring.

In some embodiments, $R^5$ and $R^6$ taken together with the atoms to which they attach form a 5-6 membered heterocycloalkyl ring. In some embodiments, $R^5$ and $R^6$ taken together with the atoms to which they attach form a 5- or 6-membered heterocycloalkyl ring. In some embodiments, $R^5$ and $R^6$ taken together with the atoms to which they attach form a 5-membered heterocycloalkyl ring.

In some embodiments, $R^5$ and $X^5$ or $X^3$ taken together with the atoms to which they attach form a 5-6 membered fused heterocycloalkyl ring.

In some embodiments, $R^5$ and $X^5$ or $X^3$ taken together with the atoms to which they attach form a 5-6 membered fused heteroaromatic ring.

In some embodiments, $R^6$ and $X^5$ or $X^3$ taken together with the atoms to which they attach form a 5-6 membered fused heterocycloalkyl ring.

As defined generally above, $R^7$ is O or optionally substituted $C_1$-$C_6$ aliphatic. In some embodiments, $R^7$ is O. In some embodiments, $R^7$ is optionally substituted $C_1$-$C_6$ aliphatic. In some embodiments, $R^7$ is methyl.

As defined generally above, $R^8$ is absent, hydrogen, or optionally substituted $C_1$-$C_6$ aliphatic. In some embodiments, $R^8$ is hydrogen or methyl.

As defined generally above, $R^8$ is absent, hydrogen, deuterium, or optionally substituted $C_1$-$C_6$ aliphatic. In some embodiments, $R^8$ is hydrogen or methyl.

In another aspect, the present disclosure provides a compound of Formula (IA):

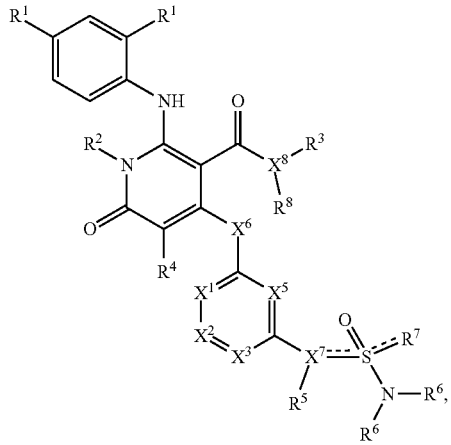

(IA)

or a pharmaceutically acceptable salt thereof, wherein. each

≡ is independently a single or double bond;

$X^1$, $X^2$, $X^3$, and $X^5$ are independently $CR^1$ or N;

$X^6$ is C(O), O, or NH;

$X^7$ is CH or N;

$X^8$ is N or O;

each $R^1$ is independently hydrogen, halo, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, or optionally substituted $C_6$-$C_{10}$ aryl;

$R^2$, $R^3$, $R^4$, and $R^5$ are independently hydrogen, halo, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, or optionally substituted $C_6$-$C_{10}$ aryl; and each $R^6$ is independently hydrogen, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, optionally substituted $C_6$-$C_{10}$ aryl, or both $R^6$ taken together with the atom to which they attach form an optionally substituted 3-7 membered hetercycloalkyl ring, or $R^5$ and $R^6$ taken together with the atoms to which they attach form a 5-6 membered heterocycloalkyl ring; or $R^6$ and $X^5$ or $X^3$ taken together with the atoms to which they attach form a 5-6 membered fused heterocycloalkyl ring;

$R^7$ is O or optionally substituted $C_1$-$C_6$ aliphatic; and $R^8$ is absent, hydrogen, or optionally substituted $C_1$-$C_6$ aliphatic.

In another aspect, the present disclosure provides a compound of Formula (IA):

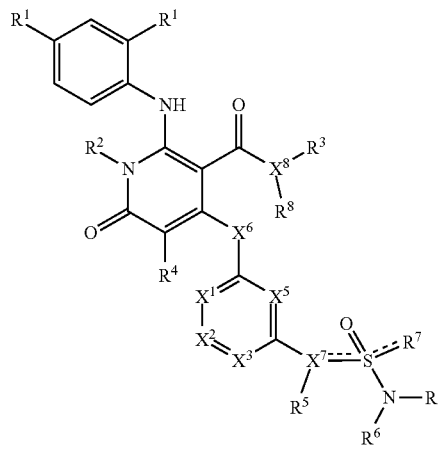

(IA)

or a pharmaceutically acceptable salt thereof, wherein: each

≡ is independently a single or double bond;

$X^1$, $X^2$, $X^3$, and $X^5$ are independently $CR^1$ or N;

$X^6$ is C(O), O, or NH;

$X^7$ is CH or N;

$X^8$ is N or O;

each $R^1$ is independently hydrogen, deuterium, halo, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, or optionally substituted $C_6$-$C_{10}$ aryl;

$R^2$, $R^3$, $R^4$, and $R^5$ are independently hydrogen, halo, $C(^2D)_3$, $OC(^2D)_3$, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, or optionally substituted $C_6$-$C_{10}$ aryl; and each $R^6$ is independently hydrogen, deuterium, $C(^2D)_3$, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, optionally substituted $C_6$-$C_{10}$ aryl, or both $R^6$ taken together with the atom to which they attach form an optionally substituted 3-7 membered hetercycloalkyl ring, or $R^5$ and $R^6$ taken together with the atoms to which they attach form a 5-6 membered heterocycloalkyl ring; or $R^5$ and $X^5$ or $X^3$ taken together with the atoms to which they attach form a 5-6 membered fused heterocycloalkyl ring;

$R^6$ and $X^5$ or $X^3$ taken together with the atoms to which they attach form a 5-6 membered fused heterocycloalkyl ring;

$R^7$ is O or optionally substituted $C_1$-$C_6$ aliphatic; and $R^8$ is absent, hydrogen, deuterium, or optionally substituted $C_1$-$C_6$ aliphatic.

As defined generally above, $X^1$, $X^2$, $X^3$, and $X^5$ are independently $CR^1$ or N. In some embodiments, $X^1$, $X^2$, $X^3$, and $X^5$ are $CR^1$. In some embodiments, $X^1$, $X^3$, and $X^5$ are $CR^1$ and $X^2$ is N. As defined generally above, $R^1$ is independently hydrogen, halo, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, and optionally substituted $C_6$-$C_{10}$ aryl. In some embodiments, $R^1$ is hydrogen, halo, or optionally substituted $C_1$-$C_6$ alkoxy. In some embodiments, $R^1$ is hydrogen, chloro, fluoro, methoxy, ethoxy, propoxy, ethoxy, or hexyloxy. In some embodiments, $R^1$ is hydrogen, fluoro, chloro, or methoxy.

As defined generally above, each

is independently a single or double bond.

As defined generally above, $X^6$ is O or NH. In some embodiments, $X^6$ is O. In some embodiments, $X^6$ is NH. In some embodiments, $X^6$ is C(O).

As defined generally above, $X^7$ is CH or N. In some embodiments, $X^7$ is CH. In some embodiments, $X^7$ is N.

As defined generally above, $X^8$ is N or O. In some embodiments, $X^8$ is N. In some embodiments, $X^8$ is O. In some embodiments, $X^8$ is N; and $R^3$ and $R^8$, taken together with the N atom to which they attach, form an optionally substituted 3-7 membered hetercycloalkyl ring.

As defined generally above, each $R^1$ is independently hydrogen, halo, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, and optionally substituted $C_6$-$C_{10}$ aryl. In some embodiments, $R^1$ is halo. In some embodiments, $R^1$ is fluoro, chloro, iodo, —$OCF_3$, cyclopropyl, —$CF_3$, or ethyne. In some embodiments, $R^1$ is fluoro or iodo. In some embodiments, $R^1$ is —CN.

As defined generally above, each $R^1$ is independently hydrogen, deuterium, halo, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, and optionally substituted $C_6$-$C_{10}$ aryl. In some embodiments, $R^1$ is halo. In some embodiments, $R^1$ is fluoro, chloro, iodo, —$OCF_3$, cyclopropyl, —$CF_3$, or ethyne. In some embodiments, $R^1$ is fluoro or iodo. In some embodiments, $R^1$ is —CN.

As defined generally above, $R^2$ is hydrogen, halo, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, or optionally substituted $C_6$-$C_{10}$ aryl. In some embodiments, $R^2$ is optionally substituted $C_1$-$C_6$ aliphatic. In some embodiments, $R^2$ is methyl, ethyl, propyl, pentyl, butyl, or hexyl. In some embodiments, $R^2$ is methyl.

As defined generally above, $R^2$ is hydrogen, halo, $C(^2D)_3$, $OC(^2D)_3$, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, or optionally substituted $C_6$-$C_{10}$ aryl. In some embodiments, $R^2$ is optionally substituted $C_1$-$C_6$ aliphatic. In some embodiments, $R^2$ is methyl, ethyl, propyl, pentyl, butyl, or hexyl. In some embodiments, $R^2$ is methyl.

As defined generally above, $R^3$ is hydrogen, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, and optionally substituted $C_6$-$C_{10}$ aryl. In some embodiments, $R^3$ is optionally substituted $C_3$-$C_{10}$ cycloalkyl. In some embodiments, $R^3$ is optionally substituted $C_3$-$C_8$ cycloalkyl. In some embodiments, $R^3$ is optionally substituted $C_3$-$C_6$ cycloalkyl. In some embodiments, $R^3$ is cyclopropyl, cyclopentyl, cyclobutyl, or cyclohexyl. In some embodiments, $R^3$ is cyclopropyl or optionally substituted cyclopropyl. In some embodiments, $R^3$ is cyclopropyl. In some embodiments, $R^3$ is —$(C_3H_3)F_2$.

As defined generally above, $R^4$ is hydrogen, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, and optionally substituted $C_6$-$C_{10}$ aryl. In some embodiments, $R^4$ is optionally substituted $C_1$-$C_6$ aliphatic. In some embodiments, $R^4$ is methyl, ethyl, propyl, pentyl, butyl, or hexyl. In some embodiments, $R^4$ is methyl. In some embodiments, $R^4$ is $CF_3$. As defined generally above, $R^4$ is hydrogen, $C(^2D)_3$, $OC(^2D)_3$, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, and optionally substituted $C_6$-$C_{10}$ aryl. In some embodiments, $R^4$ is optionally substituted $C_1$-$C_6$ aliphatic. In some embodiments, $R^4$ is methyl, ethyl, propyl, pentyl, butyl, or hexyl. In some embodiments, $R^4$ is methyl. In some embodiments, $R^4$ is $CF_3$.

As defined generally above, $R^5$ is hydrogen, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, and optionally substituted $C_6$-$C_{10}$ aryl. In some embodiments, $R^5$ is hydrogen, optionally substituted $C_1$-$C_6$ aliphatic, or optionally substituted $C_1$-$C_6$ alkoxy. In some embodiments, $R^5$ is hydrogen. In some embodiments, $R^5$ is absent when $X^7$ is N forming a double bond with the sulfur atom.

As defined generally above, each $R^6$ is independently hydrogen, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, optionally substituted $C_6$-$C_{10}$ aryl, or both $R^6$ taken together with the atom to which they attach form a 3-7 membered hetercycloalkyl ring, or $R^5$ and $R^6$ taken together with the atoms to which they attach form a 5-6 membered heterocycloalkyl ring.

As defined generally above, each $R^6$ is independently hydrogen, deuterium, $C(^2D)_3$, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, optionally substituted $C_6$-$C_{10}$ aryl, or both $R^6$ taken together with the atom to which they attach form a 3-7 membered hetercycloalkyl ring, or $R^5$ and $R^6$ taken together with the atoms to which they attach form a 5-6 membered heterocycloalkyl ring.

In some embodiments, each $R^6$ is independently hydrogen or optionally substituted $C_1$-$C_6$ aliphatic. In some embodiments, each $R^6$ is independently hydrogen, methyl, or —$(CH_2)_2N(CH_3)_2$.

In some embodiments, both $R^6$ taken together with the atom to which they attach form a 3-7 membered hetercycloalkyl ring. In some embodiments, both $R^6$ taken together with the atom to which they attach form a 3-, 4-, 5-, 6-, or 7-membered hetercycloalkyl ring.

In some embodiments, $R^5$ and $R^6$ taken together with the atoms to which they attach form a 5-6 membered heterocycloalkyl ring. In some embodiments, $R^5$ and $R^6$ taken together with the atoms to which they attach form a 5- or 6-membered heterocycloalkyl ring. In some embodiments, $R^5$ and $R^6$ taken together with the atoms to which they attach form a 5-membered heterocycloalkyl ring.

In some embodiments, $R^5$ and $X^5$ or $X^3$ taken together with the atoms to which they attach form a 5-6 membered fused heterocycloalkyl ring.

In some embodiments, $R^5$ and $X^5$ or $X^3$ taken together with the atoms to which they attach form a 5-6 membered fused heteroaromatic ring.

In some embodiments, $R^6$ and $X^5$ or $X^3$ taken together with the atoms to which they attach form a 5-6 membered fused heterocycloalkyl ring.

As defined generally above, $R^7$ is O or optionally substituted $C_1$-$C_6$ aliphatic. In some embodiments, $R^7$ is O. In some embodiments, $R^7$ is optionally substituted $C_1$-$C_6$ aliphatic. In some embodiments, $R^7$ is methyl.

As defined generally above, $R^8$ is absent, hydrogen, or optionally substituted $C_1$-$C_6$ aliphatic. In some embodiments, $R^8$ is hydrogen or methyl.

As defined generally above, $R^8$ is absent, hydrogen, deuterium, or optionally substituted $C_1$-$C_6$ aliphatic. In some embodiments, $R^8$ is hydrogen or methyl.

In some embodiments, the present disclosure provides a compound of Formulae (IB) to (IE):

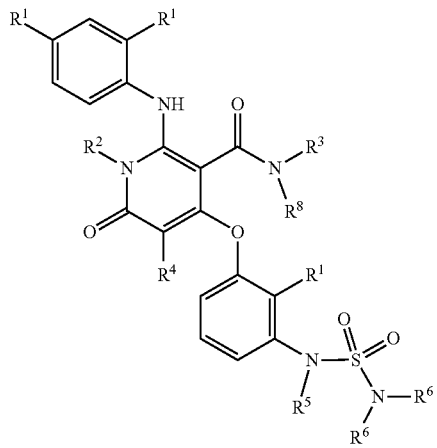

(IB)

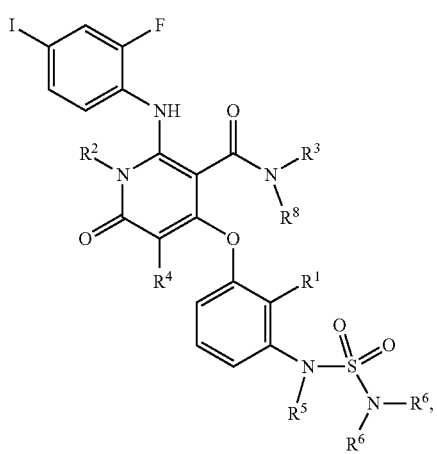

(IC)

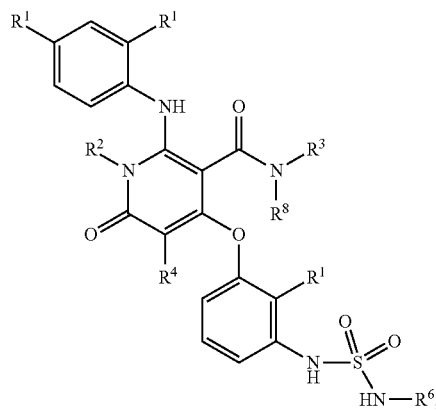

(ID)

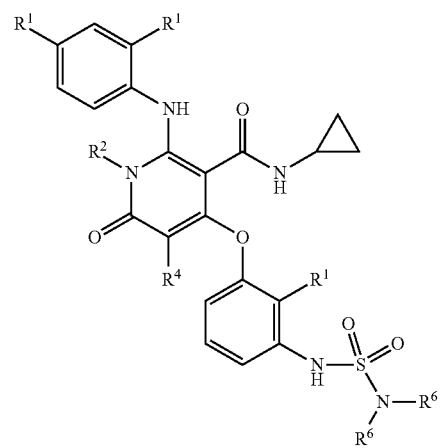

(IE)

or a pharmaceutically acceptable salt thereof, wherein each variable is independently as defined and described in embodiments herein.

TABLE 1

Exemplary Compounds.

| Compound # | Structure |
|---|---|
| I-1 | 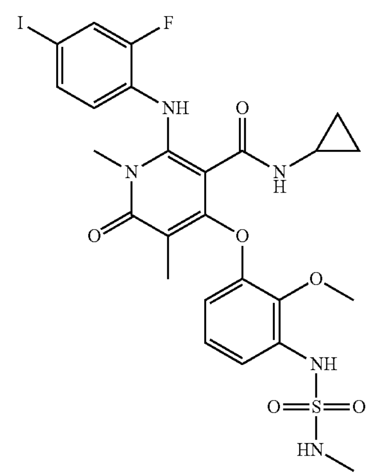 [SMILES: CNS(=O)(=O)Nc1cccc(Oc2c(C(=O)NC3CC3)c(Nc3ccc(I)cc3F)n(C)c(=O)c2C)c1OC] |

TABLE 1-continued
Exemplary Compounds.
| Compound # | Structure |
|---|---|
| I-2 | 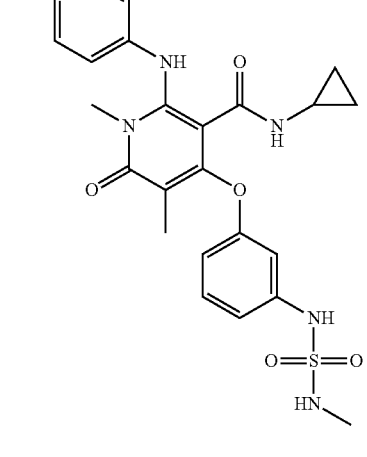 |
| I-3 | 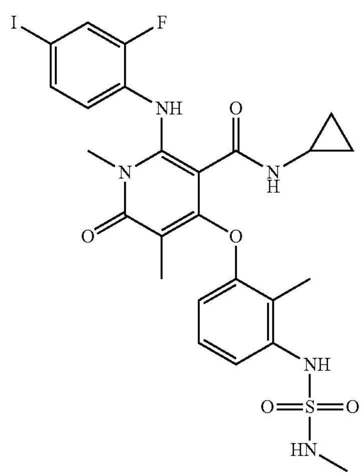 [SMILES: CNS(=O)(=O)Nc1cccc(Oc2c(C(=O)NC3CC3)c(Nc3ccc(I)cc3F)n(C)c(=O)c2C)c1C] |
| I-4 | 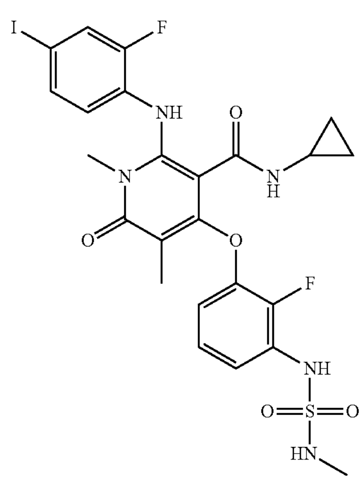 [SMILES: CNS(=O)(=O)Nc1cccc(Oc2c(C(=O)NC3CC3)c(Nc3ccc(I)cc3F)n(C)c(=O)c2C)c1F] |
| I-5 | 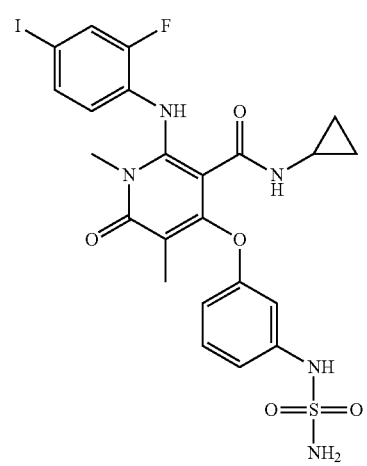 [SMILES: Cc1c(Oc2cccc(NS(N)(=O)=O)c2)c(C(=O)NC2CC2)c(Nc2ccc(I)cc2F)n(C)c1=O] |
| I-6 | |
| I-7 | 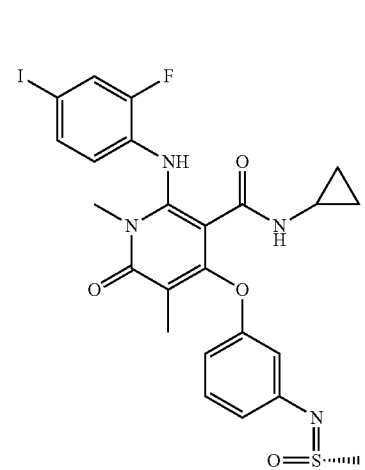 |

TABLE 1-continued

Exemplary Compounds.

| Compound # | Structure |
|---|---|
| I-8 | (structure) |
| I-9 | (structure) |
| I-10 | (structure) |
| I-11 | (structure) |
| I-12 | (structure) |
| I-13 | (structure) |

TABLE 1-continued
Exemplary Compounds.
| Compound # | Structure |
|---|---|
| I-14 | 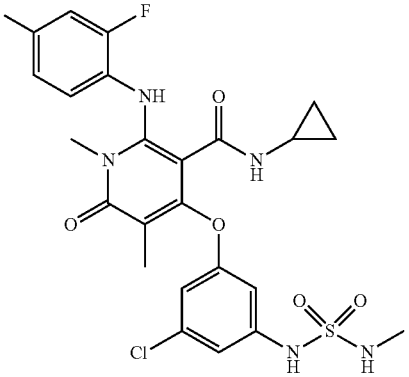 |
| I-15 | 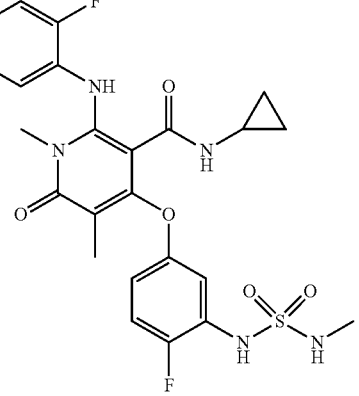 |
| I-16 | 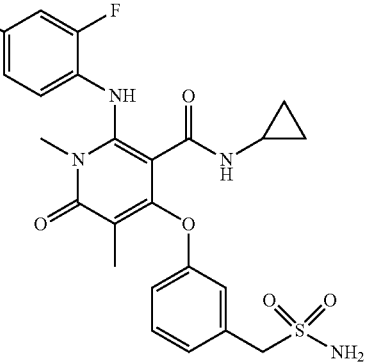 |
| I-17 | 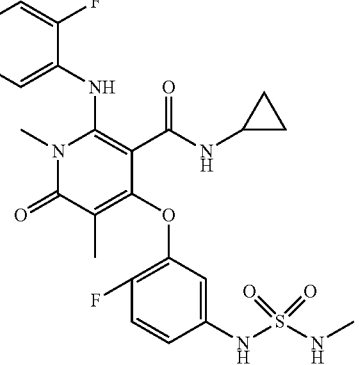 |
| I-18 | 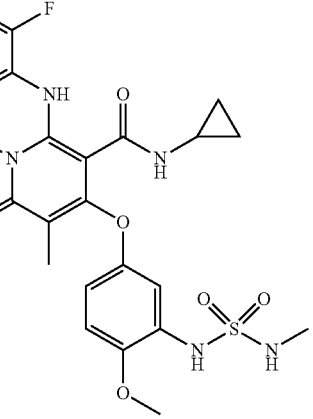 |
| I-19 | 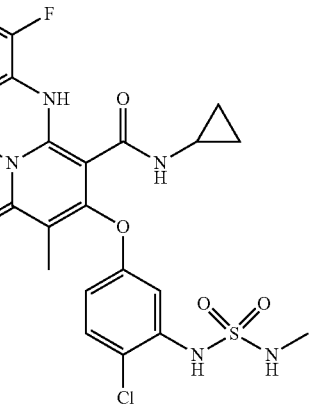 |
| I-20 | 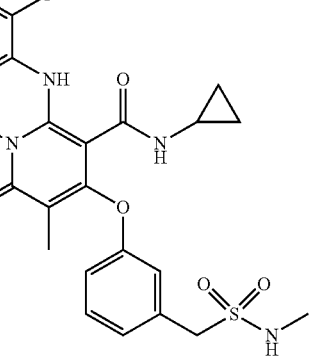 |

TABLE 1-continued

Exemplary Compounds.

| Compound # | Structure |
| --- | --- |
| I-21 | (structure) |
| I-22 | (structure) |
| I-23 | (structure) |
| I-24 | (structure) |
| I-25 | (structure) |
| I-26 | (structure) |
| I-27 | (structure) |

TABLE 1-continued
Exemplary Compounds.
| Compound # | Structure |
|---|---|
| I-28 | 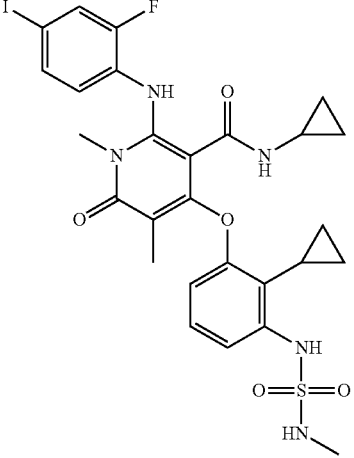 [SMILES: CNS(=O)(=O)Nc1cccc(Oc2c(C(=O)NC3CC3)c(Nc3ccc(I)cc3F)n(C)c(=O)c2C)c1C1CC1] |
| I-29 | 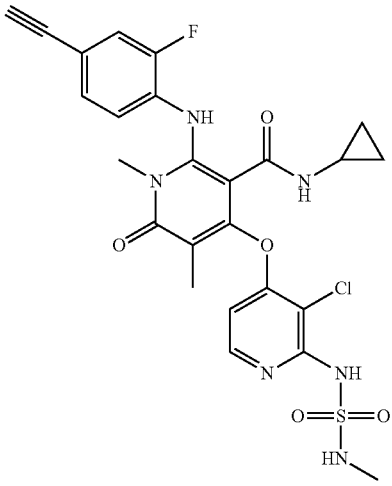 [SMILES: C#Cc1ccc(Nc2c(C(=O)NC3CC3)c(Oc3ccnc(NS(=O)(=O)NC)c3Cl)c(C)c(=O)n2C)c(F)c1] |
| I-30 | 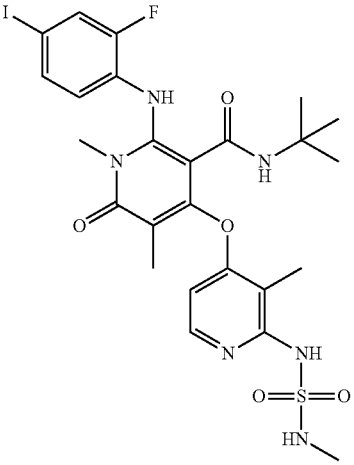 [SMILES: CNS(=O)(=O)Nc1nccc(Oc2c(C(=O)NC(C)(C)C)c(Nc3ccc(I)cc3F)n(C)c(=O)c2C)c1C] |
| I-31 | 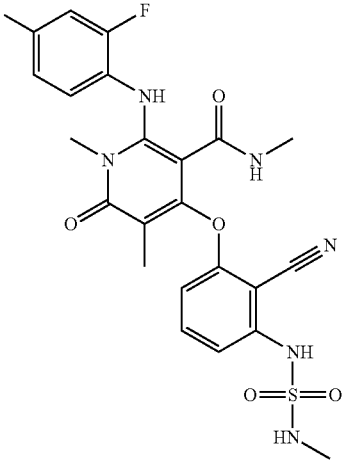 |
| I-32 | 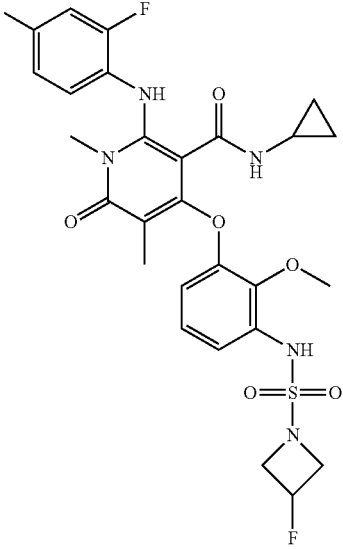 |

TABLE 1-continued

Exemplary Compounds.

| Compound # | Structure |
|---|---|
| I-33 | (structure) |
| I-34 | (structure) |
| I-35 | (structure) |
| I-36 | (structure) |
| I-37 | (structure) |

TABLE 1-continued

Exemplary Compounds.

| Compound # | Structure |
| --- | --- |
| I-38 | (structure) |
| I-39 | (structure) |
| I-40 | (structure) |
| I-41 | (structure) |
| I-42 | (structure) |
| I-43 | (structure) |
| I-44 | (structure) |
| I-45 | (structure) |

TABLE 1-continued

Exemplary Compounds.

| Compound # | Structure |
|---|---|
| I-46 | (structure) |
| I-47 | (structure) |
| I-48 | (structure) |
| I-49 | (structure) |
| I-50 | (structure) |
| I-51 | (structure) |
| I-52 | (structure) |
| I-53 | (structure) |

TABLE 1-continued
Exemplary Compounds.
| Compound # | Structure |
|---|---|
| I-54 | 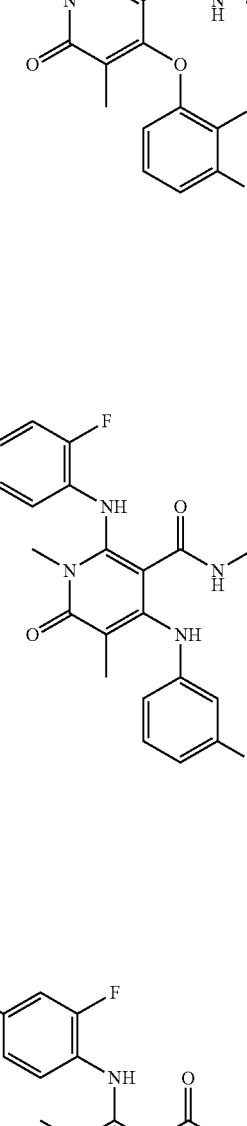 |
| I-55 | 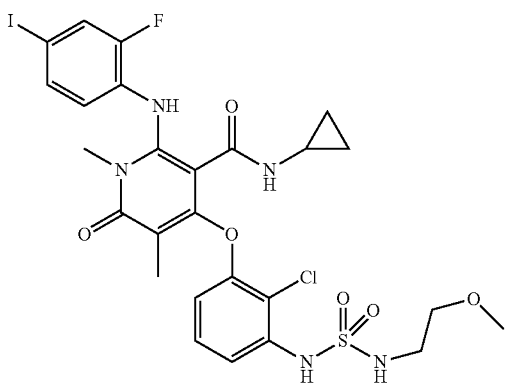 [SMILES: COCCNS(=O)(=O)Nc1cccc(Oc2c(C(=O)NC3CC3)c(Nc3ccc(I)cc3F)n(C)c(=O)c2C)c1Cl] |
| I-56 | 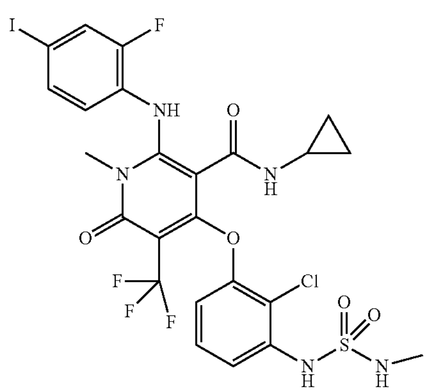 [SMILES: CNS(=O)(=O)Nc1cccc(Oc2c(C(=O)NC3CC3)c(Nc3ccc(I)cc3F)n(C)c(=O)c2C(F)(F)F)c1Cl] |
| I-57 | 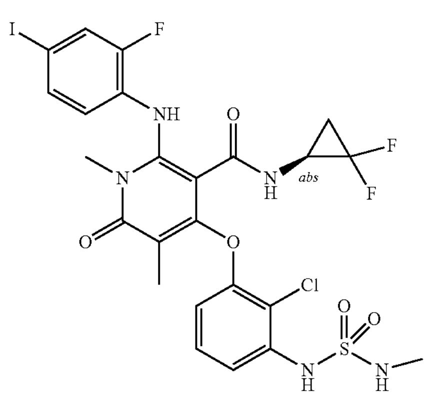 [SMILES: CNS(=O)(=O)Nc1cccc(Oc2c(C(=O)N[C@H]3CC3(F)F)c(Nc3ccc(I)cc3F)n(C)c(=O)c2C)c1Cl] |
| I-58 | 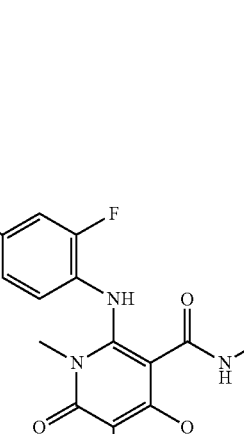 |
| I-77 | 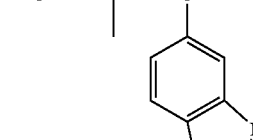 |
| I-78 | |

TABLE 1-continued

Exemplary Compounds.

| Compound # | Structure |
|---|---|
| I-79 | (structure) |
| I-87 | (structure) |
| I-88 | (structure) |
| I-89 | (structure) |
| I-90 | (structure) |
| I-91 | (structure) |
| I-92 | (structure) |
| I-93 | (structure) |

TABLE 1-continued
Exemplary Compounds.
| Compound # | Structure |
|---|---|
| I-94 | 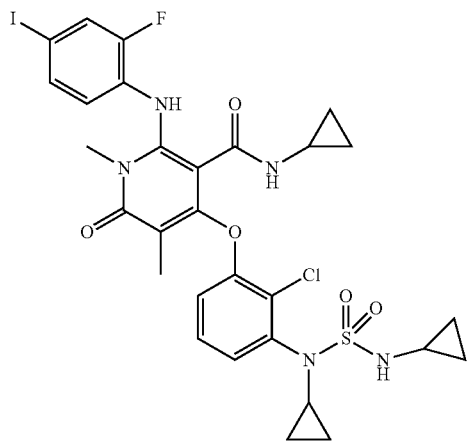 [SMILES: Cc1c(Oc2cccc(N(C3CC3)S(=O)(=O)NC3CC3)c2Cl)c(C(=O)NC2CC2)c(Nc2ccc(I)cc2F)n(C)c1=O] |
| I-95 | 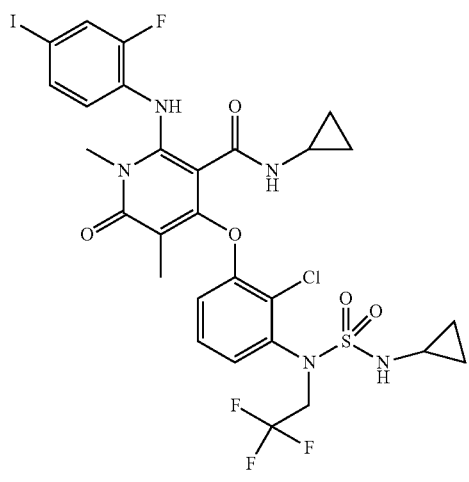 [SMILES: Cc1c(Oc2cccc(N(CC(F)(F)F)S(=O)(=O)NC3CC3)c2Cl)c(C(=O)NC2CC2)c(Nc2ccc(I)cc2F)n(C)c1=O] |
| I-96 | 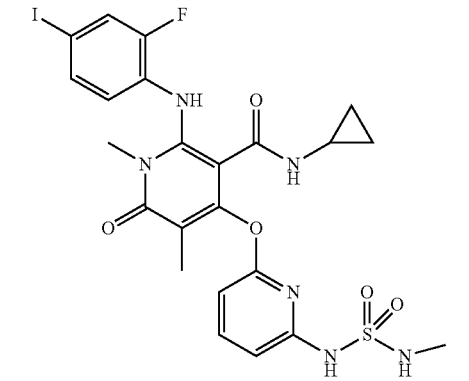 [SMILES: CNS(=O)(=O)Nc1cccc(Oc2c(C(=O)NC3CC3)c(Nc3ccc(I)cc3F)n(C)c(=O)c2C)n1] |
| I-97 | 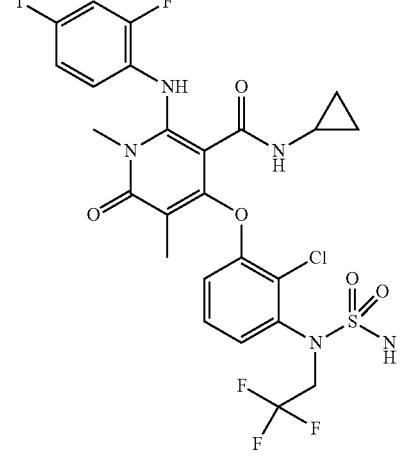 |
| I-98 | 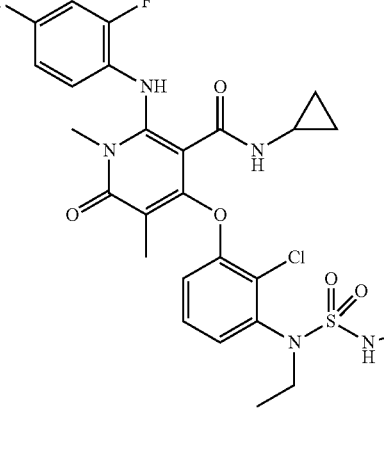 |
| I-99 | 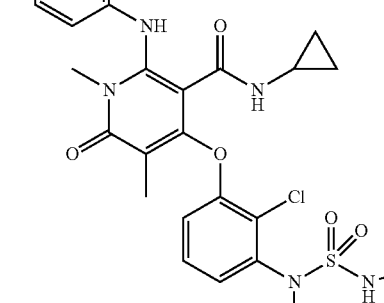 |

TABLE 1-continued
Exemplary Compounds.
| Compound # | Structure |
|---|---|
| I-100 | 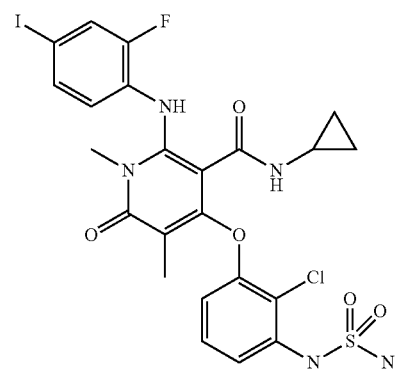 |
| I-101 | 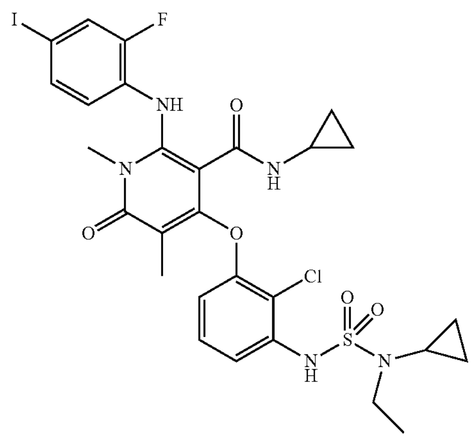 [SMILES: CCN(C1CC1)S(=O)(=O)Nc1cccc(Oc2c(C(=O)NC3CC3)c(Nc3ccc(I)cc3F)n(C)c(=O)c2C)c1Cl] |
| I-102 | 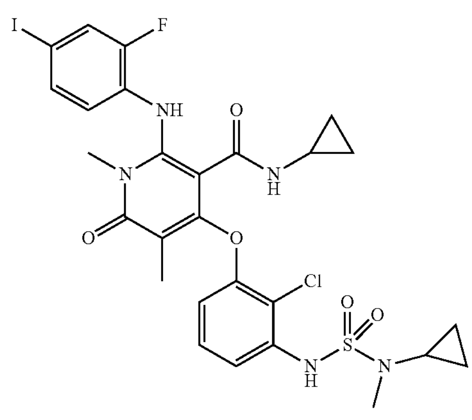 [SMILES: Cc1c(Oc2cccc(NS(=O)(=O)N(C)C3CC3)c2Cl)c(C(=O)NC2CC2)c(Nc2ccc(I)cc2F)n(C)c1=O] |
| I-103 | 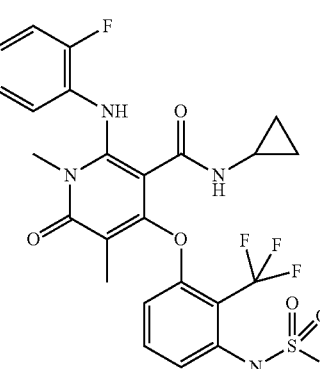 |
| I-104 | |
| I-105 | |

TABLE 1-continued
Exemplary Compounds.
| Compound # | Structure |
|---|---|
| I-106 | 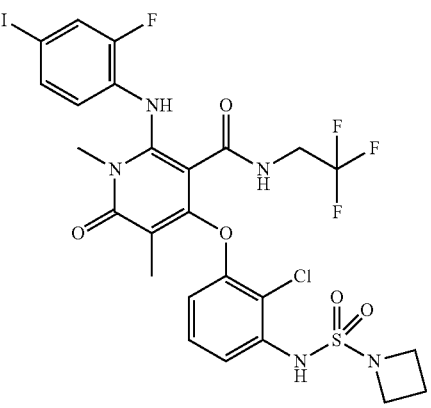 [SMILES: Cc1c(Oc2cccc(NS(=O)(=O)N3CCC3)c2Cl)c(C(=O)NCC(F)(F)F)c(Nc2ccc(I)cc2F)n(C)c1=O] |
| I-107 | 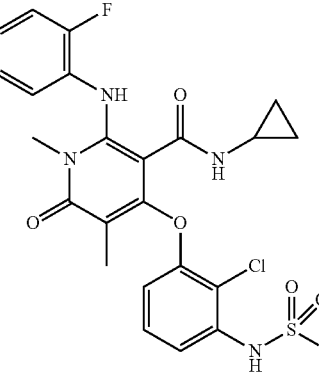 |
| I-108 | 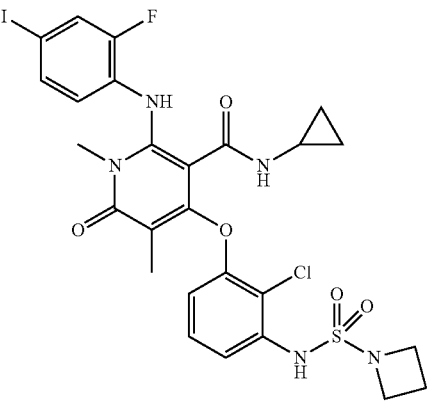 [SMILES: Cc1c(Oc2cccc(NS(=O)(=O)N3CCC3)c2Cl)c(C(=O)NC2CC2)c(Nc2ccc(I)cc2F)n(C)c1=O] |
| I-109 | 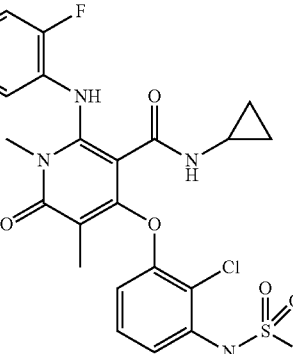 |
| I-110 | 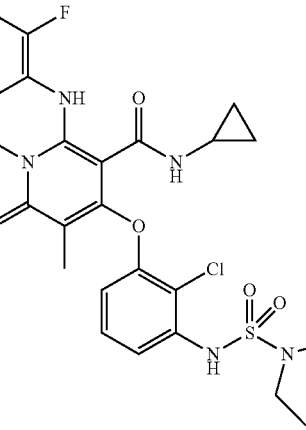 |
| I-111 | 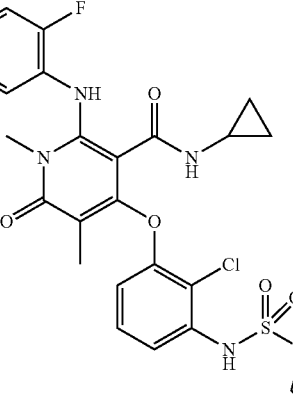 |

TABLE 1-continued

Exemplary Compounds.

| Compound # | Structure |
|---|---|
| I-112 | (structure) |
| I-113 | (structure) |
| I-114 | (structure) |
| I-115 | (structure) |
| I-116 | (structure) |
| I-117 | (structure) |
| I-118 | (structure) |
| I-119 | (structure) |

TABLE 1-continued
Exemplary Compounds.
| Compound # | Structure |
|---|---|
| I-120 | 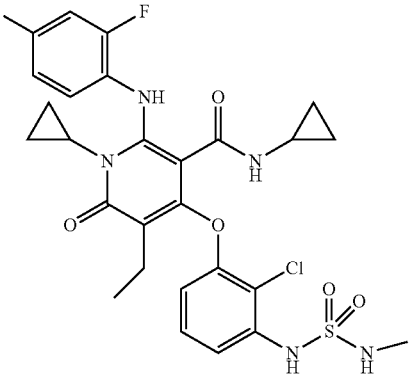 |
| I-121 | 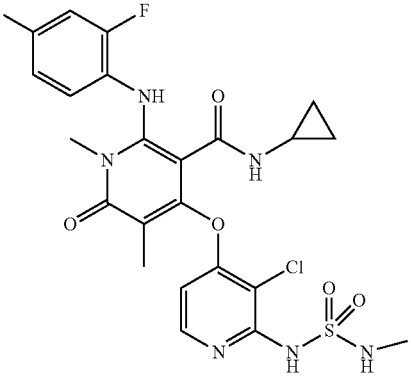 |
| I-122 | 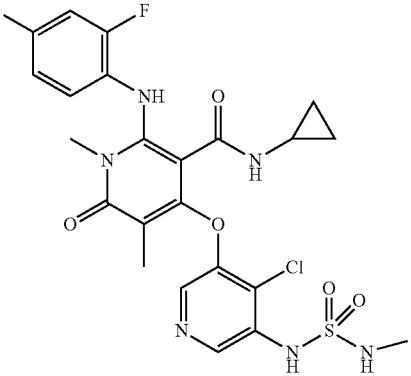 |
| I-123 | 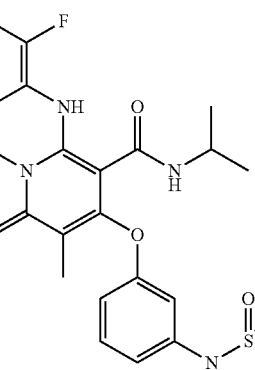 |
| I-124 | 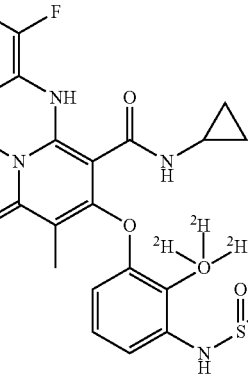 |
| I-125 | 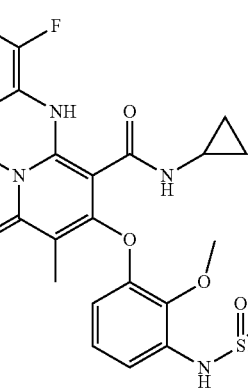 |

TABLE 1-continued
Exemplary Compounds.
| Compound # | Structure |
|---|---|
| I-126 | 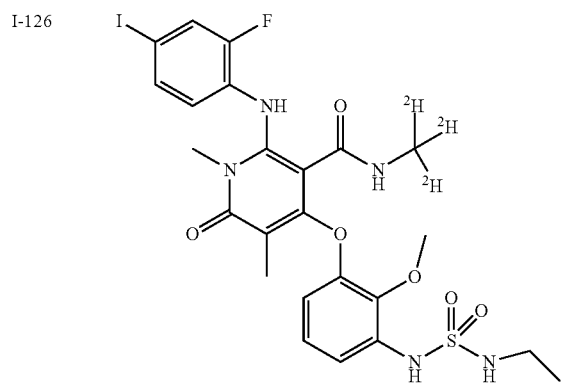 |
| I-127 | 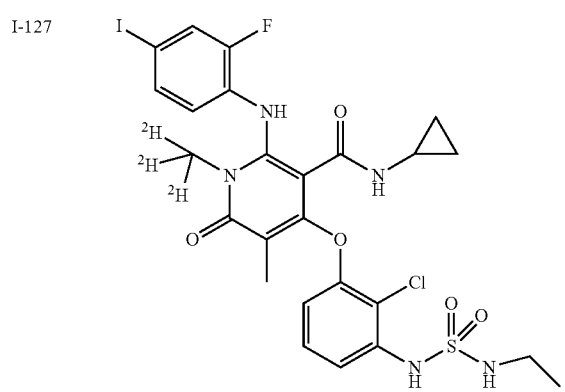 |
| I-128 | 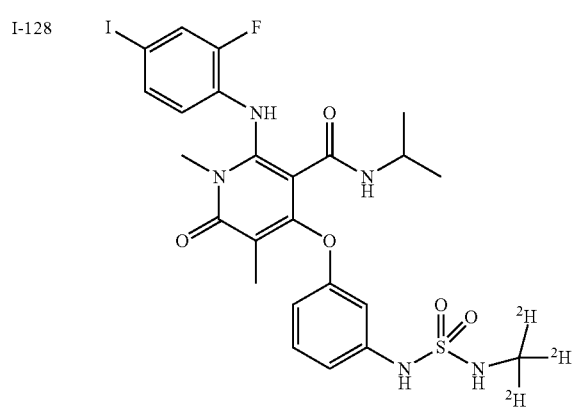 |
| I-129 | 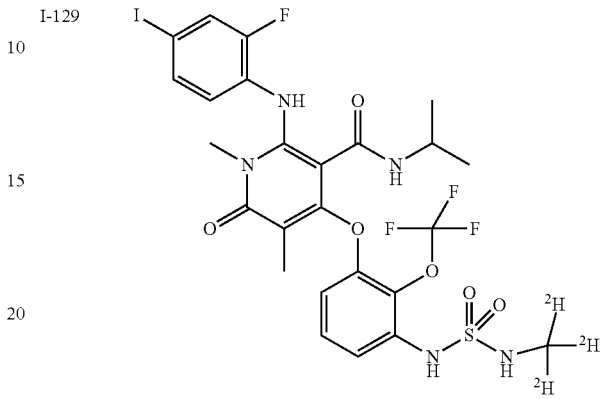 |
| I-130 | 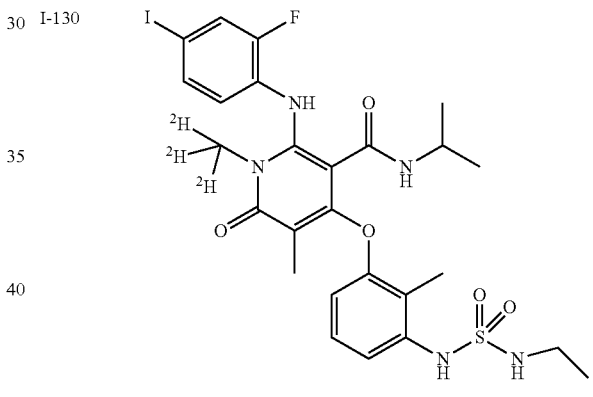 |
| I-131 | 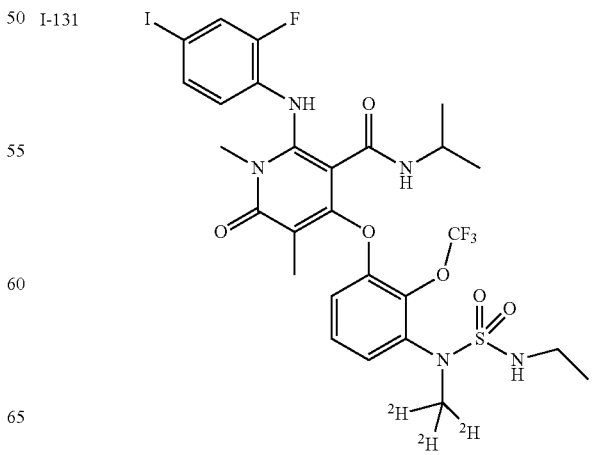 |

TABLE 1-continued

Exemplary Compounds.

| Compound # | Structure |
|---|---|
| I-132 | 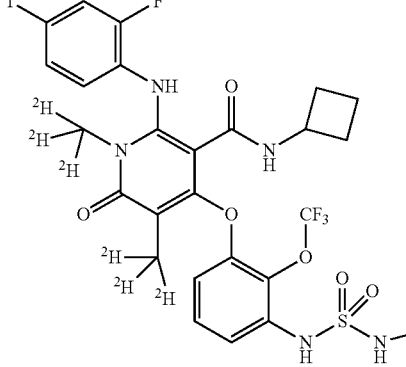 |
| I-133 | 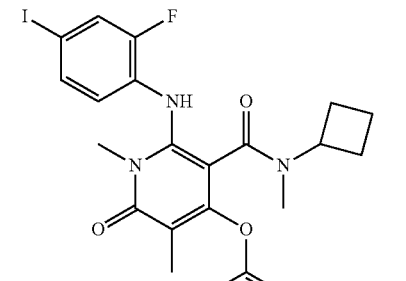 |

In some embodiments, the present disclosure provides a compound set forth in Table 1 above, or a pharmaceutically acceptable salt thereof.

In another aspect, the present disclosure provides a compound of Formula (II):

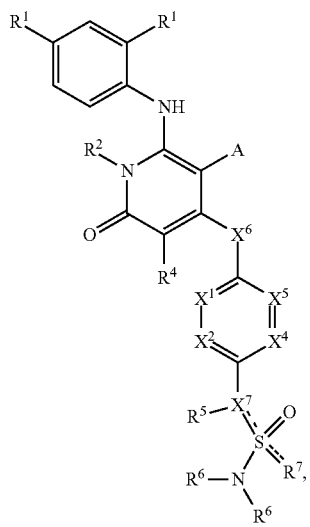

(II)

or a pharmaceutically acceptable salt thereof, wherein:

each

is independently a single or double bond;
each A is independently

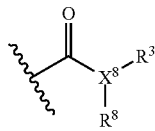

or optionally substituted 5-6 membered heteroaryl;
$X^1$, $X^2$, $X^4$, and $X^5$ are independently $CR^1$ or N;
$X^6$ is O or NH;
$X^7$ is CH or N;
$X^8$ is N or O;
each $R^1$ is independently hydrogen, deuterium, halo, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, or optionally substituted $C_6$-$C_{10}$ aryl;
$R^2$, $R^3$, $R^4$, and $R^5$ are independently hydrogen, deuterium, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, or optionally substituted $C_6$-$C_{10}$ aryl; and
each $R^6$ is independently hydrogen, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, optionally substituted $C_6$-$C_{10}$ aryl, or both $R^6$ taken together with the atom to which they attach form a 3-7 membered hetercycloalkyl ring, or
$R^5$ and $R^6$ taken together with the atoms to which they attach form a 5-6 membered heterocycloalkyl ring; or
$R^5$ and $X^2$ or $X^4$ taken together with the atoms to which they attach form a 5-6 membered fused heterocycloalkyl ring;
$R^6$ and $X^2$ or $X^4$ taken together with the atoms to which they attach form a 5-6 membered fused heterocycloalkyl ring;
$R^7$ is O or optionally substituted $C_1$-$C_6$ aliphatic; and
$R^8$ is absent, hydrogen, deuterium, or optionally substituted $C_1$-$C_6$ aliphatic.

As defined generally above, $X^1$, $X^2$, $X^4$, and $X^5$ are independently $CR^1$ or N. In some embodiments, $X^1$, $X^2$, $X^4$, and $X^5$ are $CR^1$. As defined generally above, $R^1$ is independently hydrogen, halo, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, and optionally substituted $C_6$-$C_{10}$ aryl. In some embodiments, $R^1$ is hydrogen, halo, or optionally substituted $C_1$-$C_6$ alkoxy. In some embodiments, $R^1$ is hydrogen, chloro, fluoro, methoxy, ethoxy, propoxy, ethoxy, or hexyloxy. In some embodiments, $R^1$ is hydrogen, fluoro, chloro, or methoxy.

As defined generally above, each

is independently a single or double bond.

As defined generally above, each A is independently

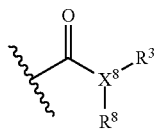

or optionally substituted 5-6 membered heteroaryl. In some embodiments, each A is independently

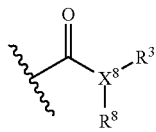

As defined generally above, $X^8$ is N or O. In some embodiments, $X^8$ is N. In some embodiments, $X^8$ is O. In some embodiments, $X^8$ is N, and $R^3$ and $R^8$, taken together with the N atom to which they attach form an optionally substituted 3-7 membered hetercycloalkyl ring.

In some embodiments, each A is independently optionally substituted 5-6 membered heteroaryl. In some embodiments, each A is independently optionally substituted 5- or 6-membered heteroaryl. In some embodiments, each A is independently optionally substituted 5-membered heteroaryl. In some embodiments, each A is optionally substituted imidazole. In some embodiments, each A is

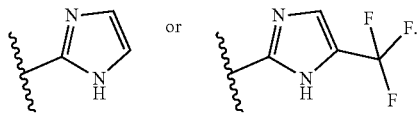 [SMILES: *c1ncc[nH]1 ; "or" ; *c1ncc(C(F)(F)F)[nH]1]

As defined generally above, $X^6$ is O or NH. In some embodiments, $X^6$ is O. In some embodiments, $X^6$ is NH. In some embodiments, $X^6$ is C(O).

As defined generally above, $X^7$ is CH or N. In some embodiments, $X^7$ is CH. In some embodiments, $X^7$ is N.

As defined generally above, each $R^1$ is independently hydrogen, deuterium, halo, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, and optionally substituted $C_6$-$C_{10}$ aryl. In some embodiments, $R^1$ is halo. In some embodiments, $R^1$ is fluoro, chloro, iodo, —$OCF_3$, cyclopropyl, —$CF_3$, or ethyne. In some embodiments, $R^1$ is fluoro or iodo. In some embodiments, $R^1$ is —CN.

As defined generally above, $R^2$ is hydrogen, halo, $C(^2D)_3$, $OC(^2D)_3$, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, or optionally substituted $C_6$-$C_{10}$ aryl. In some embodiments, $R^2$ is optionally substituted $C_1$-$C_6$ aliphatic. In some embodiments, $R^2$ is methyl, ethyl, propyl, pentyl, butyl, or hexyl. In some embodiments, $R^2$ is methyl.

As defined generally above, $R^3$ is hydrogen, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, and optionally substituted $C_6$-$C_{10}$ aryl. In some embodiments, $R^3$ is optionally substituted $C_3$-$C_{10}$ cycloalkyl. In some embodiments, $R^3$ is optionally substituted $C_3$-$C_8$ cycloalkyl. In some embodiments, $R^3$ is optionally substituted $C_3$-$C_6$ cycloalkyl. In some embodiments, $R^3$ is cyclopropyl, cyclopentyl, cyclobutyl, or cyclohexyl. In some embodiments, $R^3$ is cyclopropyl or optionally substituted cyclopropyl. In some embodiments, $R^3$ is cyclopropyl. In some embodiments, $R^3$ is —$(C_3H_3)F_2$.

As defined generally above, $R^4$ is hydrogen, $C(^2D)_3$, $OC(^2D)_3$, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, and optionally substituted $C_6$-$C_{10}$ aryl. In some embodiments, $R^4$ is optionally substituted $C_1$-$C_6$ aliphatic. In some embodiments, $R^4$ is methyl, ethyl, propyl, pentyl, butyl, or hexyl. In some embodiments, $R^4$ is methyl. In some embodiments, $R^4$ is $CF_3$.

As defined generally above, $R^5$ is hydrogen, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, and optionally substituted $C_6$-$C_{10}$ aryl. In some embodiments, $R^5$ is hydrogen, optionally substituted $C_1$-$C_6$ aliphatic, or optionally substituted $C_1$-$C_6$ alkoxy. In some embodiments, $R^5$ is hydrogen. In some embodiments, $R^5$ is absent when $X^7$ is N forming a double bond with the sulfur atom.

As defined generally above, each $R^6$ is independently hydrogen, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, optionally substituted $C_6$-$C_{10}$ aryl, or both $R^6$ taken together with the atom to which they attach form a 3-7 membered hetercycloalkyl ring, or $R^5$ and $R^6$ taken together with the atoms to which they attach form a 5-6 membered heterocycloalkyl ring.

In some embodiments, each $R^6$ is independently hydrogen or optionally substituted $C_1$-$C_6$ aliphatic. In some embodiments, each $R^6$ is independently hydrogen, methyl, or —$(CH_2)_2N(CH_3)_2$.

In some embodiments, both $R^6$ taken together with the atom to which they attach form a 3-7 membered hetercycloalkyl ring. In some embodiments, both $R^6$ taken together with the atom to which they attach form a 3-, 4-, 5-, 6-, or 7-membered hetercycloalkyl ring.

In some embodiments, $R^5$ and $R^6$ taken together with the atoms to which they attach form a 5-6 membered heterocycloalkyl ring. In some embodiments, $R^5$ and $R^6$ taken together with the atoms to which they attach form a 5- or 6-membered heterocycloalkyl ring. In some embodiments, $R^5$ and $R^6$ taken together with the atoms to which they attach form a 5-membered heterocycloalkyl ring.

In some embodiments, $R^5$ and $X^2$ or $X^4$ taken together with the atoms to which they attach form a 5-6 membered fused heterocycloalkyl ring.

In some embodiments, $R^5$ and $X^2$ or $X^4$ taken together with the atoms to which they attach form a 5-6 membered fused heteroaromatic ring.

In some embodiments, $R^6$ and $X^2$ or $X^4$ taken together with the atoms to which they attach form a 5-6 membered fused heterocycloalkyl ring.

As defined generally above, $R^7$ is O or optionally substituted $C_1$-$C_6$ aliphatic. In some embodiments, $R^7$ is O. In some embodiments, $R^7$ is optionally substituted $C_1$-$C_6$ aliphatic. In some embodiments, $R^7$ is methyl.

As defined generally above, $R^8$ is absent, hydrogen, deuterium, or optionally substituted $C_1$-$C_6$ aliphatic. In some embodiments, $R^8$ is hydrogen or methyl.

In another aspect, the present disclosure provides a compound of Formula (IIA):

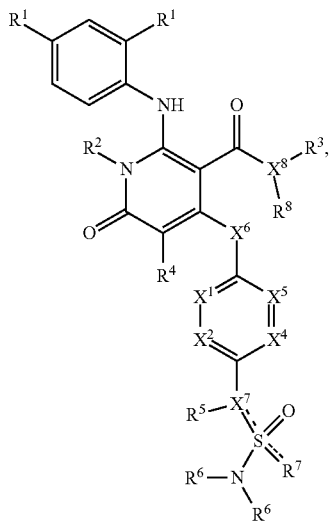

or a pharmaceutically acceptable salt thereof, wherein:
each

is independently a single or double bond;
$X^1$, $X^2$, $X^4$, and $X^5$ are independently $CR^1$ or N;
$X^6$ is O or NH;
$X^7$ is CH or N;
$X^8$ is N or O;
each $R^1$ is independently hydrogen, deuterium, halo, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, or optionally substituted $C_6$-$C_{10}$ aryl;
$R^2$, $R^3$, $R^4$, and $R^5$ are independently hydrogen, $C(^2D)_3$, $OC(^2D)_3$, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, or optionally substituted $C_6$-$C_{10}$ aryl; and
each $R^6$ is independently hydrogen, deuterium, $C(^2D)_3$, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, optionally substituted $C_6$-$C_{10}$ aryl, or both $R^6$ taken together with the atom to which they attach form a 3-7 membered hetercycloalkyl ring, or
$R^5$ and $R^6$ taken together with the atoms to which they attach form a 5-6 membered heterocycloalkyl ring; or
$R^5$ and $X^2$ or $X^4$ taken together with the atoms to which they attach form a 5-6 membered fused heterocycloalkyl ring;
$R^6$ and $X^2$ or $X^4$ taken together with the atoms to which they attach form a 5-6 membered fused heterocycloalkyl ring;
$R^7$ is O or optionally substituted $C_1$-$C_6$ aliphatic; and
$R^8$ is absent, hydrogen, deuterium, or optionally substituted $C_1$-$C_6$ aliphatic.

As defined generally above, $X^1$, $X^2$, $X^4$, and $X^5$ are independently $CR^1$ or N. In some embodiments, $X^1$, $X^2$, $X^4$, and $X^5$ are $CR^1$. As defined generally above, $R^1$ is independently hydrogen, halo, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, and optionally substituted $C_6$-$C_{10}$ aryl. In some embodiments, $R^1$ is hydrogen, halo, or optionally substituted $C_1$-$C_6$ alkoxy. In some embodiments, $R^1$ is hydrogen, chloro, fluoro, methoxy, ethoxy, propoxy, ethoxy, or hexyloxy. In some embodiments, $R^1$ is hydrogen, fluoro, chloro, or methoxy.

As defined generally above, each

is independently a single or double bond.

As defined generally above, each A is independently

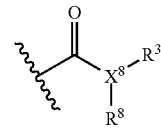

or optionally substituted 5-6 membered heteroaryl. In some embodiments, each A is independently

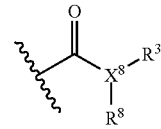

As defined generally above, $X^8$ is N or O. In some embodiments, $X^8$ is N. In some embodiments, $X^8$ is O. In some embodiments, $X^8$ is N; and $R^3$ and $R^8$, taken together with the N atom to which they attach, form an optionally substituted 3-7 membered hetercycloalkyl ring.

In some embodiments, each A is independently optionally substituted 5-6 membered heteroaryl. In some embodiments, each A is independently optionally substituted 5- or 6-membered heteroaryl. In some embodiments, each A is independently optionally substituted 5-membered heteroaryl. In some embodiments, each A is optionally substituted imidazole. In some embodiments, each A is

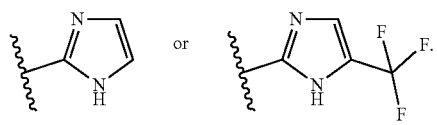

As defined generally above, $X^6$ is O or NH. In some embodiments, $X^6$ is O. In some embodiments, $X^6$ is NH. In some embodiments, $X^6$ is C(O).

As defined generally above, $X^7$ is CH or N. In some embodiments, $X^7$ is CH. In some embodiments, $X^7$ is N.

As defined generally above, each $R^1$ is independently hydrogen, deuterium, halo, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, and optionally substituted $C_6$-$C_{10}$ aryl. In some embodiments, $R^1$ is halo. In some embodiments, $R^1$ is fluoro, chloro, iodo, —$OCF_3$, cyclopropyl, —$CF_3$, or ethyne. In some embodiments, $R^1$ is fluoro or iodo. In some embodiments, $R^1$ is —CN.

As defined generally above, $R^2$ is hydrogen, $C(^2D)_3$, $OC(^2D)_3$, halo, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, or optionally substituted $C_6$-$C_{10}$ aryl. In some embodiments, $R^2$ is optionally substituted $C_1$-$C_6$ aliphatic. In some embodiments, $R^2$ is methyl, ethyl, propyl, pentyl, butyl, or hexyl. In some embodiments, $R^2$ is methyl.

As defined generally above, $R^3$ is hydrogen, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, and optionally substituted $C_6$-$C_{10}$ aryl. In some embodiments, $R^3$ is optionally substituted $C_3$-$C_{10}$ cycloalkyl. In some embodiments, $R^3$ is optionally substituted $C_3$-$C_8$ cycloalkyl. In some embodiments, $R^3$ is optionally substituted $C_3$-$C_6$ cycloalkyl. In some embodiments, $R^3$ is cyclopropyl, cyclopentyl, cyclobutyl, or cyclohexyl. In some embodiments, $R^3$ is cyclopropyl or optionally substituted cyclopropyl. In some embodiments, $R^3$ is cyclopropyl. In some embodiments, $R^3$ is —$(C_3H_3)F_2$.

As defined generally above, $R^4$ is hydrogen, $C(^2D)_3$, $OC(^2D)_3$, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, and optionally substituted $C_6$-$C_{10}$ aryl. In some embodiments, $R^4$ is optionally substituted $C_1$-$C_6$ aliphatic. In some embodiments, $R^4$ is methyl, ethyl, propyl, pentyl, butyl, or hexyl. In some embodiments, $R^4$ is methyl. In some embodiments, $R^4$ is $CF_3$.

As defined generally above, $R^5$ is hydrogen, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, and optionally substituted $C_6$-$C_{10}$ aryl. In some embodiments, $R^5$ is hydrogen, optionally substituted $C_1$-$C_6$ aliphatic, or optionally substituted $C_1$-$C_6$ alkoxy. In some embodiments, $R^5$ is hydrogen. In some embodiments, $R^5$ is absent when $X^7$ is N forming a double bond with the sulfur atom.

As defined generally above, each $R^6$ is independently hydrogen, deuterium, $C(^2D)_3$, optionally substituted $C_1$-$C_6$ aliphatic, optionally substituted $C_1$-$C_6$ alkoxy, optionally substituted $C_3$-$C_{10}$ cycloalkyl, optionally substituted $C_6$-$C_{10}$ heterocycloalkyl, optionally substituted $C_6$-$C_{10}$ aryl, or both $R^6$ taken together with the atom to which they attach form a 3-7 membered heterocycloalkyl ring, or $R^5$ and $R^6$ taken together with the atoms to which they attach form a 5-6 membered heterocycloalkyl ring.

In some embodiments, each $R^6$ is independently hydrogen or optionally substituted $C_1$-$C_6$ aliphatic. In some embodiments, each $R^6$ is independently hydrogen, methyl, or —$(CH_2)_2N(CH_3)_2$.

In some embodiments, both $R^6$ taken together with the atom to which they attach form a 3-7 membered hetercycloalkyl ring. In some embodiments, both $R^6$ taken together with the atom to which they attach form a 3-, 4-, 5-, 6-, or 7-membered heterocycloalkyl ring.

In some embodiments, $R^5$ and $R^6$ taken together with the atoms to which they attach form a 5-6 membered heterocycloalkyl ring. In some embodiments, $R^5$ and $R^6$ taken together with the atoms to which they attach form a 5- or 6-membered heterocycloalkyl ring. In some embodiments, $R^5$ and $R^6$ taken together with the atoms to which they attach form a 5-membered heterocycloalkyl ring.

In some embodiments, $R^5$ and $X^2$ or $X^4$ taken together with the atoms to which they attach form a 5-6 membered fused heterocycloalkyl ring.

In some embodiments, $R^5$ and $X^2$ or $X^4$ taken together with the atoms to which they attach form a 5-6 membered fused heteroaromatic ring.

In some embodiments, $R^6$ and $X^2$ or $X^4$ taken together with the atoms to which they attach form a 5-6 membered fused heterocycloalkyl ring.

As defined generally above, $R^7$ is O or optionally substituted $C_1$-$C_6$ aliphatic. In some embodiments, $R^7$ is O. In some embodiments, $R^7$ is optionally substituted $C_1$-$C_6$ aliphatic. In some embodiments, $R^7$ is methyl.

As defined generally above, $R^8$ is absent, hydrogen, deuterium, or optionally substituted $C_1$-$C_6$ aliphatic. In some embodiments, $R^8$ is hydrogen or methyl.

TABLE 2

Exemplary Compounds.

| Compound # | Structure |
|---|---|
| I-59 | [chemical structure: iodo-fluoro-phenyl-NH linked to N-methyl dihydropyridinone bearing cyclopropyl carboxamide and aryloxy substituent with fused benzo sulfamide ring] |
| I-60 | [chemical structure: iodo-fluoro-phenyl-NH linked to N-methyl dihydropyridinone bearing cyclopropyl carboxamide and aryloxy substituent with fused benzo N-methyl sulfamide ring] |

TABLE 2-continued
Exemplary Compounds.
| Compound # | Structure |
|---|---|
| I-61 | 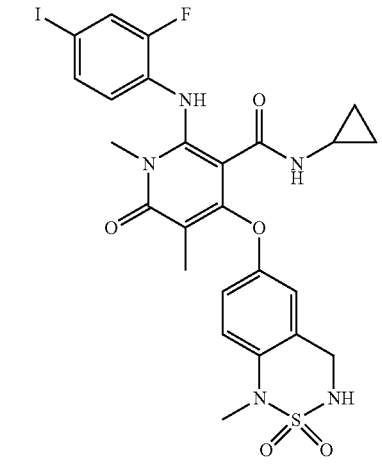 [SMILES: Cc1c(Oc2ccc3c(c2)CNS(=O)(=O)N3C)c(C(=O)NC2CC2)c(Nc2ccc(I)cc2F)n(C)c1=O] |
| I-62 | 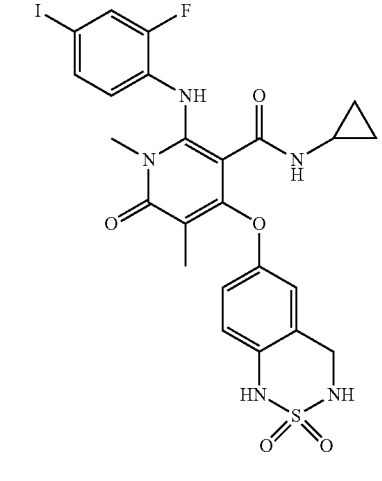 [SMILES: Cc1c(Oc2ccc3c(c2)CNS(=O)(=O)N3)c(C(=O)NC2CC2)c(Nc2ccc(I)cc2F)n(C)c1=O] |
| I-63 | 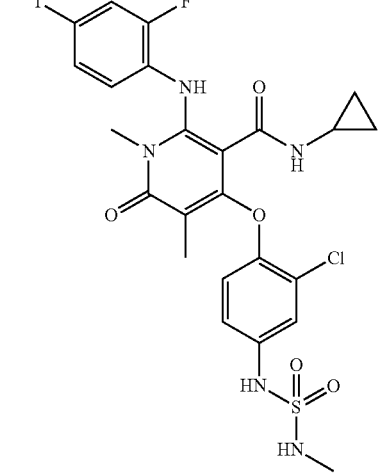 |
| I-64 | 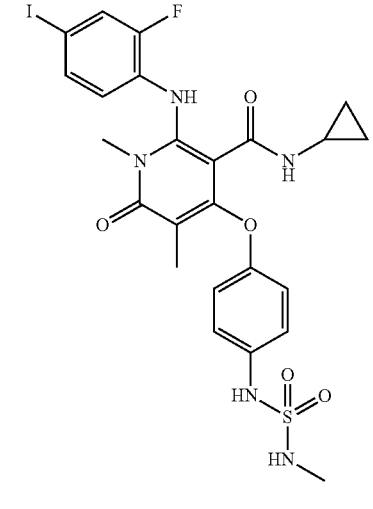 |
| I-66 | 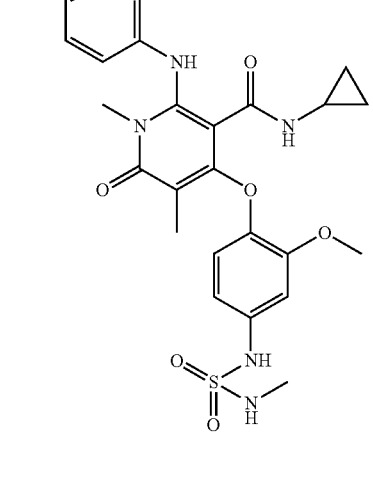 |
| I-67 | 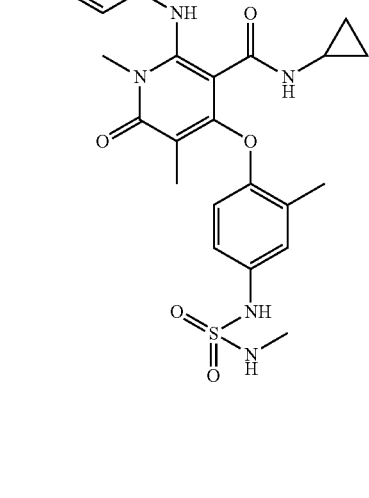 |

TABLE 2-continued
Exemplary Compounds.
| Compound # | Structure |
|---|---|
| I-68 | 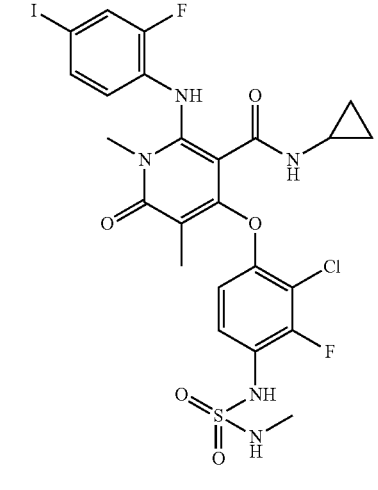 [SMILES: CNS(=O)(=O)Nc1ccc(Oc2c(C(=O)NC3CC3)c(Nc3ccc(I)cc3F)n(C)c(=O)c2C)c(Cl)c1F] |
| I-69 | 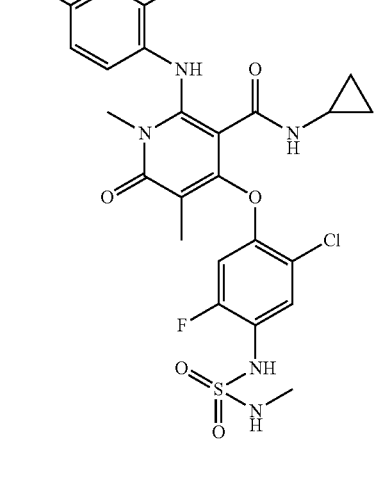 |
| I-70 | 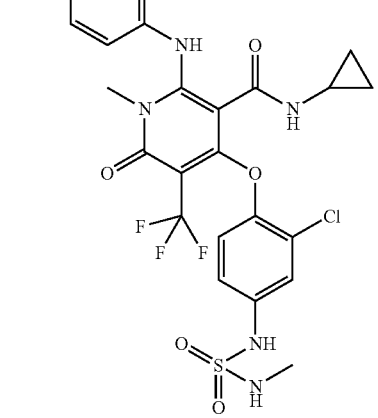 |
| I-71 |  |
| I-72 |  |
| I-73 |  |

TABLE 2-continued

Exemplary Compounds.

| Compound # | Structure |
|---|---|
| I-74 | 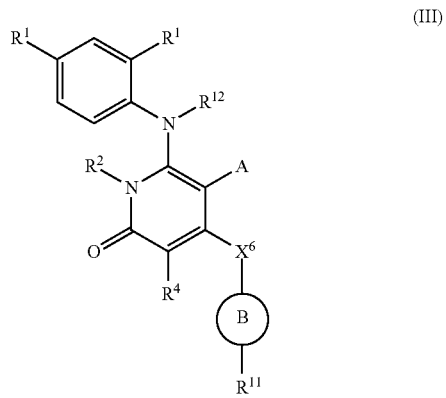 |
| I-75 | 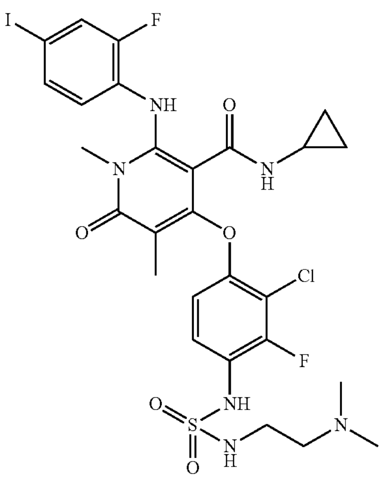 [SMILES: Cc1c(Oc2ccc(NS(=O)(=O)NCCN(C)C)c(F)c2Cl)c(C(=O)NC2CC2)c(Nc2ccc(I)cc2F)n(C)c1=O] |
| I-76 | 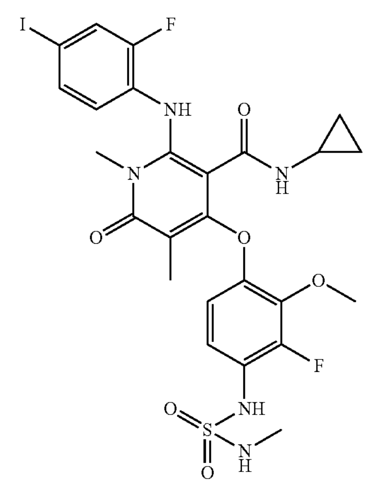 [SMILES: CNS(=O)(=O)Nc1ccc(Oc2c(C(=O)NC3CC3)c(Nc3ccc(I)cc3F)n(C)c(=O)c2C)c(OC)c1F] |

In some embodiments, the present disclosure provides a compound set forth in Table 2 above, or a pharmaceutically acceptable salt thereof.

In another aspect, the present disclosure provides a compound of Formula (III):

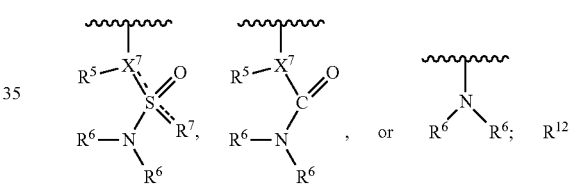

(III)

or a pharmaceutically acceptable salt thereof, wherein Ring B is an optionally substituted ring selected from $C_3$-$C_{10}$ cycloalkyl, $C_3$-$C_{10}$ heterocycloalkyl having 1-4 heteroatoms N, S, or O, phenyl, 5-6 membered heteroaryl having 1-4 heteroatoms N, S, or O, or 6-10 membered bicyclic heteroaryl having 1-4 heteroatoms N, S, or O; $R^{11}$ is H, is H or optionally substituted $C_1$-$C_6$ aliphatic; and each of $R^1$, $R^2$, $R^3$, $R^4$, $R^5$, $R^6$, $R^7$, $R^8$, $X^6$, and $X^7$ is independently as described above and described in embodiments herein.

In another aspect, the present disclosure provides a compound of Formulae (IIIA), (IIIB), or (IIC):

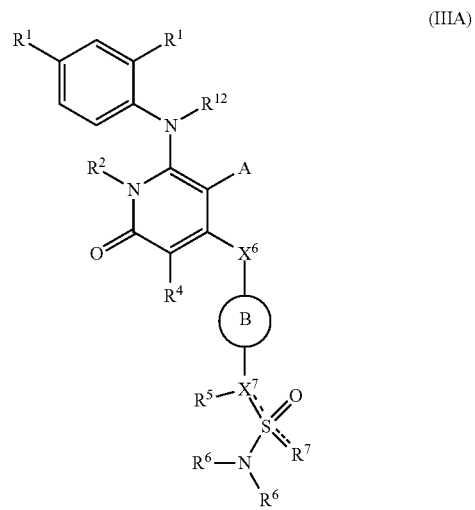

(IIIA)

-continued

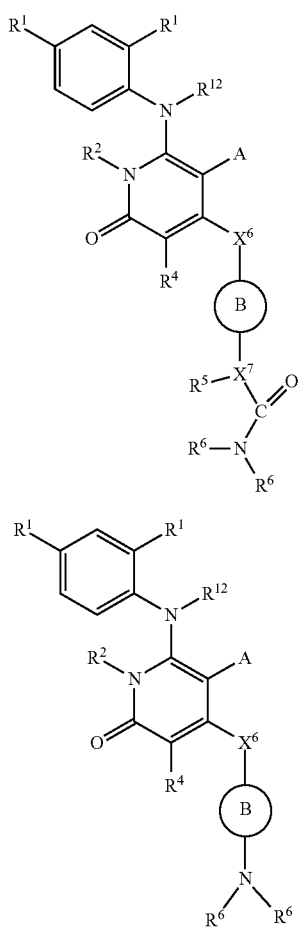

(IIIB)

(IIIC)

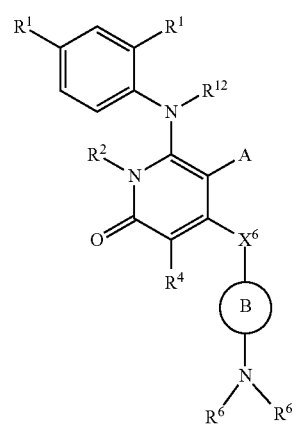

or a pharmaceutically acceptable salt thereof, wherein Ring B is an optionally substituted ring selected from $C_3$-$C_{10}$ cycloalkyl, $C_3$-$C_{10}$ heterocycloalkyl having 1-4 heteroatoms N, S, or O, phenyl, 5-6 membered heteroaryl having 1-4 heteroatoms N, S, or O, or 6-10 membered bicyclic heteroaryl having 1-4 heteroatoms N, S, or O; $R^{12}$ is H or optionally substituted $C_1$-$C_6$ aliphatic; and each of $R^1$, $R^2$, $R^3$, $R^4$, $R^5$, $R^6$, $R^7$, $R^8$, $X^6$, and $X^7$ is independently as described above and described in embodiments herein.

In some embodiments, Ring B is optionally substituted $C_3$-$C_{10}$ cycloalkyl. In some embodiments, Ring B is optionally substituted $C_3$-$C_{10}$ heterocycloalkyl having 1-4 heteroatoms N, S, or O. In some embodiments, Ring B is optionally substituted phenyl. In some embodiments, Ring B is optionally substituted 5-6 membered heteroaryl having 1-4 heteroatoms N, S, or O. In some embodiments, Ring B is optionally substituted 6-10 membered bicyclic heteroaryl having 1-4 heteroatoms N, S, or O.

In some embodiments, Ring B is optionally substituted

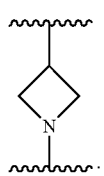

In some embodiments, Ring B is optionally substitute

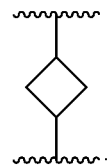

In some embodiments, Ring B is optionally substituted

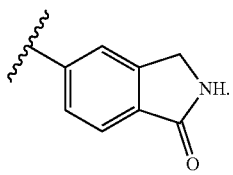 [SMILES: *c1ccc2c(c1)CNC2=O]

In some embodiments, $R^{12}$ is H or optionally substituted $C_1$-$C_6$ aliphatic. In some embodiments, $R^{12}$ is H. In some embodiments, $R^{12}$ is optionally substituted $C_1$-$C_6$ aliphatic. In some embodiments, $R^{12}$ is optionally substituted $C_1$-$C_6$ alkyl. In some embodiments, $R^{12}$ is unsubstituted $C_1$-$C_6$ alkyl. In some embodiments, $R^{12}$ is methyl.

TABLE 2B

| Compound # | Exemplary Compounds. Structure |
|---|---|
| I-80 |  |
| I-81 |  |

TABLE 2B-continued

Exemplary Compounds.

| Compound # | Structure |
|---|---|
| I-82 | (structure) |
| I-83 | (structure) |
| I-84 | (structure) |
| I-85 | (structure) |
| I-86 | (structure) |

In some embodiments, the present disclosure provides a compound set forth in Table 2B above, or a pharmaceutically acceptable salt thereof.

III. Uses, Formulation, and Administration a. Pharmaceutically Acceptable Compositions According to another embodiment, the disclosure provides a pharmaceutical composition comprising a compound of this disclosure or a pharmaceutically acceptable derivative thereof and a pharmaceutically acceptable carrier, adjuvant, or vehicle. The amount of compound in compositions of this disclosure is such that is effective to measurably inhibit MEK, or a variant or mutant thereof, in a biological sample or in a patient. In certain embodiments, the amount of compound in compositions of this disclosure is such that is effective to measurably inhibit MEK, or a variant or mutant thereof, in a biological sample or in a patient. In certain embodiments, a composition of this disclosure is formulated for administration to a patient in need of such composition. In some embodiments, a composition of this disclosure is formulated for oral administration to a patient.

As used herein, the terms "subject" and "patient" are used interchangeably and refer to organisms to be treated by the methods of the present disclosure. Such organisms preferably include, but are not limited to, mammals (e.g., murines, simians, equines, bovines, porcines, canines, felines, and the like), and, most preferably, includes humans.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this disclosure that, upon administration to a recipient, is capable of providing, either directly or indirectly, a compound of this disclosure or an active metabolite or residue thereof.

As used herein, the term "active metabolite or residue thereof" means that a metabolite or residue thereof also inhibits MEK, or a variant or mutant thereof.

Compositions of the present disclosure can be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this disclosure may be aqueous or oleaginous suspension. These suspensions can be formulated according to techniques known in the art using suitable dispersing or wetting agents and suspending agents. The sterile injectable preparation can also be a sterile injectable solution or suspension in a non-toxic parenterally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium.

For this purpose, any bland fixed oil can be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this disclosure can be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents can also be added.

Alternatively, pharmaceutically acceptable compositions of this disclosure can be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this disclosure can also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches can also be used.

For topical applications, provided pharmaceutically acceptable compositions can be formulated in a suitable ointment containing the active component suspended or dissolved in one or more carriers. Carriers for topical administration of compounds of this disclosure include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions can be formulated in an ointment such as petrolatum.

Pharmaceutically acceptable compositions of this disclosure can also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this disclosure are formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

In some embodiments, the pharmaceutical compositions of this disclosure are brain-penetrant or CNS-penetrant or provide brain exposure. As used herein, the terms "brain-penetrant, "CNS-penetrant," or "brain exposure" refers that the compounds and pharmaceutical compositions of this disclosure are capable of crossing the blood brain barrier (BBB), and thus are useful for treating a brain or CNS disease, condition, injury or disorder. In some embodiments, a brain or CNS disease, condition, injury or disorder is a neurodegenerative diseases, neuronal injury, stroke, genetic disorders, psychiatric disorders, developmental disorders, inflammation, infection or damage, and brain cancers, spinal cord injury (SCI) and traumatic brain injury (TBI). In certain embodiments, a brain disorder is selected from epilepsy, meningitis, encephalitis including HIV Encephalitis, progressive multifocal leukoencephalopathy, neuromyelitis optica, multiple sclerosis, late-stage neurological trypanosomiasis, amyotrophic lateral sclerosis (ALS), progressive bulbar palsy (PBP), primary lateral sclerosis (PLS), progressive muscular atrophy (PMA), Alzheimer's disease, Parkinson's disease, Huntington's disease, De Vivo disease, and any type of tumor, cancer or hyperproliferative disease in the brain or CNS.

In some embodiments, a brain or CNS disease, condition, injury or disorder is a neurological disorder which affects the CNS and/or which has an etiology in the CNS, which includes, but is not limited to, neuropathy, amyloidosis, cancer, an ocular disease or disorder, viral or microbial infection, inflammation, ischemia, neurodegenerative disease, seizure, behavioral disorders, and a lysosomal storage disease. For the purposes of this application, the CNS will be understood to include the eye, which is normally sequestered from the rest of the body by the blood-retina barrier. Specific examples of neurological disorders include, but are not limited to, neurodegenerative diseases (including, but not limited to, Lewy body disease, postpoliomyelitis syndrome, Shy-Draeger syndrome, olivopontocerebellar atrophy, Parkinson's disease, multiple system atrophy, striatonigral degeneration, tauopathies (including, but not limited to, Alzheimer disease and supranuclear palsy), prion diseases (including, but not limited to, bovine spongiform encephalopathy, scrapie, Creutzfeldt-Jakob syndrome, kuru, Gerstmann-Straussler-Scheinker disease, chronic wasting disease, and fatal familial insomnia), bulbar palsy, motor neuron disease, and nervous system hetero degenerative disorders (including, but not limited to, Canavan disease, Huntington's disease, neuronal ceroid-lipofuscinosis, Alexander's disease, Tourette's syndrome, Menkes kinky hair syndrome, Cockayne syndrome, Halervorden-Spatz syndrome, lafora disease, Rett syndrome, hepatolenticular degeneration, Lesch-Nyhan syndrome, and Unverricht-Lundborg syndrome), dementia (including, but not limited to, Pick's disease, and spinocerebellar ataxia), cancer (e.g. of the CNS and/or brain, including brain metastases resulting from cancer elsewhere in the body).

The "central nervous system" or "CNS" refers to the complex of nerve tissues that control bodily function, and includes the brain and spinal cord.

The amount of compounds of the present disclosure that can be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient depends upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present disclosure in the composition also depends upon the particular compound in the composition.

b. Uses of Compounds and Pharmaceutically Acceptable Compositions

In some embodiments, the present disclosure provides a method of using a compound as described herein for treating a disease or disorder associated with MEK. In some embodiments, a disease or disorder associated with MEK is a proliferative disorder. In some embodiments, a disease or disorder associated with MEK is a cancer. In some embodiments, a disease or disorder associated with MEK is a cancer as described herein.

In some aspects and embodiments, provided herein are methods of treating, reducing the severity of, delaying the onset of, or inhibiting the progress of a disease or disorder, or one or more symptoms thereof, of a disease or disorder characterized by or associated with increased MEK expression and/or increased MEK activity, comprising the step of administering to a patient in need thereof a therapeutically effective amount of a compound of the present disclosure, or pharmaceutically acceptable composition thereof. In some aspects and embodiments, provided herein are methods of treating, reducing the severity of, delaying the onset of, or inhibiting the progress of a disease or disorder, or one or more symptoms thereof of a disease or disorder in which inhibition or antagonizing of MEK activity is beneficial, comprising the step of administering to a patient in need thereof a therapeutically effective amount of a compound of the present disclosure, or pharmaceutically acceptable composition thereof.

In some embodiments, a compound as described herein is an "ATP non-competitive MEK inhibitor" that stabilizes or "glues" the complex formed between MEK and KSR, and/or BRAF/CRAF. In some embodiments, a compound as described herein allosterically binds an "inhibitor pocket" formed at an interaction interface between human MEK (MEK1 or MEK2) and human Kinase Suppressor of Ras (KSR1 or KSR2 or the KSR homolog BRAF or CRAF) adjacent to ATP in a physiological complex between MEK and KSR (or BRAF or CRAF), forming an inhibitor-inhibitor pocket complex. In some embodiments, a compound as described herein is an ATP non-competitive kinase inhibitor. In some embodiments, a compound as described herein has a structure such that when bound to the inhibitor-inhibitor pocket complex, the complex comprises the structural elements: (a) at least one moiety of the inhibitor engaging A825 of hKSR1, or P878 of hKSR2, or R662 of BRAF, or R554 of CRAF (b) at least one moiety engaging R234 of hMEK1 or R238 of hMEK2, wherein R234 is within about 5 Å to about 8 Å from any atoms of hKSR1 or hKSR2 or BRAF or CRAF. The structures of complexes described herein, including for example, the MEK and KSR (or BRAF or CRAF) complex, and the inhibitor-inhibitor pocket complex, can be found in WO 2021142345, the content of which is incorporated herein by reference in its entirety. Reference Uniprot sequences for human MEK1, human MEK2, human KSR1, human KSR2, human BRAF, and human CRAF are Uniprot ID Q02750, Uniprot ID P36507, Uniprot ID Q8IVT5, Uniprot ID Q6VAB6, Uniprot ID P15056, and Uniprot ID P04049, respectively.

In some embodiments, a compound as described herein does not engage one or more of 1216 in hMEK1 or 1220 of hMEK2 and A825 in KSR1 or P878 in KSR2. In some embodiments, a compound as described herein comprises a structural element according to (a) as described in the above paragraph, which is an H-bond acceptor, inter alia, an oxygen or nitrogen atom, or a fluorine atom attached to an aromatic ring, or an H bond donor. In some embodiments, a compound as described herein comprises a structural element according to (a) as described in the above paragraph, which is a moiety of a linker engaging the backbone of A825 of hKSR1, or P878 of hKSR2, or R662 of hBRAF, or R554 of CRAF, directly or through a water-mediated contact.

In some embodiments, a compound as described herein comprising one or more of the following:
(c) at least one moiety engaging M230 of hMEK1 or M234 of hMEK2, wherein M230 or M234 are within about 5 Å to about 8 Å from terminal atom (CB) of A825 of KSR1 or (CG) of P878 of hKSR2 or (CG) N661 of hBRAF or N553 of CRAF;

(d) at least one moiety is a H-bond acceptor or donor engaging the backbone carbonyl of N823 of hKSR1, or T876 of hKSR2 through a water-mediated contact or backbone amino group of R662 of hBRAF or R554 of hCRAF directly;

(e) at least one moiety engaging Q824 of hKSR1 or Q877 of hKSR2 or Q664 of hBRAF or Q556 of hCRAF;

(f) at least one moiety engaging a side chain atom of A826 of hKSR1 or A879 of hKSR2 or R662 of BRAF or R554 of CRAF;

(g) at least one moiety is a heteroaryl group engaging M143 of hMEK1 or M147 of hMEK2;

(h) at least one moiety is a heteroaryl group engaging F209 of hMEK1 or F213 of hMEK2; (i) at least one moiety (inter alia, a H-bond acceptor) is engaging the backbone amino group of S212 of hMEK1 or S216 of hMEK2;

(j) at least one moiety engaging L215 of hMEK1 or L219 of hMEK2;

(k) at least one moiety engaging 1216 of hMEK1 or 1220 of hMEK2; and (l) at least one moiety engaging M219 of hMEK1 or M223 of hMEK2 where hMEK1 residues 215-219 adopt a helical conformation.

In some embodiments, a moiety corresponding to (c) as described above is selected from substituted or unsubstituted alkyl or cycloalkyl.

In some embodiments, a backbone CO residue of a compound as described herein engages with T876 of hKSR2 or N823 of hKSR1.

In some embodiments, a compound as described herein engages with a binding pocket, which is lined by the hMEK1 residues R234 and M230, or hMEK2 residues R238 and M234, and P877 of KSR2 or A825 of KSR1 or R662 of BRAF or R554 of CRAF.

In some embodiments, a compound as described herein engages a binding pocket via multiple hydrogen bond contacts, including through a water mediated H-bond to Arg189 and Arg234 in hMEK1 or ARG193 and A238 of hMEK2, as well as a direct H-bond to the backbone of the pre-helix αG loop —NH— of Arg662 of BRAF or ARG 554 of CRAF.

In some embodiments, a compound as described herein engage A825 of hKSR1 or P878 of hKSR2 or R662 of BRAF or R554 of CRAF. In some embodiments, a compound as described herein has a distance of less than or equal to about 5 Å to about 8 Å from at least one moiety selected from A825 of hKSR1, P878 of hKSR2, and R662 of BRAF and R554 of CRAF.

Accordingly, in some aspects and embodiments, the present disclosure provides a method for treating one or more disorders, diseases, and/or conditions wherein the disorder, disease, or condition includes, but is not limited to, a cellular proliferative disorder, comprising administering to a patient in need thereof, a MEK inhibitor compound as described herein, or a pharmaceutical salt or composition thereof. In some embodiments, the cellular proliferative disorder is cancer. In some embodiments, the cancer is characterized by increased MEK expression and/or increased MEK activity, i.e., "increased activated MEK."

As used herein, the terms "increased," "elevated," or "enhanced," are used interchangeably and encompass any measurable increase in a biological function and/or biological activity and/or a concentration. For example, an increase can be by at least about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, about 100%, about 2-fold, about 3-fold, about 4-fold, about 5-fold, about 6-fold, about 7-fold, about 8-fold, about 9-fold, about 10-fold, about 20-fold, about 25-fold, about 50-fold, about 100-fold, or higher, relative to a control or baseline amount of a function, or activity, or concentration.

As used herein, the terms "increased expression" and/or "increased activity" of a substance, such as MEK, in a sample or cancer or patient, refers to an increase in the amount of the substance, such as MEK, of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, about 100%, about 2-fold, about 3-fold, about 4-fold, about 5-fold, about 6-fold, about 7-fold, about 8-fold, about 9-fold, about 10-fold, about 20-fold, about 25-fold, about 50-fold, about 100-fold, or higher, relative to the amount of the substance, such as MEK, in a control sample or control samples, such as an individual or group of individuals who are not suffering from the disease or disorder (e.g., cancer) or an internal control, as determined by techniques known in the art. A subject can also be determined to have an "increased expression" or "increased activity" of MEK if the expression and/or activity of MEK is increased by one standard deviation, two standard deviations, three standard deviations, four standard deviations, five standard deviations, or more, relative to the mean (average) or median amount of MEK in a control group of samples or a baseline group of samples or a retrospective analysis of patient samples. As practiced in the art, such control or baseline expression levels can be previously determined, or measured prior to the measurement in the sample or cancer or subject, or can be obtained from a database of such control samples.

c. Cancer

In some embodiments, the present disclosure provides a method for treating or preventing or reducing the risk of a cancer in patient comprising administering to the patient a compound of the disclosure, or a pharmaceutically acceptable salt thereof, or a pharmaceutical composition thereof.

A "cancer," as used herein, refers to a broad group of various diseases characterized by the uncontrolled growth of abnormal cells in the body. Unregulated cell division and growth divide and grow results in the formation of malignant tumors that invade neighboring tissues and can also metastasize to distant parts of the body through the lymphatic system or bloodstream.

The cancer or proliferative disorder or tumor to be treated using the compounds and methods and uses described herein include, but are not limited to, a hematological cancer, a lymphoma, a myeloma, a leukemia, a neurological cancer, skin cancer, breast cancer, a prostate cancer, a colorectal cancer, lung cancer, head and neck cancer, a gastrointestinal cancer, a liver cancer, a pancreatic cancer, a genitourinary cancer, a bone cancer, renal cancer, and a vascular cancer.

In some embodiments, the cancer is a K-Ras mutant cancer. In some embodiments, the K-Ras mutant cancer is an activated mutant K-Ras cancer. In some embodiments, the K-Ras mutant cancer is a cancer having a mutant or variant K-Ras G12. In some embodiments, the mutant or variant K-Ras G12 is K-Ras G12D, K-Ras G12V, K-Ras G12C, K-Ras G12R, K-Ras G12A, or any combination thereof. In some embodiments, the mutant or variant K-Ras G12 is K-Ras G12D, K-Ras G12V, K-Ras G12C, K-Ras G12R, K-Ras G12A, K-Ras G12S, or any combination thereof. In some embodiments, the mutant or variant K-Ras G12 is K-Ras G12D. In some embodiments, the mutant or variant K-Ras G12 is K-Ras G12V. In some embodiments, the mutant or variant K-Ras G12 is K-Ras G12C. In some embodiments, the mutant or variant K-Ras G12 is K-Ras G12R. In some embodiments, the mutant or variant K-Ras G12 is K-Ras G12A. In some embodiments, the mutant or variant K-Ras G12 is K-Ras G12S. In some embodiments, the K-Ras mutant cancer is a cancer having a mutant or variant K-Ras G13. In some embodiments, the mutant or variant K-Ras G13 is K-Ras G13D, K-Ras G13C, or any combination thereof. In some embodiments, the K-Ras mutant cancer is a cancer having a mutant or variant K-Ras Q61. In some embodiments, the mutant or variant K-Ras Q61 is K-Ras Q61H, K-Ras Q61R, or any combination thereof. In some embodiments, the K-Ras mutant cancer is a cancer having a mutant or variant K-Ras A146. In some embodiments, the mutant or variant K-Ras A146 is K-Ras A146T. In some embodiments, the K-Ras mutant cancer is a cancer having a mutant or variant K-Ras G12D, K-Ras G12V, K-Ras G12C, K-Ras G12R, K-Ras G12A, K-Ras G13D, K-Ras G13C, K-Ras Q61H, K-Ras Q61R, K-Ras A146T, or any combination thereof. In some embodiments, the K-Ras mutant cancer is a cancer having a mutant or variant K-Ras G12D, K-Ras G12V, K-Ras G12C, K-Ras G12R, K-Ras G12A, K-Ras G12S, K-Ras G13D, K-Ras G13C, K-Ras Q61H, K-Ras Q61R, K-Ras A146T, or any combination thereof.

In some embodiments, the cancer is a mutant B-Raf cancer. In some embodiments, the mutant B-Raf cancer comprises a B-Raf amplification. As used herein, a "B-Raf amplification" refers to a cancer or cancer cell comprising at least three B-Raf copies, at least four B-Raf copies, at least five B-Raf copies, at least six B-Raf copies, at least seven B-Raf copies, at least eight B-Raf copies, at least nine B-Raf copies, at least ten B-Raf copies, or more. In some embodiments, the mutant B-Raf cancer is a cancer having a mutant or variant B-Raf V600, also referred to as a "Class I B-Raf mutation." In some embodiments, the mutant or variant B-Raf V600 is B-Raf V600E, V600K, V600D, V600R, or any combination thereof. In some embodiments, the mutant or variant B-Raf V600 is B-Raf V600E, V600K, V600D, V600R, V600M, or any combination thereof. In some embodiments, the mutant B-Raf cancer is a cancer having a mutant or variant B-Raf K601, B-Raf P367, B-Raf G464, B-Raf L485, B-Raf E586, B-Raf T588, B-Raf T599, B-Raf L597, B-Raf G469, or any combination thereof, which are also collectively referred to as "Class II B-Raf mutations." In some embodiments, the mutant B-Raf cancer is a cancer having a mutant or variant B-Raf K601, B-Raf P367, B-Raf G464, B-Raf G469, B-Raf G496, B-Raf L485, B-Raf E586, B-Raf T588, B-Raf T599, B-Raf L597, B-Raf fusions, such as, for example, B-Raf fusions combining the kinase domain of B-Raf with the N-terminal portion of a distinct gene product allowing for RAS-independent B-Raf dimerization, or any combination thereof, which are also collectively referred to as "Class II B-Raf mutations." In some embodiments, the mutant B-Raf K601 is B-Raf K601E, K601N, K601T, or any combination thereof. In some embodiments, the mutant B-Raf P367 is B-Raf P367L, P367S, or any combination thereof. In some embodiments, the mutant B-Raf G464 is B-Raf G464V, G464E, or any combination thereof. In some embodiments, the mutant B-Raf G496 is B-Raf G496V. In some embodiments, the mutant B-Raf L485 is L485W. In some embodiments, the mutant B-Raf E586 is E586K. In some embodiments, the mutant B-Raf T599 is T588TT, T588TS, T599I, T599K, or any combination thereof. In some embodiments, the mutant B-Raf L597 is B-Raf L597Q, L597R, L597S, L597V, or any combination thereof. In some embodiments, the mutant B-Raf G469 is B-Raf G469A, G469V, G469R, or any combination thereof. In some embodiments, the mutant B-Raf is a B-Raf fusion. In some embodiments, the mutant B-Raf cancer is a cancer having a mutant or variant B-Raf D287, B-Raf V459, B-Raf G466, B-Raf S467, B-Raf G469, B-Raf N581, B-Raf D594, B-Raf F595, B-Raf G596, or any combination thereof, which are also collectively referred to as "Class III B-Raf mutations." In some embodiments, the mutant B-Raf D287 is B-Raf D287N. In some embodiments, the mutant B-Raf V459 is B-Raf B459L. In some embodiments, the mutant B-Raf G466 is B-Raf G466A, B-Raf G466E, B-Raf G466V, or any combination thereof. In some embodiments, the mutant B-Raf S467 is B-Raf S467L. In some embodiments, the mutant B-Raf G469 is B-Raf-G469E. In some embodiments, the mutant B-Raf N581 is B-Raf N581I, B-Raf N581S, B-Raf N581T, or any combination thereof. In some embodiments, the mutant B-Raf D594 is B-Raf D594A, B-Raf D594G, B-Raf D594H, B-Raf D594N, or any combination thereof. In some embodiments, the mutant B-Raf F595 is B-Raf F595L. In some embodiments, the mutant B-Raf G596 is B-Raf G596D, B-Raf G596R, or any combination thereof. In some embodiments, the mutant B-Raf cancer comprises a B-Raf amplification and at least one B-Raf mutant or variant B-Raf Class I, Class II, or Class III mutation.

In some embodiments, the cancer is an N-Ras mutant cancer. In some embodiments, the N-Ras mutant cancer is an activated mutant N-Ras cancer. In some embodiments, the N-Ras mutant cancer is a cancer having a mutant or variant N-Ras G12. In some embodiments, the mutant or variant N-Ras G12 is N-Ras G12D, N-Ras G12V, N-Ras G12C, N-Ras G12A, N-Ras G12R, N-Ras G12S, or any combination thereof. In some embodiments, the mutant or variant N-Ras G12 is N-Ras G12D. In some embodiments, the mutant or variant N-Ras G12 is N-Ras is N-Ras G12V. In some embodiments, the mutant or variant N-Ras G12 is N-Ras G12C. In some embodiments, the mutant or variant N-Ras G12 is N-Ras G12R. In some embodiments, the mutant or variant N-Ras G12 is N-Ras is N-Ras G12A. In some embodiments, the mutant or variant N-Ras G12 is N-Ras G12S. In some embodiments, the N-Ras mutant cancer is a cancer having a mutant or variant N-Ras Q61. In some embodiments, mutant or variant N-Ras Q61 is N-Ras Q61R, N-Ras Q61K, N-Ras Q61L, N-Ras Q61H, N-Ras Q61P, or any combination thereof. In some embodiments, the mutant or variant N-Ras Q61 is N-Ras Q61R. In some embodiments, the mutant or variant N-Ras Q61 is N-Ras Q61K. In some embodiments, the mutant or variant N-Ras Q61 is N-Ras Q61L. In some embodiments, the mutant or variant N-Ras Q61 is N-Ras Q61H. In some embodiments, the mutant or variant N-Ras Q61 is N-Ras Q61P. In some embodiments, the N-Ras mutant cancer is a cancer having a mutant or variant N-Ras G12D, N-Ras G12V, N-Ras G12C, N-Ras G12R, N-Ras G12A, N-Ras G12S, N-Ras Q61, or any combination thereof.

In some embodiments, the cancer is a C-Raf mutant cancer. In some embodiments, the mutant C-Raf cancer comprises a C-Raf amplification. As used herein, a "C-Raf amplification" refers to a cancer cell comprising at least three C-Raf copies, at least four C-Raf copies, at least five C-Raf copies, at least six C-Raf copies, at least seven C-Raf copies, at least eight C-Raf copies, at least nine C-Raf copies, at least ten C-Raf copies, or more. In some embodiments, the mutant C-Raf cancer is a cancer having a mutant or variant C-Raf S427. In some embodiments, the mutant or variant C-Raf S427 is C-Raf S427G. In some embodiments, the mutant C-Raf cancer is a cancer having a mutant or variant C-Raf 1448. In some embodiments, the mutant C-Raf 1448 is C-Raf I448V. In some embodiments, the mutant C-Raf cancer comprises a C-Raf amplification and/or at least one C-Raf mutant or variant C-Raf.

In some embodiments, the cancer is an NF1 and/or NF2 mutant cancer. As used herein, an "NF1 mutant cancer" refers to a cancer having a mutant or variant gene encoding the neurofibromin protein, and includes deletion mutations, loss-of-function mutations, microdeletion mutations, missense mutations, copy number loss mutations, and substitution mutations. As used herein, an "NF2 mutant cancer" refers to a cancer having a mutant or variant gene encoding the Merlin protein (also known as schwannomin protein), and includes deletion mutations, loss-of-function mutations, microdeletion mutations, missense mutations, copy number loss mutations, and substitution mutations.

In some embodiments of the methods and uses described herein, the cancer is selected from non-small cell lung cancer (NSCLC), pancreatic cancer, colorectal cancer (CRC), uterine carcinoma, endometrial carcinoma, bladder cancer, head and neck cancer, thyroid cancer, melanoma, multiple myeloma, acute myeloid leukemia (AML), low-grade serous ovarian cancer, neurofibroma, and glioma.

In some embodiments of the methods and uses described herein, the cancer is a K-Ras mutant non-small cell lung cancer (NSCLC). In some embodiments of the methods and uses described herein, the cancer is a K-Ras mutant pancreatic cancer. In some embodiments of the methods and uses described herein, the cancer is a K-Ras mutant colorectal cancer. In some embodiments of the methods and uses described herein, the cancer is a K-Ras mutant uterine carcinoma. In some embodiments of the methods and uses described herein, the cancer is a K-Ras mutant endometrial carcinoma. In some embodiments of the methods and uses described herein, the cancer is a K-Ras mutant bladder cancer. In some embodiments of the methods and uses described herein, the cancer is a K-Ras mutant head and neck cancer. In some embodiments of the methods and uses described herein, the cancer is a K-Ras mutant thyroid cancer. In some embodiments of the methods and uses described herein, the cancer is a K-Ras mutant low-grade serous ovarian cancer. In some embodiments of the methods and uses described herein, the cancer is an N-Ras mutant melanoma. In some embodiments of the methods and uses described herein, the cancer is an N-Ras mutant multiple myeloma. In some embodiments of the methods and uses described herein, the cancer is an N-Ras mutant acute myeloid leukemia (AML). In some embodiments of the methods and uses described herein, the cancer is an N-Ras mutant Bladder cancer. In some embodiments of the methods and uses described herein, the cancer is a K-Ras mutant low-grade serous ovarian cancer. In some embodiments of the methods and uses described herein, the cancer is a B-Raf mutant non-small cell lung cancer (NSCLC). In some embodiments of the methods and uses described herein, the cancer is a C-Raf mutant bladder cancer. In some embodiments of the methods and uses described herein, the cancer is an NF1 mutant glioma. In some embodiments of the methods and uses described herein, the cancer is an NF1 mutant non-small cell lung cancer (NSCLC). In some embodiments of the methods and uses described herein, the cancer is an NF2 mutant neurofibroma.

In some embodiments of the methods and uses described herein, the cancer is lung cancer, thyroid cancer, ovarian cancer, colorectal cancer, prostate cancer, cancer of the pancreas, cancer of the esophagus, liver cancer, breast cancer, skin cancer, or mesothelioma. In some embodiments, the cancer is mesothelioma, such as malignant mesothelioma.

In some embodiments, a cancer includes, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, and retinoblastoma).

In some embodiments, a cancer is glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, or retinoblastoma.

In some embodiments, a cancer is acoustic neuroma, astrocytoma (e.g. Grade I—Pilocytic Astrocytoma, Grade II—Low-grade Astrocytoma, Grade III—Anaplastic Astrocytoma, or Grade IV—Glioblastoma (GBM)), chordoma, CNS lymphoma, craniopharyngioma, brain stem glioma, ependymoma, mixed glioma, optic nerve glioma, subependymoma, medulloblastoma, meningioma, metastatic brain tumor, oligodendroglioma, pituitary tumors, primitive neuroectodermal (PNET) tumor, or schwannoma. In some embodiments, the cancer is a type found more commonly in children than adults, such as brain stem glioma, craniopharyngioma, ependymoma, juvenile pilocytic astrocytoma (JPA), medulloblastoma, optic nerve glioma, pineal tumor, primitive neuroectodermal tumors (PNET), or rhabdoid tumor. In some embodiments, the patient is an adult human. In some embodiments, the patient is a child or pediatric patient.

Cancer includes, in another embodiment, without limitation, mesothelioma, hepatobilliary (hepatic and billiary duct), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, non-Hodgkins's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

In some embodiments, a cancer is a solid tumor, such as a sarcoma, carcinoma, or lymphoma. Solid tumors generally comprise an abnormal mass of tissue that typically does not include cysts or liquid areas. In some embodiments, the cancer is selected from renal cell carcinoma, or kidney cancer; hepatocellular carcinoma (HCC) or hepatoblastoma, or liver cancer; melanoma; breast cancer; colorectal carcinoma, or colorectal cancer; colon cancer; rectal cancer; anal cancer; lung cancer, such as non-small cell lung cancer (NSCLC) or small cell lung cancer (SCLC); ovarian cancer, ovarian epithelial cancer, ovarian carcinoma, or fallopian tube cancer; papillary serous cystadenocarcinoma or uterine papillary serous carcinoma (UPSC); prostate cancer; testicular cancer; gallbladder cancer; hepatocholangiocarcinoma; soft tissue and bone synovial sarcoma; rhabdomyosarcoma; osteosarcoma; chondrosarcoma; Ewing sarcoma; anaplastic thyroid cancer; adrenocortical carcinoma; pancreatic cancer; pancreatic ductal carcinoma or pancreatic adenocarcinoma; gastrointestinal/stomach (GIST) cancer; lymphoma; squamous cell carcinoma of the head and neck (SCCHN); salivary gland cancer; glioma, or brain cancer; neurofibromatosis-1 associated malignant peripheral nerve sheath tumors (MPNST); Waldenstrom's macroglobulinemia; or medulloblastoma.

In some embodiments, a cancer is hepatocellular carcinoma (HCC). In some embodiments, the cancer is hepatoblastoma. In some embodiments, the cancer is colon cancer. In some embodiments, the cancer is rectal cancer. In some embodiments, the cancer is ovarian cancer, or ovarian carcinoma. In some embodiments, the cancer is ovarian epithelial cancer. In some embodiments, the cancer is fallopian tube cancer. In some embodiments, the cancer is papillary serous cystadenocarcinoma. In some embodiments, the cancer is uterine papillary serous carcinoma (UPSC). In some embodiments, the cancer is hepatocholangiocarcinoma. In some embodiments, the cancer is soft tissue and bone synovial sarcoma. In some embodiments, the cancer is rhabdomyosarcoma. In some embodiments, the cancer is osteosarcoma. In some embodiments, the cancer is anaplastic thyroid cancer. In some embodiments, the cancer is adrenocortical carcinoma. In some embodiments, the cancer is pancreatic cancer, or pancreatic ductal carcinoma. In some embodiments, the cancer is pancreatic adenocarcinoma. In some embodiments, the cancer is glioma. In some embodiments, the cancer is malignant peripheral nerve sheath tumors (MPNST). In some embodiments, the cancer is neurofibromatosis-1 associated MPNST. In some embodiments, the cancer is Waldenstrom's macroglobulinemia. In some embodiments, the cancer is medulloblastoma.

In some embodiments, a cancer is a viral-associated cancer, including human immunodeficiency virus (HIV) associated solid tumors, human papilloma virus (HPV)-16 positive incurable solid tumors, and adult T-cell leukemia, which is caused by human T-cell leukemia virus type I (HTLV-I) and is a highly aggressive form of CD4+ T-cell leukemia characterized by clonal integration of HTLV-I in leukemic cells (See https://clinicaltrials.gov/ct2/show/study/NCT02631746); as well as virus-associated tumors in gastric cancer, nasopharyngeal carcinoma, cervical cancer, vaginal cancer, vulvar cancer, squamous cell carcinoma of the head and neck, and Merkel cell carcinoma. (See https://clinicaltrials.gov/ct2/show/study/NCT02488759; see also https://clinicaltrials.gov/ct2/show/study/NCT0240886; https://clinicaltrials.gov/ct2/show/NCT02426892)

In some embodiments, the methods or uses described herein inhibit or reduce or arrest or ameliorate the growth or spread of a cancer or tumor. In some embodiments, the tumor is treated by arresting, reducing, or inhibiting further growth of the cancer or tumor. In some embodiments, the methods or uses described herein increase or potentiate or activate one or more immune responses to inhibit or reduce or arrest or ameliorate the growth or spread of a cancer or tumor. In some embodiments, the cancer or tumor is treated by reducing the size (e.g., volume or mass) of the cancer or tumor by at least 5%, at least 10%, at least 25%, at least 50%, at least 75%, at least 90%, at least 95%, at least 96%, at least 97%, at least 98%, or at least 99% relative to the size of the cancer or tumor prior to treatment. In some embodiments, cancers or tumors are treated by reducing the quantity of the cancers or tumors in the patient by at least 5%, at least 10%, at least 25%, at least 50%, at least 75%, at least 90%, at least 95%, at least 96%, at least 97%, at least 98%, or at least 99% relative to the quantity of cancers or tumors prior to treatment.

In some embodiments, a patient treated using the methods or uses described herein exhibits progression-free survival of at least about one month, at least about 2 months, at least about 3 months, at least about 4 months, at least about 5 months, at least about 6 months, at least about 7 months, at least about 8 months, at least about 9 months, at least about 10 months, at least about 11 months, at least about one year, at least about eighteen months, at least about two years, at least about three years, at least about four years, or at least about five years after the treatment is initiated. In some embodiments, a patient treated using the methods or uses described herein exhibits an overall survival of at least about one month, at least about 2 months, at least about 3 months, at least about 4 months, at least about 5 months, at least about 6 months, at least about 7 months, at least about 8 months, at least about 9 months, at least about 10 months, at least about 11 months, at least about one year, at least about 14 months, at least about 16 months, at least about 18 months, at least about 20 months, at least about 22 months, at least about two years, at least about three years, at least about four years, or at least about five years after the treatment is initiated.

In some embodiments, a patient treated using the methods or uses described herein exhibits an objective response rate (ORR) of at least about 15%, at least about 20%, at least about 25%, at least about 30%, about 35%, about 40%, about 45%, about 50%, about 55%, about 60%, about 65%, about 70%, about 75%, about 80%, about 85%, about 90%, about 95%, or about 100%.

The compounds and compositions, according to the method of the present disclosure, may be administered using any amount and any route of administration effective for inhibiting MEK and treating or lessening the severity of a disease, for example, as those described herein. The exact amount required will vary from subject to subject, depending on the species, age, and general condition of the subject, the severity of the disease or condition, the particular agent, its mode of administration, and the like. Compounds of the disclosure are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this disclosure can be administered to humans and other animals orally, rectally, parenterally, intracisternally, intravaginally, intraperitoneally, topically (as by powders, ointments, or drops), bucally, as an oral or nasal spray, or the like, depending on the severity of the disease or disorder being treated. In certain embodiments, the compounds of the disclosure may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present disclosure, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this disclosure with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this disclosure include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this disclosure. Additionally, the present disclosure contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

d. Co-Administration with One or More Other Therapeutic Agent(s)

Depending upon the particular condition, or disease, to be treated, additional therapeutic agents that are normally administered to treat that condition, can also be present in the compositions of this disclosure. As used herein, additional therapeutic agents that are normally administered to treat a particular disease, or condition, are known as "appropriate for the disease, or condition, being treated."

In some embodiments, the present disclosure provides a method of treating a disclosed disease or condition comprising administering to a patient in need thereof an effective amount of a compound disclosed herein or a pharmaceutically acceptable salt thereof and co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents. In some embodiments, the combination of the disclosed compound and the additional therapeutic agent or agents acts synergistically.

A compound of the current disclosure can be administered alone or in combination with one or more other therapeutic compounds, possible combination therapy taking the form of fixed combinations or the administration of a compound of the disclosure and one or more other therapeutic compounds being staggered or given independently of one another, or the combined administration of fixed combinations and one or more other therapeutic compounds.

One or more other therapeutic agent(s) can be administered separately from a compound or composition of the disclosure, as part of a multiple dosage regimen. Alternatively, one or more other therapeutic agent(s) may be part of a single dosage form, mixed together with a compound of this disclosure in a single composition. If administered as a multiple dosage regime, one or more other therapeutic agent(s) and a compound or composition of the disclosure can be administered simultaneously, sequentially or within a period of time from one another, for example within 1, 2, 3, 4, 5, 6, 7, 8, 9, 10, 11, 12, 13, 14, 15, 16, 17, 18, 19, 20, 21, 22, 23, or 24 hours from one another. In some embodiments, one or more other therapeutic agent(s) and a compound or composition of the disclosure are administered as a multiple dosage regimen within greater than 24 hours apart.

As used herein, the term "combination," "combined," and related terms refers to the simultaneous or sequential administration of therapeutic agents in accordance with this disclosure. For example, a compound of the present disclosure can be administered with one or more other therapeutic agent(s) simultaneously or sequentially in separate unit dosage forms or together in a single unit dosage form. Accordingly, the present disclosure provides a single unit dosage form comprising a compound of the current disclosure, one or more other therapeutic agent(s), and a pharmaceutically acceptable carrier, adjuvant, or vehicle.

The amount of a compound of the disclosure and one or more other therapeutic agent(s) (in those compositions which comprise an additional therapeutic agent as described above) that can be combined with the carrier materials to produce a single dosage form varies depending upon the host treated and the particular mode of administration. Preferably, a composition of the disclosure should be formulated so that a dosage of between 0.01-100 mg/kg body weight/day of a compound of the disclosure can be administered.

In those compositions which comprise one or more other therapeutic agent(s), the one or more other therapeutic agent(s) and a compound of the disclosure can act synergistically. Therefore, the amount of the one or more other therapeutic agent(s) in such compositions may be less than that required in a monotherapy utilizing only that therapeutic agent. In such compositions a dosage of between 0.01-1,000 g/kg body weight/day of the one or more other therapeutic agent(s) can be administered.

The amount of one or more other therapeutic agent(s) present in the compositions of this disclosure may be no more than the amount that would normally be administered in a composition comprising that therapeutic agent as the only active agent. Preferably the amount of one or more other therapeutic agent(s) in the presently disclosed compositions ranges from about 50% to 100% of the amount normally present in a composition comprising that agent as the only therapeutically active agent. In some embodiments, one or more other therapeutic agent(s) is administered at a dosage of about 50%, about 55%, about 60%, about 65%, about 70%, about 75%, about 80%, about 85%, about 90%, or about 95% of the amount normally administered for that agent. As used herein, the phrase "normally administered" means the amount an FDA approved therapeutic agent is approved for dosing per the FDA label insert.

The compounds of this disclosure, or pharmaceutical compositions thereof, can also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by precoating the device with a pharmaceutically acceptable composition comprising a kinase inhibitor. Implantable devices coated with a compound of this disclosure are another embodiment of the present disclosure.

e. Exemplary Other Therapeutic Agents

In some embodiments, the one or more other therapeutic agent is a TEAD inhibitor. In certain embodiments, the TEAD inhibitor is selected from those described in WO 2020/243415, the contents of which are herein incorporated by reference in their entirety. In certain embodiments, the TEAD inhibitor is selected from those described in WO 2020/243423, the contents of which are herein incorporated by reference in their entirety. In certain embodiments, the TEAD inhibitor is selected from those described in U.S. Pat. No. 11,247,082, the contents of which are herein incorporated by reference in their entirety. In certain embodiments, the TEAD inhibitor is selected from those described in WO 2022/120353, the contents of which are herein incorporated by reference in their entirety. In certain embodiments, the TEAD inhibitor is selected from those described in WO 2022/120354, the contents of which are herein incorporated by reference in their entirety.

In certain embodiments, the second anti-cancer agent is a TEAD degrader. In certain embodiments, the TEAD degrader is selected from those described in WO 2022/120355, the contents of which are herein incorporated by reference in their entirety.

TEAD inhibitors can be produced by organic synthesis methods known to one of ordinary skill in the art. Additionally, certain TEAD inhibitors can be prepared as described in Pobbati et al., "Targeting the Central Pocket in Human Transcription Factor TEAD as a Potential Cancer Therapeutic Strategy," Structure 2015, 23, 2076-2086; Gibault et al., "Targeting Transcriptional Enhanced Associate Domains (TEADs)," J. Med. Chem. 2018, 61, 5057-5072; Bum-Erdene et al., "Small-Molecule Covalent Modification of Conserved Cysteine Leads to Allosteric Inhibition of the TEADoYap Protein-Protein Interaction," Cell Chemical Biology 2019, 26, 1-12; Holden et al., "Small Molecule Dysregulation of TEAD Lipidation Induces a Dominant-Negative Inhibition of HippoPathway Signaling," Cell Reports 2020, 31, 107809; WO 2017/053706, WO 2017/111076, WO 2018/204532, WO 2018/235926, US 20190010136, WO 2019/040380, WO 2019/113236, WO 2019/222431, WO 2019/232216, WO 2020/051099, WO 2020/081572, WO 2020/097389, WO 2020/190774, WO 2020/214734, PCT/US2020/35098, and PCT/US2020/35111, the contents of each of which are herein incorporated by reference in its entirety.

In some embodiments, the one or more other therapeutic agent is an ERK5 inhibitor. In certain embodiments, the ERK5 inhibitor is selected from those described in WO 2022/051567, the contents of which are herein incorporated by reference in their entirety. In certain embodiments, the ERK5 inhibitor is selected from those described in WO 2022/051565, the contents of which are herein incorporated by reference in their entirety. In certain embodiments, the ERK5 inhibitor is selected from those described in WO 2022/051569, the contents of which are herein incorporated by reference in their entirety. In certain embodiments, the ERK5 inhibitor is selected from those described in WO 2022/051568, the contents of which are herein incorporated by reference in their entirety.

In some embodiments, the one or more other therapeutic agent is a KRAS inhibitor, such as a KRAS G12C inhibitor. As used herein, a "KRAS G12C inhibitor" refers to any inhibitor or blocker or antagonist that binds to and/or inhibits signaling through KRAS. In certain embodiments, a KRAS G12C inhibitor is selected from adagrasib (KRAZATI®, Mirati Therapeutics), sotorasib (LUMAKRAS® and LUMYKRAS®, Amgen), or a pharmaceutically acceptable salt and/or solvate of any of the foregoing. Other examples of KRAS G12C inhibtiors for use in the methods and uses described herein include, but are not limited to, JDQ-443 (Novartis AG), D-1553 (Inventisbio Shanghai), GF-105 (GenFleet Therapeutics), GH-35 (Suzhou GenHouse Bio Co.), JAB-21822 (Jacobio Pharmaceuticals), JMKX-001899 (Shanghi Jiyu Pharmaceuticals), TAS-119 (Taiho Pharmaceuticals), XNW-14010 (Suzhou Sinovent Pharmaceuticals), YL-15293 (Shanghai Yingli Pharmaceuticals), ZG-19018 (Suzhou Zelgen Biopharma), BEBT-607 (Guangzhou Bibet Pharmaceuticals), BI-1701963 (Forma Therapeutics Holdings), BI-1823911 (Boehringer Ingelheim Gmbh), BPI-421286 (Betta Pharmaceuticals), D3S-001 (D3 Bio), ERAS-3490 (Regents of the University of California), GEC-255 (GenEros BioPhrma LTD), and JS116 (Shanghai Junshi Biosceinces). Other examples of KRAS G12C inhibitors in the methods and uses described herein include, but are not limited to, those described in international patent publications WO 2021/120890 the contents of each of which are herein incorporated by reference in their entireties.

In some embodiments, the one or more other therapeutic agent is a pan-RAF inhibitor. As used herein, a "Pan-RAF inhibitor" refers to any inhibitor or blocker or antagonist that binds to all known members of the serine/threonine protein kinase Raf family including A-Raf, B-Raf, and C-Raf protein kinases, with potential antineoplastic activity. In certain embodiments, a Pan-RAF inhibitor is selected from tovorafenib (TAK580, Day On Biopharmaceuticals), TAK-632 (Takeda Pharmaceuticals), lifirafenib (BGB-283, BeiGene), exarafeinib (Kinnate Biophanna), naporafenib (LXH-254, Erasca), or a pharmaceutically acceptable salt and/or solvate of any of the foregoing. In certain embodiments, a Pan-RAF inhibitor is selected from tovorafenib TAK-632, lifirafenib, exarafenib, or a pharmaceutically acceptable salt and/or solvate of any of the foregoing. Other examples of Pan-RAF inhibitors useful with the compositions, methods, and uses described herein include, but are not limited to, those described in international patent publications WO2015/075483, WO2015/075483, and WO2014/151616 the contents of each of which are herein incorporated by reference in their entireties.

In some embodiments, one or more other therapeutic agent is a Poly ADP ribose polymerase (PARP) inhibitor. In some embodiments, a PARP inhibitor is selected from olaparib (LYNPARZA®, AstraZeneca); rucaparib (RUBRACA®, Clovis Oncology); niraparib (ZEJULA®, Tesaro); talazoparib (MDV3800/BMN 673/LT00673, Medivation/Pfizer/Biomarin); veliparib (ABT-888, AbbVie); and BGB-290 (BeiGene, Inc.).

In some embodiments, one or more other therapeutic agent is a histone deacetylase (HDAC) inhibitor. In some embodiments, an HDAC inhibitor is selected from vorinostat (ZOLINZA®, Merck); romidepsin (ISTODAX®, Celgene); panobinostat (FARYDAK®, Novartis); belinostat (BELEODAQ®, Spectrum Pharmaceuticals); entinostat (SNDX-275, Syndax Pharmaceuticals) (NCT00866333); and chidamide (EPIDAZA®, HBI-8000, Chipscreen Biosciences, China).

In some embodiments, one or more other therapeutic agent is a CDK inhibitor, such as a CDK4/CDK6 inhibitor. In some embodiments, a CDK 4/6 inhibitor is selected from palbociclib (IBRANCE®, Pfizer); ribociclib (KISQALI®, Novartis); abemaciclib (Ly2835219, Eli Lilly); and trilaciclib (G1T28, G1 Therapeutics).

In some embodiments, one or more other therapeutic agent is a phosphatidylinositol 3 kinase (PI3K) inhibitor. In some embodiments, a PI3K inhibitor is selected from idelalisib (ZYDELIG®, Gilead), alpelisib (BYL719, Novartis), taselisib (GDC-0032, Genentech/Roche); pictilisib (GDC-0941, Genentech/Roche); copanlisib (BAY806946, Bayer); duvelisib (formerly IPI-145, Infinity Pharmaceuticals); PQR309 (Piqur Therapeutics, Switzerland); and TGR1202 (formerly RP5230, TG Therapeutics). In some embodiments, a PI3K inhibitor is selected from inavolisib (GDC-077, Genentech), idelalisib (ZYDELIG®, Gilead), alpelisib (BYL719, Novartis), taselisib (GDC-0032, Genentech/Roche); pictilisib (GDC-0941, Genentech/Roche); copanlisib (BAY806946, Bayer); duvelisib (formerly IPI-145, Infinity Pharmaceuticals); PQR309 (Piqur Therapeutics, Switzerland); and TGR1202 (formerly RP5230, TG Therapeutics).

In some embodiments, one or more other therapeutic agent is a platinum-based therapeutic, also referred to as platins. Platins cause cross-linking of DNA, such that they inhibit DNA repair and/or DNA synthesis, mostly in rapidly reproducing cells, such as cancer cells.

In some embodiments, a platinum-based therapeutic is selected from cisplatin (PLATINOL®, Bristol-Myers Squibb); carboplatin (PARAPLATIN®, Bristol-Myers Squibb; also, Teva; Pfizer); oxaliplatin (ELOXITIN® Sanofi-Aventis); nedaplatin (AQUPLA®, Shionogi), picoplatin (Poniard Pharmaceuticals); and satraplatin (JM-216, Agennix).

In some embodiments, one or more other therapeutic agent is a taxane compound, which causes disruption of microtubules, which are essential for cell division. In some embodiments, a taxane compound is selected from paclitaxel (TAXOL®, Bristol-Myers Squibb), docetaxel (TAXOTERE®, Sanofi-Aventis); DOCEFREZ®, Sun Pharmaceutical), albumin-bound paclitaxel (ABRAXANE®; Abraxis/Celgene), cabazitaxel (JEVTANA®, Sanofi-Aventis), and SID530 (SK Chemicals, Co.) (NCT00931008).

In some embodiments, one or more other therapeutic agent is a nucleoside inhibitor, or a therapeutic agent that interferes with normal DNA synthesis, protein synthesis, cell replication, or will otherwise inhibit rapidly proliferating cells.

In some embodiments, a nucleoside inhibitor is selected from trabectedin (guanidine alkylating agent, YONDELIS®, Janssen Oncology), mechlorethamine (alkylating agent, VALCHLOR®, Aktelion Pharmaceuticals); vincristine (ONCOVIN®, Eli Lilly; VINCASAR®, Teva Pharmaceuticals; MARQIBO®, Talon Therapeutics); temozolomide (prodrug to alkylating agent 5-(3-methyltriazen-1-yl)-imidazole-4-carboxamide (MTIC) TEMODAR®, Merck); cytarabine injection (ara-C, antimetabolite cytidine analog, Pfizer); lomustine (alkylating agent, CEENU®, Bristol-Myers Squibb; GLEOSTINE®, NextSource Biotechnology); azacitidine (pyrimidine nucleoside analog of cytidine, VIDAZA®, Celgene); omacetaxine mepesuccinate (cephalotaxine ester) (protein synthesis inhibitor, SYNRIBO®; Teva Pharmaceuticals); asparaginase *Erwinia chrysanthemi* (enzyme for depletion of asparagine, ELSPAR®, Lundbeck; ERWINAZE®, EUSA Pharma); eribulin mesylate (microtubule inhibitor, tubulin-based antimitotic, HALAVEN®, Eisai); cabazitaxel (microtubule inhibitor, tubulin-based antimitotic, JEVTANA®, Sanofi-Aventis); capacetrine (thymidylate synthase inhibitor, XELODA®, Genentech); bendamustine (bifunctional mechlorethamine derivative, believed to form interstrand DNA cross-links, TREANDA®, Cephalon/Teva); ixabepilone (semi-synthetic analog of epothilone B, microtubule inhibitor, tubulin-based antimitotic, IXEMPRA®, Bristol-Myers Squibb); nelarabine (prodrug of deoxyguanosine analog, nucleoside metabolic inhibitor, ARRANON®, Novartis); clorafabine (prodrug of ribonucleotide reductase inhibitor, competitive inhibitor of deoxycytidine, CLOLAR®, Sanofi-Aventis); and trifluridine and tipiracil (thymidine-based nucleoside analog and thymidine phosphorylase inhibitor, LONSURF®, Taiho Oncology).

In some embodiments, one or more other therapeutic agent is a kinase inhibitor or VEGF-R antagonist. Approved VEGF inhibitors and kinase inhibitors useful in the present disclosure include: bevacizumab (AVASTIN®, Genentech/Roche) an anti-VEGF monoclonal antibody; ramucirumab (CYRAMZA®, Eli Lilly), an anti-VEGFR-2 antibody and ziv-aflibercept, also known as VEGF Trap (ZALTRAP®; Regeneron/Sanofi). VEGFR inhibitors, such as regorafenib (STIVARGA®, Bayer); vandetanib (CAPRELSA®, AstraZeneca); axitinib (INLYTA®, Pfizer); and lenvatinib (LENVIMA®, Eisai); Raf inhibitors, such as sorafenib (NEXAVAR®, Bayer AG and Onyx); dabrafenib (TAFINLAR®, Novartis); and vemurafenib (ZELBORAF®, Genentech/Roche); MEK inhibitors, such as cobimetanib (COTELLIC®, Exelexis/Genentech/Roche); trametinib (MEK1NIST®, Novartis); Bcr-Abl tyrosine kinase inhibitors, such as imatinib (GLEEVEC®, Novartis); nilotinib (TASIGNA®, Novartis); dasatinib (SPRYCEL®, BristolMyersSquibb); bosutinib (BOSULIF®, Pfizer); and ponatinib (INCLUSIG®, Ariad Pharmaceuticals); Her2 and EGFR inhibitors, such as gefitinib (IRESSA®, AstraZeneca); erlotinib (TARCEEVA®, Genentech/Roche/Astellas); lapatinib (TYKERB®, Novartis); afatinib (GILOTRIF®, Boehringer Ingelheim); osimertinib (targeting activated EGFR, TAGRISSO®, AstraZeneca); and brigatinib (ALUNBRIG®, Ariad Pharmaceuticals); c-Met and VEGFR2 inhibitors, such as cabozanitib (COMETRIQ®, Exelexis); and multikinase inhibitors, such as sunitinib (SUTENT®, Pfizer); pazopanib (VOTRIENT®, Novartis); ALK inhibitors, such as crizotinib (XALKORI®, Pfizer); ceritinib (ZYKADIA®, Novartis); and alectinib (ALECENZa®, Genentech/Roche); Bruton's tyrosine kinase inhibitors, such as ibrutinib (IBRUVICA®, Pharmacyclics/Janssen); and Flt3 receptor inhibitors, such as midostaurin (RYDAPT®, Novartis).

Other kinase inhibitors and VEGF-R antagonists that are in development and may be used in the present disclosure include tivozanib (Aveo Pharmaecuticals); vatalanib (Bayer/Novartis); lucitanib (Clovis Oncology); dovitinib (TK1258, Novartis); Chiauanib (Chipscreen Biosciences); CEP-11981 (Cephalon); linifanib (Abbott Laboratories); neratinib (HKI-272, Puma Biotechnology); radotinib (SUPECT®, IY5511, Il-Yang Pharmaceuticals, S. Korea); ruxolitinib (JAKAFI®, Incyte Corporation); PTC299 (PTC Therapeutics); CP-547, 632 (Pfizer); foretinib (Exelexis, GlaxoSmithKline); quizartinib (Daiichi Sankyo) and motesanib (Amgen/Takeda).

In some embodiments, a one or more other therapeutic agent is an EGFR inhibitor. As used herein, an "EGFR inhibitor" refers to any inhibitor or blocker or antagonist that binds to and/or inhibits epidermal growth factor receptor (EGFR). In some embodiments, an EGFR inhibitor is selected from those as described in Ayati et al., "A review on progression of epidermal growth factor receptor (EGFR) inhibitors as an efficient approach in cancer targeted therapy," Bioorganic Chemistry 2020, 99: 103811, the contents of which are incorporated herein by reference in their entirety. In some embodiments, an EGFR inhibitor is selected from cetuximab, necitumumab, panitumumab, zalutumumab, nimotuzumab, and matuzumab. In some embodiments, an EGFR inhibitor is cetuximab. In some embodiments, an EGFR inhibitor is necitumumab. In some embodiments, an EGFR inhibitor is panitumumab. In some embodiments, an EGFR inhibitor is zalutumumab. In some embodiments, an EGFR inhibitor is nimotuzumab. In some embodiments, an EGFR inhibitor is matuzumab.

In some embodiments, an EGFR inhibitor is selected from osimertinib, gefitinib, erlotinib, lapatinib, neratinib, vandetanib, afatinib, brigatinib, dacomitinib, and icotinib. In some embodiments, an EGFR inhibitor is osimertinib. In some embodiments, an EGFR inhibitor is gefitinib. In some embodiments, an EGFR inhibitor is erlotinib. In some embodiments, an EGFR inhibitor is lapatinib. In some embodiments, an EGFR inhibitor is neratinib. In some embodiments, an EGFR inhibitor is vandetanib. In some embodiments, an EGFR inhibitor is afatinib. In some embodiments, an EGFR inhibitor is brigatinib. In some embodiments, an EGFR inhibitor is dacomitinib. In some embodiments, an EGFR inhibitor is icotinib.

In some embodiments, an EGFR inhibitor is a "1st generation EGFR tyrosine kinase inhibitor" ("1st generation TKI"). A 1st generation TKI refers to reversible EGFR inhibitors, such as gefitinib and erlotinib, which are effective in first-line treatment of, for example, NSCLC harboring EGFR activating mutations, such as deletions in exon 19 and exon 21 L858R mutation.

In some embodiments, an EGFR inhibitor is a "2nd generation EGFR tyrosine kinase inhibitor" ("2nd generation TKI"). A 2nd generation TKI refers to covalent irreversible EGFR inhibitors, such as afatinib and dacomitib, which are effective in first-line treatment of NSCLC harboring EGFR activating mutations, such as deletions in exon 19 and exon 21 L858R mutation.

In some embodiments, an EGFR inhibitor is a "3rd generation EGFR tyrosine kinase inhibitor" ("3rd generation TKI"). A 3rd generation TKI refers to covalent irreversible EGFR inhibitors, such as osimertinib and lazertinib, which are selective to the EGFR activating mutations, such as deletions in exon 19 and exon 21 L858R, alone or in combination with T790M mutation, and have lower inhibitory activity against wild-type EGFR.

In some embodiments, one or more other therapeutic agent is an mTOR inhibitor, which inhibits cell proliferation, angiogenesis and glucose uptake. In some embodiments, an mTOR inhibitor is everolimus (AFINITOR®, Novartis); temsirolimus (TORISEL®, Pfizer); and sirolimus (RAPAMUNE®, Pfizer).

In some embodiments, a one or more other therapeutic agent is a SOS1 (son of sevenless 1) inhibitor. In some embodiments, a SOS1 inhibitor is selected from BI-3406, BAY-293, MRTX0902, and BI-1701963. Other exemplary SOS1 inhibitors for use with the compositions, methods, and uses described herein include, but are not limited to, those SOS1 inhibitors described in patent publications WO2020180768A1, WO2021130731A1, WO2022271679A1, WO2022266248A1, WO2022058344A1, and WO2019122129A1, the contents of each of which are herein incorporated by reference in their entireties.

In some embodiments, a one or more other therapeutic agent is a SHP2 (Src homology 2 domain-containing protein tyrosine phosphatase) inhibitor. In some embodiments, a SHP2 inhibitor is selected from RMC-4550, RMC-4630, BBP-398, SHP836, SHP099, SHP394, BPI-442096, and ETS-001. Other exemplary SHP2 inhibitors for use with the compositions, methods, and uses described herein include, but are not limited to, those SHP2 inhibitors described in patent publications WO2017211303A1, WO2017216706A1, WO2018013597A1, WO2018057884A1, WO2018172984A1, WO2018081091A1, WO2018136265A1, WO2018136264A1, WO2019051084A1, WO2019067843A1, WO2019075265A1, WO2019118909A1, WO2019165073A1, WO2019183367A1, WO2019183364A1, WO2019233810A1, WO2020022323A1, WO2020061103A1, WO2020063760A1, WO2020108590A1, WO2020081848A1, WO2020156242A1, WO2020156243A1, WO2021033153A1, WO2021061515A1, WO2021074227A1, WO2021110796A1, WO2021143680A1, WO2021143823A1, WO2021218752A1, WO2021218755A1, WO2021249449A1, WO2022017444A1, WO2022033430A1, WO2022089389A1, WO2022089406A1, WO2022161222A1, WO2023280283A1, and WO2023282702A1, the contents of each of which are herein incorporated by reference in their entireties.

In some embodiments, one or more other therapeutic agent is a proteasome inhibitor. Approved proteasome inhibitors useful in the present disclosure include bortezomib (VELCADE®, Takeda); carfilzomib (KYPROLIS®, Amgen); and ixazomib (NINLARO®, Takeda).

In some embodiments, one or more other therapeutic agent is a growth factor antagonist, such as an antagonist of platelet-derived growth factor (PDGF), or epidermal growth factor (EGF) or its receptor (EGFR). Approved PDGF antagonists which may be used in the present disclosure include olaratumab (LARTRUVO®; Eli Lilly). Approved EGFR antagonists which may be used in the present disclosure include cetuximab (ERBITUX®, Eli Lilly); necitumumab (PORTRAZZA®, Eli Lilly), panitumumab (VECTIBIX®, Amgen); and osimertinib (targeting activated EGFR, TAGRISSO®, AstraZeneca).

In some embodiments, one or more other therapeutic agent is an aromatase inhibitor. In some embodiments, an aromatase inhibitor is selected from exemestane (AROMASIN®, Pfizer); anastazole (ARIMIDEX®, AstraZeneca) and letrozole (FEMARA®, Novartis).

In some embodiments, one or more other therapeutic agent is an antagonist of the hedgehog pathway. Approved hedgehog pathway inhibitors which may be used in the present disclosure include sonidegib (ODOMZO®, Sun Pharmaceuticals); and vismodegib (ERIVEDGE®, Genentech), both for treatment of basal cell carcinoma.

In some embodiments, one or more other therapeutic agent is a folic acid inhibitor. Approved folic acid inhibitors useful in the present disclosure include pemetrexed (ALIMTA®, Eli Lilly).

In some embodiments, one or more other therapeutic agent is a CC chemokine receptor 4 (CCR4) inhibitor. CCR4 inhibitors being studied that may be useful in the present disclosure include mogamulizumab (POTELIGEO®, Kyowa Hakko Kirin, Japan).

In some embodiments, one or more other therapeutic agent is an isocitrate dehydrogenase (IDH) inhibitor. IDH inhibitors being studied which may be used in the present disclosure include AG120 (Celgene; NCT02677922); AG221 (Celgene, NCT02677922; NCT02577406); BAY1436032 (Bayer, NCT02746081); IDH305 (Novartis, NCT02987010).

In some embodiments, one or more other therapeutic agent is an arginase inhibitor. Arginase inhibitors being studied which may be used in the present disclosure include AEB1102 (pegylated recombinant arginase, Aeglea Biotherapeutics), which is being studied in Phase 1 clinical trials for acute myeloid leukemia and myelodysplastic syndrome (NCT02732184) and solid tumors (NCT02561234); and CB-1158 (Calithera Biosciences).

In some embodiments, one or more other therapeutic agent is a glutaminase inhibitor. Glutaminase inhibitors being studied which may be used in the present disclosure include CB-839 (Calithera Biosciences).

In some embodiments, one or more other therapeutic agent is an antibody that binds to tumor antigens, that is, proteins expressed on the cell surface of tumor cells. Approved antibodies that bind to tumor antigens which may be used in the present disclosure include rituximab (RITUXAN®, Genentech/BiogenIdec); ofatumumab (anti-CD20, ARZERRA®, GlaxoSmithKline); obinutuzumab (anti-CD20, GAZYVA®, Genentech), ibritumomab (anti-CD20 and Yttrium-90, ZEVALIN®, Spectrum Pharmaceuticals); daratumumab (anti-CD38, DARZALEX®, Janssen Biotech), dinutuximab (anti-glycolipid GD2, UNITUXIN®, United Therapeutics); trastuzumab (anti-HER2, HERCEPTIN®, Genentech); ado-trastuzumab emtansine (anti-HER2, fused to emtansine, KADCYLA®, Genentech); and pertuzumab (anti-HER2, PERJETA®, Genentech); and brentuximab vedotin (anti-CD30-drug conjugate, ADCETRIS®, Seattle Genetics).

In some embodiments, one or more other therapeutic agent is a topoisomerase inhibitor. Approved topoisomerase inhibitors useful in the present disclosure include irinotecan (ONIVYDE®, Merrimack Pharmaceuticals); topotecan (HYCAMTIN®, GlaxoSmithKline). Topoisomerase inhibitors being studied which may be used in the present disclosure include pixantrone (PIXUVRI®, CTI Biopharma).

In some embodiments, one or more other therapeutic agent is an inhibitor of anti-apoptotic proteins, such as BCL-2. Approved anti-apoptotics which may be used in the present disclosure include venetoclax (VENCLEXTA®, AbbVie/Genentech); and blinatumomab (BLINCYTO®, Amgen). Other therapeutic agents targeting apoptotic proteins which have undergone clinical testing and may be used in the present disclosure include navitoclax (ABT-263, Abbott), a BCL-2 inhibitor (NCT02079740).

In some embodiments, one or more other therapeutic agent is an androgen receptor inhibitor. Approved androgen receptor inhibitors useful in the present disclosure include enzalutamide (XTANDI®, Astellas/Medivation); approved inhibitors of androgen synthesis include abiraterone (ZYTIGA®, Centocor/Ortho); approved antagonist of gonadotropin-releasing hormone (GnRH) receptor (degaralix, FIRMAGON®, Ferring Pharmaceuticals).

In some embodiments, one or more other therapeutic agent is a selective estrogen receptor modulator (SERM), which interferes with the synthesis or activity of estrogens. Approved SERMs useful in the present disclosure include raloxifene (EVISTA®, Eli Lilly).

In some embodiments, one or more other therapeutic agent is an inhibitor of bone resorption. An approved therapeutic which inhibits bone resorption is Denosumab (XGEVA®, Amgen), an antibody that binds to RANKL, prevents binding to its receptor RANK, found on the surface of osteoclasts, their precursors, and osteoclast-like giant cells, which mediates bone pathology in solid tumors with osseous metastases. Other approved therapeutics that inhibit bone resorption include bisphosphonates, such as zoledronic acid (ZOMETA®, Novartis).

In some embodiments, one or more other therapeutic agent is an inhibitor of interaction between the two primary p53 suppressor proteins, MDMX and MDM2. Inhibitors of p53 suppression proteins being studied which may be used in the present disclosure include ALRN-6924 (Aileron), a stapled peptide that equipotently binds to and disrupts the interaction of MDMX and MDM2 with p53. ALRN-6924 is currently being evaluated in clinical trials for the treatment of AML, advanced myelodysplastic syndrome (MDS) and peripheral T-cell lymphoma (PTCL) (NCT02909972; NCT02264613).

In some embodiments, one or more other therapeutic agent is an inhibitor of transforming growth factor-beta (TGF-beta or TGF-β). Inhibitors of TGF-beta proteins being studied which may be used in the present disclosure include NIS793 (Novartis), an anti-TGF-beta antibody being tested in the clinic for treatment of various cancers, including breast, lung, hepatocellular, colorectal, pancreatic, prostate and renal cancer (NCT 02947165). In some embodiments, the inhibitor of TGF-beta proteins is fresolimumab (GC1008; Sanofi-Genzyme), which is being studied for melanoma (NCT00923169); renal cell carcinoma (NCT00356460); and non-small cell lung cancer (NCT02581787). Additionally, in some embodiments, the additional therapeutic agent is a TGF-beta trap, such as described in Connolly et al. (2012) Int'l J. Biological Sciences 8:964-978. One therapeutic compound currently in clinical trials for treatment of solid tumors is M7824 (Merck KgaA—formerly MSB0011459X), which is a bispecific, anti-PD-L1/TGF-β trap compound (NCT02699515); and (NCT02517398). M7824 is comprised of a fully human IgG1 antibody against PD-L1 fused to the extracellular domain of human TGF-beta receptor II, which functions as a TGF-β "trap."

In some embodiments, one or more other therapeutic agent is selected from glembatumumab vedotin-monomethyl auristatin E (MMAE) (Celldex), an anti-glycoprotein NMB (gpNMB) antibody (CR011) linked to the cytotoxic MMAE. gpNMB is a protein overexpressed by multiple tumor types associated with cancer cells' ability to metastasize.

In some embodiments, one or more other therapeutic agents is an antiproliferative compound. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (TEMODAL*); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, $AZd_6244$ from AstraZeneca, PD181461 from Pfizer and leucovorin.

The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name AROMASIN™. Formestane is marketed under the trade name LENTARON™. Fadrozole is marketed under the trade name AFEMA™. Anastrozole is marketed under the trade name ARIMIDEX™. Letrozole is marketed under the trade names FEMARA™ or FEMAr™ Aminoglutethimide is marketed under the trade name ORIMETEN™. A combination of the disclosure comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name NOLVADEX™. Raloxifene hydrochloride is marketed under the trade name EVISTA™. Fulvestrant can be administered under the trade name FASLODEX™. Fulvestrant can be administered under the trade name FASLODEX™. A combination of the disclosure comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (CASODEX™). The term "gonadorelin agonist" as used herein includes, but is not limited to abarelix, goserelin, and goserelin acetate. Goserelin can be administered under the trade name ZOLADEX™

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g., in the form as it is marketed, e.g., under the trademark CAMPTOSAR™. Topotecan is marketed under the trade name HYCAMPTIN™.

The term "topoisomerase II inhibitor" as used herein includes, but is not limited to the anthracyclines such as doxorubicin (including liposomal formulation, such as CAELYX™) daunorubicin, epirubicin, idarubicin and nemorubicin, the anthraquinones mitoxantrone and losoxantrone, and the podophillotoxines etoposide and teniposide. Etoposide is marketed under the trade name ETOPOPHOS™. Teniposide is marketed under the trade name VM 26-Bristol Doxorubicin is marketed under the trade name ACRIBLASTIN™ or ADRIAMYCIN™ Epirubicin is marketed under the trade name FARMORUBICIN™. Idarubicin is marketed. under the trade name ZAVEDOS™. Mitoxantrone is marketed under the trade name NOVANTRON™.

The term "microtubule active agent" relates to microtubule stabilizing, microtubule destabilizing compounds and microtublin polymerization inhibitors including, but not limited to taxanes, such as paclitaxel and docetaxel; *vinca* alkaloids, such as vinblastine or vinblastine sulfate, vincristine or vincristine sulfate, and vinorelbine; discodermolides; cochicine and epothilones and derivatives thereof. Paclitaxel is marketed under the trade name TAXOL™ Docetaxel is marketed under the trade name TAXOTERE™. Vinblastine sulfate is marketed under the trade name VINBLASTIN R.P™. Vincristine sulfate is marketed under the trade name FARMISTIN™.

The term "alkylating agent" as used herein includes, but is not limited to, cyclophosphamide, ifosfamide, melphalan or nitrosourea (BCNU or Gliadel). Cyclophosphamide is marketed under the trade name CYCLOSTIN™. Ifosfamide is marketed under the trade name HOLOXAN™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name XELODA™. Gemcitabine is marketed under the trade name GEMZAR™.

The term "platin compound" as used herein includes, but is not limited to, carboplatin, cis-platin, cisplatinum and oxaliplatin. Carboplatin can be administered, e.g., in the form as it is marketed, e.g., under the trademark CARBOPLAT™. Oxaliplatin can be administered, e.g., in the form as it is marketed, e.g. under the trademark ELOXATIN™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g., BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (HERCEPTIN™), cetuximab (ERBITUX™), Iressa, Tarceva, OSI-774, C$_1$-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this disclosure include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

Further examples of BTK inhibitory compounds, and conditions treatable by such compounds in combination with compounds of this disclosure can be found in WO2008039218 and WO2011090760, the entirety of which are incorporated herein by reference.

Further examples of SYK inhibitory compounds, and conditions treatable by such compounds in combination with compounds of this disclosure can be found in WO2003063794, WO2005007623, and WO2006078846, the entirety of which are incorporated herein by reference.

Further examples of P13K inhibitory compounds, and conditions treatable by such compounds in combination with compounds of this disclosure can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this disclosure can be found in WO2009114512, WO2008109943, WO2007053452, WO2000142246, and WO2007070514, the entirety of which are incorporated herein by reference.

Further anti-angiogenic compounds include compounds having another mechanism for their activity, e.g., unrelated to protein or lipid kinase inhibition e.g., thalidomide (THALOMID™) and TNP-470.

Examples of proteasome inhibitors useful for use in combination with compounds of the disclosure include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g., inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (CELEBREX™), rofecoxib (VIOXX™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name DIDRONEL™. Clodronic acid is marketed under the trade name BONEFOS™. Tiludronic acid is marketed under the trade name Skelid™. Pamidronic acid is marketed under the trade name AREDIA™. Alendronic acid is marketed under the trade name FOSAMAX™. Ibandronic acid is marketed under the trade name BONDRANAT™. Risedronic acid is marketed under the trade name ACTONEL™. Zoledronic acid is marketed under the trade name ZOMETA™. The term "mTOR inhibitors" relates to compounds which inhibit the mammalian target of rapamycin (mTOR) and which possess antiproliferative activity such as sirolimus (RAPAMUNE®), everolimus (CERTICAN™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (ZARNESTRA™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (VELCADE™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g., hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino,17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (HERCEPTIN™), Trastuzumab-DM1, erbitux, bevacizumab (AVASTIN™) rituximab (RITUXAN©), PR064553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current disclosure can be used in combination with standard leukemia therapies, especially in combination with therapies used for the treatment of AML. In particular, compounds of the current disclosure can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-

(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; ANGIOSTATIN™; ENDOSTATIN™; anthranilic acid amides; ZD4190; Zd$_6$474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgG1 antibody, Angiozyme (RPI 4610) and Bevacizumab (AVASTIN™).

Photodynamic therapy as used herein refers to therapy which uses certain chemicals known as photosensitizing compounds to treat or prevent cancers. Examples of photodynamic therapy include treatment with compounds, such as VISUDYNE™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code numbers, generic or trade names may be taken from the actual edition of the standard compendium "The Merck Index" or from databases, e.g., Patents International (e.g., IMS World Publications).

f. Exemplary Immuno-Oncology Agents

In some embodiments, a one or more other therapeutic agent is an immuno-oncology agent. As used herein, the term "an immuno-oncology agent" refers to an agent which is effective to enhance, stimulate, and/or up-regulate immune responses in a subject. In some embodiments, the administration of an immuno-oncology agent with a compound of the disclosure has a synergic effect in treating a cancer.

An immuno-oncology agent can be, for example, a small molecule drug, an antibody, or a biologic or small molecule. Examples of biologic immuno-oncology agents include, but are not limited to, cancer vaccines, antibodies, and cytokines. In some embodiments, an antibody is a monoclonal antibody. In some embodiments, a monoclonal antibody is humanized or human.

In some embodiments, an immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses.

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, NGFR.

In some embodiments, an immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In some embodiments, a combination of a compound of the disclosure and an immuno-oncology agent can stimulate T cell responses. In some embodiments, an immuno-oncology agent is: (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4; or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

In some embodiments, an immuno-oncology agent is an antagonist of inhibitory receptors on NK cells or an agonist of activating receptors on NK cells. In some embodiments, an immuno-oncology agent is an antagonist of KIR, such as lirilumab.

In some embodiments, an immuno-oncology agent is an agent that inhibits or depletes macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In some embodiments, an immuno-oncology agent is selected from agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell energy or exhaustion) and agents that trigger innate immune activation and/or inflammation at tumor sites.

In some embodiments, an immuno-oncology agent is a CTLA-4 antagonist. In some embodiments, a CTLA-4 antagonist is an antagonistic CTLA-4 antibody. In some embodiments, an antagonistic CTLA-4 antibody is YERVOY (ipilimumab) or tremelimumab.

In some embodiments, an immuno-oncology agent is a PD-1 antagonist. In some embodiments, a PD-1 antagonist is administered by infusion. In some embodiments, an immuno-oncology agent is an antibody or an antigen-binding portion thereof that binds specifically to a Programmed Death-1 (PD-1) receptor and inhibits PD-1 activity. In some embodiments, a PD-1 antagonist is an antagonistic PD-1 antibody. In some embodiments, an antagonistic PD-1 antibody is OPDIVO (nivolumab), KEYTRUDA (pembrolizumab), or MEDI-0680 (AMP-514; WO2012/145493). In some embodiments, an immuno-oncology agent may be pidilizumab (CT-011). In some embodiments, an immuno-oncology agent is a recombinant protein composed of the extracellular domain of PD-L2 (B7-DC) fused to the Fc portion of IgG1, called AMP-224.

In some embodiments, an immuno-oncology agent is a PD-L1 antagonist. In some embodiments, a PD-L1 antagonist is an antagonistic PD-L1 antibody. In some embodiments, a PD-L1 antibody is MPDL3280A (RG7446; WO2010/077634), durvalumab (MEDI4736), BMS-936559 (WO2007/005874), and MSB0010718C (WO2013/79174).

In some embodiments, an immuno-oncology agent is a LAG-3 antagonist. In some embodiments, a LAG-3 antagonist is an antagonistic LAG-3 antibody. In some embodiments, a LAG3 antibody is BMS-986016 (WO10/19570, WO14/08218), or IMP-731 or IMP-321 (WO08/132601, WO009/44273).

In some embodiments, an immuno-oncology agent is a CD137 (4-1BB) agonist. In some embodiments, a CD137 (4-1BB) agonist is an agonistic CD137 antibody. In some embodiments, a CD137 antibody is urelumab or PF-05082566 (WO12/32433).

In some embodiments, an immuno-oncology agent is a GITR agonist. In some embodiments, a GITR agonist is an agonistic GITR antibody. In some embodiments, a GITR antibody is BMS-986153, BMS-986156, TRX-518 (WO006/105021, WO009/009116), or MK-4166 (WO11/028683).

In some embodiments, an immuno-oncology agent is an indoleamine (2,3)-dioxygenase (IDO) antagonist. In some embodiments, an IDO antagonist is selected from epacadostat (INCB024360, Incyte); indoximod (NLG-8189, NewLink Genetics Corporation); capmanitib (INC280, Novartis); GDC-0919 (Genentech/Roche); PF-06840003 (Pfizer); BMS:F001287 (Bristol-Myers Squibb); Phy906/KD108 (Phytoceutica); an enzyme that breaks down kynurenine (Kynase, Ikena Oncology, formerly known as Kyn Therapeutics); and NLG-919 (WO09/73620, WO009/1156652, WO11/56652, WO12/142237).

In some embodiments, an immuno-oncology agent is an OX40 agonist. In some embodiments, an OX40 agonist is an agonistic OX40 antibody. In some embodiments, an OX40 antibody is MEDI-6383 or MEDI-6469.

In some embodiments, an immuno-oncology agent is an OX40L antagonist. In some embodiments, an OX40L antagonist is an antagonistic OX40 antibody. In some embodiments, an OX40L antagonist is RG-7888 (WO06/029879).

In some embodiments, an immuno-oncology agent is a CD40 agonist. In some embodiments, a CD40 agonist is an agonistic CD40 antibody. In some embodiments, an immuno-oncology agent is a CD40 antagonist. In some embodiments, a CD40 antagonist is an antagonistic CD40 antibody. In some embodiments, a CD40 antibody is lucatumumab or dacetuzumab.

In some embodiments, an immuno-oncology agent is a CD27 agonist. In some embodiments, a CD27 agonist is an agonistic CD27 antibody. In some embodiments, a CD27 antibody is varlilumab.

In some embodiments, an immuno-oncology agent is MGA271 (to $B7H_3$) (WO11/109400).

In some embodiments, an immuno-oncology agent is abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab.

In some embodiments, an immuno-oncology agent is an immunostimulatory agent. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med. 8. The anti-PD-1 antibody nivolumab (OPDIVO©, Bristol-Myers Squibb, also known as ONO-4538, MDX1106 and BMS-936558), has shown potential to improve the overall survival in patients with RCC who had experienced disease progression during or after prior anti-angiogenic therapy.

In some embodiments, the immunomodulatory therapeutic specifically induces apoptosis of tumor cells. Approved immunomodulatory therapeutics which may be used in the present disclosure include pomalidomide (POMALYST®, Celgene); lenalidomide (REVLIMID®, Celgene); ingenol mebutate (PICATO®, LEO Pharma).

In some embodiments, an immuno-oncology agent is a cancer vaccine. In some embodiments, the cancer vaccine is selected from sipuleucel-T (PROVENGE®, Dendreon/Valeant Pharmaceuticals), which has been approved for treatment of asymptomatic, or minimally symptomatic metastatic castrate-resistant (hormone-refractory) prostate cancer; and talimogene laherparepvec (IMLYGIC®, BioVex/Amgen, previously known as T-VEC), a genetically modified oncolytic viral therapy approved for treatment of unresectable cutaneous, subcutaneous and nodal lesions in melanoma. In some embodiments, an immuno-oncology agent is selected from an oncolytic viral therapy such as pexastimogene devacirepvec (PexaVec/JX-594, SillaJen/formerly Jennerex Biotherapeutics), a thymidine kinase-(TK−) deficient vaccinia virus engineered to express GM-CSF, for hepatocellular carcinoma (NCT02562755) and melanoma (NCT00429312); pelareorep (REOLYSIN®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT 00861627); enadenotucirev (NG-348, PsiOxus, formerly known as ColoAdl), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-1h68/GLV-1h153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In some embodiments, an immuno-oncology agent is selected from JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TGO1 and TG02 (Targovax/formerly Oncos), peptide-based immunotherapy agents targeted for difficult-to-treat RAS mutations; and TILT-123 (TILT Biotherapeutics), an engineered adenovirus designated: Ad5/3-E2F-delta24-hTNFα-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific CD8$^+$ T cell response.

In some embodiments, an immuno-oncology agent is a T-cell engineered to express a chimeric antigen receptor, or CAR. The T-cells engineered to express such chimeric antigen receptor are referred to as a CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARs link to endogenous signaling pathways in the effector cell and generate activating signals similar to those initiated by the TCR complex.

For example, in some embodiments the CAR-T cell is one of those described in U.S. Pat. No. 8,906,682 (June et al.; hereby incorporated by reference in its entirety), which discloses CAR-T cells engineered to comprise an extracellular domain having an antigen binding domain (such as a domain that binds to CD19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Over 200 clinical trials are currently in progress employing CAR-T in a wide range of indications. [https://clinicaltrials.gov/ct2/results?term=chimeric+antigen+receptors&pg=1].

In some embodiments, an immunostimulatory agent is an activator of retinoic acid receptor-related orphan receptor γ (RORγt). RORγt is a transcription factor with key roles in the differentiation and maintenance of Type 17 effector subsets of CD4+(Th17) and CD8+(Tc17) T cells, as well as the differentiation of IL-17 expressing innate immune cell subpopulations such as NK cells. In some embodiments, an activator of RORγt is LYC-55716 (Lycera), which is currently being evaluated in clinical trials for the treatment of solid tumors (NCT02929862).

In some embodiments, an immunostimulatory agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present disclosure include motolimod (VTX-2337, VentiRx Pharmaceuticals) which is being studied for squamous cell cancer of the head and neck (NCTO2124850) and ovarian cancer (NCT02431559).

Other immuno-oncology agents that can be used in the present disclosure include urelumab (BMS-663513, Bristol-Myers Squibb), an anti-CD137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; MK-4166 (Merck & Co.), an anti-GITR monoclonal antibody.

In some embodiments, an immunostimulatory agent is selected from elotuzumab, mifamurtide, an agonist or activator of a toll-like receptor, and an activator of RORγt.

In some embodiments, an immunostimulatory therapeutic is recombinant human interleukin 15 (rhIL-15). rhIL-15 has been tested in the clinic as a therapy for melanoma and renal cell carcinoma (NCT01021059 and NCT01369888) and leukemias (NCT02689453). In some embodiments, an immunostimulatory agent is recombinant human interleukin 12 (rhIL-12). In some embodiments, an IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). In some embodiments, a recombinant human interleukin 12 (rhIL-12) is NM-IL-12 (Neumedicines, Inc.), NCT02544724, or NCT02542124.

In some embodiments, an immuno-oncology agent is selected from those descripted in Jerry L. Adams et al., "Big opportunities for small molecules in immuno-oncology," Cancer Therapy 2015, Vol. 14, pages 603-622, the content of which is incorporated herein by reference in its entirety. In some embodiments, an immuno-oncology agent is selected from the examples described in Table 1 of Jerry L. Adams et al. In some embodiments, an immuno-oncology agent is a small molecule targeting an immuno-oncology target selected from those listed in Table 2 of Jerry L. Adams et al. In some embodiments, an immuno-oncology agent is a small molecule agent selected from those listed in Table 2 of Jerry L. Adams et al.

In some embodiments, an immuno-oncology agent is selected from the small molecule immuno-oncology agents described in Peter L. Toogood, "Small molecule immuno-oncology therapeutic agents," Bioorganic & Medicinal Chemistry Letters 2018, Vol. 28, pages 319-329, the content of which is incorporated herein by reference in its entirety. In some embodiments, an immuno-oncology agent is an agent targeting the pathways as described in Peter L. Toogood.

In some embodiments, an immuno-oncology agent is selected from those described in Sandra L. Ross et al., "Bispecific T cell engager (BITE®) antibody constructs can mediate bystander tumor cell killing", PLoS ONE 12(8): e0183390, the content of which is incorporated herein by reference in its entirety. In some embodiments, an immuno-oncology agent is a bispecific T cell engager (BITE®) antibody construct. In some embodiments, a bispecific T cell engager (BITE®) antibody construct is a CD19/CD3 bispecific antibody construct. In some embodiments, a bispecific T cell engager (BITE®) antibody construct is an EGFR/CD3 bispecific antibody construct. In some embodiments, a bispecific T cell engager (BITE®) antibody construct activates T cells. In some embodiments, a bispecific T cell engager (BITE®) antibody construct activates T cells, which release cytokines inducing upregulation of intercellular adhesion molecule 1 (ICAM-1) and FAS on bystander cells. In some embodiments, a bispecific T cell engager (BITE®) antibody construct activates T cells which result in induced bystander cell lysis. In some embodiments, the bystander cells are in solid tumors. In some embodiments, the bystander cells being lysed are in proximity to the BITE®-activated T cells. In some embodiment, the bystander cells comprises tumor-associated antigen (TAA) negative cancer cells. In some embodiment, the bystander cells comprise EGFR-negative cancer cells. In some embodiments, an immuno-oncology agent is an antibody which blocks the PD-L1/PD1 axis and/or CTLA4. In some embodiments, an immuno-oncology agent is an ex vivo expanded tumor-infiltrating T cell. In some embodiments, an immuno-oncology agent is a bispecific antibody construct or chimeric antigen receptors (CARs) that directly connect T cells with tumor-associated surface antigens (TAAs).

g. Exemplary Immune Checkpoint Inhibitors

In some embodiments, an immuno-oncology agent is an immune checkpoint inhibitor as described herein.

The term "checkpoint inhibitor" as used herein relates to agents useful in preventing cancer cells from avoiding the immune system of the patient. One of the major mechanisms of anti-tumor immunity subversion is known as "T-cell exhaustion," which results from chronic exposure to antigens that has led to up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular "gatekeepers" that allow extracellular information to dictate whether cell cycle progression and other intracellular signaling processes should proceed.

In some embodiments, an immune checkpoint inhibitor is an antibody to PD-1. PD-1 binds to the programmed cell death 1 receptor (PD-1) to prevent the receptor from binding to the inhibitory ligand PDL-1, thus overriding the ability of tumors to suppress the host anti-tumor immune response.

In one aspect, the checkpoint inhibitor is a biologic therapeutic or a small molecule. In another aspect, the checkpoint inhibitor is a monoclonal antibody, a humanized antibody, a fully human antibody, a fusion protein or a combination thereof. In a further aspect, the checkpoint inhibitor inhibits a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an additional aspect, the checkpoint inhibitor interacts with a ligand of a checkpoint protein selected from CTLA-4, PDL 1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an aspect, the checkpoint inhibitor is an immunostimulatory agent, a T cell growth factor, an interleukin, an antibody, a vaccine or a combination thereof. In a further aspect, the interleukin is IL-7 or IL-15. In a specific aspect, the interleukin is glycosylated IL-7. In an additional aspect, the vaccine is a dendritic cell (DC) vaccine.

Checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative checkpoint molecules that can be targeted for blocking or inhibition include, but are not limited to, CTLA-4, PDL1, PDL2, PD1, B7-H3, B7-H$_4$, BTLA, HVEM, GAL9, LAG3, TIM3, VISTA, KIR, 2B4 (belongs to the CD2 family of molecules and is expressed on all NK, T6, and memory CD8+(ap) T cells), CD160 (also referred to as BY55), CGEN-15049, CHK 1 and CHK2 kinases, A2aR, and various B-7 family ligands. B7 family ligands include, but are not limited to, B7-1, B7-2, B7-DC, B7-H1, B7-H2, B7-H3, B7-H$_4$, B7-H5, B7-H6 and B7-H7. Checkpoint inhibitors include antibodies, or antigen binding fragments thereof, other binding proteins, biologic therapeutics, or small molecules, that bind to and block or inhibit the activity of one or more of CTLA-4, PDL1, PDL2, PD1, BTLA, HVEM, TIM3, GAL9, LAG3, VISTA, KIR, 2B4, CD 160 and CGEN-15049. Illustrative immune checkpoint inhibitors include, but are not limited to, Tremelimumab (CTLA-4 blocking antibody), anti-OX40, PD-L1 monoclonal Antibody (Anti-B7-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280 Å (anti-PDL1 antibody), MSB0010718C (anti-PDL1 antibody), and ipilimumab (anti-CTLA-4 checkpoint inhibitor). Checkpoint protein ligands include, but are not limited to PD-L1, PD-L2, B7-H3, B7-H4, CD28, CD86 and TIM-3.

In certain embodiments, the immune checkpoint inhibitor is selected from a PD-1 antagonist, a PD-L1 antagonist, and a CTLA-4 antagonist. In some embodiments, the checkpoint inhibitor is selected from the group consisting of nivolumab (OPDIVO®), ipilimumab (YERVOY®), and pembrolizumab (KEYTRUDA®). In some embodiments, the checkpoint inhibitor is selected from nivolumab (anti-PD-1 antibody, OPDIVO®, Bristol-Myers Squibb); pembrolizumab (anti-PD-1 antibody, KEYTRUDA®, Merck); ipilimumab (anti-CTLA-4 antibody, YERVOY®, Bristol-Myers Squibb); durvalumab (anti-PD-L1 antibody, IMFINZI®, AstraZeneca); and atezolizumab (anti-PD-L1 antibody, TECENTRIQ®, Genentech).

In some embodiments, the checkpoint inhibitor is selected from the group consisting of lambrolizumab (MK-3475), nivolumab (BMS-936558), pidilizumab (CT-011), AMP-224, MDX-1105, MEDI4736, MPDL3280A, BMS-936559, ipilimumab, lirlumab, IPH2101, pembrolizumab (KEYTRUDA®), and tremelimumab.

In some embodiments, an immune checkpoint inhibitor is REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (BAVENCIO®, Pfizer/Merck KGaA), also known as MSB0010718C), a fully human IgG1 anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; or PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; AstraZeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

In some embodiments, a checkpoint inhibitor is an inhibitor of T-cell immunoglobulin mucin containing protein-3 (TIM-3). TIM-3 inhibitors that may be used in the present disclosure include TSR-022, LY3321367 and MBG453. TSR-022 (TESARO) is an anti-TIM-3 antibody which is being studied in solid tumors (NCT02817633). LY3321367 (Eli Lilly) is an anti-TIM-3 antibody which is being studied in solid tumors (NCT03099109). MBG453 (Novartis) is an anti-TIM-3 antibody which is being studied in advanced malignancies (NCT02608268).

In some embodiments, a checkpoint inhibitor is an inhibitor of T cell immunoreceptor with Ig and ITIM domains, or TIGIT, an immune receptor on certain T cells and NK cells. TIGIT inhibitors that may be used in the present disclosure include BMS-986207 (Bristol-Myers Squibb), an anti-TIGIT monoclonal antibody (NCT02913313); OMP-313M32 (Oncomed); and anti-TIGIT monoclonal antibody (NCT03119428).

In some embodiments, a checkpoint inhibitor is an inhibitor of Lymphocyte Activation Gene-3 (LAG-3). LAG-3 inhibitors that may be used in the present disclosure include BMS-986016 and REGN3767 and IMP321. BMS-986016 (Bristol-Myers Squibb), an anti-LAG-3 antibody, is being studied in glioblastoma and gliosarcoma (NCT02658981). REGN3767 (Regeneron), is also an anti-LAG-3 antibody, and is being studied in malignancies (NCT03005782). IP321 (Immutep S.A.) is an LAG-3-Ig fusion protein, being studied in melanoma (NCT02676869); adenocarcinoma (NCT02614833); and metastatic breast cancer (NCT00349934).

Checkpoint inhibitors that may be used in the present disclosure include OX40 agonists. OX40 agonists that are being studied in clinical trials include PF-04518600/PF-8600 (Pfizer), an agonistic anti-OX40 antibody, in metastatic kidney cancer (NCT03092856) and advanced cancers and neoplasms (NCT02554812; NCT05082566); GSK3174998 (Merck), an agonistic anti-OX40 antibody, in Phase 1 cancer trials (NCT02528357); MEDI0562 (Medimmune/AstraZeneca), an agonistic anti-OX40 antibody, in advanced solid tumors (NCT02318394 and NCT02705482); MEDI6469, an agonistic anti-OX40 antibody (Medimmune/AstraZeneca), in patients with colorectal cancer (NCT02559024), breast cancer (NCT01862900), head and neck cancer (NCT02274155) and metastatic prostate cancer (NCT01303705); and BMS-986178 (Bristol-Myers Squibb) an agonistic anti-OX40 antibody, in advanced cancers (NCT02737475).

Checkpoint inhibitors that may be used in the present disclosure include CD137 (also called 4-1BB) agonists. CD137 agonists that are being studied in clinical trials include utomilumab (PF-05082566, Pfizer) an agonistic anti-CD137 antibody, in diffuse large B-cell lymphoma (NCT02951156) and in advanced cancers and neoplasms (NCT02554812 and NCT05082566); urelumab (BMS-663513, Bristol-Myers Squibb), an agonistic anti-CD137 antibody, in melanoma and skin cancer (NCT02652455) and glioblastoma and gliosarcoma (NCT02658981); and CTX-471 (Compass Therapeutics), an agonistic anti-CD137 antibody in metastatic or locally advanced malignancies (NCT03881488).

Checkpoint inhibitors that may be used in the present disclosure include CD27 agonists. CD27 agonists that are being studied in clinical trials include varlilumab (CDX-1127, Celldex Therapeutics) an agonistic anti-CD27 antibody, in squamous cell head and neck cancer, ovarian carcinoma, colorectal cancer, renal cell cancer, and glioblastoma (NCT02335918); lymphomas (NCT01460134); and glioma and astrocytoma (NCT02924038).

Checkpoint inhibitors that may be used in the present disclosure include glucocorticoid-induced tumor necrosis factor receptor (GITR) agonists. GITR agonists that are being studied in clinical trials include TRX518 (Leap Therapeutics), an agonistic anti-GITR antibody, in malignant melanoma and other malignant solid tumors (NCT01239134 and NCT02628574); GWN323 (Novartis), an agonistic anti-GITR antibody, in solid tumors and lymphoma (NCT 02740270); INCAGN01876 (Incyte/Agenus), an agonistic anti-GITR antibody, in advanced cancers (NCT02697591 and NCT03126110); MK-4166 (Merck), an agonistic anti-GITR antibody, in solid tumors (NCT02132754) and MEDI1873 (Medimmune/AstraZeneca), an agonistic hexameric GITR-ligand molecule with a human IgG1 Fc domain, in advanced solid tumors (NCT02583165).

Checkpoint inhibitors that may be used in the present disclosure include inducible T-cell co-stimulator (ICOS, also known as CD278) agonists. ICOS agonists that are being studied in clinical trials include MEDI-570 (Medimmune), an agonistic anti-ICOS antibody, in lymphomas (NCT02520791); GSK3359609 (Merck), an agonistic anti-ICOS antibody, in Phase 1 (NCT02723955); JTX-2011 (Jounce Therapeutics), an agonistic anti-ICOS antibody, in Phase 1 (NCT02904226).

Checkpoint inhibitors that may be used in the present disclosure include killer IgG-like receptor (KIR) inhibitors. KIR inhibitors that are being studied in clinical trials include lirilumab (IPH2102/BMS-986015, Innate Pharma/Bristol-Myers Squibb), an anti-KIR antibody, in leukemias (NCT01687387, NCT02399917, NCT02481297, NCT02599649), multiple myeloma (NCT02252263), and lymphoma (NCT01592370); IPH2101 (1-7F9, Innate Pharma) in myeloma (NCT01222286 and NCT01217203); and IPH4102 (Innate Pharma), an anti-KIR antibody that binds to three domains of the long cytoplasmic tail (KIR3DL2), in lymphoma (NCT02593045).

Checkpoint inhibitors that may be used in the present disclosure include CD47 inhibitors of interaction between CD47 and signal regulatory protein alpha (SIRPa). CD47/SIRPa inhibitors that are being studied in clinical trials include ALX-148 (Alexo Therapeutics), an antagonistic variant of (SIRPa) that binds to CD47 and prevents CD47/SIRPa-mediated signaling, in phase 1 (NCT03013218); TTI-621 (SIRPa-Fc, *Trillium* Therapeutics), a soluble recombinant fusion protein created by linking the N-terminal CD47-binding domain of SIRPa with the Fc domain of human IgG1, acts by binding human CD47, and preventing it from delivering its "do not eat" signal to macrophages, is in clinical trials in Phase 1 (NCT02890368 and NCT02663518); CC-90002 (Celgene), an anti-CD47 antibody, in leukemias (NCT02641002); and Hu5F9-G4 (Forty Seven, Inc.), in colorectal neoplasms and solid tumors (NCT02953782), acute myeloid leukemia (NCT02678338) and lymphoma (NCT02953509).

Checkpoint inhibitors that may be used in the present disclosure include CD73 inhibitors. CD73 inhibitors that are being studied in clinical trials include MEDI9447 (Medimmune), an anti-CD73 antibody, in solid tumors (NCT02503774); and BMS-986179 (Bristol-Myers Squibb), an anti-CD73 antibody, in solid tumors (NCT02754141).

Checkpoint inhibitors that may be used in the present disclosure include agonists of stimulator of interferon genes protein (STING, also known as transmembrane protein 173, or TMEM173). Agonists of STING that are being studied in clinical trials include MK-1454 (Merck), an agonistic synthetic cyclic dinucleotide, in lymphoma (NCT03010176); and ADU-S100 (MIW815, Aduro Biotech/Novartis), an agonistic synthetic cyclic dinucleotide, in Phase 1 (NCT02675439 and NCT03172936).

Checkpoint inhibitors that may be used in the present disclosure include CSF1R inhibitors. CSF1R inhibitors that are being studied in clinical trials include pexidartinib (PLX3397, Plexxikon), a CSF1R small molecule inhibitor, in colorectal cancer, pancreatic cancer, metastatic and advanced cancers (NCT02777710) and melanoma, non-small cell lung cancer, squamous cell head and neck cancer, gastrointestinal stromal tumor (GIST) and ovarian cancer (NCT02452424); and IMC-CS4 (LY3022855, Lilly), an anti-CSF-1R antibody, in pancreatic cancer (NCT03153410), melanoma (NCT03101254), and solid tumors (NCT02718911); and BLZ945 (4-[2((1R,2R)-2-hydroxycyclohexylamino)-benzothiazol-6-yloxyl]-pyridine-2-carboxylic acid methylamide, Novartis), an orally available inhibitor of CSF1R, in advanced solid tumors (NCT02829723).

Checkpoint inhibitors that can be used in the present disclosure include NKG2A receptor inhibitors. NKG2A receptor inhibitors that are being studied in clinical trials include monalizumab (IPH2201, Innate Pharma), an anti-NKG2A antibody, in head and neck neoplasms (NCT02643550) and chronic lymphocytic leukemia (NCT02557516).

In some embodiments, the immune checkpoint inhibitor is selected from nivolumab, pembrolizumab, ipilimumab, avelumab, durvalumab, atezolizumab, or pidilizumab.

EXAMPLES

The following examples are included to demonstrate various aspects of the present disclosure. It should be appreciated by those of skill in the art that the techniques disclosed in the examples that follow represent techniques discovered by the inventors to function well in the practice of the disclosure, and thus can be considered to constitute preferred modes for its practice. However, those of skill in the art should, in light of the present disclosure, appreciate that many changes can be made in the specific examples which are disclosed and still obtain a like or similar result without departing from the spirit and scope of the disclosure.

Methods for preparing compounds described herein are illustrated in the following synthetic Schemes. The Schemes are given for the purpose of illustrating the disclosure, and are not intended to limit the scope or spirit of the present disclosure. Starting materials shown in the Schemes can be obtained from commercial sources or can be prepared based on procedures described in the literature.

In the Schemes, it is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated (for example, use of protecting groups or alternative reactions). Protecting group chemistry and strategy is well known in the art, for example, as described in detail in "Protecting Groups in Organic synthesis", T. W. Greene and P. G. M. Wuts, 3rd edition, John Wiley & Sons, 1999, the entire contents of which are hereby incorporated by reference.

Example 1: Synthesis of N-cyclopropyl-2-((2-fluoro-4-iodophenyl)amino)-1,5-dimethyl-4-(3-((N-methylsulfamoyl)amino)phenoxy)-6-oxo-1,6-dihydropyridine-3-carboxamide (I-5)

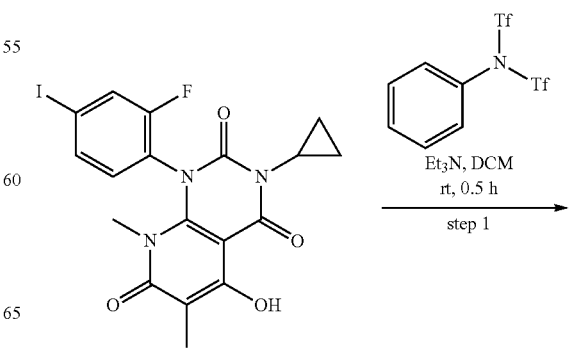

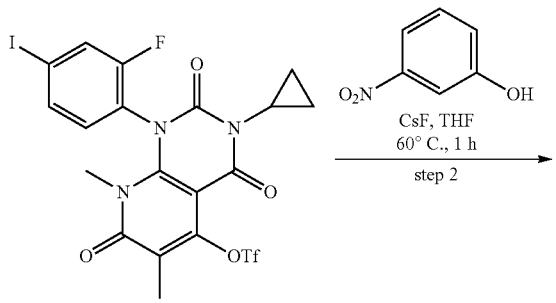

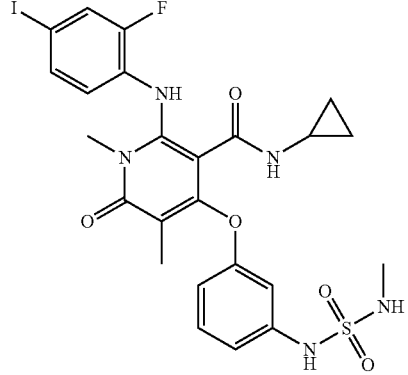 [SMILES: CNS(=O)(=O)Nc1cccc(Oc2c(C(=O)NC3CC3)c(Nc3ccc(I)cc3F)n(C)c(=O)c2C)c1]

Step 1: 3-Cyclopropyl-1-(2-fluoro-4-iodophenyl)-6,8-dimethyl-2,4,7-trioxo-1,2,3,4,7,8-hexahydropyrido[2,3-d]pyrimidin-5-yl trifluoromethanesulfonate

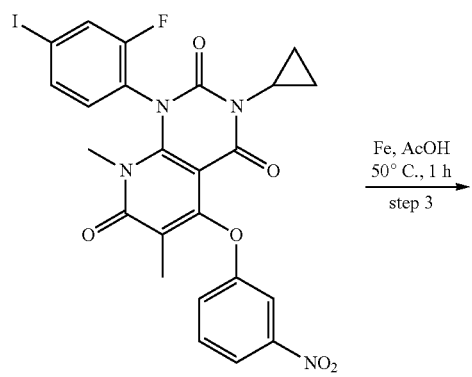

To the solution of 3-cyclopropyl-1-(2-fluoro-4-iodophenyl)-5-hydroxy-6,8-dimethylpyrido[2,3-d]pyrimidine-2,4,7-trione (5.0 g, 10.34 mmol, 1.0 equiv) and phenyl(trifluoromethanesulfonyloxy)amino trifluoromethanesulfonate (8.0 g, 20.69 mmol, 2.0 equiv) in DCM (100.0 mL) was added Et$_3$N (4.2 g, 41.39 mmol, 4.0 equiv) at room temperature under nitrogen atmosphere. The resulting mixture was stirred for 30 min at room temperature under nitrogen atmosphere. The reaction was monitored by LCMS. The reaction was quenched by the addition of water (20 mL) at room temperature. The resulting mixture was extracted with CH$_2$Cl$_2$ (3×30 mL). The combined organic layers were washed with brine (30 mL), dried over anhydrous Na$_2$SO$_4$. After filtration, the filtrate was concentrated under reduced pressure. The residue was purified by silica gel column chromatography, eluted with PE/EA (2:1) to afford 3-cyclopropyl-1-(2-fluoro-4-iodophenyl)-6,8-dimethyl-2,4,7-trioxopyrido[2,3-d]pyrimidin-5-yl trifluoromethanesulfonate (5.0 g, 78%) as a white solid. ES-LCMS m/z 616 [M+H]$^+$.

$^1$H NMR (400 MHz, DMSO-d$_6$) δ 7.99-7.92 (m, 1H), 7.77-7.69 (m, 1H), 7.36-7.23 (m, 2H), 2.77 (s, 3H), 2.74-2.64 (m, 1H), 2.02 (s, 3H), 1.13-0.96 (m, 2H), 0.70-0.56 (m, 2H).

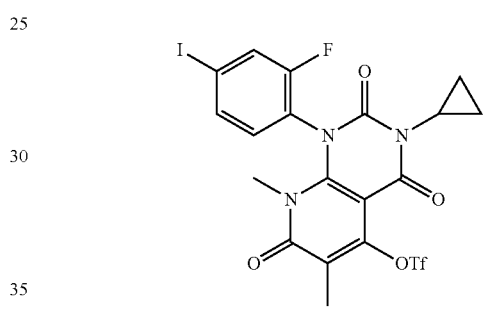

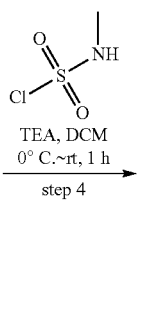

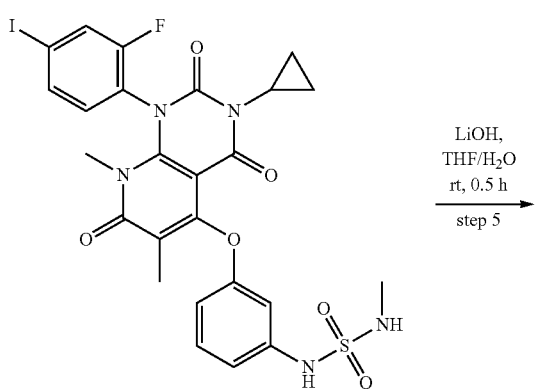

Step 2: 3-Cyclopropyl-1-(2-fluoro-4-iodophenyl)-6,8-dimethyl-5-(3-nitrophenoxy)pyrido[2,3-d]pyrimidine-2,4,7(1H,3H,8H)-trione

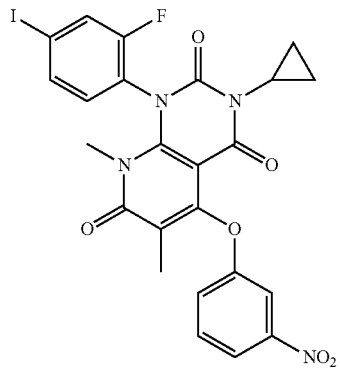 [SMILES: Cc1c(Oc2cccc([N+](=O)[O-])c2)c2c(=O)n(C3CC3)c(=O)n(-c3ccc(I)cc3F)c2n(C)c1=O]

To a stirred solution of 3-cyclopropyl-1-(2-fluoro-4-iodophenyl)-6,8-dimethyl-2,4,7-trioxopyrido[2,3-d]pyrimidin-5-yl trifluoromethanesulfonate (2.5 g, 4.06 mmol, 1.0 equiv) and 3-nitrophenol (1.1 g, 8.13 mmol, 2.0 equiv) in THF (30.0 mL) were added CsF (1.9 g, 12.19 mmol, 3.0 equiv) in portions at room temperature under nitrogen atmosphere. The resulting mixture was stirred for 1 h at 60° C. under nitrogen atmosphere. The reaction was monitored by LCMS. The mixture was allowed to cool down to room temperature and quenched by the addition of water (50 mL). The resulting mixture was extracted with EtOAc (3×50 mL). The combined organic layers were washed with brine (50 mL), dried over anhydrous $Na_2SO_4$. After filtration, the filtrate was concentrated under reduced pressure. The residue was purified by silica gel column chromatography, eluted with PE/EA (1:1) to afford 3-cyclopropyl-1-(2-fluoro-4-iodophenyl)-6,8-dimethyl-5-(3-nitrophenoxy)pyrido[2,3-d]pyrimidine-2,4,7-trione (1.3 g, 52%) as a white solid. ES-LCMS m/z 605 $[M+H]^+$.

$^1$H NMR (300 MHz, DMSO-$d_6$) δ 8.01-7.87 (m, 2H), 7.81-7.71 (m, 2H), 7.68-7.57 (m, 1H), 7.53-7.44 (m, 1H), 7.42-7.31 (m, 1H), 2.59-2.52 (s, 3H), 2.54 (m, 1H), 1.84 (s, 3H), 0.94-0.85 (m, 2H), 0.65-0.27 (m, 2H).

Step 3: 5-(3-Aminophenoxy)-3-cyclopropyl-1-(2-fluoro-4-iodophenyl)-6,8-dimethylpyrido[2,3-d]pyrimidine-2,4,7(1H,3H,8H)-trione

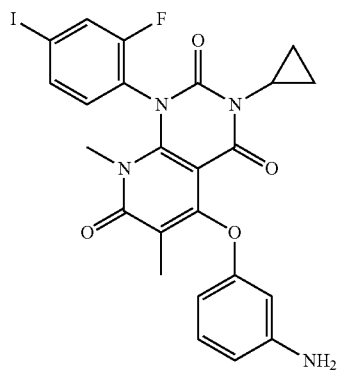

To a stirred solution of 3-cyclopropyl-1-(2-fluoro-4-iodophenyl)-6,8-dimethyl-5-(3-nitrophenoxy)pyrido[2,3-d]pyrimidine-2,4,7-trione (900 mg, 1.49 mmol, 1.0 equiv) in AcOH (10.0 mL) were added Fe (831 mg, 14.89 mmol, 10.0 equiv) in portions at 50° C. under air atmosphere. The resulting mixture was stirred for 1 h at 50° C. under nitrogen atmosphere. The reaction was monitored by LCMS. The mixture was allowed to cool down to room temperature and quenched by the addition of water (50 mL) at room temperature. The mixture was neutralized to pH 7 with saturated $NaHCO_3$ (aq.). The resulting mixture was extracted with EtOAc (3×50 mL). The combined organic layers were washed with brine (3×50 mL), dried over anhydrous $Na_2SO_4$. After filtration, the filtrate was concentrated under reduced pressure. The residue was purified by silica gel column chromatography, eluted with PE/EA (1:1) to afford 5-(3-aminophenoxy)-3-cyclopropyl-1-(2-fluoro-4-iodophenyl)-6,8-dimethylpyrido[2,3-d]pyrimidine-2,4,7-trione (690 mg, 80%) as a white solid. ES-LCMS m/z 575 $[M+H]^+$.

$^1$H NMR (400 MHz, DMSO-$d_6$) δ 7.96 (dd, 1H), 7.74 (dd, 1H), 7.37-7.28 (m, 1H), 6.95-6.86 (m, 1H), 6.28-6.21 (m, 1H), 6.21-6.16 (m, 1H), 6.11-6.04 (m, 1H), 5.27 (s, 2H), 2.80 (s, 3H), 2.59-2.52 (m, 1H), 1.80 (s, 3H), 0.96-0.82 (m, 2H), 0.59-0.38 (m, 2H).

Step 4: 3-Cyclopropyl-1-(2-fluoro-4-iodophenyl)-6,8-dimethyl-5-{3-[(methylsulfamoyl)amino]phenoxy]pyrido[2,3-d]pyrimidine-2,4,7-trione

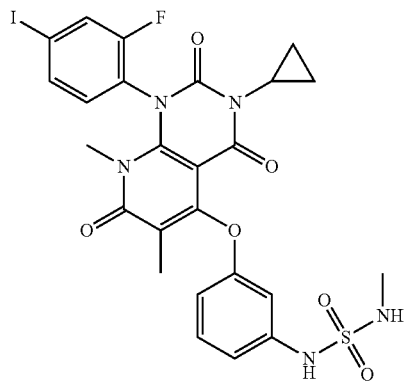 [SMILES: CNS(=O)(=O)Nc1cccc(Oc2c(C)c(=O)n(C)c3c2c(=O)n(C2CC2)c(=O)n3-c2ccc(I)cc2F)c1]

To a stirred solution of 5-(3-aminophenoxy)-3-cyclopropyl-1-(2-fluoro-4-iodophenyl)-6,8-dimethylpyrido[2,3-d]pyrimidine-2,4,7-trione (320 mg, 0.55 mmol, 1.0 equiv) and TEA (169 mg, 1.67 mmol, 3.0 equiv) in DCM (5.0 mL) was added N-methylsulfamoyl chloride (86 mg, 0.67 mmol, 1.2 equiv) dropwise at 0° C. under nitrogen atmosphere. The resulting mixture was stirred for 1 h at room temperature. The reaction was quenched with water (10 mL) and then extracted with EtOAc (3×10 mL). The organic layer was dried over anhydrous $Na_2SO_4$, filtered and the filtrate was concentrated under reduced pressure. To afford 3-cyclopropyl-1-(2-fluoro-4-iodophenyl)-6,8-dimethyl-5-{3-[(methylsulfamoyl)amino]phenoxy}pyrido[2,3-d]pyrimidine-2,4,7-trione (200 mg, 53%, crude) as a yellow solid. The crude product was used in the next step directly without further purification. ES-LCMS m/z 668 $[M+H]^+$.

Step 5: N-cyclopropyl-2-((2-fluoro-4-iodophenyl)amino)-1,5-dimethyl-4-(3-((N-methylsulfamoyl)amino)phenoxy)-6-oxo-1,6-dihydropyridine-3-carboxamide

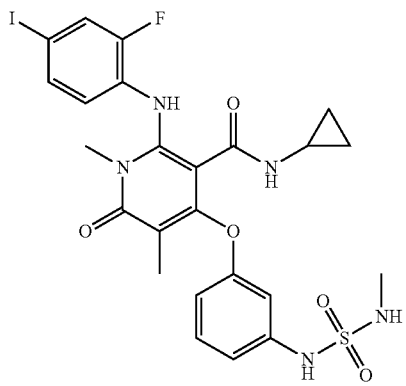

Into a 40 mL vial were added 3-cyclopropyl-1-(2-fluoro-4-iodophenyl)-6,8-dimethyl-5-{3-[(methylsulfamoyl)amino]phenoxy}pyrido[2,3-d]pyrimidine-2,4,7-trione (200 mg, 0.30 mmol, 1.0 equiv), LiOH·H$_2$O (125 mg, 3.00 mmol, 10.0 equiv), THF (2.0 mL) and H$_2$O (2.0 mL) at room temperature. The resulting mixture was stirred for 30 min at room temperature. The residue was diluted with H$_2$O (20 mL). The resulting mixture was extracted with EtOAc (3×20 mL). The combined organic layers were washed with brine (30 mL), dried over anhydrous Na$_2$SO$_4$. After filtration, the filtrate was concentrated under reduced pressure. The crude product was purified by Prep-HPLC [Column: Welch XB-C18, 50*250 mm, 10 μm Mobile Phase A: Water (0.1% TFA), Mobile Phase B: ACN; Flow rate: 90 mL/min; Gradient: 15% B to 50% B in 15 min, Wave Length: 254/220 nm] to afford N-cyclopropyl-2-[(2-fluoro-4-iodophenyl)amino]-1,5-dimethyl-4-{3-[(methylsulfamoyl)amino]phenoxy}-6-oxopyridine-3-carboxamide (120 mg, TFA salt, 62%) as an off-white solid. ES-LCMS m/z 642.2 [M+H]$^+$.
$^1$H NMR (400 MHz, DMSO-d$_6$) δ 9.76 (s, 1H), 8.63 (s, 1H), 8.05 (d, J=3.5 Hz, 1H), 7.64-7.57 (m, 1H), 7.40-7.33 (m, 1H), 7.32-7.27 (m, 1H), 7.25-7.17 (m, 1H), 6.92-6.85 (m, 1H), 6.77-6.72 (m, 1H), 6.63-6.54 (m, 1H), 6.52-6.44 (m, 1H), 3.38 (s, 3H), 2.47 (s, 3H), 2.28-2.18 (m, 1H), 1.86 (s, 3H), 0.46-0.37 (m, 2H), 0.02-0.05 (m, 2H).

Example 2: Synthesis of (R)-4-(3-((amino(methyl)oxo-lambda6-sulfaneylidene)amino)phenoxy)-N-cyclopropyl-2-((2-fluoro-4-iodophenyl)amino)-1,5-dimethyl-6-oxo-1,6-dihydropyridine-3-carboxamide (I-8)

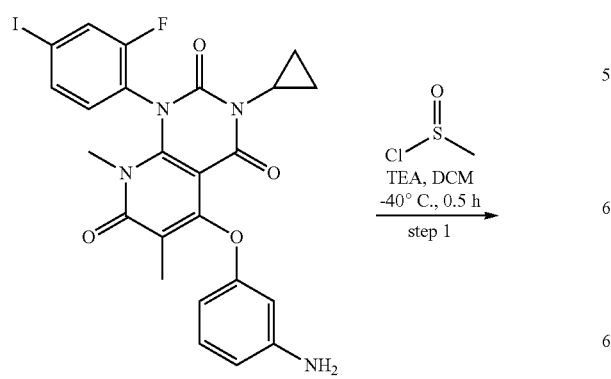

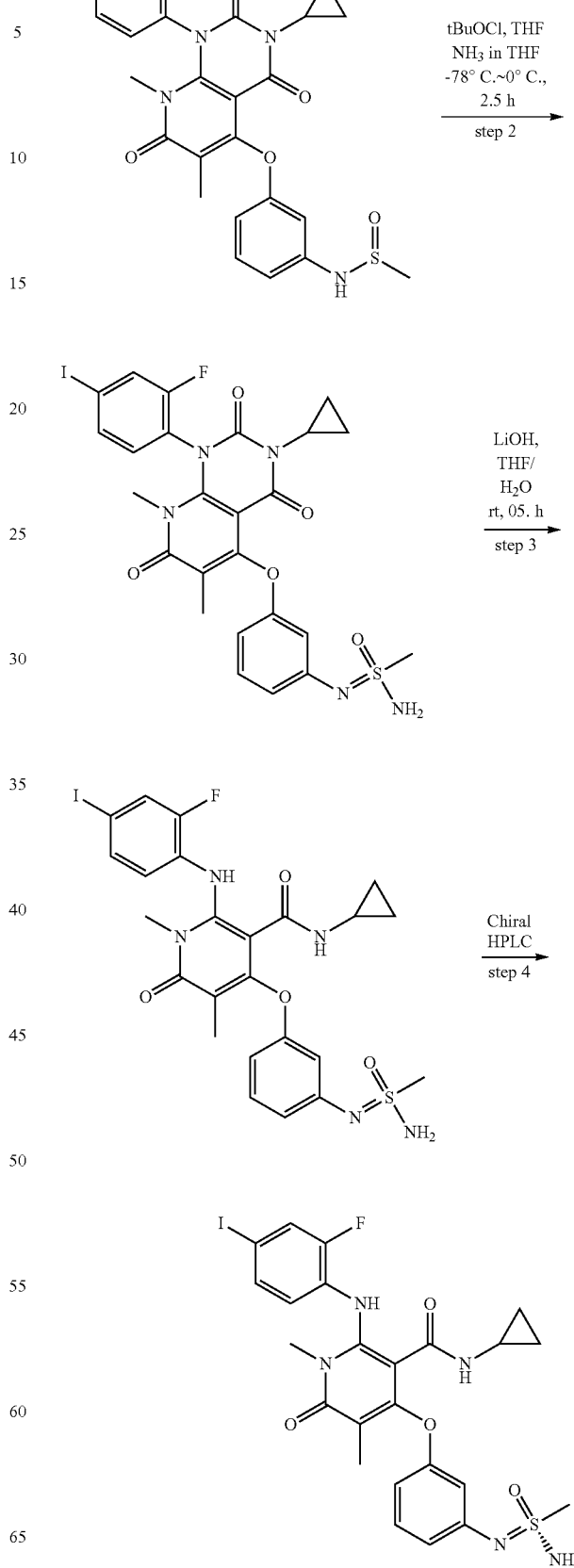

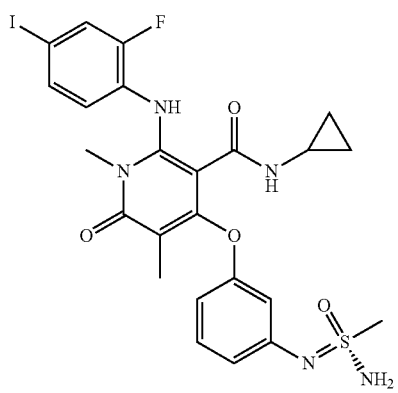

Step 1: N-(3-((3-cyclopropyl-1-(2-fluoro-4-iodophenyl)-6,8-dimethyl-2,4,7-trioxo-1,2,3,4,7,8-hexahydropyrido[2,3-d]pyrimidin-5-yl)oxy)phenyl)methanesulfinamide

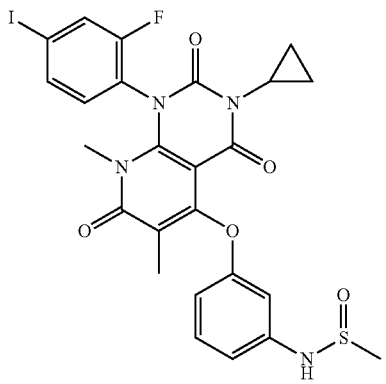 [SMILES: Cc1c(Oc2cccc(NS(C)=O)c2)c2c(=O)n(C3CC3)c(=O)n(-c3ccc(I)cc3F)c2n(C)c1=O]

To a stirred solution of 5-(3-aminophenoxy)-3-cyclopropyl-1-(2-fluoro-4-iodophenyl)-6,8-dimethylpyrido[2,3-d]pyrimidine-2,4,7-trione (500 mg, 0.87 mmol, 1.0 equiv) and TEA (264 mg, 2.61 mmol, 3.0 equiv) in DCM (10.0 mL) was added methanesulfinyl chloride (102 mg in 1.0 mL DCM, 1.04 mmol, 1.2 equiv) dropwise at −40° C. under nitrogen atmosphere. The resulting mixture was stirred for 0.5 h at −40° C. The reaction was monitored by LCMS. The reaction was quenched with water at −40° C. The resulting mixture was extracted with EtOAc (3×10 mL). The combined organic layers were washed with brine (10 mL), dried over anhydrous Na$_2$SO$_4$. After filtration, the filtrate was concentrated under reduced pressure. The residue was purified by silica gel column chromatography, eluted with PE/EA (1:1) to afford N-(3-{[3-cyclopropyl-1-(2-fluoro-4-iodophenyl)-6,8-dimethyl-2,4,7-trioxopyrido[2,3-d]pyrimidin-5-yl]oxy}phenyl)methanesulfinamide (390 mg, 70%) as a yellow solid. ES-LCMS m/z 637 [M+H]$^+$.

Step 2: N-(3-((3-cyclopropyl-1-(2-fluoro-4-iodophenyl)-6,8-dimethyl-2,4,7-trioxo-1,2,3,4,7,8-hexahydropyrido[2,3-d]pyrimidin-5-yl)oxy)phenyl)methanesulfonimidamide

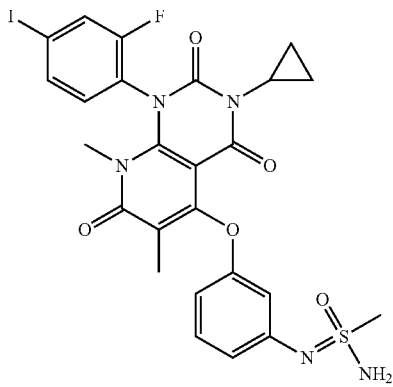 [SMILES: Cc1c(Oc2cccc(N=S(C)(N)=O)c2)c2c(=O)n(C3CC3)c(=O)n(-c3ccc(I)cc3F)c2n(C)c1=O]

To a stirred solution of N-(3-{[3-cyclopropyl-1-(2-fluoro-4-iodophenyl)-6,8-dimethyl-2,4,7-trioxopyrido[2,3-d]pyrimidin-5-yl]oxy}phenyl)methanesulfinamide (370 mg, 0.58 mmol, 1.0 equiv) in THF (5.0 mL) was added t-butyl hypochlorite (94 mg in 1.0 mL THF, 0.87 mmol, 1.5 equiv) dropwise at 0° C. under nitrogen atmosphere. The resulting mixture was stirred for 1.5 h at 0° C. The reaction mass was then cooled to −78° C., and added NH$_3$ (g) in THF (0.5M) (5.0 mL), the mixture was slowly allowed to come up to room temperature within 1 h. The reaction was quenched with water at 0° C. The resulting mixture was extracted with EtOAc (3×20 mL). The combined organic layers were washed with brine (30 mL), dried over anhydrous Na$_2$SO$_4$. After filtration, the filtrate was concentrated under reduced pressure. The residue was purified by silica gel column chromatography, eluted with PE/EA (1:1) to afford N-(3-{[3-cyclopropyl-1-(2-fluoro-4-iodophenyl)-6,8-dimethyl-2,4,7-trioxopyrido[2,3-d]pyrimidin-5-yl]oxy}phenyl)methanesulfonoimidamide (300 mg, 79%) as a yellow solid. ES-LCMS m/z 652 [M+H]$^+$.

Step 3: 4-(3-((amino(methyl)oxo-lambda6-sulfaneylidene)amino)phenoxy)-N-cyclopropyl-2-((2-fluoro-4-iodophenyl)amino)-1,5-dimethyl-6-oxo-1,6-dihydropyridine-3-carboxamide

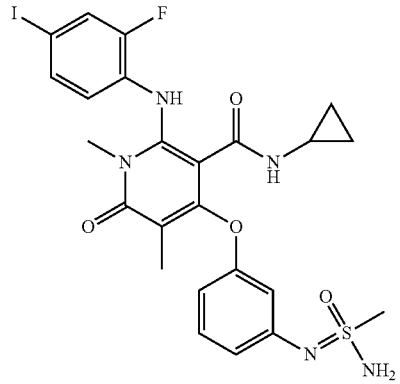 [SMILES: Cc1c(Oc2cccc(N=S(C)(N)=O)c2)c(C(=O)NC2CC2)c(Nc2ccc(I)cc2F)n(C)c1=O]

Into a 40 mL vial were added N-(3-{[3-cyclopropyl-1-(2-fluoro-4-iodophenyl)-6,8-dimethyl-2,4,7-trioxopyrido[2,3-d]pyrimidin-5-yl]oxy}phenyl)methanesulfonoimidamide (300 mg, 0.46 mmol, 1.0 equiv), LiOH·H$_2$O (110 mg, 4.61 mmol, 10.0 equiv), THF (2.0 mL) and H$_2$O (2.0 mL) at room temperature. The resulting mixture was stirred for 30 min at room temperature. The residue was dissolved in H$_2$O (20 mL). The resulting mixture was extracted with EtOAc (3×20 mL). The combined organic layers were washed with brine (30 mL), dried over anhydrous Na$_2$SO$_4$. After filtration, the filtrate was concentrated under reduced pressure. The crude product was purified by HPLC to afford 4-(3-{[amino(methyl)oxo-lambda6-sulfanylidene]amino}phenoxy)-N-cyclopropyl-2-[(2-fluoro-4-iodophenyl)amino]-1,5-dimethyl-6-oxopyridine-3-carboxamide (150 mg, 52%) as a yellow solid. ES-LCMS m/z 626 [M+H]$^+$.

Step 4: (R)-4-(3-((amino(methyl)oxo-lambda6-sulfaneylidene)amino)phenoxy)-N-cyclopropyl-2-((2-fluoro-4-iodophenyl)amino)-1,5-dimethyl-6-oxo-1,6-dihydropyridine-3-carboxamide

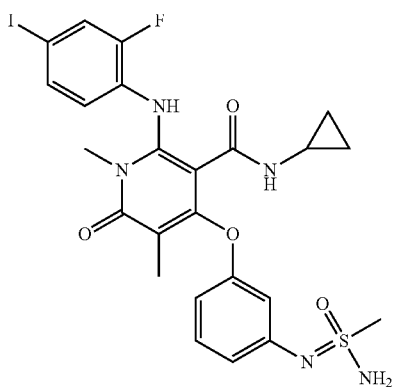 [SMILES: Cc1c(Oc2cccc(N=S(C)(N)=O)c2)c(C(=O)NC2CC2)c(Nc2ccc(I)cc2F)n(C)c1=O]

4-(3-{[amino(methyl)oxo-lambda6-sulfanylidene]amino}phenoxy)-N-cyclopropyl-2-[(2-fluoro-4-iodophenyl)amino]-1,5-dimethyl-6-oxopyridine-3-carboxamide (150 mg) was purified by CHIRAL-HPLC with the following conditions (Column: CHIRALPAK IE, 3*25 cm, 5 m; Mobile Phase A: HEX: DCM=3:1, Mobile Phase B: EtOH; Flow rate: 30 mL/min; Gradient: 30% B to 30% B in 16 min; Wave Length: 220/254 nm; $RT_1$ (min): 12; $RT_2$ (min): 14; Sample Solvent: EtOH: DCM=1:1; Injection Volume: 1.5 mL; Number Of Runs: 8) to afford (R)-4-(3-((amino(methyl)oxo-lambda6-sulfaneylidene)amino)phenoxy)-N-cyclopropyl-2-((2-fluoro-4-iodophenyl)amino)-1,5-dimethyl-6-oxo-1,6-dihydropyridine-3-carboxamide (47 mg, 31%) as a off-white solid. ES-LCMS m/z 626.2 $[M+H]^+$.

$^1$H NMR (400 MHz, DMSO-$d_6$) δ 8.64 (s, 1H), 7.91 (d, J=3.7 Hz, 1H), 7.60-7.53 (m, 1H), 7.37-7.30 (m, 1H), 7.09-7.00 (m, 1H), 6.81-6.66 (m, 3H), 6.57-6.48 (m, 1H), 6.45-6.40 (m, 1H), 6.35-6.28 (m, 1H), 3.33 (s, 3H), 3.09 (s, 3H), 2.31-2.22 (m, 1H), 1.80 (s, 3H), 0.44-0.35 (m, 2H), 0.05-0.01 (m, 2H).

Example 3: Synthesis of (S)-4-(3-((amino(methyl)oxo-lambda6-sulfaneylidene)amino)phenoxy)-N-cyclopropyl-2-((2-fluoro-4-iodophenyl)amino)-1,5-dimethyl-6-oxo-1,6-dihydropyridine-3-carboxamide (I-7)

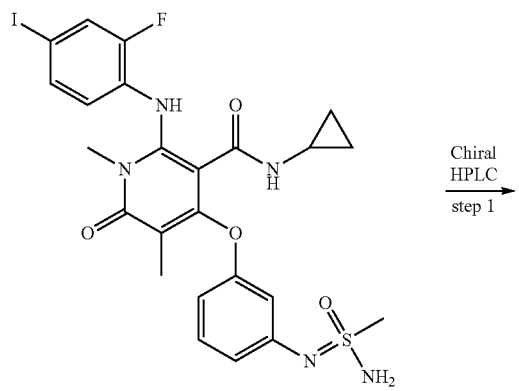

Chiral HPLC step 1

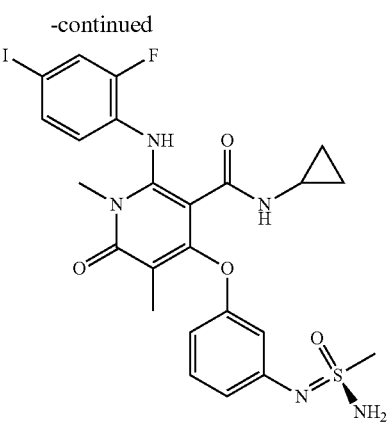

Step 1: (S)-4-(3-((amino(methyl)oxo-lambda6-sulfaneylidene)amino)phenoxy)-N-cyclopropyl-2-((2-fluoro-4-iodophenyl)amino)-1,5-dimethyl-6-oxo-1,6-dihydropyridine-3-carboxamide

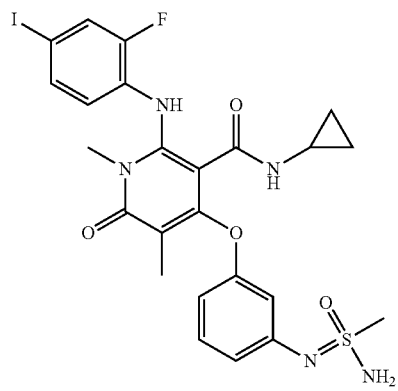 [SMILES: Cc1c(Oc2cccc(N=S(C)(N)=O)c2)c(C(=O)NC2CC2)c(Nc2ccc(I)cc2F)n(C)c1=O]

4-(3-{[amino(methyl)oxo-lambda6-sulfanylidene]amino}phenoxy)-N-cyclopropyl-2-[(2-fluoro-4-iodophenyl)amino]-1,5-dimethyl-6-oxopyridine-3-carboxamide (150 mg) was purified by CHIRAL-HPLC with the following conditions (Column: CHIRALPAK IE, 3*25 cm, 5 m; Mobile Phase A: HEX: DCM=3:1, Mobile Phase B: EtOH; Flow rate: 30 mL/min; Gradient: 30% B to 30% B in 16 min; Wave Length: 220/254 nm; $RT_1$ (min): 12; $RT_2$ (min): 14; Sample Solvent: EtOH: DCM=1:1; Injection Volume: 1.5 mL; Number Of Runs: 8) to afford (S)-4-(3-((amino(methyl)oxo-lambda6-sulfaneylidene)amino)phenoxy)-N-cyclopropyl-2-((2-fluoro-4-iodophenyl)amino)-1,5-dimethyl-6-oxo-1,6-dihydropyridine-3-carboxamide (49 mg, 32%) as a off-white solid. ES-LCMS m/z 626.2 $[M+H]^+$.

$^1$H NMR (400 MHz, DMSO-$d_6$) δ 8.64 (s, 1H), 7.91 (d, J=3.7 Hz, 1H), 7.61-7.53 (m, 1H), 7.37-7.30 (m, 1H), 7.09-7.00 (m, 1H), 6.82-6.65 (m, 3H), 6.57-6.48 (m, 1H), 6.45-6.40 (m, 1H), 6.35-6.28 (m, 1H), 3.33 (s, 3H), 3.09 (s, 3H), 2.31-2.22 (m, 1H), 1.80 (s, 3H), 0.44-0.35 (m, 2H), 0.05-0.01 (m, 2H).

Example 4: Synthesis of N-cyclopropyl-2-((2-fluoro-4-iodophenyl)amino)-1,5-dimethyl-4-(3-((N-methylsulfamoyl)methyl)phenoxy)-6-oxo-1,6-dihydropyridine-3-carboxamide (I-23)

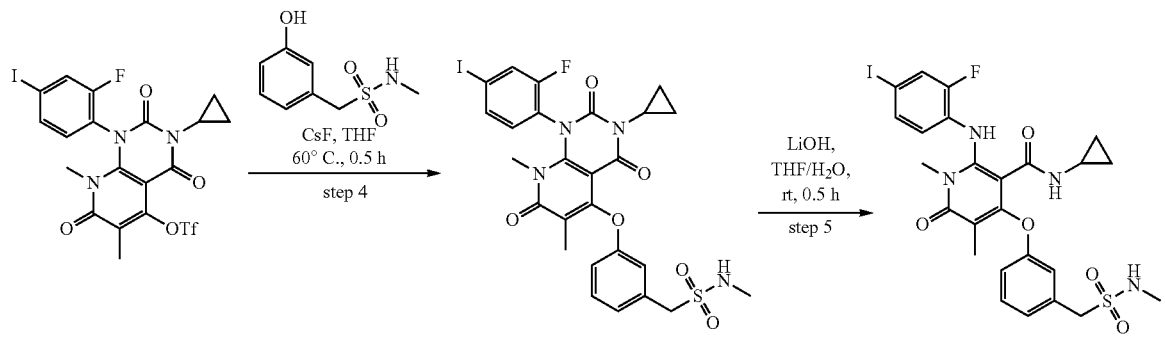

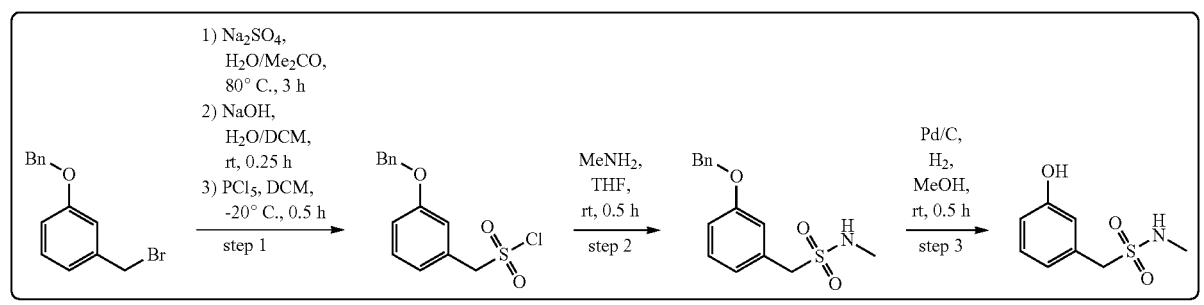

Step 1: (3-(benzyloxy)phenyl)methanesulfonyl chloride

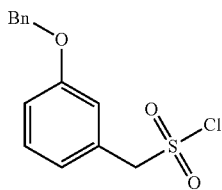 [SMILES: O=S(=O)(Cl)Cc1cccc(OCc2ccccc2)c1]

A solution of 1-(benzyloxy)-3-(bromomethyl)benzene (2.60 g, 9.38 mmol, 1.0 equiv) and sodium sulfonate (1.30 g, 10.31 mmol, 1.1 equiv) in water (20.0 mL) and acetone (20.0 mL) was stirred for 3 h at 80° C. The resulting mixture was concentrated under vacuum to afford sodium [3-(benzyloxy)phenyl]methanesulfonate (2.80 g, crude, 99%), the crude product mixture was used in the next step directly without further purification. Then to a stirred solution of tetrabutylammonium hydrogen sulfate (2.26 g, 9.32 mmol, 1.0 equiv) and NaOH (3.73 g, 93.24 mmol, 10.0 equiv) in DCM (40.0 mL) and water (10.0 mL) added sodium [3-(benzyloxy)phenyl]methanesulfonate (2.80 g, crude, 9.32 mmol, 1.0 equiv) at room temperature. The resulting mixture was stirred for additional 15 min at room temperature. The resulting mixture was extracted with DCM (3×30 mL). The combined organic layers were washed with brine (50 mL), dried over anhydrous Na₂SO₄. After filtration, the filtrate was concentrated under reduced pressure to afford sodium tetrabutylammonium ion [3-(benzyloxy)phenyl]methanesulfonate (2.50 g, crude, 51%), the crude product mixture was used in the next step directly without further purification. Then to a stirred solution of tetrabutylammonium ion [3-(benzyloxy)phenyl]methanesulfonate (1.20 g, crude, 2.30 mmol, 1.0 equiv) in DCM was added pentachloro-lambda5-phosphane (0.48 g, 2.30 mmol, 1.0 equiv) dropwise at −20° C. The resulting mixture was stirred for 0.5 h at −20° C. then concentrated under reduced pressure. The residue was purified by silica gel column chromatography, eluted with PE/THE (1:1) to afford [3-(benzyloxy)phenyl]methanesulfonyl chloride (361 mg, 52%) as an off-white solid.

Step 2: 1-(3-(benzyloxy)phenyl)-N-methylmethanesulfonamide

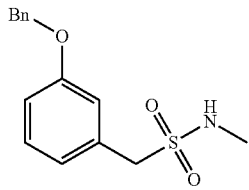 [SMILES: CNS(=O)(=O)Cc1cccc(OCc2ccccc2)c1]

A solution of [3-(benzyloxy)phenyl]methanesulfonyl chloride (360 mg, 0.67 mmol, 1.0 equiv) in Methylamine (2.0 mL, 2 M in THF) and THF (1.0 mL) was stirred for 30 min at room temperature. The solvent was removed under vacuum to afford 1-[3-(benzyloxy)phenyl]-N-methylmethanesulfonamide (300 mg, crude, 84%), the crude product mixture was used in the next step directly without further purification. ES-LCMS m/z 290 [M−H]⁻.

Step 3:
1-(3-hydroxyphenyl)-N-methylmethanesulfonamide

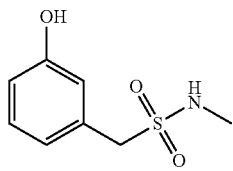

To a solution of 1-[3-(benzyloxy)phenyl]-N-methylmethanesulfonamide (300 mg, 1.03 mmol, 1.0 equiv) in MeOH (4.0 mL) was added Pd/C (10%, 0.05 g) in a pressure tank. The mixture was hydrogenated at room temperature under 30 psi of hydrogen pressure for 30 min, filtered through a Celite pad and concentrated under reduced pressure. The resulting mixture was filtered, the filter cake was washed with MeOH (3×5 mL). The filtrate was concentrated under reduced pressure. The crude product was purified by Prep-HPLC [Column: YMC-Actus Triart C18 ExRS, 30*150 mm, 5 μm; Mobile Phase A: Water (10 mmol/L $NH_4HCO_3$+0.1% $NH_3 \cdot H_2O$), Mobile Phase B: ACN; Flow rate: 30 mL/min; Gradient: 15% B to 55% B in 9 min; Detector, UV 220&254 nm] to afford 1-(3-hydroxyphenyl)-N-methylmethanesulfonamide (116 mg, 55%) as a light brown solid. ES-LCMS m/z 200 [M−H]⁻.

Step 4: 1-(3-((3-cyclopropyl-1-(2-fluoro-4-iodophenyl)-6,8-dimethyl-2,4,7-trioxo-1,2,3,4,7,8-hexahydropyrido[2,3-d]pyrimidin-5-yl)oxy)phenyl)-N-methylmethanesulfonamide

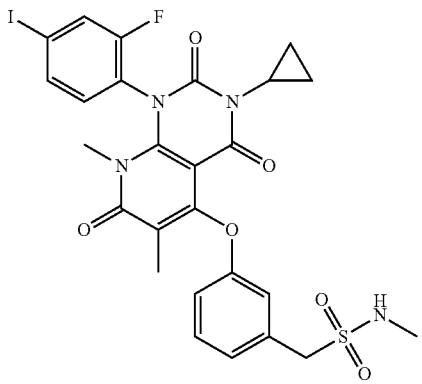 [SMILES: CNS(=O)(=O)Cc1cccc(Oc2c(C)c(=O)n(C)c3c2c(=O)n(C2CC2)c(=O)n3-c2ccc(I)cc2F)c1]

A solution of 3-cyclopropyl-1-(2-fluoro-4-iodophenyl)-6,8-dimethyl-2,4,7-trioxopyrido[2,3-d]pyrimidin-5-yl trifluoromethanesulfonate (200 mg, 0.32 mmol, 1.0 equiv), 1-(3-hydroxyphenyl)-N-methylmethanesulfonamide (116 mg, 0.57 mmol, 1.7 equiv) and caesium fluoride (148 mg, 0.975 mmol, 3 equiv) in THF was stirred for 30 min at 60° C. The reaction was quenched with water (20 mL) and extracted with EA (3×20 mL). The combined organic layers were washed with brine (20 mL), dried over anhydrous $Na_2SO_4$. After filtration, the filtrate was concentrated under reduced pressure. The residue was purified by silica gel column chromatography, eluted with PE/THF (1:1) to afford 1-(3-{[3-cyclopropyl-1-(2-fluoro-4-iodophenyl)-6,8-dimethyl-2,4,7-trioxopyrido[2,3-d]pyrimidin-5-yl]oxy}phenyl)-N-methylmethanesulfonamide (106 mg, 48%) as an off-white solid. ES-LCMS m/z 667 [M+H]1.

Step 5: N-cyclopropyl-2-((2-fluoro-4-iodophenyl)amino)-1,5-dimethyl-4-(3-((N-methylsulfamoyl)methyl)phenoxy)-6-oxo-1,6-dihydropyridine-3-carboxamide

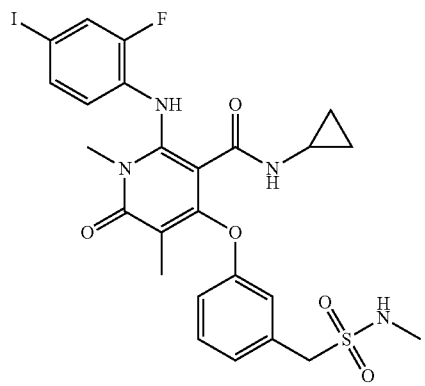 [SMILES: CNS(=O)(=O)Cc1cccc(Oc2c(C(=O)NC3CC3)c(Nc3ccc(I)cc3F)n(C)c(=O)c2C)c1]

To a stirred solution of 1-(3-{[3-cyclopropyl-1-(2-fluoro-4-iodophenyl)-6,8-dimethyl-2,4,7-trioxopyrido[2,3-d]pyrimidin-5-yl]oxy}phenyl)-N-methylmethanesulfonamide (106 mg, 0.15 mmol, 1.0 equiv) in THF (2.0 mL) and water (2.0 mL) was added LiOH (38 mg, 1.59 mmol, 10.0 equiv) in portions at room temperature. The resulting mixture was stirred 30 min at room temperature and dissolved in $H_2O$ (20 mL). The resulting mixture was extracted with EtOAc (3×20 mL). The combined organic layers were washed with brine (30 mL), dried over anhydrous $Na_2SO_4$. After filtration, the filtrate was concentrated under reduced pressure. The crude product was purified by Prep-HPLC [Column: Welch XB-C18, 50*250 mm, 10 m Mobile Phase A: Water (0.1% TFA), Mobile Phase B: ACN; Flow rate: 90 mL/min; Gradient: 15% B to 50% B in 15 min, Wave Length: 254/220 nm] to afford N-cyclopropyl-2-[(2-fluoro-4-iodophenyl)amino]-1,5-dimethyl-4-{3-[(methylsulfamoyl)methyl]phenoxy}-6-oxopyridine-3-carboxamide (53 mg, 52%) as an off-white solid. ES-LCMS m/z 641.2 [M+H]⁺.

¹H NMR (400 MHz, DMSO-$d_6$) δ 8.50 (s, 1H), 7.94 (d, J=3.7 Hz, 1H), 7.59-7.52 (m, 1H), 7.36-7.26 (m, 2H), 7.08-7.01 (m, 1H), 6.88-6.79 (m, 3H), 6.60-6.49 (m, 1H), 4.30 (s, 2H), 3.36 (s, 3H), 2.53 (s, 3H), 2.21-2.14 (m, 1H), 1.82 (s, 3H), 0.41-0.31 (m, 2H), −0.03-0.08 (m, 1H).

Example 5: Synthesis of N-cyclopropyl-4-((2,2-dioxido-3,4-dihydro-1H-benzo[c][1,2,6]thiadiazin-7-yl)oxy)-2-((2-fluoro-4-iodophenyl)amino)-1,5-dimethyl-6-oxo-1,6-dihydropyridine-3-carboxamide (I-14)

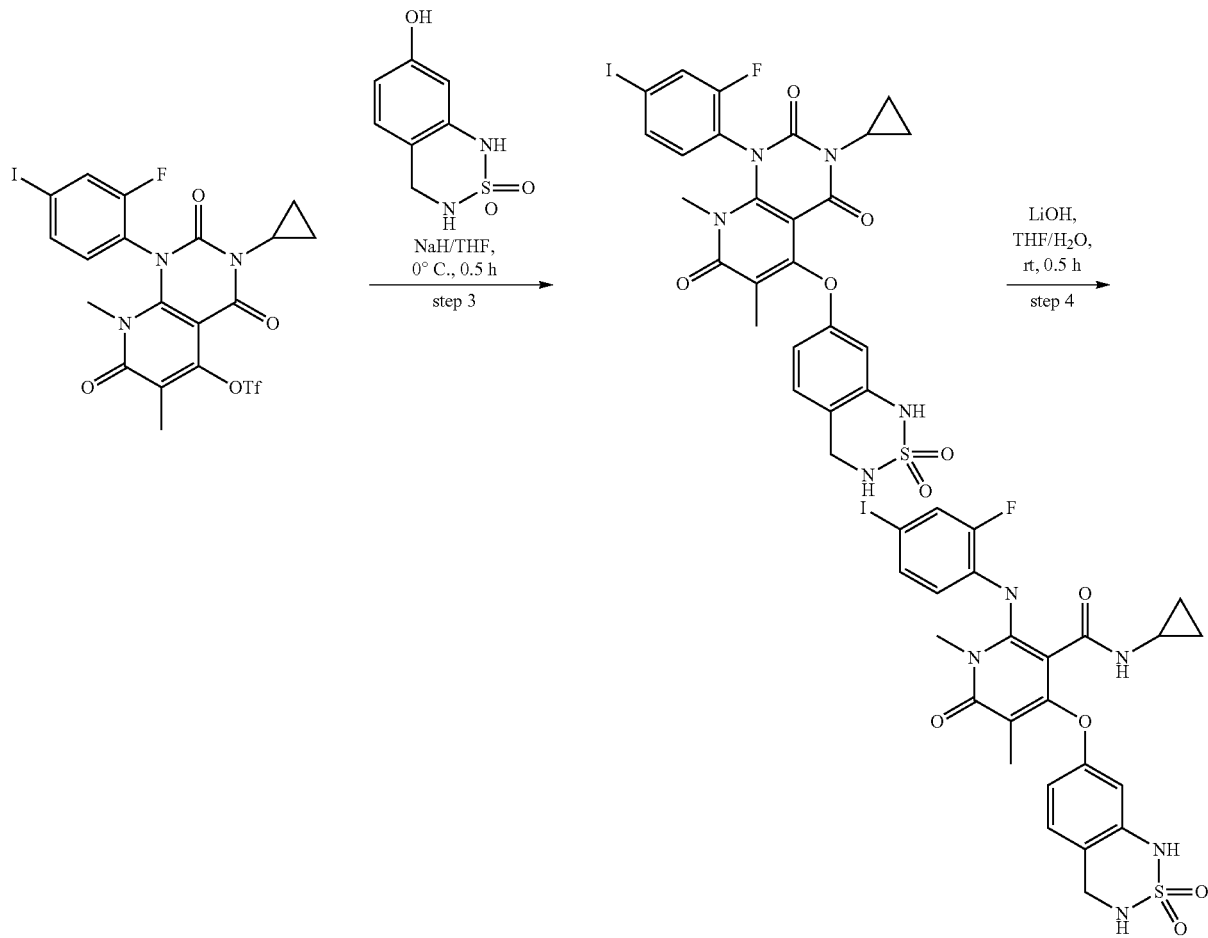

Step 1: 3-amino-4-(aminomethyl)phenol

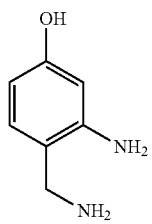

The solution of 2-amino-4-hydroxybenzamide (600 mg, 3.94 mmol, 1.0 equiv) in THF (2.0 mL) and BH$_3$·Me$_2$S (2.0 mL) was stirred for 4 h at 80° C. The reaction was quenched with MeOH (20 mL) at 0° C. and concentrated under reduced pressure to afford 3-amino-4-(aminomethyl)phenol (370 mg, 67%) as an off-white solid. The crude product was used in the next step directly without further purification. ES-LCMS m/z 139 [M+H]$^+$.

Step 2: 7-hydroxy-3,4-dihydro-1H-benzo[c][1,2,6]thiadiazine 2,2-dioxide

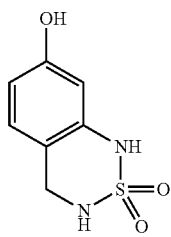 [SMILES: O=S1(=O)NCc2ccc(O)cc2N1]

A solution of 3-amino-4-(aminomethyl)phenol (370 mg, 2.67 mmol, 1.0 equiv) and sulfamide (772 mg, 8.03 mmol, 3.0 equiv) in pyridine (10.0 mL) was stirred for 6 h at 120° C. The reaction was monitored by LCMS. After the reaction was completed, the mixture was then concentrated under reduced pressure. The residue was purified by reverse flash chromatography with the following conditions: column, C18 silica gel; mobile phase, MeCN in Water (10 mmol/L NH$_4$HCO$_3$), 10% to 40% gradient in 10 min; detector, UV 254 nm. To afford 7-hydroxy-3,4-dihydro-1H-2lambda6,1,3-benzothiadiazine-2,2-dione (270 mg, 50%) as a off-white solid. ES-LCMS m/z 201 [M+H]$^+$.

Step 3: 3-cyclopropyl-5-((2,2-dioxido-3,4-dihydro-1H-benzo[c][1,2,6]thiadiazin-7-yl)oxy)-1-(2-fluoro-4-iodophenyl)-6,8-dimethylpyrido[2,3-d]pyrimidine-2,4,7(1H,3H,8H)-trione

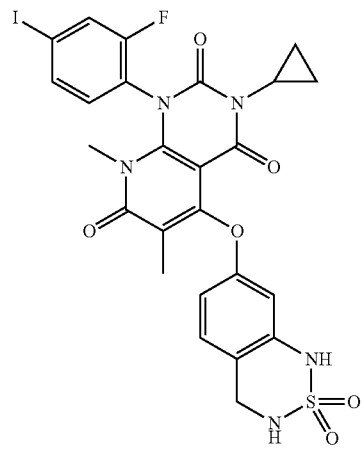 [SMILES: Cc1c(Oc2ccc3c(c2)NS(=O)(=O)NC3)c2c(=O)n(C3CC3)c(=O)n(-c3ccc(I)cc3F)c2n(C)c1=O]

A solution of 7-hydroxy-3,4-dihydro-1H-2lambda6,1,3-benzothiadiazine-2,2-dione (84 mg, 0.42 mmol, 1.3 equiv) in THF was treated with NaH (23 mg, 0.97 mmol, 3.0 equiv) for 15 min at 0° C. followed by the addition of 3-cyclopropyl-1-(2-fluoro-4-iodophenyl)-6,8-dimethyl-2,4,7-trioxopyrido[2,3-d]pyrimidin-5-yl trifluoromethanesulfonate (200 mg in THF, 0.32 mmol, 1.0 equiv) dropwise at 0° C. The resulting mixture was stirred for additional 30 min at 60° C. Then quenched by the addition of water (20 mL) and extracted with EA (3×20 mL). The combined organic layers were washed with brine (20 mL), dried over anhydrous Na$_2$SO$_4$. After filtration, the filtrate was concentrated under reduced pressure. The residue was purified by silica gel column chromatography, eluted with PE/THF (1:1) to afford 3-cyclopropyl-5-[(2,2-dioxo-3,4-dihydro-1H-2lambda6,1,3-benzothiadiazin-7-yl)oxy]-1-(2-fluoro-4-iodophenyl)-6,8-dimethylpyrido[2,3-d]pyrimidine-2,4,7-trione (170 mg, 78%) as an off-white solid. ES-LCMS m/z 666 [M+H]$^+$.

Step 4: N-cyclopropyl-4-((2,2-dioxido-3,4-dihydro-1H-benzo[c][1,2,6]thiadiazin-7-yl)oxy)-2-((2-fluoro-4-iodophenyl)amino)-1,5-dimethyl-6-oxo-1,6-dihydropyridine-3-carboxamide

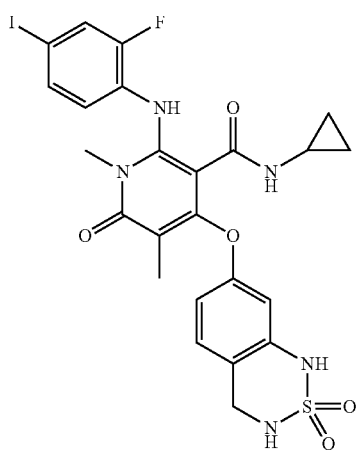 [SMILES: Cc1c(Oc2ccc3c(c2)NS(=O)(=O)NC3)c(C(=O)NC2CC2)c(Nc2ccc(I)cc2F)n(C)c1=O]

To a stirred solution of 3-cyclopropyl-5-[(2,2-dioxo-3,4-dihydro-1H-2lambda6,1,3-benzothiadiazin-7-yl)oxy]-1-(2-fluoro-4-iodophenyl)-6,8-dimethylpyrido[2,3-d]pyrimidine-2,4,7-trione (170 mg, 0.25 mmol, 1.0 equiv) in THF (1.0 mL) and water (1.0 mL) was added LiOH (61 mg, 2.55 mmol, 10.0 equiv) in portions at room temperature. The resulting mixture was stirred for additional 30 min at room temperature. The residue was dissolved in H$_2$O (20 mL) and extracted with EA (3×20 mL). The combined organic layers were washed with brine (20 mL), dried over anhydrous Na$_2$SO$_4$. After filtration, the filtrate was concentrated under reduced pressure. The crude product was purified by Prep-HPLC [Column: YMC C18 30*150 mm, 5 um Mobile Phase A: Water (0.050% NH$_3$·H$_2$O), Mobile Phase B: ACN; Flow rate: 35 mL/min; Gradient: 40% B to 75% B in 8 min, Wave Length: 254/220 nm] to afford N-cyclopropyl-4-[(2,2-dioxo-3,4-dihydro-1H-2lambda6,1,3-benzothiadiazin-7-yl)oxy]-2-[(2-fluoro-4-iodophenyl)amino]-1,5-dimethyl-6-oxopyridine-3-carboxamide (40 mg, 24%) as an off-white solid. ES-LCMS m/z 640.2 [M+H]$^+$.

$^1$H NMR (300 MHz, DMSO-d$_6$) δ 7.99 (d, J=3.8 Hz, 1H), 7.63-7.53 (m, 1H), 7.39-7.30 (m, 1H), 7.07-6.99 (m, 1H), 6.61-6.49 (m, 1H), 6.44-6.35 (m, 1H), 6.22-6.15 (m, 1H), 4.34 (s, 2H), 3.35 (s, 3H), 2.31-2.23 (m, 1H), 1.80 (s, 3H), 0.48-0.36 (m, 2H), 0.11-0.03 (m, 2H).

Example 6: Synthesis of N-cyclopropyl-4-{2-fluoro-3-](methylsulfamoyl)amino]phenoxy}-2-[(2-fluoro-4-iodophenyl)amino]-1,5-dimethyl-6-oxopyridine-3-carboxamide (1-4)

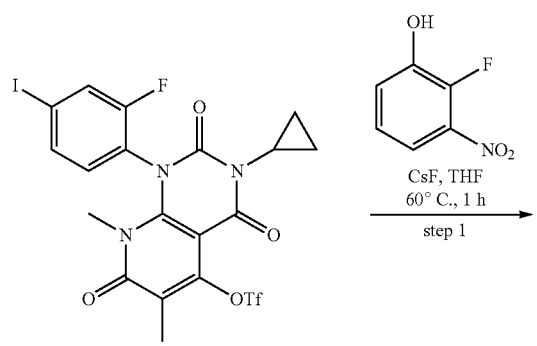
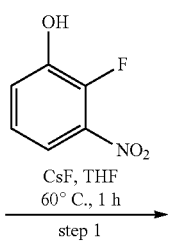
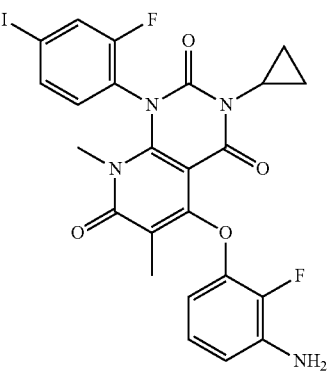 [SMILES: Cc1c(Oc2cccc([N+](=O)[O-])c2F)c2c(=O)n(C3CC3)c(=O)n(-c3ccc(I)cc3F)c2n(C)c1=O]
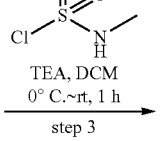
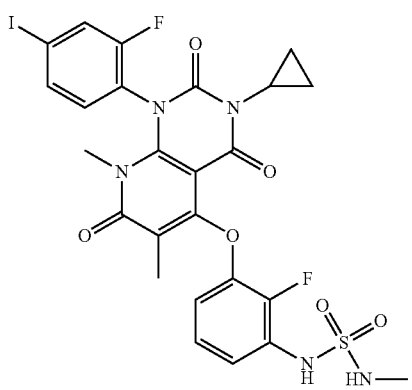 [SMILES: CNS(=O)(=O)Nc1cccc(Oc2c(C)c(=O)n(C)c3c2c(=O)n(C2CC2)c(=O)n3-c2ccc(I)cc2F)c1F]
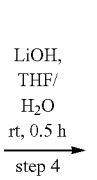
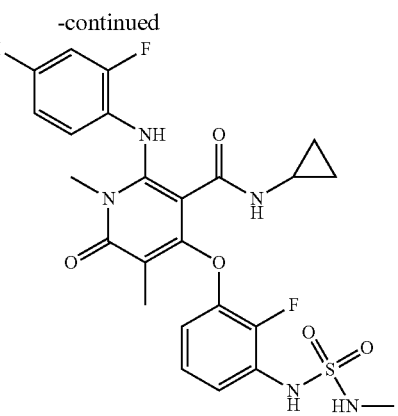
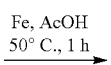

Step 1: 3-cyclopropyl-5-(2-fluoro-3-nitrophenoxy)-1-(2-fluoro-4-iodophenyl)-6,8-dimethylpyrido[2,3-d]pyrimidine-2,4,7-trione To a stirred solution of 3-cyclopropyl-1-(2-fluoro-4-iodophenyl)-6,8-dimethyl-2,4,7-trioxopyrido[2,3-d]pyrimidin-5-yl trifluoromethanesulfonate (1.2 g, 2.03 mmol, 1.0 equiv) and 2-fluoro-3-nitrophenol (0.6 g, 4.06 mmol, 2.0 equiv) in THF (15.0 mL) was added caesium fluoride (0.9 g, 6.09 mmol, 3.0 equiv) in portions at room temperature. The reaction mixture was stirred for additional 1 h at 60° C. The mixture was allowed to cool down to room temperature and quenched by the addition of water (50 mL). The resulting mixture was extracted with EtOAc (3×50 mL). The combined organic layers were washed with brine (50 mL), dried over anhydrous $Na_2SO_4$. After filtration, the filtrate was concentrated under reduced pressure. The residue was purified by silica gel column chromatography, eluted with PE/EA (3:1) to afford 3-cyclopropyl-5-(2-fluoro-3-nitrophenoxy)-1-(2-fluoro-4-iodophenyl)-6,8-dimethylpyrido[2,3-d]pyrimidine-2,4,7-trione (370 mg, 29%) as a white solid. ES-LCMS m/z 623 [M+H]⁺.

Step 2: 5-(3-amino-2-fluorophenoxy)-3-cyclopropyl-1-(2-fluoro-4-iodophenyl)-6,8-dimethylpyrido[2,3-d]pyrimidine-2,4,7-trione

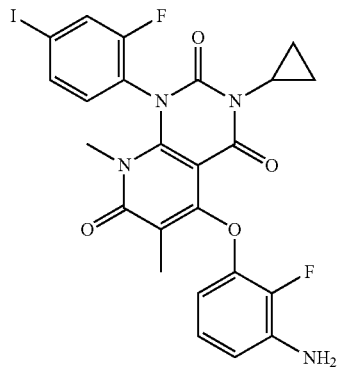

To a stirred solution of 3-cyclopropyl-5-(2-fluoro-3-nitrophenoxy)-1-(2-fluoro-4-iodophenyl)-6,8-dimethylpyrido[2,3-d]pyrimidine-2,4,7-trione (370 mg, 0.54 mmol, 1.0 equiv) in AcOH (4.0 mL) was added Fe (304 mg, 5.46 mmol, 10.0 equiv) in portions at 50° C. under air atmosphere. The reaction mixture was stirred for additional 1 h at room temperature. The resulting mixture was diluted with water (50 mL) and neutralized to pH 7 with saturated Na$_2$CO$_3$ (aq.), then extracted with DCM (3×50 mL). The combined organic layers were washed with brine (50 mL), dried over anhydrous Na$_2$SO$_4$. After filtration, the filtrate was concentrated under reduced pressure. The residue was purified by silica gel column chromatography, eluted with PE/THF (2:1) to afford 5-(3-amino-2-fluorophenoxy)-3-cyclopropyl-1-(2-fluoro-4-iodophenyl)-6,8-dimethylpyrido[2,3-d]pyrimidine-2,4,7-trione (180 mg, 55%) as a white solid. ES-LCMS m/z 593 [M+H]$^+$.

Step 3: 3-cyclopropyl-5-{2-fluoro-3-[(methylsulfamoyl)amino]phenoxy}-1-(2-fluoro-4-iodophenyl)-6,8-dimethylpyrido[2,3-d]pyrimidine-2,4,7-trione

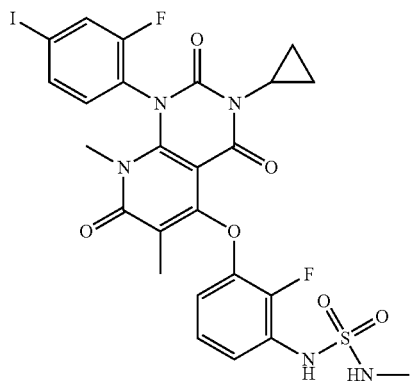

To a stirred solution of 5-(3-amino-2-fluorophenoxy)-3-cyclopropyl-1-(2-fluoro-4-iodophenyl)-6,8-dimethylpyrido[2,3-d]pyrimidine-2,4,7-trione (270 mg, 0.45 mmol, 1.0 equiv) and triethylamine (138 mg, 1.36 mmol, 3.0 equiv) in DCM (25.0 mL) was added N-methylsulfamoyl chloride (177 mg, 1.36 mmol, 3.0 equiv) dropwise at 0° C. The resulting mixture was stirred for additional 0.5 h at room temperature. The resulting mixture was quenched with water (0.5 mL) and concentrated under reduced pressure. The crude product was used in the next step directly without further purification. ES-LCMS m/z 686 [M+H]$^+$.

Step 4: N-cyclopropyl-4-{2-fluoro-3-[(methylsulfamoyl)amino]phenoxy]-2-[(2-fluoro-4-iodophenyl)amino]-1,5-dimethyl-6-oxopyridine-3-carboxamide

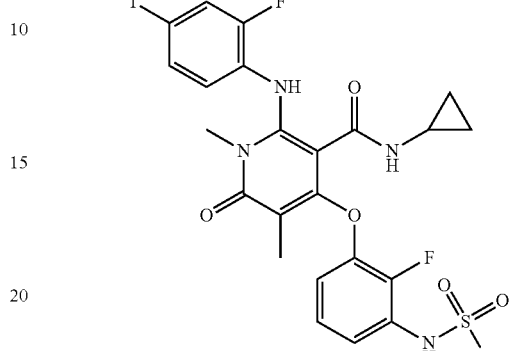

To a stirred solution of 3-cyclopropyl-5-{2-fluoro-3-[(methylsulfamoyl)amino]phenoxy}-1-(2-fluoro-4-iodophenyl)-6,8-dimethylpyrido[2,3-d]pyrimidine-2,4,7-trione (230 mg, 0.33 mmol, 1.0 equiv) in THF (3 mL) was added LiOH (41.2 mg, in 3.0 mL H$_2$O, 1.72 mmol, 10 equiv) at room temperature under air atmosphere. The resulting mixture was stirred for 30 min at room temperature. Then the resulting mixture was diluted with water (30 mL) and extracted with EtOAc (3×30 mL). The combined organic layers were washed with brine (30 mL), dried over anhydrous Na$_2$SO$_4$. After filtration, the filtrate was concentrated under reduced pressure. The crude product was purified by Prep-HPLC (YMC C18 30*150 mm, Sum Mobile Phase A: Water (0.05% NH$_3$·H$_2$O), Mobile Phase B: ACN; Flow rate: 35 mL/min; Gradient: 40% B to 80% B in 8 min, Wave Length: 254/220 nm) to afford N-cyclopropyl-4-{2-fluoro-3-[(methylsulfamoyl)amino]phenoxy}-2-[(2-fluoro-4-iodophenyl)amino]-1,5-dimethyl-6-oxopyridine-3-carboxamide (53.2 mg, 24%) as a white solid. ES-LCMS m/z 660.2 [M+H]$^+$.
$^1$H NMR (400 MHz, DMSO-d$_6$) δ 9.87 (br, s, 1H), 8.41 (s, 1H), 8.02 (d, J=3.5 Hz, 1H), 7.59-7.51 (m, 1H), 7.35-7.27 (m, 2H), 7.14-7.06 (m, 1H), 7.01-6.92 (m, 1H), 6.60-6.48 (m, 2H), 3.35 (s, 3H), 2.53 (d, 3H), 2.23-2.15 (m, 1H), 1.81 (s, 3H), 0.43-0.34 (m, 2H), −0.01-0.05 (m, 2H).

Example 7: Synthesis of 4-(2-chloro-3-((N-methylsulfamoyl)amino)phenoxy)-N-cyclopropyl-2-((2-fluoro-4-iodophenyl)amino)-1,5-dimethyl-6-oxo-1,6-dihydropyridine-3-carboxamide (I-2)

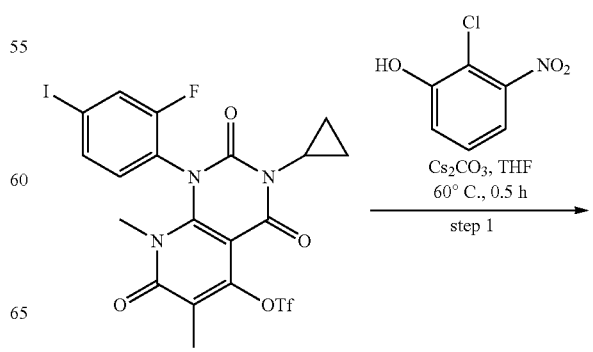

-continued

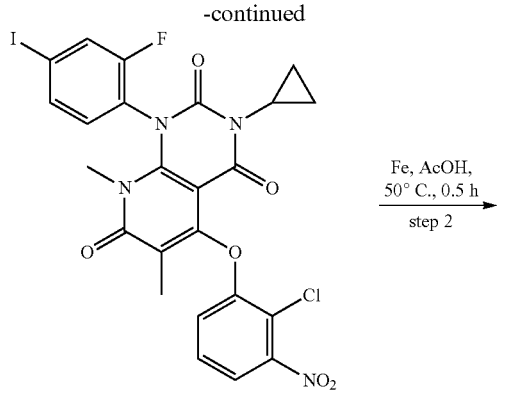

Fe, AcOH,
50° C., 0.5 h
⟶
step 2

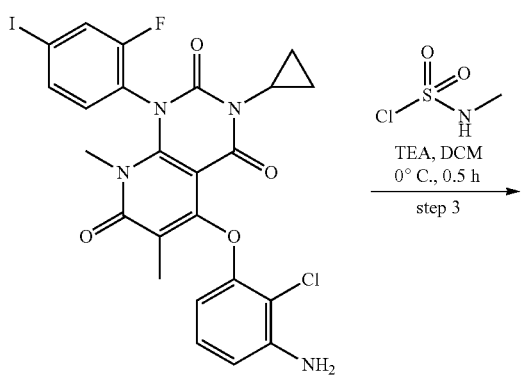

TEA, DCM
0° C., 0.5 h
⟶
step 3

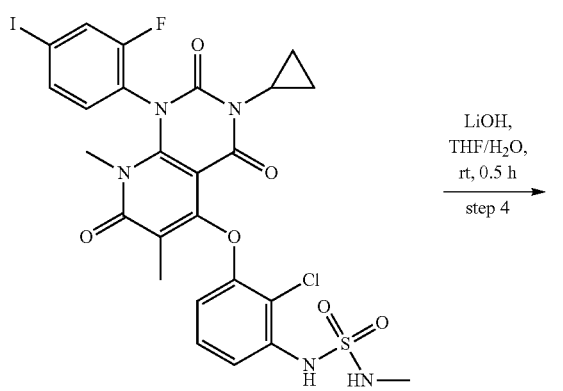

LiOH,
THF/H₂O,
rt, 0.5 h
⟶
step 4

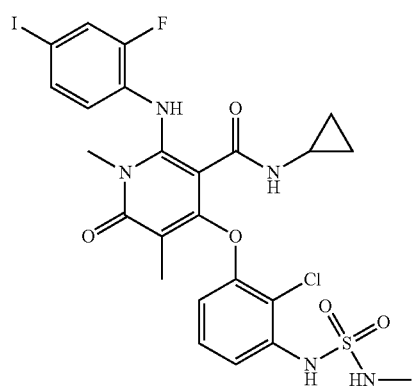

Step 1: 5-(2-chloro-3-nitrophenoxy)-3-cyclopropyl-1-(2-fluoro-4-iodophenyl)-6,8-dimethylpyrido[2,3-d]pyrimidine-2,4,7(1H,3H,8H)-trione

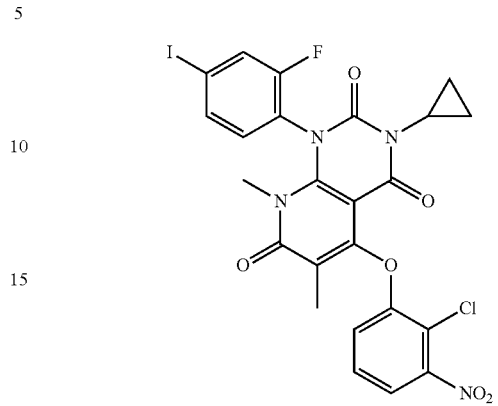

To a stirred mixture of 3-cyclopropyl-1-(2-fluoro-4-iodophenyl)-6,8-dimethyl-2,4,7-trioxopyrido[2,3-d]pyrimidin-5-yl trifluoromethanesulfonate (1.00 g, 1.62 mmol, 1.0 equiv) and 2-chloro-5-nitrophenol (0.85 g, 4.87 mmol, 3.0 equiv) in THF was added caesium fluoride (0.74 g, 4.87 mmol, 3.0 equiv) in portions at 60° C. The reaction mixture was stirred for additional 30 min at 60° C. The resulting mixture was diluted with water (30 mL) and extracted with EA (3×30 mL). The combined organic layers were washed with brine (50 mL), dried over anhydrous Na₂SO₄. After filtration, the filtrate was concentrated under reduced pressure. The residue was purified by silica gel column chromatography, eluted with PE/THE (1:1) to afford 5-(2-chloro-3-nitrophenoxy)-3-cyclopropyl-1-(2-fluoro-4-iodophenyl)-6,8-dimethylpyrido[2,3-d]pyrimidine-2,4,7-trione (540 mg, 52%) as a light yellow solid. ES-LCMS m/z 639 [M+H]⁺.

Step 2: 5-(3-amino-2-chlorophenoxy)-3-cyclopropyl-1-(2-fluoro-4-iodophenyl)-6,8-dimethylpyrido[2,3-d]pyrimidine-2,4,7(1H,3H,8H)-trione

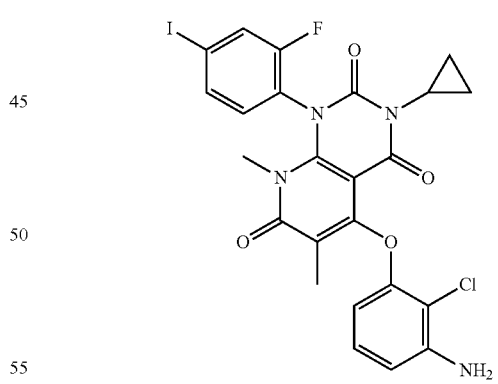

To a stirred mixture of 5-(2-chloro-3-nitrophenoxy)-3-cyclopropyl-1-(2-fluoro-4-iodophenyl)-6,8-dimethylpyrido[2,3-d]pyrimidine-2,4,7-trione (540 mg, 0.84 mmol, 1.0 equiv) in AcOH was added iron (472 mg, 8.45 mmol, 10.0 equiv) in portions at 50° C. The resulting mixture was stirred for additional 30 min at 50° C. The mixture was diluted with water (50 mL) and neutralized to pH 7 with saturated NaHCO₃ (aq.), then extracted with EA (3×20 mL). The combined organic layers were washed with brine 50 mL), dried over anhydrous Na₂SO₄. After filtration, the filtrate was concentrated under reduced pressure. This resulted in 5-(3-amino-2-chlorophenoxy)-3-cyclopropyl-1-(2-fluoro-4- iodophenyl)-6,8-dimethylpyrido[2,3-d]pyrimidine-2,4,7-trione (195 mg, crude, 37%) as a light brown solid. ES-LCMS m/z 609 [M+H]$^+$.

Step 3: 5-{2-chloro-3-[(methylsulfamoyl)amino]phenoxy]-3-cyclopropyl-1-(2-fluoro-4-iodophenyl)-6,8-dimethylpyrido[2,3-d]pyrimidine-2,4,7-trione

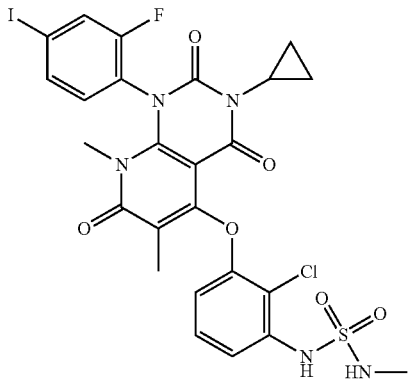 [SMILES: CNS(=O)(=O)Nc1cccc(Oc2c(C)c(=O)n(C)c3c2c(=O)n(C2CC2)c(=O)n3-c2ccc(I)cc2F)c1Cl]

To a stirred mixture of 5-(3-amino-2-chlorophenoxy)-3-cyclopropyl-1-(2-fluoro-4-iodophenyl)-6,8-dimethylpyrido[2,3-d]pyrimidine-2,4,7-trione (195 mg, crude, 0.32 mmol, 1.0 equiv) in DCM was added triethylamine (64 mg, 0.64 mmol, 2.0 equiv) at 0° C., then N-methylsulfamoyl chloride (83 mg, 0.64 mmol, 2.0 equiv) was added dropwise over 2 min at 0° C. The reaction mixture was stirred for additional 30 min at 0° C. The reaction was quenched with water (10 mL) and then extracted with EtOAc (3×10 mL). The organic layer was dried over anhydrous Na$_2$SO$_4$, filtered and the filtrate was concentrated under reduced pressure to afford 5-{2-chloro-3-[(methylsulfamoyl)amino]phenoxy}-3-cyclopropyl-1-(2-fluoro-4-iodophenyl)-6,8-dimethylpyrido[2,3-d]pyrimidine-2,4,7-trione (130 mg, crude, 57%). The crude product mixture was used in the next step directly without further purification. ES-LCMS m/z 702 [M+H]$^+$.

Step 4: 4-(2-chloro-3-((N-methylsulfamoyl)amino)phenoxy)-N-cyclopropyl-2-((2-fluoro-4-iodophenyl)amino)-1,5-dimethyl-6-oxo-1,6-dihydropyridine-3-carboxamide

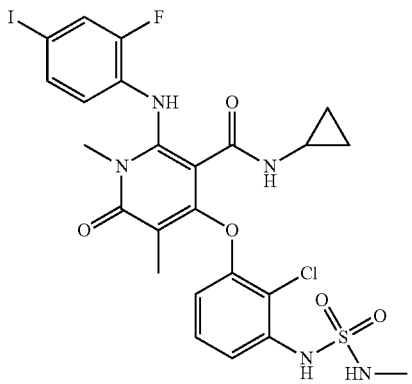 [SMILES: CNS(=O)(=O)Nc1cccc(Oc2c(C(=O)NC3CC3)c(Nc3ccc(I)cc3F)n(C)c(=O)c2C)c1Cl]

To a stirred solution of 5-{2-chloro-3-[(methylsulfamoyl)amino]phenoxy}-3-cyclopropyl-1-(2-fluoro-4-iodophenyl)-6,8-dimethylpyrido[2,3-d]pyrimidine-2,4,7-trione (130 mg, 0.18 mmol, 1.0 equiv) in THF (1.0 mL) and water (1.0 mL) was added LiOH (44 mg, 1.85 mmol, 10.0 equiv) in portions at room temperature. The reaction mixture was stirred for additional 30 min at room temperature. The resulting mixture was diluted with water (10 mL) and extracted with EA (3×10 mL). The combined organic layers were washed with brine (1×20 mL), dried over anhydrous Na$_2$SO$_4$. After filtration, the filtrate was concentrated under reduced pressure. The crude product was purified by Prep-HPLC [Column: YMC C18 30*150 mm, Sum Mobile Phase A: Water (0.05% NH3·H$_2$O), Mobile Phase B: ACN; Flow rate: 35 mL/min; Gradient: 40% B to 75% B in 8 min, Wave Length: 254/220 nm] to afford 4-{2-chloro-3-[(methylsulfamoyl)amino]phenoxy}-N-cyclopropyl-2-[(2-fluoro-4-iodophenyl)amino]-1,5-dimethyl-6-oxopyridine-3-carboxamide (51 mg, 41%) as an off-white solid. ES-LCMS m/z 676.1 [M+H]$^+$.

$^1$H NMR (400 MHz, DMSO-d$_6$) δ 9.01 (br, s, 1H), 8.41 (br, s, 1H), 7.98 (d, J=3.6 Hz, 1H), 7.59-7.51 (m, 1H), 7.39-7.27 (m, 2H), 7.23-7.12 (m, 2H), 6.63-6.55 (m, 1H), 6.55-6.48 (m, 1H), 3.36 (s, 3H), 2.53 (d, J=2.6 Hz, 3H), 2.21-2.11 (m, 1H), 1.76 (s, 3H), 0.42-0.33 (m, 2H), −0.01-−0.05 (m, 2H).

Example 8: Synthesis of N-cyclopropyl-2-((2-fluoro-4-iodophenyl)amino)-N1,5-trimethyl-4-(2-methyl-3-((N-methylsulfamoyl)amino)phenoxy)-6-oxo-1,6-dihydropyridine-3-carboxamide (I-28)

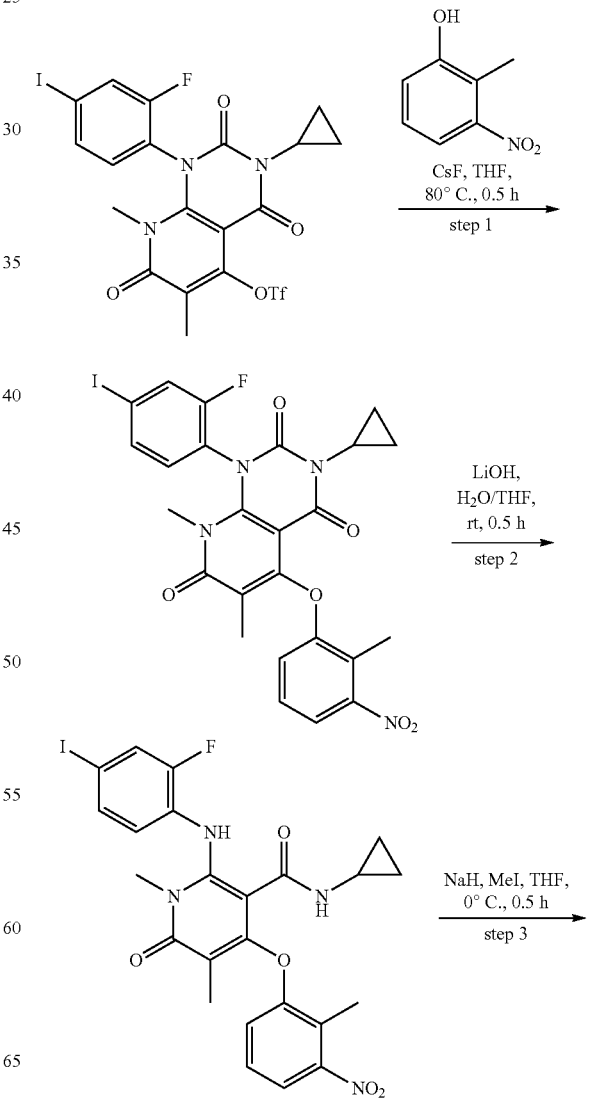

-continued

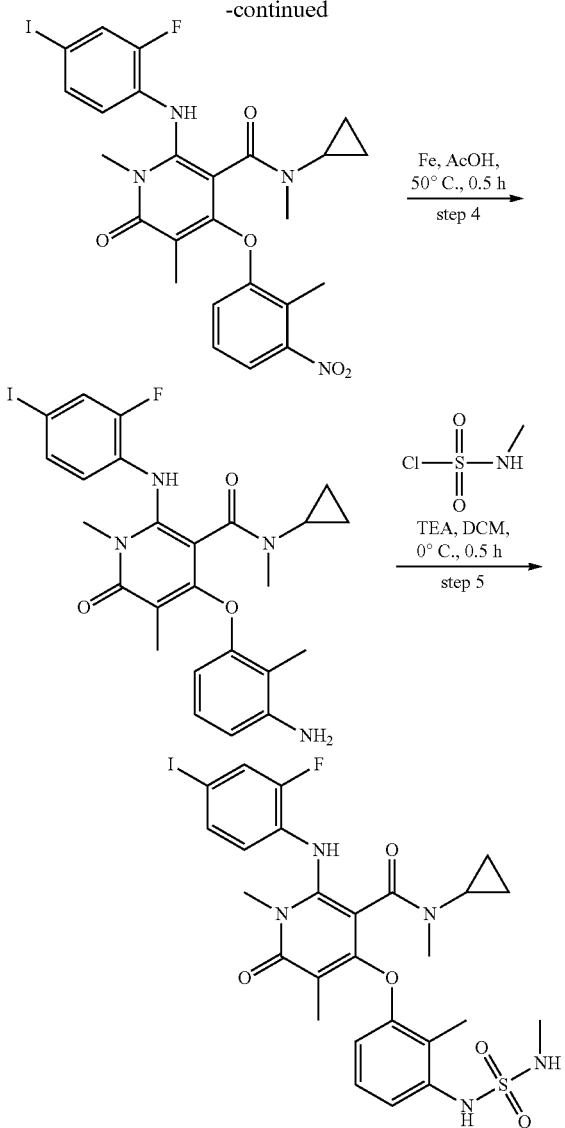

Step 1: 3-cyclopropyl-1-(2-fluoro-4-iodophenyl)-6,8-dimethyl-5-(2-methyl-3-nitrophenoxy) pyrido[2,3-d]pyrimidine-2,4,7(1H,3H,8H)-trione

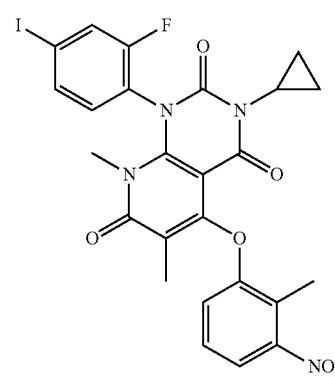

To a stirred mixture of 3-cyclopropyl-1-(2-fluoro-4-iodophenyl)-6,8-dimethyl-2,4,7-trioxopyrido[2,3-d]pyrimidin-5-yl trifluoromethanesulfonate (1.00 g, 1.62 mmol, 1.0 equiv) and 2-methyl-3-nitrophenol (497 mg, 3.25 mmol, 2.0 equiv) in THF was added caesium fluoride (740 mg, 4.87 mmol, 3.0 equiv) in portions at 80° C. The reaction mixture was stirred for additional 30 min at 80° C. The resulting mixture was diluted with water (30 mL) and extracted with EA (3×30 mL). The combined organic layers were washed with brine (50 mL), dried over anhydrous Na₂SO₄. After filtration, the filtrate was concentrated under reduced pressure. The residue was purified by silica gel column chromatography, eluted with PE/THF (1:1) to afford 3-cyclopropyl-1-(2-fluoro-4-iodophenyl)-6,8-dimethyl-5-(2-methyl-3-nitrophenoxy)pyrido[2,3-d]pyrimidine-2,4,7-trione (470 mg, 46%) as a brown solid. ES-LCMS m/z 619 [M+H]⁺.

Step 2: N-cyclopropyl-2-((2-fluoro-4-iodophenyl)amino)-1,5-dimethyl-4-(2-methyl-3-nitrophenoxy)-6-oxo-1,6-dihydropyridine-3-carboxamide

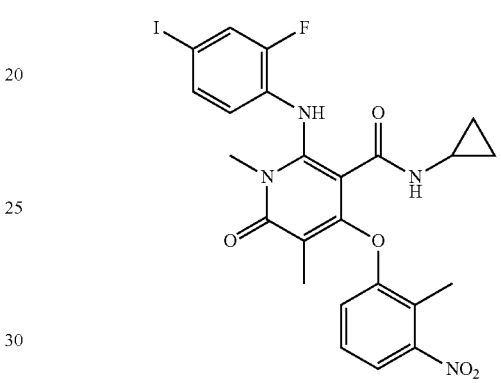

To a stirred mixture of 3-cyclopropyl-1-(2-fluoro-4-iodophenyl)-6,8-dimethyl-5-(2-methyl-3-nitrophenoxy)pyrido[2,3-d]pyrimidine-2,4,7-trione (470 mg, 0.76 mmol, 1.0 equiv) in THF (2.0 mL) and water (2.0 mL) was added LiOH (182 mg, 7.60 mmol, 10.0 equiv) in portions at room temperature. The reaction mixture was stirred for additional 30 min at room temperature. The resulting mixture was diluted with water (10 mL) and extracted with EA (3×10 mL). The combined organic layers were washed with brine (20 mL), dried over anhydrous Na₂SO₄. After filtration, the filtrate was concentrated under reduced pressure. This resulted in N-cyclopropyl-2-[(2-fluoro-4-iodophenyl)amino]-1,5-dimethyl-4-(2-methyl-3-nitrophenoxy)-6-oxopyridine-3-carboxamide (175 mg, crude, 38%) as a light yellow solid. ES-LCMS m/z 593 [M+H]⁺.

Step 3: N-cyclopropyl-2-((2-fluoro-4-iodophenyl)amino)-N,3,5-trimethyl-6-(2-methyl-3-nitrophenoxy)-4-oxocyclohexa-1,5-diene-1-carboxamide

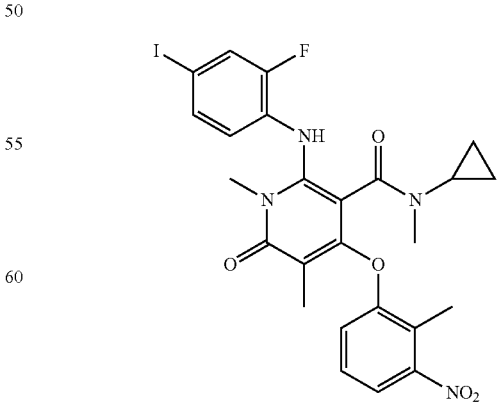

A solution of N-cyclopropyl-2-[(2-fluoro-4-iodophenyl)amino]-1,5-dimethyl-4-(2-methyl-3-nitrophenoxy)-6- oxopyridine-3-carboxamide (175 mg, crude, 0.29 mmol, 1.0 equiv) in THF was treated with sodium hydride (28 mg, 1.18 mmol, 4.0 equiv) for 30 min at 0° C., then methyl iodide (251 mg, 1.77 mmol, 6.0 equiv) was added dropwise at 0° C. The reaction mixture was stirred for additional 30 min at room temperature. The resulting mixture was diluted with water (10 mL) and extracted with EA (3×10 mL). The combined organic layers were washed with brine (20 mL), dried over anhydrous $Na_2SO_4$. After filtration, the filtrate was concentrated under reduced pressure. The residue was purified by silica gel column chromatography, eluted with PE/THF (1:1) to afford N-cyclopropyl-2-[(2-fluoro-4-iodophenyl)amino]-N1,5-trimethyl-4-(2-methyl-3-nitrophenoxy)-6-oxopyridine-3-carboxamide (100 mg, 55%) as a light brown solid. ES-LCMS m/z 607 $[M+H]^+$.

Step 4: 4-(3-amino-2-methylphenoxy)-N-cyclopropyl-2-((2-fluoro-4-iodophenyl)amino)-N1,5-trimethyl-6-oxo-1,6-dihydropyridine-3-carboxamide

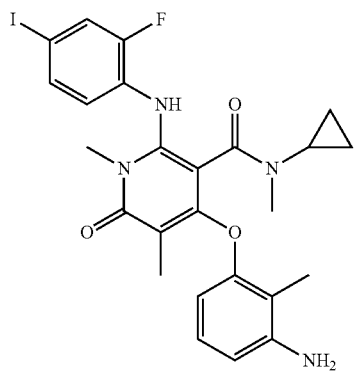 [SMILES: Cc1c(Oc2c(C(=O)N(C)C3CC3)c(Nc3ccc(I)cc3F)n(C)c(=O)c2C)cccc1[N+](=O)[O-]]

To a stirred mixture of N-cyclopropyl-2-[(2-fluoro-4-iodophenyl)amino]-N1,5-trimethyl-4-(2-methyl-3-nitrophenoxy)-6-oxopyridine-3-carboxamide (100 mg, 0.16 mmol, 1.0 equiv) in AcOH was added Fe powder (92 mg, 1.65 mmol, 10.0 equiv) in portions at 50° C. The reaction mixture was stirred for additional 30 min at 50° C. The mixture was diluted with water (10 mL) and neutralized to pH 7 with saturated $NaHCO_3$ (aq.), extracted with EA (3×20 mL). The combined organic layers were washed with brine (10 mL), dried over anhydrous $Na_2SO_4$. After filtration, the filtrate was concentrated under reduced pressure. This resulted in 4-(3-amino-2-methylphenoxy)-N-cyclopropyl-2-[(2-fluoro-4-iodophenyl)amino]-N1,5-trimethyl-6-oxopyridine-3-carboxamide (67 mg, crude, 70%) as an off-white solid.

Step 5: N-cyclopropyl-2-((2-fluoro-4-iodophenyl)amino)-N1,5-trimethyl-4-(2-methyl-3-((N-methylsulfamoyl)amino)phenoxy)-6-oxo-1,6-dihydropyridine-3-carboxamide

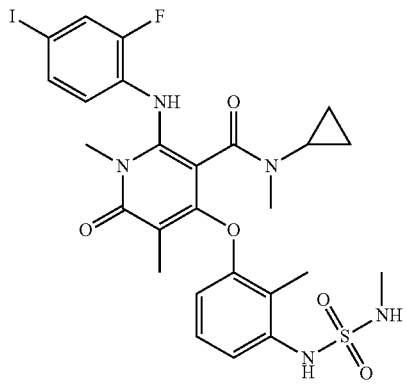 [SMILES: CNS(=O)(=O)Nc1cccc(Oc2c(C(=O)N(C)C3CC3)c(Nc3ccc(I)cc3F)n(C)c(=O)c2C)c1C]

To a stirred mixture of 4-(3-amino-2-methylphenoxy)-N-cyclopropyl-2-[(2-fluoro-4-iodophenyl)amino]-N1,5-trimethyl-6-oxopyridine-3-carboxamide (67 mg, crude, 0.11 mmol, 1.0 equiv) in DCM was added triethylamine (35 mg, 0.34 mmol, 3.0 equiv) dropwise at 0° C., Then N-methylsulfamoyl chloride (22 mg, 0.17 mmol, 1.5 equiv) was added dropwise over 2 min at 0° C. The reaction mixture was stirred for additional 30 min at room temperature. The resulting mixture was diluted with water (20 mL) and extracted with EA (3×20 mL). The combined organic layers were washed with brine (20 mL), dried over anhydrous $Na_2SO_4$. After filtration, the filtrate was concentrated under reduced pressure. The crude product was purified by Prep-HPLC [Column: YMC C18 30*150 mm, 5 µm Mobile Phase A: Water (0.05% $NH_3 \cdot H_2O$), Mobile Phase B: ACN; Flow rate: 35 mL/min; Gradient: 40% B to 80% B in 8 min, Wave Length: 254/220 nm] to afford N-cyclopropyl-2-[(2-fluoro-4-iodophenyl)amino]-N1,5-trimethyl-4-{2-methyl-3-[(methylsulfamoyl)amino]phenoxy}-6-oxopyridine-3-carboxamide (17 mg, 21%) as an off-white solid. ES-LCMS m/z 670.2 $[M+H]^+$.

$^1$H NMR (300 MHz, DMSO-$d_6$) δ 8.93-8.74 (m, 1H), 8.24-8.12 (m, 1H), 7.59-7.46 (m, 1H), 7.41-7.26 (m, 1H), 7.15-6.96 (m, 3H), 6.73-6.58 (m, 1H), 6.53-6.39 (m, 1H), 3.53-3.40 (m, 3H), 3.30-3.21 (m, 3H), 2.89-2.70 (m, 1H), 2.66-2.53 (m, 3H), 2.20 (s, 3H), 1.80-1.56 (m, 3H), 0.68-0.48 (m, 2H), 0.45-0.32 (m, 1.5H), 0.01-0.31 (m, 0.5H).

Example 9: Synthesis of N-cyclopropyl-2-[(2-fluoro-4-iodophenyl)amino]-4-(3-methanesulfonoimidamidophenoxy)-1,5-dimethyl-6-oxopyridine-3-carboxamide (I-20)

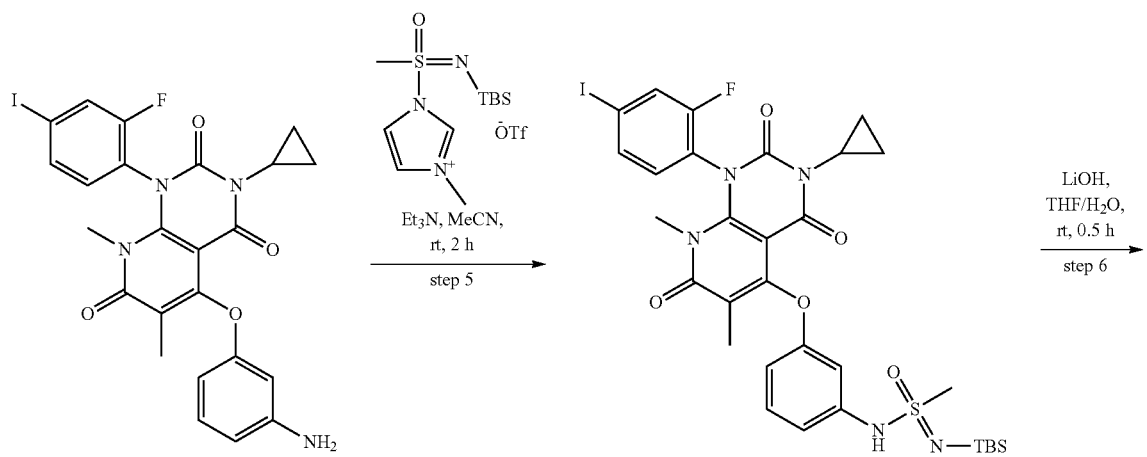

145 146

-continued

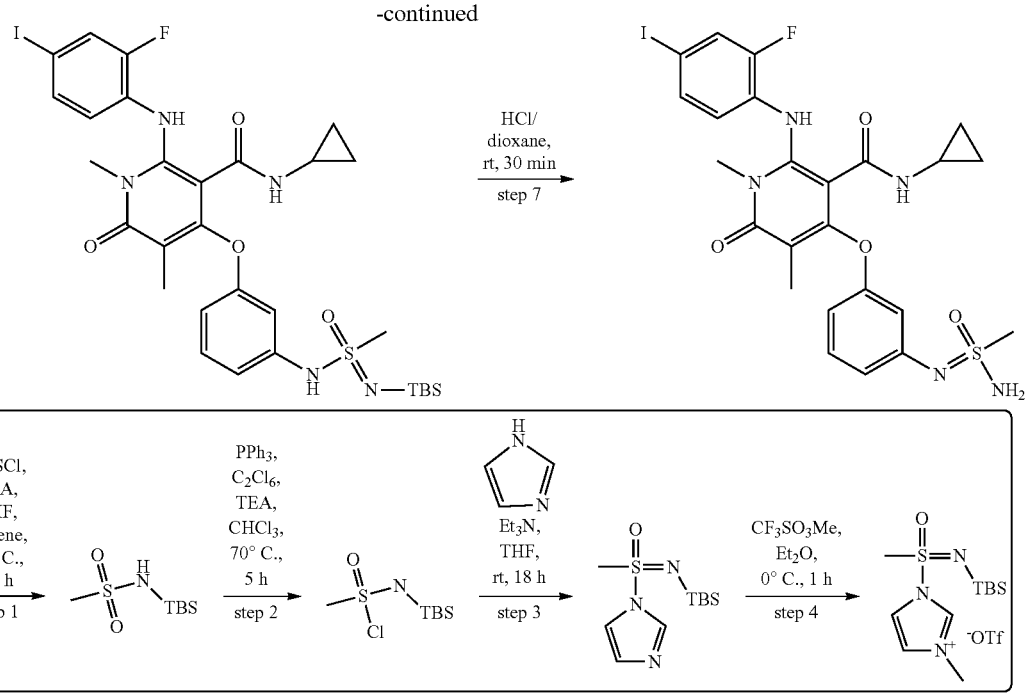

Step 1: N-(tert-butyldimethylsilyl)methanesulfonamide

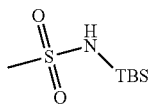

In a 250 mL round bottom flask, a solution of TBSCl (18.54 g, 123.0 mmol, 1.2 equiv) in toluene (20.0 mL) was added dropwise to a stirred solution of methanesulfonamide (10.00 g, 105.1 mmol, 1.2 equiv) and Et₃N (21.28 g, 210.3 mmol, 2.0 equiv) in THF (50.0 mL). The reaction mixture was stirred overnight at 60° C. The reaction was cool to rt and filtrated. The filter cake was washed with THF and then triturated with hexane. The final solid was collected after filtration. This resulted in N-(tert-butyldimethylsilyl)methanesulfonamide (19.00 g, 86%) as a white solid. ¹H NMR (300 MHz, Chloroform-d) δ 4.71 (s, 1H), 3.02 (s, 3H), 0.95 (s, 9H), 0.29 (s, 6H).

Step 2: N-(tert-butyldimethylsilyl)methanesulfonimidoyl chloride

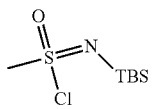

A solution of PPh₃ (26.18 g, 99.8 mmol, 1.1 equiv) and hexachloroethane (23.63 g, 99.8 mmol, 1.1 equiv) in CHCl₃ (50.0 mL) was stirred for 5 h at 70° C. under nitrogen atmosphere, the formation of a white suspension was observed. The mixture was allowed to cool down to room temperature and TEA (13.77 g, 136.1 mmol, 1.5 equiv) was added. After stirring for 10 min, the mixture was allowed to cool down to 0° C. and a solution of N-(tert-butyldimethylsilyl)methanesulfonamide (19.00 g, 90.7 mmol, 1.0 equiv) in CHCl₃ (200.0 mL) were added dropwise. The reaction mixture was stirred for 30 min at 0° C. The resulting mixture was used in the next step directly without further purification.

Step 3: 1-(N-(tert-butyldimethylsilyl)-S-methylsulfonimidoyl)-1H-imidazole

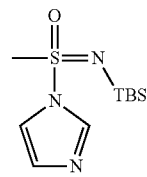

To a solution of N-(tert-butyldimethylsilyl)methanesulfonimidoyl chloride (5.00 g, 21.8 mmol, 1.0 equiv) in THF (17.0 mL), imidazole (1.48 g, 21.8 mmol, 1.0 equiv) and TEA (2.20 g, 21.7 mmol, 1.0 equiv) were added. The mixture was stirred 18 h at room temperature. The resulting mixture was concentrated under reduced pressure. The residue was dissolved in CH₂Cl₂ and washed with H₂O. The organic phase was dried over anhydrous Na₂SO₄ and concentrated under reduced pressure. The residue was purified by flash chromatography (10:90 petroleum ether/THF) to afford (tert-butyldimethylsilyl)[imidazol-1-yl(methyl)oxo-lambda6-sulfanylidene]amine (0.40 g, 7%) as a colorless solid. ES-LCMS m/z 260 [M+H]+. 1H NMR (400 MHz, Chloroform-d) δ 7.95 (s, 1H), 7.30 (s, 1H), 7.14 (s, 1H), 3.24 (s, 3H), 0.94 (s, 9H), 0.11 (s, 6H).

Step 4: 1-(N-(tert-butyldimethylsilyl)-S-methyl-sulfonimidoyl)-3-methyl-1H-imidazol-3-ium trifluoromethanesulfonate

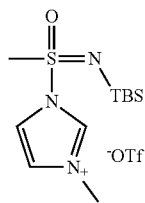

A solution of (tert-butyldimethylsilyl)[imidazol-1-yl(methyl)oxo-lambda6-sulfanylidene]amine (375.00 mg, 1.5 mmol, 1.0 equiv) in Et2O (2.0 mL) under nitrogen atmosphere was cooled to 0° C. Methyl trifluoromethanesulfonate (237.19 mg, 1.5 mmol, 1.0 equiv) in Et2O (2.0 mL) was added dropwise and the resulting mixture was stirred for 1 h at 0° C. The obtained solids were filtered, washed with Et2O and dried under vacuum. This resulted in 1-(N-(tert-butyldimethylsilyl)-S-methylsulfonimidoyl)-3-methyl-1H-imidazol-3-ium trifluoromethanesulfonate (380 mg, 95%) as a white solid.

Step 5: N'-(tert-butyldimethylsilyl)-N-(3-((3-cyclopropyl-1-(2-fluoro-4-iodophenyl)-6,8-dimethyl-2,4,7-trioxo-1,2,3,4,7,8-hexahydropyrido[2,3-d]pyrimidin-5-yl)oxy)phenyl)methanesulfonimidamide

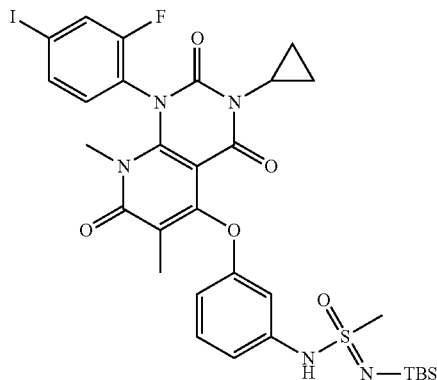

To a solution of 5-(3-aminophenoxy)-3-cyclopropyl-1-(2-fluoro-4-iodophenyl)-6,8-dimethylpyrido[2,3-d]pyrimidine-2,4,7-trione (235 mg, 0.4 mmol, 1.0 equiv) and TEA (124 mg, 1.2 mmol, 3.0 equiv) in CH3CN (4.5 mL), 1-(N-(tert-butyldimethylsilyl)-S-methylsulfonimidoyl)-3-methyl-1H-imidazol-3-ium trifluoromethanesulfonate (449 mg, 1.6 mmol, 4.0 equiv) was added at an ice bath. The resulting mixture was stirred for 2 h at room temperature under nitrogen atmosphere. The resulting mixture was concentrated under reduced pressure, to afford N'-(tert-butyldimethylsilyl)-N-(3-((3-cyclopropyl-1-(2-fluoro-4-iodophenyl)-6,8-dimethyl-2,4,7-trioxo-1,2,3,4,7,8-hexahydropyrido[2,3-d]pyrimidin-5-yl)oxy)phenyl)methanesulfonimidamide (240 mg, 76%) as a white crude solid. The crude product was used in the next step directly without further purification. ES-LCMS m/z 766 [M+H]+.

Step 6: 4-{3-[N-(tert-butyldimethylsilyl)methane-sulfonoimidamido]phenoxy]-N-cyclopropyl-2-[(2-fluoro-4-iodophenyl)amino]-1,5-dimethyl-6-oxopyridine-3-carboxamide

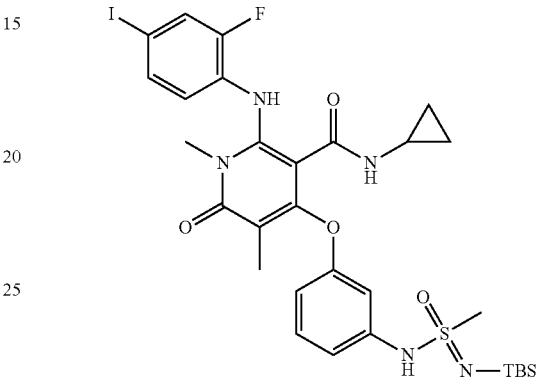

To a solution of N-(tert-butyldimethylsilyl)-N-(3-{[3-cyclopropyl-1-(2-fluoro-4-iodophenyl)-6,8-dimethyl-2,4,7-trioxopyrido[2,3-d]pyrimidin-5-yl]oxy}phenyl)methanesulfonoimidamide (240 mg, 0.3 mmol, 1.0 equiv) in THF (2.0 mL) and H2O (3.0 mL), LiOH (75 mg, 3.1 mmol, 10.0 equiv) was added. The reaction mixture was stirred for 30 min at room temperature. The resulting mixture was diluted with water (10 mL) and extracted with EtOAc (3×10 mL). The combined organic layers were washed with brine, dried over anhydrous Na2SO4. After filtration, the filtrate was concentrated under reduced pressure. The residue was purified by Prep-TLC (PE:THF=1:1) to afford 4-{3-[N-(tert-butyldimethylsilyl)methanesulfonoimidamido]phenoxy}-N-cyclopropyl-2-[(2-fluoro-4-iodophenyl)amino]-1,5-dimethyl-6-oxopyridine-3-carboxamide (90 mg, 38%) as a yellow solid. ES-LCMS m/z 740 [M+H]+.

Step 7: N-cyclopropyl-2-[(2-fluoro-4-iodophenyl)amino]-4-(3-methanesulfonoimidamidophenoxy)-1,5-dimethyl-6-oxopyridine-3-carboxamide

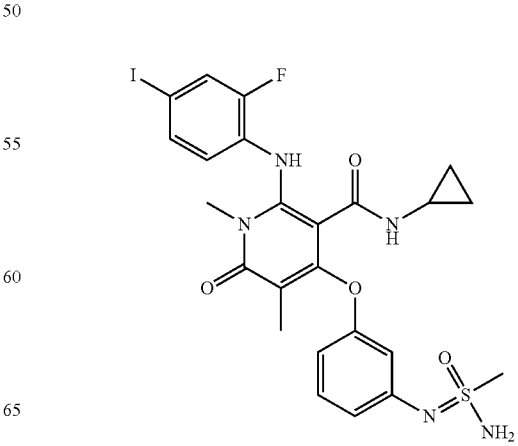

Into a 8 mL vial were added 4-{3-[N-(tert-butyldimethylsilyl)methanesulfonoimidamido]phenoxy}-N-cyclopropyl-2-[(2-fluoro-4-iodophenyl)amino]-1,5-dimethyl-6-oxopyridine-3-carboxamide (90 mg, 0.1 mmol, 1.0 equiv) and HCl (4 M in 1,4-dioxane) (1.0 mL). The reaction mixture was stirred for 30 min at room temperature. The resulting mixture was concentrated under reduced pressure. The residue was purified by Prep-HPLC (Column: YMC C18 30*150 mm, 5 um Mobile Phase A: Water (0.05% $NH_3 \cdot H_2O$), Mobile Phase B: ACN; Flow rate: 35 mL/min; Gradient: 40% B to 80% B in 8 min, Wave Length: 254/220 nm) to afford N-cyclopropyl-2-[(2-fluoro-4-iodophenyl)amino]-4-(3-methanesulfonoimidamidophenoxy)-1,5-dimethyl-6-oxopyridine-3-carboxamide (17.7 mg, 23%) as a white solid. ES-LCMS m/z 626.2.

$^1$H NMR (400 MHz, DMSO-$d_6$) δ 8.64 (s, 1H), 7.91 (d, J=3.6 Hz, 1H), 7.60-7.53 (m, 1H), 7.37-7.30 (m, 1H), 7.09-7.00 (m, 1H), 6.81-6.65 (m, 3H), 6.57-6.48 (m, 1H), 6.44-6.40 (m, 1H), 6.35-6.28 (m, 1H), 3.33 (s, 3H), 3.09 (s, 3H), 2.31-2.22 (m, 1H), 1.80 (s, 3H), 0.44-0.35 (m, 2H), 0.05-0.00 (m, 2H).

Example 10: SPR Assays

MEK-RAF Binding Assay

Compound effects on binding affinity of MEK to BRAF or CRAF were followed by surface plasmon resonance (SPR) with single-cycle kinetic analysis. GST-BRAF or GST-CRAF was immobilized onto a chip and increasing concentrations of His-tagged MEK1 were flowed over the sensor chip. 500 mM ATP was added to the running buffer. The dissociation constant for MEK1 binding to either BRAF or CRAF was calculated in the absence and presence of compound. Analyses were carried out on a Biacore 8K instrument. Sensorgrams were double-reference and DMSO corrected. Data was fit to a single-cycle kinetic model. The activity is classified as A-D, wherein A represents $IC_{50}$<100 nM; B represents 100 nM≤$IC_{50}$<1 uM; C represents 1≤$IC_{50}$<10 uM; and D represents $IC_{50}$≥10 uM.

Experimental results are provided in Table 3, below.

TABLE 3

| Compound # | uMEK/BRAF HTRF: Average IC50 (nM) |
|---|---|
| I-1 | A |
| I-2 | A |
| I-3 | A |
| I-4 | A |
| I-5 | A |
| I-6 | A |
| I-7 | A |
| I-8 | A |
| I-9 | A |
| I-62 | A |
| I-10 | A |
| I-11 | A |
| I-12 | A |
| I-13 | B |
| I-14 | B |
| I-15 | B |
| I-16 | B |
| I-59 | B |
| I-60 | B |
| I-17 | B |
| I-18 | B |
| I-19 | B |
| I-20 | B |
| I-21 | B |
| I-22 | B |
| I-23 | B |
| I-61 | B |

TABLE 3-continued

| Compound # | uMEK/BRAF HTRF: Average IC50 (nM) |
|---|---|
| I-24 | C |
| I-25 | C |
| I-26 | C |
| I-38 | A |
| I-39 | A |
| I-42 | A |
| I-43 | A |
| I-45 | A |
| I-46 | A |
| I-55 | A |
| I-78 | B |
| I-79 | B |
| I-63 | B |
| I-64 | B |
| I-86 | A |

MEK-KSR Binding Assay

Compound effects on binding affinity of MEK to KSR1 or KSR2 are followed by surface plasmon resonance (SPR) with single-cycle kinetic analysis. GST-KSR1 or GST-KSR2 is immobilized onto a chip and increasing concentrations of His-tagged MEK1 are flowed over the sensor chip. 500 mM ATP is added to the running buffer. The dissociation constant for MEK1 binding to either BRAF or CRAF is calculated in the absence and presence of compound. Analyses are carried out on a Biacore 8K instrument. Sensorgrams are double-reference and DMSO corrected. Data is fit to a single-cycle kinetic model.

Example 11: Immunoprecipitation Assay

Immunoprecipitation experiments were performed by plating about 450,000 HCT116 cells per well in 6-well plates. Cells were plated for 48 h so as to reach approximately 70% confluency before transfection. Then, 24 h after transfection, cells were treated with vehicle (0.1% DMSO) or a compound (about 200 nM) for 1 h. Cells were washed twice in cold PBS and then transferred to a pre-chilled tube in 0.6 ml of PBS solution. Cells were spun at 1,800 g in a cold centrifuge for 10 min, and supernatant was aspirated. To lyse cells, pellets were resuspended in NP-40 buffer (50 mM Tris pH 7.8, 100 mM NaCl, 0.5% (v/v) NP-40, 10% (v/v) glycerol, 1 mM EDTA) supplemented with protease and phosphatase inhibitor cocktail (Thermo Fisher, 78440) and incubated on ice for 30 min. Lysates were centrifuged for 20 min at 2,100 g, and supernatants are collected. Cleared lysates were quantified using BCA reagent (Pierce, 23225), with BSA as a standard. Five micrograms of rabbit anti-MEK1 antibody (Millipore-Sigma, 07-641), or rabbit IgG (Millipore Sigma, 12-370), was immobilized on 50 µl of Sepharose Protein A Resin (Thermo Fisher, 53139) and washed three times in 300 µl NP-40 buffer before initiating immunoprecipitations.

Next, for MEK1 immunoprecipitation, 250 µg of total cell lysate in a total volume of 0.6 ml was mixed with the pre-immobilized anti-MEK1 antibody pre-conjugated to Protein A resin. Samples were incubated at 4° C. on an end-over-end rotator for 4 h, followed by three washes in 0.6 ml volume of NP-40 buffer. Next, proteins were denatured and released from resin by the addition of 80 µl volume of 1×SDS sample buffer. Samples were boiled at 90° C. for 2 min, spun, and then applied to a 4-12% bis-tris glycine gel (Bio-Rad, 3450125) ran in MOPS-SDS buffer (Thermo Fisher, NP0001) for 60 min at 150 V. Gels were then transferred onto nitrocellulose in 20% methanol in Tris-glycine buffer (95 V, 250 A). Transfers were confirmed using Ponceau red and then analyzed by western blot. Signals for MEK, Flag-tagged proteins, BRAF, and GAPDH were detected by enhanced chemiluminescence on a ChemDoc XRS+ imaging system (Biorad). The activity is classified as A-D, wherein A represents $IC_{50}<100$ nM; B represents 100 nM≤$IC_{50}$<1 uM; C represents 1≤$IC_{50}$<10 uM; and D represents $IC_{50}$≥10 uM.

Experimental results are provided in Table 4, below.

TABLE 4

| Compound # | pERK HCT-116 (G13D) ICW (4 hour): Average IC50 (nM) |
|---|---|
| I-1 | A |
| I-2 | A |
| I-3 | A |
| I-4 | A |
| I-5 | A |
| I-6 | A |
| I-7 | A |
| I-8 | A |
| I-62 | A |
| I-10 | A |
| I-11 | B |
| I-12 | C |
| I-13 | B |
| I-15 | B |
| I-16 | B |
| I-59 | B |
| I-60 | A |
| I-17 | B |
| I-18 | C |
| I-20 | B |
| I-22 | C |
| I-23 | C |
| I-61 | B |
| I-24 | B |
| I-25 | C |
| I-26 | C |

4 Hour—PERK1/2 HTRF Assay

AsPC1 cells were seeded at 20,000 cells/well overnight in 96-well plates, then treated with a 12-point dose response of compounds (Starting dose of 3000 nM and 3-fold dilution) for 4 hours. AsPC1 cells are a K-Ras mutant cell line. Phosphorylation of ERK1/2 on residues Thr202 and Tyr204 were detected using a Homogenous Time-Resolved Fluorescence (HTRF) assay (Cisbio Cat #64ERKPEG). Briefly, ERK phosphorylation was detected using a sandwich assay format using two phospho-ERK specific antibodies, one labelled with $EU^{3+}$—Cryptate (donor) and the second with d2 (acceptor). The Fluorescence Resonance Energy Transfer (FRET) towards the d2 acceptor was detected at a wavelength of 665 nm. ERK1/2 phosphorylation levels were normalized to total ERK1/2 protein levels in each well. $IC_{50}$ values were determined by fitting a variable slope, four parameters curve to the compound concentration to normalized Phospho-ERK1/2 relationship. The activity is classified as A-D, wherein A represents $IC_{50}<100$ nM; B represents 100 nM≤$IC_{50}$<1 uM; C represents 1≤$IC_{50}$≤10 uM; and D represents $IC_{50}$≥10 uM. Experimental results are provided in Table 5 below.

TABLE 5

| Compound # | pERK AsPC-1 HTRF (4 hour): Average IC50 (nM) |
|---|---|
| I-38 | A |
| I-39 | A |
| I-42 | A |
| I-43 | A |
| I-45 | A |
| I-46 | A |
| I-55 | A |
| I-78 | C |
| I-79 | A |
| I-63 | B |
| I-64 | B |
| I-86 | A |
| I-92 | B |
| I-93 | A |
| I-94 | B |
| I-95 | A |
| I-96 | B |
| I-97 | B |
| I-98 | B |
| I-99 | A |
| I-100 | A |
| I-101 | A |
| I-102 | A |
| I-103 | A |
| I-104 | A |
| I-105 | A |
| I-106 | A |
| I-107 | A |
| I-108 | A |
| I-109 | A |
| I-110 | A |
| I-111 | A |
| I-112 | A |
| I-47 | A |
| I-113 | A |
| I-40 | A |
| I-115 | A |
| I-116 | C |
| I-117 | C |
| I-118 | A |
| I-119 | A |
| I-120 | C |
| I-121 | A |
| I-122 | B |

4 Hour—PMEK1/2 MSD Assay

AsPC1 cells were seeded at 10,000 cells/well overnight in 96-well plates, then treated with a 12-point dose response of compounds (Starting dose of 1000 nM and 3-fold dilution) for 4 hours. AsPC1 cells are a K-Ras mutant (G12D) pancreatic cancer cell line. Phosphorylation of MEK1/2 on residues Ser217 and Ser221 were detected using a MesoScale Discovery (MSD) assay (MSD Cat #K15129D-2). MEK1/2 phosphorylation levels were normalized to total MEK1/2 protein detected in each well on the same MSD plate. $IC_{50}$ values were determined by fitting a variable slope, four parameters curve to the compound concentration to normalized Phospho-MEK1/2 relationship. The activity is classified as A-D, wherein A represents $IC_{50}<100$ nM; B represents 100 nM≤$IC_{50}$<1 uM; C represents 1≤$IC_{50}$<10 uM; and D represents $IC_{50}$≥10 uM. Experimental results are provided in Table 6 below.

TABLE 6

| Compound | pMEK IC50 (nM) |
|---|---|
| I-1 | A |
| I-2 | A |

Example 12: Synthesis of 4-{2-chloro-3-[(methyl-sulfamoyl)amino]phenoxy}-N-cyclopropyl-2-[(2-fluoro-4-iodophenyl)amino]-1,5-dimethyl-6-oxopyridine-3-carboxamide (1-2)

Alternate Synthesis of I-2

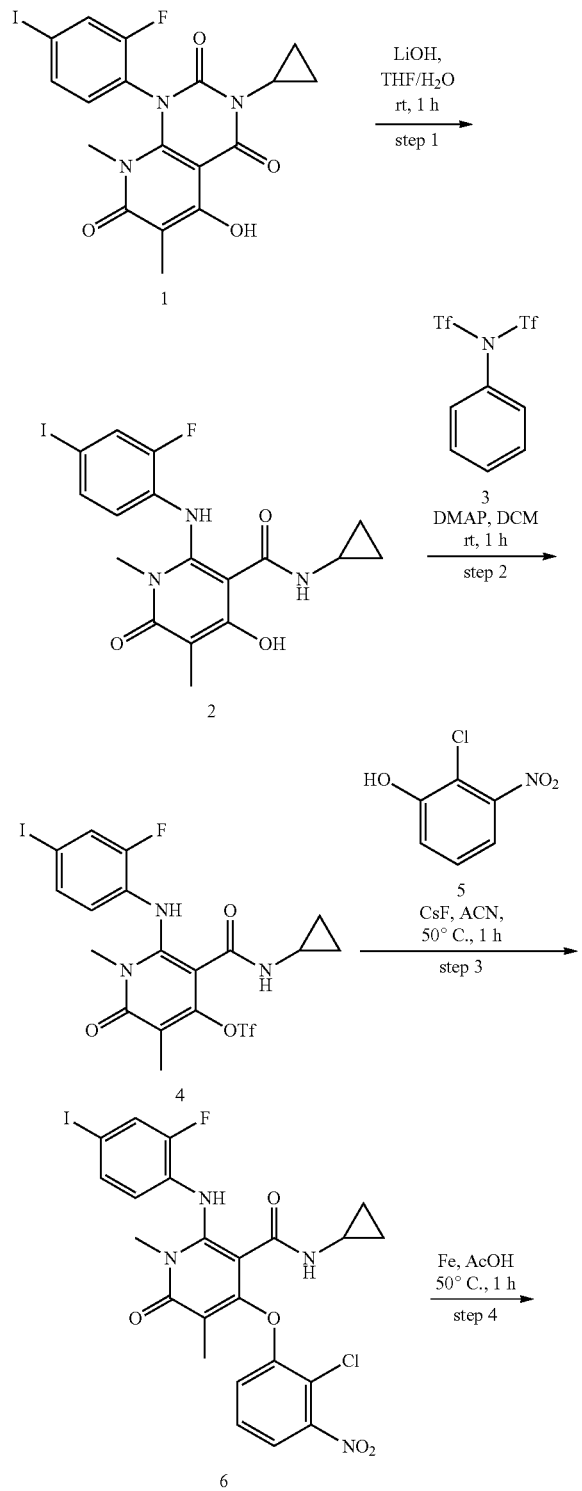

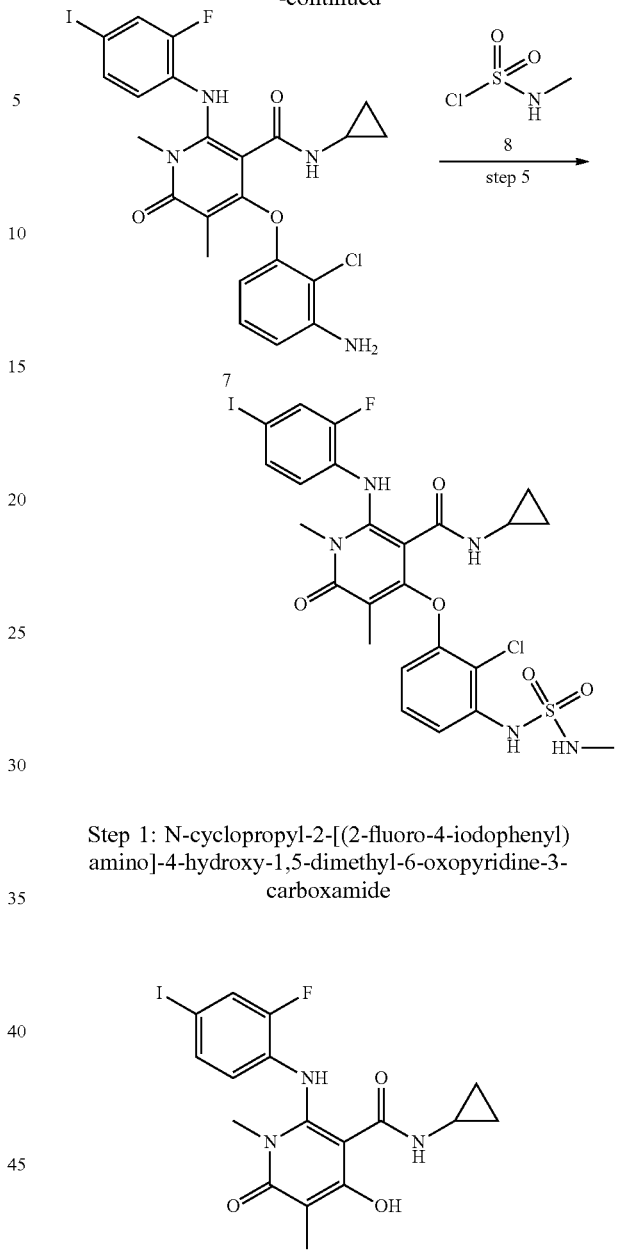

Step 1: N-cyclopropyl-2-[(2-fluoro-4-iodophenyl)amino]-4-hydroxy-1,5-dimethyl-6-oxopyridine-3-carboxamide To a stirred solution of 3-cyclopropyl-1-(2-fluoro-4-iodophenyl)-5-hydroxy-6,8-dimethylpyrido[2,3-d]pyrimidine-2,4,7-trione (8.0 g, 16 mmol, 1.0 eq) and LiOH·H$_2$O (6.9 g, 165 mmol, 10.0 eq) in THF (100 mL) were added H$_2$O (100 mL) dropwise at room temperature under air atmosphere. The resulting mixture was stirred for 30 min at room temperature under air atmosphere and reaction was monitored by LCMS. After the reaction was completed, the resulting mixture was extracted with EtOAc (3×100 mL), dried over anhydrous Na$_2$SO$_4$. After filtration, the filtrate was concentrated under reduced pressure. The residue was purified by trituration with hexane (200 mL). The precipitated solids were collected by filtration and washed with hexane (2×30 mL). This resulted in N-cyclopropyl-2-[(2-fluoro-4-iodophenyl)amino]-4-hydroxy-1,5-dimethyl-6-oxopyridine-3-carboxamide (7.5 g, 99%) as a white solid. ES-LCMS m/z 458 [M+H]$^+$.

Step 2: 3-(cyclopropylcarbamoyl)-2-[(2-fluoro-4-iodophenyl)amino]-1,5-dimethyl-6-oxopyridin-4-yl trifluoromethanesulfonate

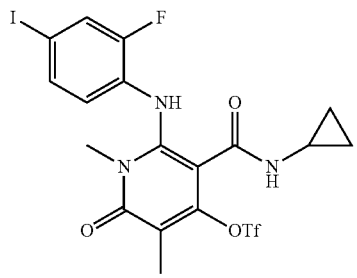 [SMILES: Cc1c(OS(=O)(=O)C(F)(F)F)c(C(=O)NC2CC2)c(Nc2ccc(I)cc2F)n(C)c1=O]

To a stirred solution of N-cyclopropyl-2-[(2-fluoro-4-iodophenyl)amino]-4-hydroxy-1,5-dimethyl-6-oxopyridine-3-carboxamide (7.2 g, 15 mmol, 1.0 eq) and DMAP (0.96 g, 7.8 mmol, 0.5 eq) in DCM (100 mL) were added 1,1,1-trifluoro-N-phenyl-N-trifluoromethanesulfonylmethanesulfonamide (8.4 g, 23 mmol, 1.5 eq) in DCM (100 mL) dropwise at 0° C. under air atmosphere. The resulting mixture was stirred for 30 min at room temperature under air atmosphere. The reaction was monitored by LCMS. After the reaction was completed, it was quenched by the addition of water (50 mL) and then extracted with EtOAc (3×100 mL). The combined organic layers were washed with brine (3×100 mL), dried over anhydrous $Na_2SO_4$. After filtration, the filtrate was concentrated under reduced pressure. The residue was purified by silica gel column chromatography, eluted with PE/THE (3:1) to afford 3-(cyclopropylcarbamoyl)-2-[(2-fluoro-4-iodophenyl)amino]-1,5-dimethyl-6-oxopyridin-4-yl trifluoromethanesulfonate (8.0 g, 86%) as a white solid.

ES-LCMS m/z 590 [M+H]$^+$.

$^1$H NMR (300 MHz, DMSO-$d_6$) δ 8.49 (s, 1H), 8.36-8.24 (m, 1H), 7.62-7.54 (m, 1H), 7.39-7.32 (m, 1H), 6.62-6.54 (m, 1H), 3.38 (s, 3H), 2.44-2.33 (m, 1H), 2.06 (s, 3H), 0.59-0.45 (m, 2H), 0.26-0.13 (m, 2H).

Step 3: 4-(2-chloro-3-nitrophenoxy)-N-cyclopropyl-2-[(2-fluoro-4-iodophenyl)amino]-1,5-dimethyl-6-oxopyridine-3-carboxamide

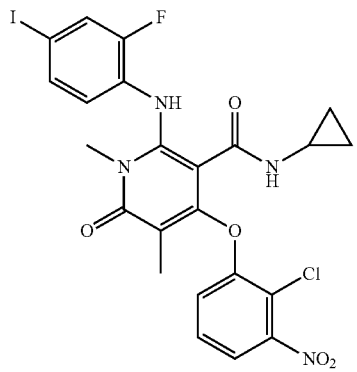

To a stirred solution of 3-(cyclopropylcarbamoyl)-2-[(2-fluoro-4-iodophenyl)amino]-1,5-dimethyl-6-oxopyridin-4-yl trifluoromethanesulfonate (11.5 g, 19 mmol, 1.0 eq) and TEA (5.9 g, 58 mmol, 3.0 eq) in ACN (200 mL) were added 2-chloro-3-nitrophenol (6.8 g, 39 mmol, 2.0 eq) dropwise at room temperature under nitrogen atmosphere. The resulting mixture was stirred for 2 h at 50° C. under nitrogen atmosphere. The reaction was monitored by LCMS. The mixture was allowed to cool down to room temperature and quenched by the addition of water (200 mL) at room temperature. The resulting mixture was extracted with EtOAc (3×100 mL). The combined organic layers were washed with brine (3×100 mL), dried over anhydrous $Na_2SO_4$. After filtration, the filtrate was concentrated under reduced pressure. Then was purified by silica gel column chromatography, eluted with PE/EA (1:1) to afford 4-(2-chloro-3-nitrophenoxy)-N-cyclopropyl-2-[(2-fluoro-4-iodophenyl)amino]-1,5-dimethyl-6-oxopyridine-3-carboxamide (6.8 g, 56%) as a white solid.

ES-LCMS m/z 613 [M+H]$^+$.

Step 4: 4-(3-amino-2-chlorophenoxy)-N-cyclopropyl-2-[(2-fluoro-4-iodophenyl)amino]-1,5-dimethyl-6-oxopyridine-3-carboxamide

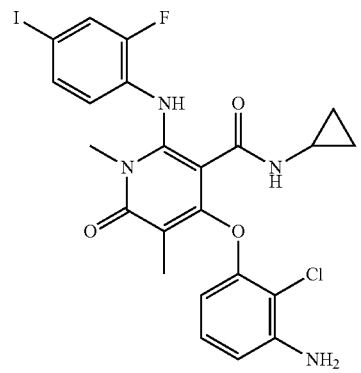 [SMILES: Cc1c(Oc2cccc([N+](=O)[O-])c2Cl)c(C(=O)NC2CC2)c(Nc2ccc(I)cc2F)n(C)c1=O]

To a stirred solution of 4-(2-chloro-3-nitrophenoxy)-N-cyclopropyl-2-[(2-fluoro-4-iodophenyl)amino]-1,5-dimethyl-6-oxopyridine-3-carboxamide (8.0 g, 13 mmol, 1.0 eq) in AcOH (50 mL) were added Fe (7.3 g, 130 mmol, 10.0 eq) in portions at 50° C. under air atmosphere. The resulting mixture was stirred for 2 h at 50° C. under air atmosphere. The reaction was monitored by LCMS. The mixture was allowed to cool down to room temperature and quenched by the addition of water (100 mL) at room temperature. The mixture was neutralized to pH 7 with saturated $NaHCO_3$. The resulting mixture was extracted with EtOAc (3×100 mL). The combined organic layers were washed with brine (1×100 mL), dried over anhydrous $Na_2SO_4$. After filtration, the filtrate was concentrated under reduced pressure. This resulted in 4-(3-amino-2-chlorophenoxy)-N-cyclopropyl-2-[(2-fluoro-4-iodophenyl)amino]-1,5-dimethyl-6-oxopyridine-3-carboxamide (6.5 g, 85%) as a white solid.

ES-LCMS m/z 583 [M+H]$^+$.

Step 5: 4-{2-chloro-3-[(methylsulfamoyl)amino]phenoxy}-N-cyclopropyl-2-[(2-fluoro-4-iodophenyl)amino]-1,5-dimethyl-6-oxopyridine-3-carboxamide

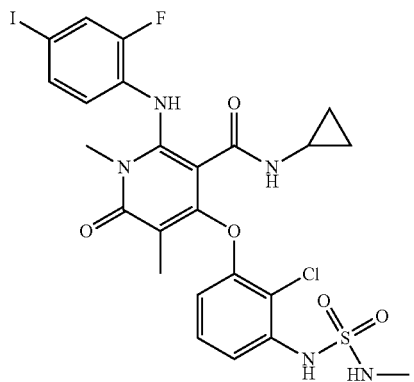 [SMILES: CNS(=O)(=O)Nc1cccc(Oc2c(C(=O)NC3CC3)c(Nc3ccc(I)cc3F)n(C)c(=O)c2C)c1Cl]

To a stirred solution of 4-(3-amino-2-chlorophenoxy)-N-cyclopropyl-2-[(2-fluoro-4-iodophenyl)amino]-1,5-dimethyl-6-oxopyridine-3-carboxamide (6.5 g, 11 mmol, 1.0 eq) and Pyridine (3.4 g, 33 mmol, 3.0 eq) in DMF (80 mL) was added N-methylsulfamoyl chloride (2.2 g, 16.7 mmol, 1.5 eq) in ACN (5 mL) dropwise at 0° C. under air atmosphere. The resulting mixture was stirred for 30 min at 0° C. under air atmosphere. The reaction was monitored by LCMS. After the reaction was completed, the reaction mixture was diluted with water. The solid was collected by filtration and then triturated with isopropyl ether (100 mL). The precipitated solids were collected by filtration to afford 4-{2-chloro-3-[(methylsulfamoyl)amino]phenoxy}-N-cyclopropyl-2-[(2-fluoro-4-iodophenyl)amino]-1,5-dimethyl-6-oxopyridine-3-carboxamide (5.3 g, 71%) as a white solid.

ES-LCMS m/z 676.2 [M+H]$^+$.

1H NMR (300 MHz, Methanol-$d_4$) δ 7.53-7.43 (m, 1H), 7.43-7.29 (m, 2H), 7.14 (t, J=8.3 Hz, 1H), 6.60 (t, J=8.6 Hz, 1H), 6.52-6.42 (m, 1H), 3.53 (s, 3H), 2.63 (s, 3H), 2.24-2.10 (m, 1H), 1.92 (s, 3H), 0.52-0.43 (m, 2H), 0.09-0.03 (m, 2H).

Example 13: Pharmacokinetic Studies

Exemplary compounds were tested to determine their pharmacokinetic properties in mice using cassette dosing protocols. Assay procedures and results are described below.

Part I—Procedures for Cassette Pharmacokinetics Studies

Pharmacokinetics studies were conducted using cassette dosing protocols, with test compounds administered per mouse. Treatment groups were 3 mice (~6-8 weeks old, ~20-30 g Balb/c male mice) per route of administration. Compounds were formulated in 5% DMSO and 95% PEG400 with final concentrations of 0.5 mg/mL for IV and PO dosing. Compounds were dosed at 2 mg/kg for IV dosing and 5 mg/kg for PO dosing. Blood samples were withdrawn at 0.083, 0.25, 0.5, 1.0, 2.0, 4.0, 6.0, 8.0, and 24 hours following IV dosing, and 0.25, 0.5, 1.0, 2.0, 4.0, 6.0, 8.0, and 24 hours following PO dosing. Blood samples were centrifuged at 4,000 g for 5 minutes at 4° C. to obtain plasma samples. Plasma samples were diluted with acetonitrile containing internal standard, vortexed for 30 seconds, then centrifuged at 4,000 rpm for 15 minutes at 4° C. The supernatant was diluted with water, and compound concentration was determined by HPLC/MS/MS compared to calibration standards of 0.5-1,000 ng/mL.

Part II— Results

Experimental results are provided in Table 7, below. Where route is listed as "IV*", the compound was dosed IV at 1 mg/kg.

TABLE 7

| Compound No. | Species | Route | Dose (mg/kg) | $C_{max}$ (ng/mL) | $t_{max}$ (h) | $t_{1/2}$ (h) | Vdss (L/kg) | Cl (mL/min/kg) | $AUC_{0\text{-}last}$ (ng * h/mL) | $AUC_{0\text{-}inf}$ (ng * h/mL) |
|---|---|---|---|---|---|---|---|---|---|---|
| 1-1 | Mouse | PO | 5 | 432 | 0.4 | 11.6 | | | 614 | 635 |
| 1-1 | Mouse | IV | 2 | | | 1.67 | 3.2 | 74.9 | 452 | 455 |
| 1-1 | Rat | IV | 0.2 | | | 2.4 | 4.2 | 31.9 | 100 | 107 |
| 1-2 | Mouse | PO | 5 | 1660 | 0.5 | 7.99 | | | 3956 | 4042 |
| 1-2 | Mouse | IV | 2 | | | 1.04 | 1.3 | 17.2 | 1939 | 1947 |
| 1-2 | Rat | IV | 1 | | | 4.22 | 2.2 | 16.6 | 1071 | 1077 |
| 1-37 | Mouse | PO | 5 | 1733 | 1.7 | 1.99 | | | 12898 | 12903 |
| 1-40 | Mouse | PO | 5 | 783 | 0.8 | 1.82 | | | 2751 | 2937 |
| 1-41 | Mouse | PO | 5 | 1263 | 0.5 | 1.62 | | | 3335 | 3472 |
| 1-42 | Mouse | PO | 5 | 418 | 0.4 | 1.11 | | | 506 | 511 |
| 1-42 | Rat | IV | 1 | | | 2.09 | 9.9 | 76.8 | 205 | 217 |
| 1-43 | Mouse | PO | 5 | 488 | 0.3 | 3.92 | | | 763 | 803 |
| 1-46 | Mouse | PO | 5 | 1427 | 0.6 | 2.8 | | | 3770 | 3799 |
| 1-46 | Rat | IV | 1 | | | 1.86 | 1 | 10.5 | 1546 | 1593 |
| 1-54 | Mouse | PO | 5 | 1670 | 0.5 | 1.6 | | | 4386 | 4541 |
| 1-55 | Mouse | PO | 5 | 801 | 0.4 | 1.58 | | | 1088 | 1094 |
| 1-64 | Mouse | PO | 5 | 231 | 0.8 | 2.1 | | | 492 | 505 |
| 1-112 | Mouse | PO | 5 | 979 | 1.3 | 2.27 | | | 5370 | 5830 |
| 1-133 | Mouse | PO | 5 | 41.2 | 0.2 | 0.4 | | | 27 | 28 |

Example 14: In Vivo Efficacy Studies Using Human MIA PaCa-2 Xenografts in Mice The antitumor activity of MEK inhibitor compounds was evaluated in vivo using a human cell line derived xenograft grown from MIA PaCa-2 cell line in immunodeficient mice. MIA PaCa-2 cells are a K-Ras mutant (G12C) pancreatic tumor cell line. The tumor cell lines are maintained in vitro as monolayer culture in medium at 37° C. in an atmosphere of 500 $CO_2$ in air. The tumor cells are routinely sub-cultured before confluence by trypsin-EDTA treatment, not to exceed 4-5 passages. The cells growing in an exponential growth phase are harvested for tumor inoculation. MIA PaCa-2 tumor cells ($1 \times 10^6$ cells) are implanted into Nu/Nu nude mice subcutaneously on the right flank with tumor cells in a 1:1 mixture with matrigel. Tumors are allowed to grow to approximately 250 mm³. At this time, mice are assigned to groups such that the mean tumor volume is the same for each treatment group (n=8 mice/group). Compounds are administrated to the tumor-bearing mice via QD oral gavage at a dose of 1 mg/kg. After 10 days of dosing, when tumors in the vehicle control mice reach the ethical endpoint (mean tumor volume >1500 mm³), all the mice are sacrificed and final measurements are recorded. Throughout the study, mouse body weight and tumor volume are recorded. The measurement of tumor size is conducted twice weekly with a caliper and recorded. The tumor volume (mm³) is estimated using the formula: $TV=a \times b^2/2$, where "a" and "b" are long and short diameters of a tumor, respectively.

Percent tumor growth inhibition (TGI) for exemplary MEK inhibitors, including I-2, as determined on day 10, was shown to be 86.2%, 96.2%, and 82.3%. The average body weight loss observed on day 10 for the exemplary MEK inhibitors, including I-2, was 5.5%, 2.5%, and 3.8%, respectively.

Example 15: Stabilization of MEK1-CRAF Complex Assay

Exemplary MEK inhibitor compounds were tested to determine effect of MEK inhibitor compounds in stabilizing MEK1-CRAF complex, by comparing the dissociation constants ($K_D$) of MEK1 and CRAF in the absence and presence of exemplary MEK inhibitor compounds.

Part I. Experimental Procedure

Preparation of 4×stocks of reagents: all reagents were diluted in AlphaLISA buffer. MEK1 was diluted to 4 nM, and nickel chelate donor beads and glutathione acceptor beads were diluted to 80 μg/mL. CRAF was diluted to a top concentration of 160 nM, which was subsequently diluted to 80, 40, 20, 10, 5, 2.5, 1.25, and 0.625 nM through 1:2 serial dilution.

Exemplary MEK inhibitor compounds (0, 0.01, 0.1, or 1 μM) were added to a 384-AlphaPlate (PerkinElmer, 6008350) by a digital liquid dispenser (Tecan D300e) based on a total volume of 20 μL reaction mixture.

5 μL 4× MEK1 stock solution was added to wells A1-P20 by multichannel pipettes. The plate was sealed with clear olefin sealing tape (Thermo Scientific, 232701), centrifuged at 1000 rpm for 1 minute, and incubated at room temperature for 30 minutes.

5 μL 4× CRAF stock solution at different concentrations or 5 μL or 10 μL AlphaLISA buffer was added by multichannel pipettes. The plate was sealed, centrifuged at 1000 rpm for 1 minute, and incubated at room temperature for 60 minutes.

5 μL 4× glutathione acceptor beads were first added to all wells by multichannel pipettes. The ambient light was subsequently adjusted to <100 lux (light meter) before adding 5 μL 4× nickel chelate donor beads to the same wells. From this step on, the plate was covered with a black plate cover, centrifuged at 1000 rpm for 1 minute, and incubated at room temperature for 60 minutes.

Part II. Data Collection

Data were collected on a PHERAStar FSX (BMG LABTECH) using the AlphaLISA module (excitation: 680 nm, emission: 615 nm), with a gain of 3600. The excitation time was 0.30 seconds, and data collection started after a 0.04-second delay for a total integration time of 0.60 seconds.

Part III. Data Analysis

The individual AlphaLISA counts of wells with exemplary MEK inhibitor compound were divided by the average AlphaLISA counts of wells without compound to obtain AlphaLISA signal/background ratio (S/B). The dissociation constant ($K_D$) of MEK1-CRAF was calculated using non-linear regression curve fit in GraphPad PRISM® 9.0 software.

Part IV. Results

Experimental results are provided in Table 8, below. The corresponding KD ratios of the compounds (0.01, 0.1, or 1 μM) to DMSO were calculated and are provided in Table 8, below. The symbol n represents the number of independent experiments run for each exemplary MEK inhibitor compound. Data from multiple experiments using the same compound were averaged and treated as a single value (compound I-1 has an n of 3, compound I-2 has an n of 7; compound I-45 has an n of 3; compound I-45 has an n of 3; compound I-43 has an n of 3; compound I-55 has an n of 3; compound I-41 has an n 3; compound I-54 has an n of 3; and compound I-40 has an n of 3).

TABLE 8

| Compound No. | Treatment (μM) | $K_D$ (nM) | $K_D$ Ratio (mean) | SD ($K_D$ ratio) |
|---|---|---|---|---|
| I-1 | 0 | 1.00 | 1.00 | N/D |
| I-1 | 0.01 | 0.80 | 0.80 | 0.01 |
| I-1 | 0.1 | 0.55 | 0.55 | 0.02 |
| I-1 | 1 | 0.42 | 0.42 | 0.01 |
| I-2 | 0 | 1.00 | 1.00 | N/D |
| I-2 | 0.01 | 0.63 | 0.63 | 0.09 |
| I-2 | 0.1 | 0.44 | 0.44 | 0.07 |
| I-2 | 1 | 0.37 | 0.37 | 0.05 |
| I-45 | 0 | 1.00 | 1.00 | N/D |
| I-45 | 0.01 | 0.62 | 0.62 | 0.05 |
| I-45 | 0.1 | 0.42 | 0.42 | 0.05 |
| I-45 | 1 | 0.38 | 0.38 | 0.03 |
| I-42 | 0 | 1.00 | 1.00 | N/D |
| I-42 | 0.01 | 0.78 | 0.78 | 0.03 |
| I-42 | 0.1 | 0.57 | 0.57 | 0.04 |
| I-42 | 1 | 0.57 | 0.57 | 0.12 |
| I-43 | 0 | 1.00 | 1.00 | N/D |
| I-43 | 0.01 | 0.69 | 0.69 | 0.10 |
| I-43 | 0.1 | 0.52 | 0.52 | 0.04 |
| I-43 | 1 | 0.51 | 0.51 | 0.05 |
| I-55 | 0 | 1.00 | 1.00 | N/D |
| I-55 | 0.01 | 0.76 | 0.76 | 0.00 |
| I-55 | 0.1 | 0.58 | 0.58 | 0.03 |
| I-55 | 1 | 0.51 | 0.51 | 0.04 |
| I-41 | 0 | 1.00 | 1.00 | N/D |
| I-41 | 0.01 | 0.79 | 0.79 | 0.05 |
| I-41 | 0.1 | 0.57 | 0.57 | 0.05 |
| I-41 | 1 | 0.48 | 0.48 | 0.04 |
| I-54 | 0 | 1.00 | 1.00 | N/D |
| I-54 | 0.01 | 0.58 | 0.58 | 0.02 |
| I-54 | 0.1 | 0.36 | 0.36 | 0.01 |
| I-54 | 1 | 0.35 | 0.35 | 0.05 |
| I-40 | 0 | 1.00 | 1.00 | N/D |
| I-40 | 0.01 | 0.87 | 0.87 | 0.08 |
| I-40 | 0.1 | 0.62 | 0.62 | 0.08 |
| I-40 | 1 | 0.47 | 0.47 | 0.08 |

*N/D is not determined

Example 16: In Vivo Efficacy Studies Using Human Xenografts in Mice

The antitumor activity of exemplary MEK inhibitor compounds is evaluated in vivo using human cell line derived xenografts (CDX) grown in immunodeficient mice. For these studies, AsPC1 (pancreatic cell line with KRAS G12D mutation), NCI-H2122 (lung cell line with KRAS G12C mutation), and 5637 (bladder cell line with CRAF amplification) models are used. In addition, HCT-116 (colorectal cell line with KRAS G13D mutation), SKM-1 (AML cell line with KRAS K117N mutation), and OCI-AML-3 (AML cell line with NRAS Q61L mutation) models are used. The tumor cell lines (AsPC-1, NCI-H2122, 5637, and HCT-116 cells) are maintained in vitro as monolayer culture in medium at 37° C. in an atmosphere of 5% $CO_2$ in air. The tumor cell lines (SKM-1 and OCI-AML-3 cells) are maintained in vitro as a suspension in medium at 37° C. in an atmosphere of 5% CO2 in air. The tumor cells are routinely sub-cultured before confluence by trypsin-EDTA treatment, not to exceed 4-5 passages. The cells growing in an exponential growth phase are harvested for tumor inoculation. AsPC1, NCI-H2122, and OCI-AML-3 tumors are implanted into Balb/c nude mice. HCT-116 tumors are implanted into Nu/Nu mice. 5637 and SKM-1 tumors are implanted into NOG mice. Each mouse is inoculated subcutaneously on the right flank with tumor cells in a 1:1 mixture with matrigel. Tumors are allowed to grow to approximately 150-200 $mm^3$. At this time, mice are assigned to groups such that the mean tumor volume is the same for each treatment group. The MEK inhibitor compound treatments are administrated to the tumor-bearing mice via oral gavage. Throughout the study, mouse body weight and tumor volume are recorded. The measurement of tumor size is conducted twice weekly with a caliper and recorded. The tumor volume ($mm^3$) is estimated using the formula: $TV = a \times b^2 / 2$, where "a" and "b" are long and short diameters of a tumor, respectively.

In the AsPC-1 model, exemplary MEK inhibitor I-2 was treated at 3 mg/kg QD and a percent TGI (tumor growth inhibition) on Day 21 of 83.4% was observed. The average body weight gain observed on Day 21 was 2.4%.

In the NCI-H2122 model, exemplary MEK inhibitor 1-2 was treated at 3 mg/kg QD and a percent TGI on Day 31 of 104% was observed. The average body weight loss observed on Day 31 was 1.5%.

In the 5637 model, exemplary MEK inhibitor I-2 was treated at 3 mg/kg QD and a percent TGI on Day 21 of 111% was observed. The average body weight loss observed on Day 21 was 6.8%.

In the HCT-116 model, exemplary MEK inhibitor I-2 was treated at 2 mg/kg QD, 3 mg/kg QOD or 6 mg/kg QOD and a percent TGIs on Day 20 of 102.9%, 98.1%, and 98%, respectively, were observed. The average body weight gain observed on Day 20 was 4%, 5.5%, and 12.1%, respectively.

In the SKM-1 model, exemplary MEK inhibitor I-2 was treated at 1 mg/kg QD, 3 mg/kg QD or 6 mg/kg QOD and venetoclax was treated at 100 mg/kg QD and a percent TGIs on Day 22 of 97.7%, 98.4%, 96.2%, and 46.6% respectively, were observed. The average body weight loss observed on Day 22 for the 3 mg/kg QD group was 1.2%, whereas weight gain was observed in 1 mg/kg QD, 6 mg/kg QOD and venetoclax groups (1.2%, 3.9, and 7.5%, respectively).

In the OCI-AML-3 model, exemplary MEK inhibitor I-2 was treated at 1 mg/kg QD, 3 mg/kg QD or 6 mg/kg QOD, and venetoclax was treated at 100 mg/kg QD and a percent TGIs on Day 15 of 94.8, 98.6, 95.2, and 13% respectively, were observed. The average body weight loss observed on Day 15 for the 1 and 3 mg/kg QD group was 2.9% and 7.8%, respectively, whereas weight gain was observed in 6 mg/kg QOD and venetoclax groups (3.3% and 8.3%, respectively).

Example 17: Assay to Assess Stabilization of MEK1-BRAF and CRAF Complexes

Exemplary MEK inhibitor compounds were tested to determine effect of MEK inhibitor compounds in stabilizing MEK1-CRAF complex, by comparing the dissociation constants ($K_D$) of MEK1 and CRAF in the absence and presence of exemplary MEK inhibitor compounds.

Part I. Experimental Procedure

Preparation of 4× stocks of reagents: all reagents were diluted in AlphaLISA buffer (50 mM HEPES (pH 7.4), 100 mM NaCl, 0.5% TRITON X-100, 0.5% BSA and 200 nM AMP-PNP). MEK1 was diluted to 4 nM, and nickel chelate donor beads and glutathione acceptor beads were diluted to 80 μg/mL. GST-tagged BRAF (433-726) and CRAF (306-648, Y340D, Y341D) was diluted to a top concentration of 160 nM, which was subsequently diluted to 80, 40, 20, 10, 5, 2.5, 1.25, and 0.625 nM through 1:2 serial dilution.

Exemplary MEK inhibitor compounds (0, 0.01, 0.1, or 1 μM) were added to a 384-AlphaPlate (PerkinElmer, 6008350) by a digital liquid dispenser (Tecan D300e) based on a total volume of 20 μL reaction mixture.

5 μL 4× MEK1 stock solution was added to wells A1-P20 by multichannel pipettes. The plate was sealed with clear olefin sealing tape (Thermo Scientific, 232701), centrifuged at 1000 rpm for 1 minute, and incubated at room temperature for 30 minutes.

5 μL 4× BRAF or CRAF stock solution at different concentrations or 10 μL AlphaLISA buffer (background) were added to the plates. The plate was sealed, centrifuged at 1000 rpm for 1 minute, and incubated at room temperature for 60 minutes.

5 μL 4× glutathione acceptor beads were first added to all wells by multichannel pipettes. The ambient light was subsequently adjusted to <100 lux (light meter) before adding 5 μL 4× nickel chelate donor beads to the same wells. From this step on, the plate was covered with a black plate cover, centrifuged at 1000 rpm for 1 minute, and incubated at room temperature for 60 minutes.

Part II. Data Collection

Data were collected on a PHERAStar FSX (BMG LABTECH) using the AlphaLISA module (excitation: 680 nm, emission: 615 nm), with a gain of 3600. The excitation time was 0.30 seconds, and data collection started after a 0.04-second delay for a total integration time of 0.60 seconds.

Part III. Data Analysis

The individual AlphaLISA counts of wells with exemplary MEK inhibitor compound were divided by the average AlphaLISA counts of wells without compound to obtain AlphaLISA signal/background ratio (S/B). The dissociation constant ($K_D$) of MEK1-BRAF or MEK1-CRAF was calculated using nonlinear regression curve fit in GraphPad PRISM® 9.0 software.

Part IV. Results

Experimental results showing mean KD Ratios of MEK1-BRAF or MEK1-CRAF in the absence and presence of exemplary MEK inhibitor compounds, such as I-2, are provided in Table 9, below. The corresponding KD ratios of the compounds (0.01, 0.1, or 1 μM) to DMSO were calculated and are provided in Table 9, below. The data demonstrates that I-2 stabilizes the MEK-RAF complex in an inactive conformation, locking in the αC-helix of MEK in an inactive form.

TABLE 9

| RAF | Compound | Mean ($K_{D,I-2}/K_{D,DMSO}$) | SD ($K_{D,I-2}/K_{D,DMSO}$) |
|---|---|---|---|
| BRAF (n = 9) | 0 μM I-2 (DMSO) | 1.00 | / |
|  | 0.01 μM I-2 | 0.86 | 0.09 |
|  | 0.1 μM I-2 | 0.78 | 0.08 |
|  | 1 μM I-2 | 0.66 | 0.13 |
| CRAF (n = 7) | 0 μM I-2 (DMSO) | 1.00 | / |
|  | 0.01 μM I-2 | 0.63 | 0.09 |
|  | 0.1 μM I-2 | 0.44 | 0.07 |
|  | 1 μM I-2 | 0.37 | 0.05 |

Example 18: Surface Plasmon Resonance (SPR) Assay Binding Kinetics Testing

The binding kinetics of exemplary MEK inhibitor compounds, I-2 and avutometinib (VS6766) to unphosphorylated MEK1 were tested and compared using SPR.

Part I: Experimental Procedures

The binding kinetics experiments were performed on Biacore S200 (Cytiva).

Biotinylated, unphosphorylated MEK1 was diluted to 1 uM by SPR buffer A (50 mM Tris-HCl (pH 7.6), 150 mM NaCl, 0.05% Tween 20, 10 mM MgCl2) and immobilized on sensor chip CAP, with 300 second injection of the biotin capture reagent followed by 900 second injection of 1 uM MEK1, both at a flow rate of 2 µL/min, to reach an immobilization level of 2500-3000 RU.

Exemplary MEK inhibitor compounds, I-2 and avutometinib (VS6766) were diluted to a concentration of 0.411, 1.23, 3.70, 11.1, 33.3, 100 nM in SPR buffer B (50 mM Tris-HCl (pH 7.6), 150 mM NaCl, 0.05% Tween 20, 10 mM MgCl2, 50 µM ATP, 1 mM DTT and 2% DMSO) and injected over the chip in a single cycle kinetic (SCK) mode with SPR buffer B as the running buffer, at a flow rate of 30 µL/min and with a 90 second on-time and a 1200 second (I-2) or 600 second (avutometinib (VS6766)) off-time.

The resultant sensorgrams were double-referenced, DMSO-calibrated, and fitted to obtain kinetic parameters of compound binding in the Biacore S200 evaluation software using the 1:1 binding model and accounting for the surface drift.

Part II. Results

The results from the above-described assays are shown in Table 10 and demonstrate that I-2 binds to MEK with much slower off-rate kinetics when compared to avutometinib (VS-6766).

TABLE 10

| Compound | $k_{on}$ (M$^{-1}$ s$^{-1}$) | $k_{off}$ (s$^{-1}$) | $K_D$ (nM) |
|---|---|---|---|
| I-2 | 8.24E+04 | 6.09E−04 | 7.39 |
| Avutometinib (VS6766) | 1.69E+05 | 7.08E−03 | 41.8 |

The stabilization effect of I-2 and avutometinib (VS6766) on MEK1-CRAF complex were tested and compared using SPR.

Part I: Experimental Procedures

The experiments were performed on Biacore S200 (Cytiva). Biotinylated, unphosphorylated MEK1 was diluted to 0.1 uM by SPR buffer C (20 mM Tris-HCl (pH 7.4), 150 mM NaCl, 0.05% Tween 20, 10 mM MgCl2) and immobilized on sensor chip SA to reach an immobilization level of 60-100 RU.

Tag-free CRAF (306-648, Y340D, Y341D) were diluted to a concentration of 3.75, 7.5, 15, 30, 60, 120 nM, and I-2 and avutometinib (VS6766) were diluted to 50 nM in SPR buffer D (20 mM Tris-HCl (pH 7.4), 150 mM NaCl, 0.05% Tween 20, 10 mM MgCl2, and 1% DMSO). I-2 or avutometinib (VS6766) was first injected over the chip surface at 30 µL/min with a 60 second on-time and 0 second off-time, followed by injection of CRAF in a single cycle kinetic (SCK) mode, at a flow rate of 30 µL/min and with a 60 second on-time and a 900 second off-time.

The resultant sensorgrams were double-referenced and fitted to obtain kinetic parameters of MEK1-CRAF complex formation in the presence of exemplary MEK inhibitor compounds in the Biacore 5200 evaluation software using the two-state reaction model.

Part II. Results

The results from the above-described assays are shown in Table 11 and demonstrate that I-2 induces a more stable MEK-CRAF complex when compared to avutometinib (VS-6766).

TABLE 11

| Compound | $K_D$ (nM) | $k_{on,1}$ (M$^{-1}$s$^{-1}$) | $k_{off,1}$ (s$^{-1}$) | $k_{on,2}$ (s$^{-1}$) | $k_{off,2}$ (s$^{-1}$) |
|---|---|---|---|---|---|
| I-2 | 0.144 | 1.16E+6 | 6.28E−3 | 2.41E−3 | 6.59E−5 |
| avutometinib (VS6766) | 2.22 | 1.64E+6 | 1.52E−2 | 1.26E−3 | 3.94-4 |

Example 19: ARAF-, BRAF-, and CRAF-MEK Stabilization in Cells

The stabilization of ARAF, BRAF and CRAF in complex with MEK in MEK immunoprecipitates isolated from cellular lysates. For these studies, HCT-116 (colorectal cell line with KRAS G13D mutation), SKMEL-2 (melanoma cell line with NRAS Q61K mutation), HT-29 (colorectal cell line with BRAF Class I mutation), NCI-H1755 (lung cancer cell line with BRAF Class II mutation), and NCI-H1666 (lung cancer cell line with BRAF Class III mutation) models are used. The tumor cell lines are maintained in vitro as monolayer culture in medium at 37° C. in an atmosphere of 5% $CO_2$ in air. Cell lines are treated with exemplary MEK inhibitors at a concentration of 3 nM for 4 hours. Cells are lysed and MEK is immunoprecipitated from the lysates overnight. Denatured immunoprecipitates are run on SDS-PAGE, transferred to nitrocellulose membranes and associated ARAF, BRAF, or CRAF are detected by Western analysis. Stabilization was defined as >1.5-fold induction of RAF-MEK interaction over vehicle control.

The association of ARAF with MEK in HCT-116 and NCI-H1755 cells was enhanced following 4 hours of treatment with the exemplary MEK inhibitor, I-2. Wild-type BRAF-MEK association was augmented in HCT-116 and SKMEL-2 cells, whereas mutant BRAF-MEK interaction was enhanced in HT-29 (BRAF Class I), NCI-H1755 (BRAF Class II), and NCI-H1666 (BRAF Class III) following treatment with exemplary MEK inhibitor, I-2. MEK inhibitor-induced MEK-CRAF stabilization was observed in HCT-116 and NCI-H1666 cells with exemplary MEK inhibitor, I-2.

Example 20: MEK Inhibitor Sensitivity in KRAS, NRAS and BRAF Class I and III Mutant and CRAF-Altered Cell Lines 240 cell lines representative of multiple cancer indications with known alterations in the MAPK pathway, including KRAS, NRAS, HRAS, NF1, EGFR, BRAF and CRAF mutations, were seeded overnight in 386-well plates, then treated with a 9-point dose response of exemplary MEK inhibitors (starting dose of 100 nM and 3-fold dilution) for 5 days. Cell viability was determined using a Cell Titer Glo (CTG) assay. Percent inhibition was calculated for all compounds utilizing staurosporine (1000 nM) treatment as a measure of maximal inhibition. $IC_{50}$ and area under the curve (AUC) values were determined by fitting a variable slope, four parameters curve to the compound concentration to percent inhibition relationship.

Compared to RAS/RAF wild-type cell lines, increased sensitivity to MEK inhibitors, such as I-2, was observed in cell lines with KRAS, NRAS, BRAF Class I and III mutations, as well as CRAF-alterations (both CRAF mutations and fusions). Cell lines with mutations in PIK3CA, PTEN, NF1, EGFR and HRAS showed similar sensitivity to MEK inhibition to RAS/RAF wild-type cell lines.

Example 21: Evaluation of In Vitro MEK Inhibitor Drug Combinations

The combination synergy between the exemplary MEK inhibitor, I-2, and KRAS G12C, Pan-RAF, SOS1, SHP2, PI3Kα, and mTOR, and a monoclonal antibody to EGFR was assessed in cancer cell lines. Cells were plated in 384-well plates and treated with increasing doses of the exemplary MEK inhibitor, I-2, (Max dose 100 nM, 10-fold dilution) and combination inhibitor (Max dose 1000 nM, 3-fold dilution) for 5 days. Cell viability was determined by Cell Titer Glo assay. Normalized Loewe sum of synergy scores for the combinations were determined using the ComBenefit software (Di Veroli G Y et al. Combenefit: an interactive platform for the analysis and visualization of drug combinations. Bioinformatics 2016). A normalized Loewe sum of synergy score of >10 was considered synergistic, <10, but >−10 additive, and <−10 antagonistic. Experimental results for all combinations are provided in Table 12.

TABLE 12

| Combination Target | Inhibitor | Cell Lines | Loewe Synergy Score > 10 |
|---|---|---|---|
| KRAS G12C | Sotorasib | NCI-H358, NCI-H1373, | 4/5 cell lines |
| | Adagrasib | NCI-H2122, MiaPACA2, NCI-H2030 | 4/5 cell lines |
| Pan-RAF | LXH254 | AsPC-1, HPAF, MiaPACA2, NCI-H1373, NCI-H2122, PANC03276 | 6/6 cell lines |
| | Lifirafenib | NCI-H358, NCI-H1373, NCI-H2122 | 3/3 cell lines |
| SOS1 | BI3406 | AsPC-1, HPAF, MiaPACA2, NCI-H1373, NCI-H2122, PANC03276 | 4/6 cell lines |
| SHP2 | RMC-4550 | AsPC-1, HPAF, MiaPACA2, NCI-H1373, NCI-H2122, PANC03276 | 3/6 cell lines |
| PI3Kα | Inavolisib | AsPC-1, HPAF, MiaPACA2, NCI-H1373, NCI-H2122, PANC03276 | 5/6 cell lines |
| mTOR | Everolimus | AsPC-1, HPAF, MiaPACA2, NCI-H1373, NCI-H2122, PANC03276 | 5/6 cell lines |
| EGFR | Cetuximab | HCA7, HCT-116, SW620, SW48, CACO2, DLD-1, RKO, HT-29 | 6/8 cell lines |

While a number of embodiments of this disclosure are described, it is apparent that the basic examples may be altered to provide other embodiments that utilize the compounds and methods of this disclosure. Therefore, it will be appreciated that the scope of this disclosure is to be defined by the application and appended claims rather than by the specific embodiments that have been represented by way of example.

INCORPORATION BY REFERENCE

The entire disclosure of each of the patent documents and scientific articles referred to herein is incorporated by reference for all purposes.

EQUIVALENTS

The disclosure may be embodied in other specific forms without departing from the spirit or essential characteristics thereof. The foregoing embodiments are therefore to be considered in all respects illustrative rather than limiting the disclosure described herein. Scope of the disclosure is thus indicated by the appended claims rather than by the foregoing description, and all changes that come within the meaning and range of equivalency of the claims are intended to be embraced therein.

What is claimed is:

1. A compound selected from:

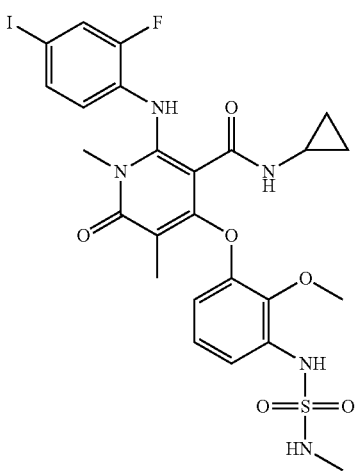 [SMILES: CNS(=O)(=O)Nc1cccc(Oc2c(C(=O)NC3CC3)c(Nc3ccc(I)cc3F)n(C)c(=O)c2C)c1OC]

I-1

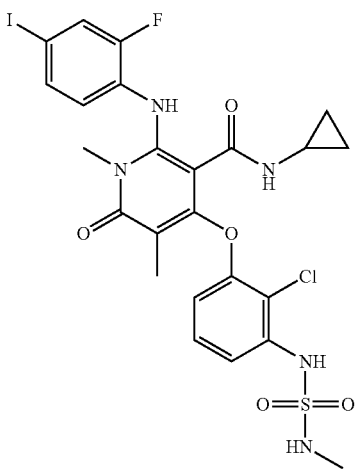 [SMILES: CNS(=O)(=O)Nc1cccc(Oc2c(C(=O)NC3CC3)c(Nc3ccc(I)cc3F)n(C)c(=O)c2C)c1Cl]

I-2

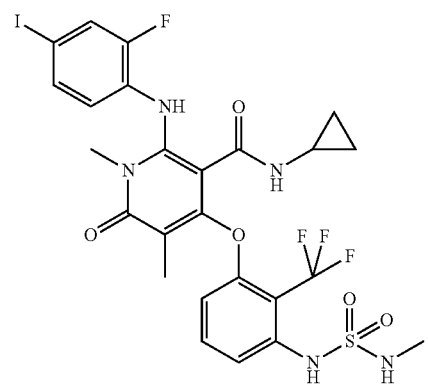 [SMILES: CNS(=O)(=O)Nc1cccc(Oc2c(C(=O)NC3CC3)c(Nc3ccc(I)cc3F)n(C)c(=O)c2C)c1C(F)(F)F]

I-37

-continued
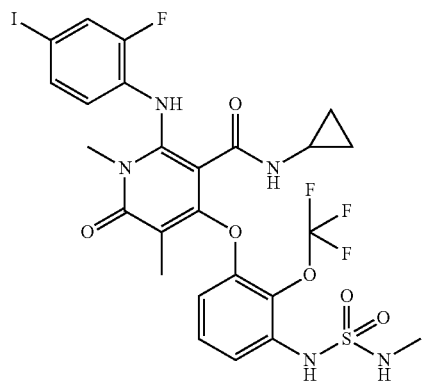 [SMILES: CNS(=O)(=O)Nc1cccc(Oc2c(C(=O)NC3CC3)c(Nc3ccc(I)cc3F)n(C)c(=O)c2C)c1OC(F)(F)F]
I-40
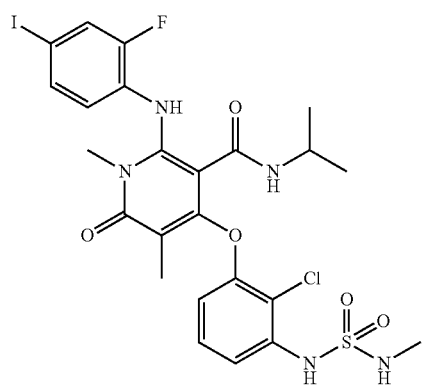 [SMILES: CNS(=O)(=O)Nc1cccc(Oc2c(C(=O)NC(C)C)c(Nc3ccc(I)cc3F)n(C)c(=O)c2C)c1Cl]
I-41
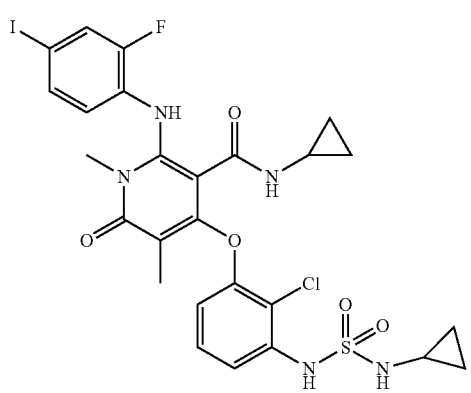 [SMILES: Cc1c(Oc2cccc(NS(=O)(=O)NC3CC3)c2Cl)c(C(=O)NC2CC2)c(Nc2ccc(I)cc2F)n(C)c1=O]
I-42
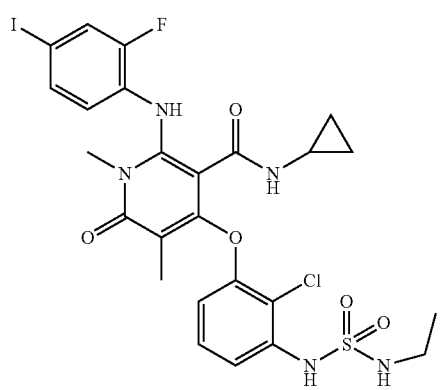 [SMILES: CCNS(=O)(=O)Nc1cccc(Oc2c(C(=O)NC3CC3)c(Nc3ccc(I)cc3F)n(C)c(=O)c2C)c1Cl]
I-43
-continued
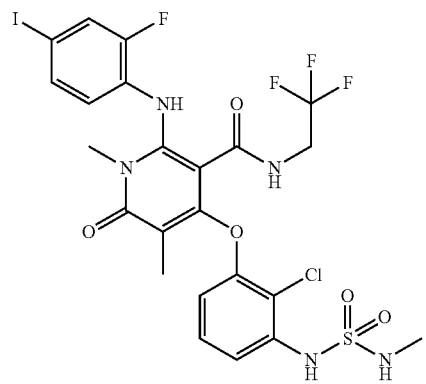 [SMILES: CNS(=O)(=O)Nc1cccc(Oc2c(C(=O)NCC(F)(F)F)c(Nc3ccc(I)cc3F)n(C)c(=O)c2C)c1Cl]
I-45
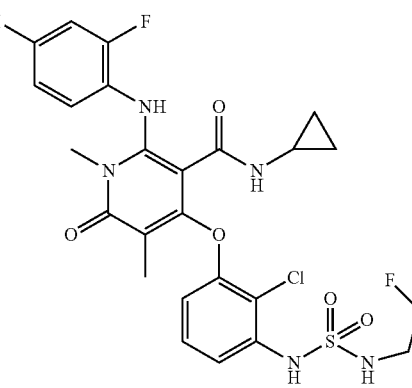
I-46
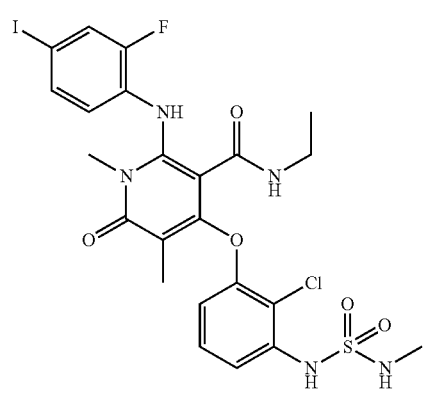 [SMILES: CCNC(=O)c1c(Oc2cccc(NS(=O)(=O)NC)c2Cl)c(C)c(=O)n(C)c1Nc1ccc(I)cc1F]
I-54
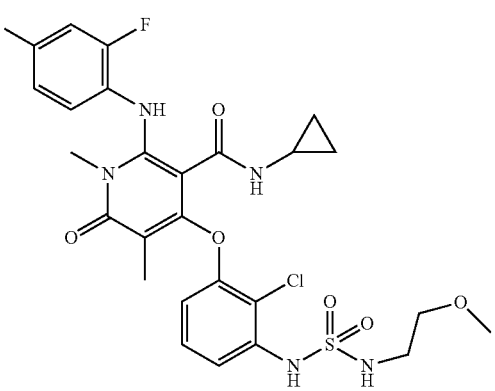
I-55

-continued
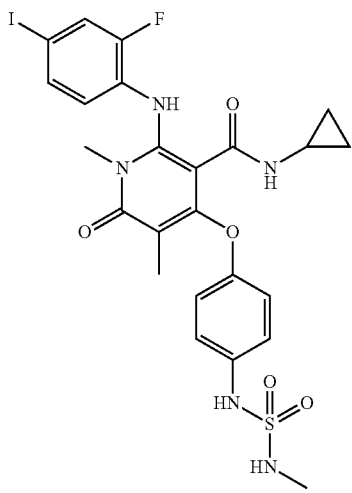 [SMILES: CNS(=O)(=O)Nc1ccc(Oc2c(C(=O)NC3CC3)c(Nc3ccc(I)cc3F)n(C)c(=O)c2C)cc1]
I-64
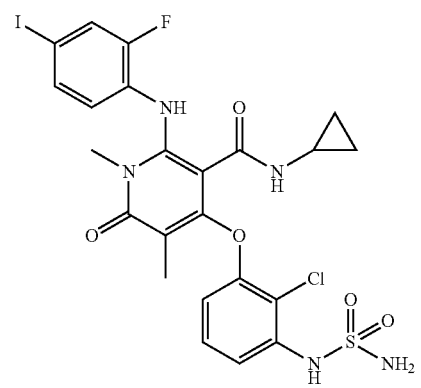 [SMILES: Cc1c(Oc2cccc(NS(N)(=O)=O)c2Cl)c(C(=O)NC2CC2)c(Nc2ccc(I)cc2F)n(C)c1=O]
I-112
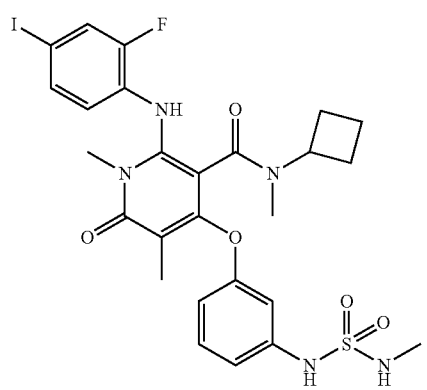 [SMILES: CNS(=O)(=O)Nc1cccc(Oc2c(C(=O)N(C)C3CCC3)c(Nc3ccc(I)cc3F)n(C)c(=O)c2C)c1]
I-133
or a pharmaceutically acceptable salt thereof.
2. The compound of claim 1, which is:
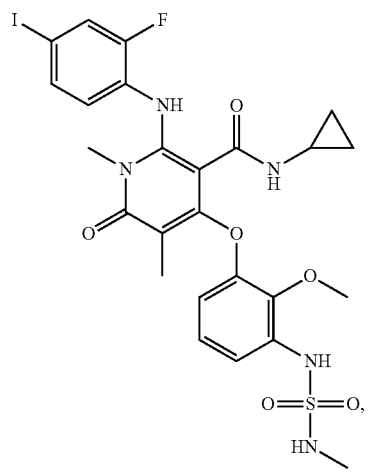
I-1
or a pharmaceutically acceptable salt thereof.
3. The compound of claim 1, which is:
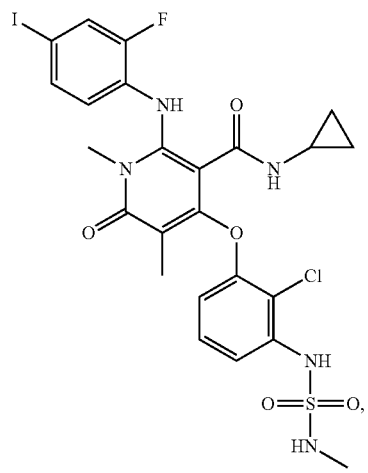
I-2
or a pharmaceutically acceptable salt thereof.
4. The compound of claim 1, which is:
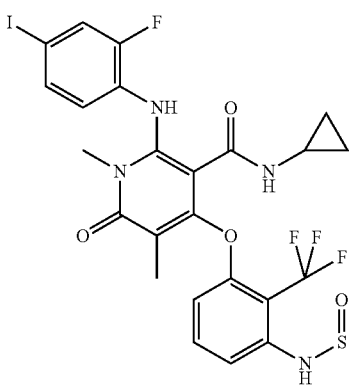
I-37
or a pharmaceutically acceptable salt thereof.

5. The compound of claim 1, which is:

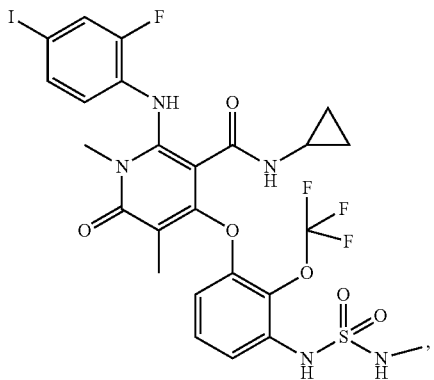

I-40 or a pharmaceutically acceptable salt thereof.

6. The compound of claim 1, which is:

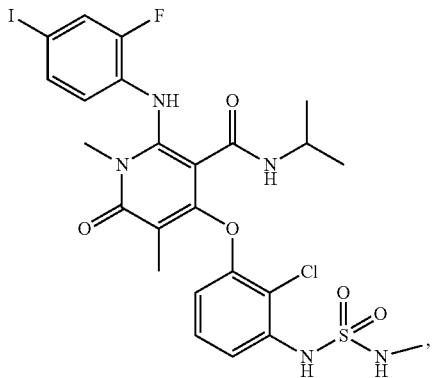

I-41 or a pharmaceutically acceptable salt thereof.

7. The compound of claim 1, which is:

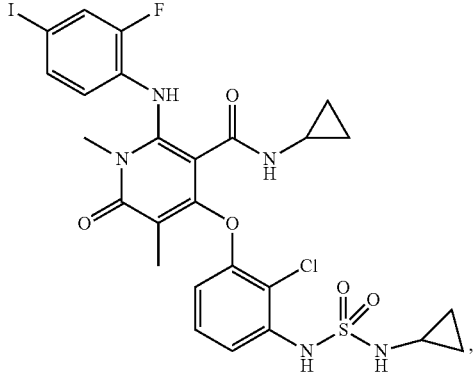

I-42 or a pharmaceutically acceptable salt thereof.

8. The compound of claim 1, which is:

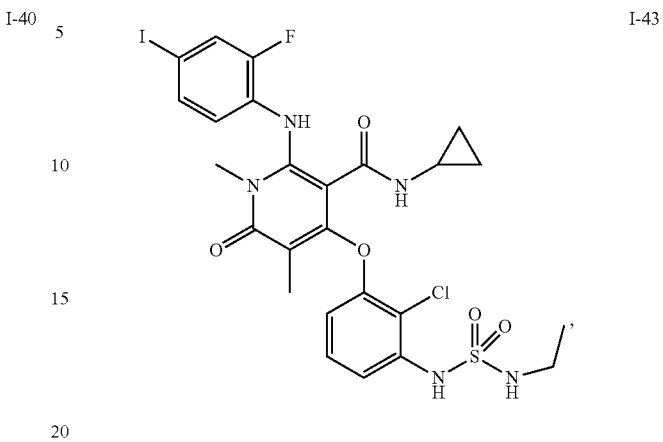

I-43 or a pharmaceutically acceptable salt thereof.

9. The compound of claim 1, which is:

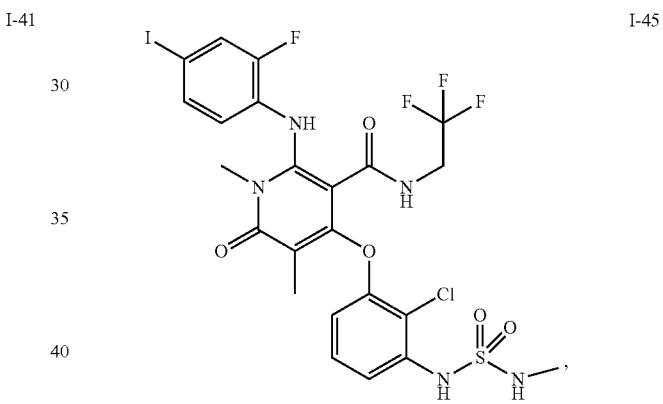

I-45 or a pharmaceutically acceptable salt thereof.

10. The compound of claim 1, wherein the compound is

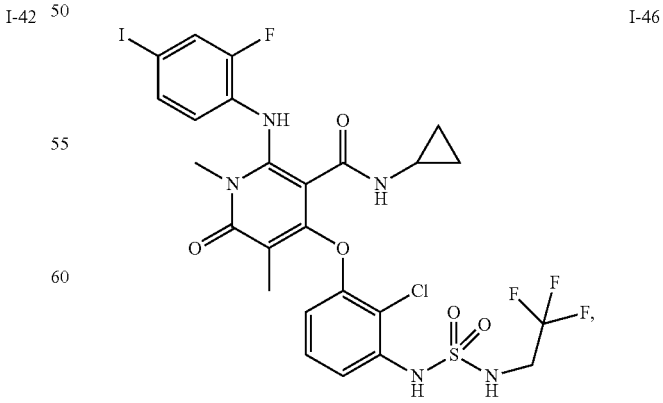

I-46 or a pharmaceutically acceptable salt thereof.

11. A pharmaceutical composition comprising a compound selected from:
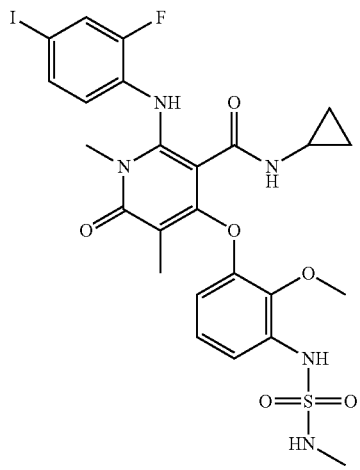 [SMILES: CNS(=O)(=O)Nc1cccc(Oc2c(C(=O)NC3CC3)c(Nc3ccc(I)cc3F)n(C)c(=O)c2C)c1OC]
I-1
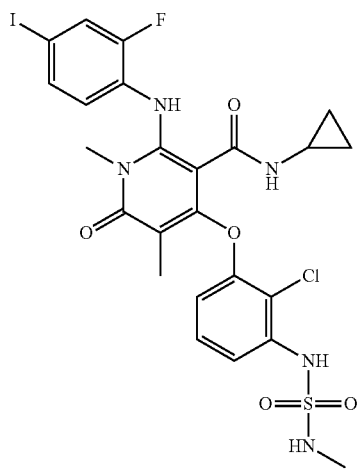
I-2
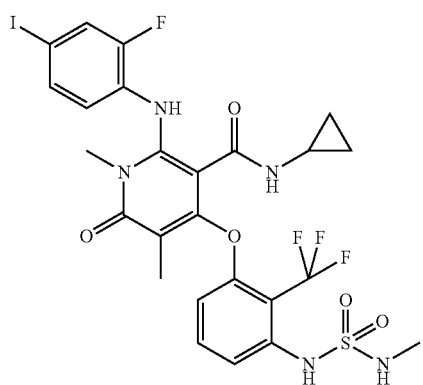 [SMILES: CNS(=O)(=O)Nc1cccc(Oc2c(C(=O)NC3CC3)c(Nc3ccc(I)cc3F)n(C)c(=O)c2C)c1C(F)(F)F]
I-37
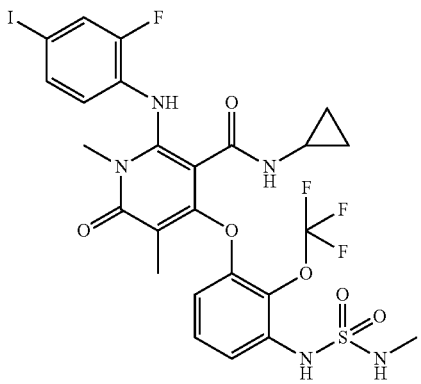 [SMILES: CNS(=O)(=O)Nc1cccc(Oc2c(C(=O)NC3CC3)c(Nc3ccc(I)cc3F)n(C)c(=O)c2C)c1OC(F)(F)F]
I-40
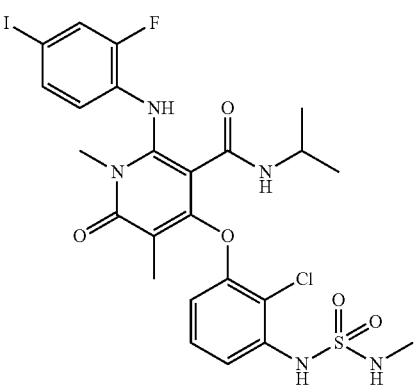 [SMILES: CNS(=O)(=O)Nc1cccc(Oc2c(C(=O)NC(C)C)c(Nc3ccc(I)cc3F)n(C)c(=O)c2C)c1Cl]
I-41
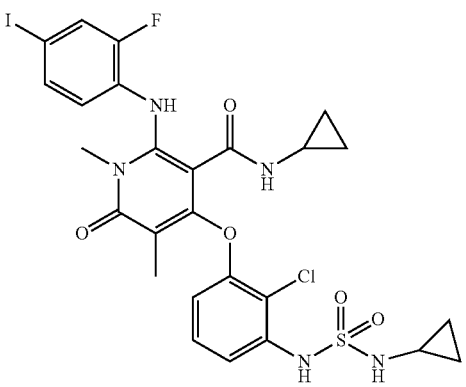
I-42
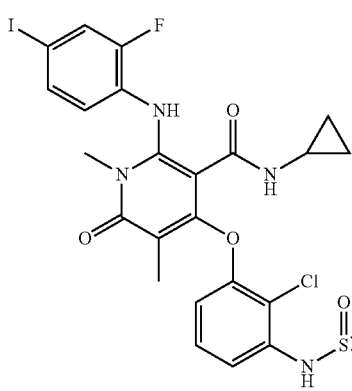
I-43

-continued
I-45
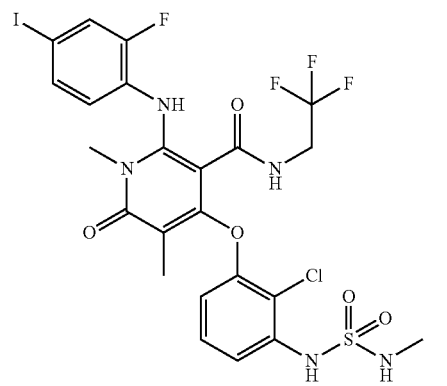 [SMILES: CNS(=O)(=O)Nc1cccc(Oc2c(C(=O)NCC(F)(F)F)c(Nc3ccc(I)cc3F)n(C)c(=O)c2C)c1Cl]
I-46
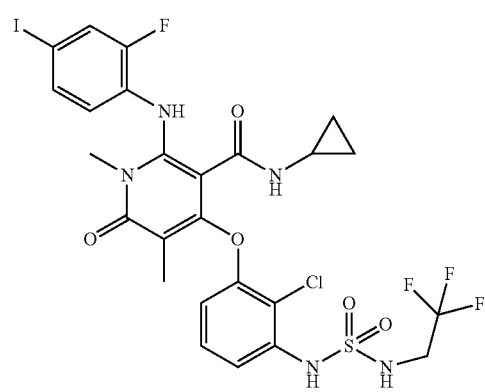 [SMILES: Cc1c(Oc2cccc(NS(=O)(=O)NCC(F)(F)F)c2Cl)c(C(=O)NC2CC2)c(Nc2ccc(I)cc2F)n(C)c1=O]
I-54
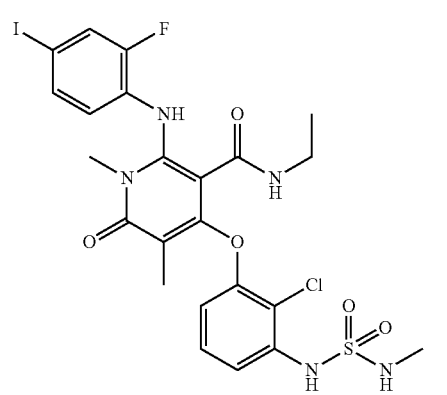
I-55
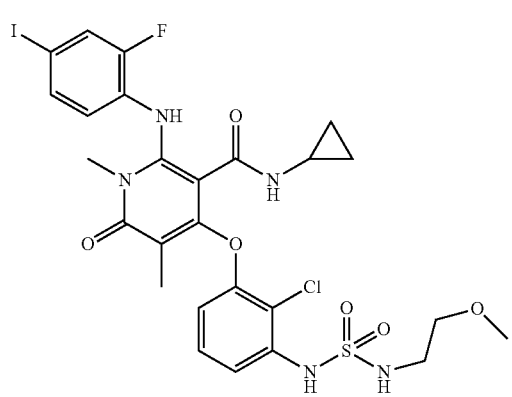 [SMILES: COCCNS(=O)(=O)Nc1cccc(Oc2c(C(=O)NC3CC3)c(Nc3ccc(I)cc3F)n(C)c(=O)c2C)c1Cl]
-continued
I-64
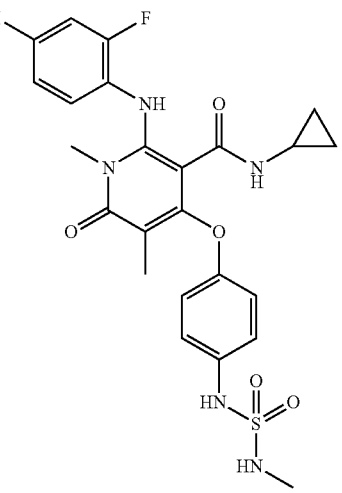
I-112
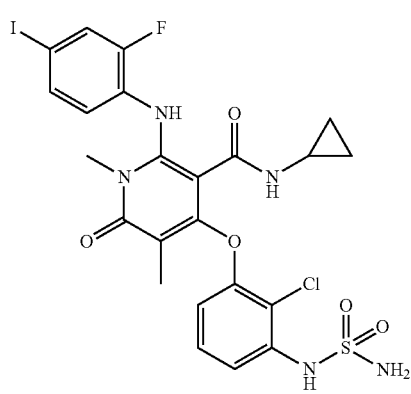 [SMILES: Cc1c(Oc2cccc(NS(N)(=O)=O)c2Cl)c(C(=O)NC2CC2)c(Nc2ccc(I)cc2F)n(C)c1=O]
I-133
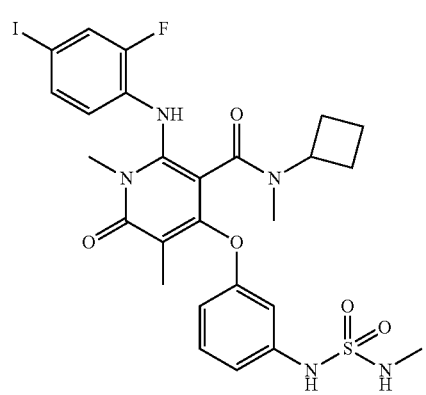 [SMILES: CNS(=O)(=O)Nc1cccc(Oc2c(C(=O)N(C)C3CCC3)c(Nc3ccc(I)cc3F)n(C)c(=O)c2C)c1]
or a pharmaceutically acceptable salt thereof, and a pharmaceutically acceptable carrier, adjuvant, or vehicle.
12. The pharmaceutical composition of claim 11, wherein the compound is

I-1

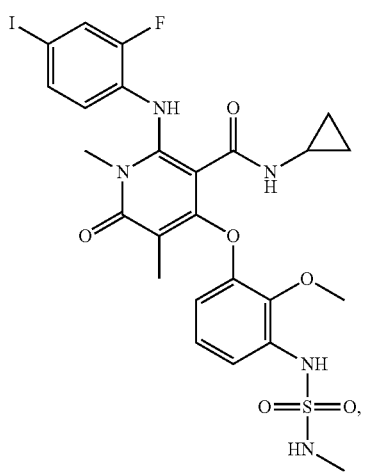

or a pharmaceutically acceptable salt thereof.

13. The pharmaceutical composition of claim 11, wherein the compound is

I-2

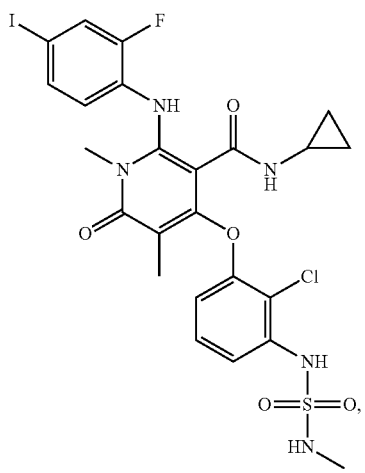

or a pharmaceutically acceptable salt thereof.

14. The pharmaceutical composition of claim 11, wherein the compound is

I-37

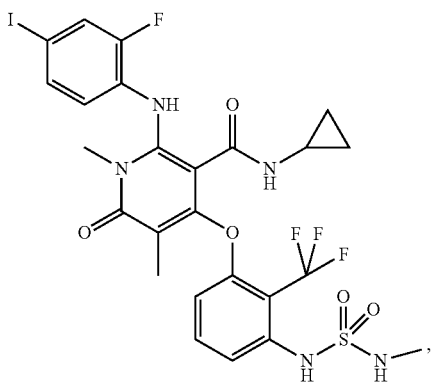

or a pharmaceutically acceptable salt thereof.

15. The pharmaceutical composition of claim 11, wherein the compound is

I-40

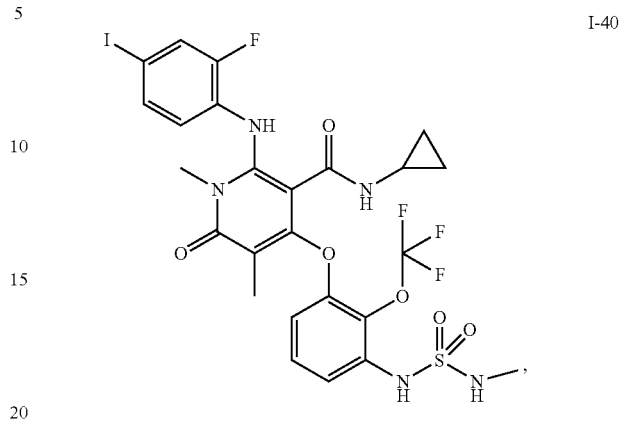

or a pharmaceutically acceptable salt thereof.

16. The pharmaceutical composition of claim 11, wherein the compound is

I-41

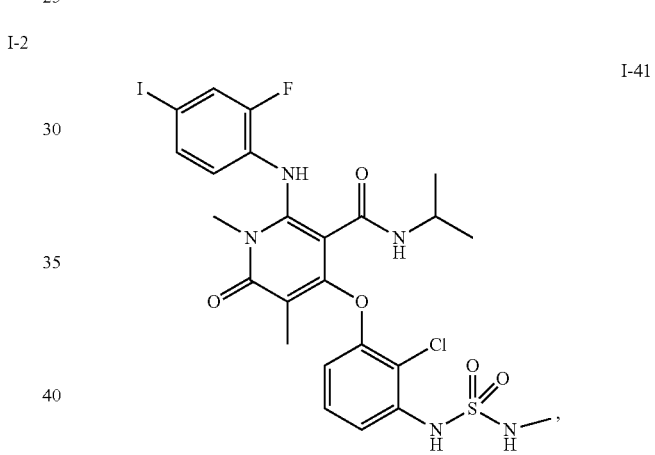

or a pharmaceutically acceptable salt thereof.

17. The pharmaceutical composition of claim 11, wherein the compound is

I-42

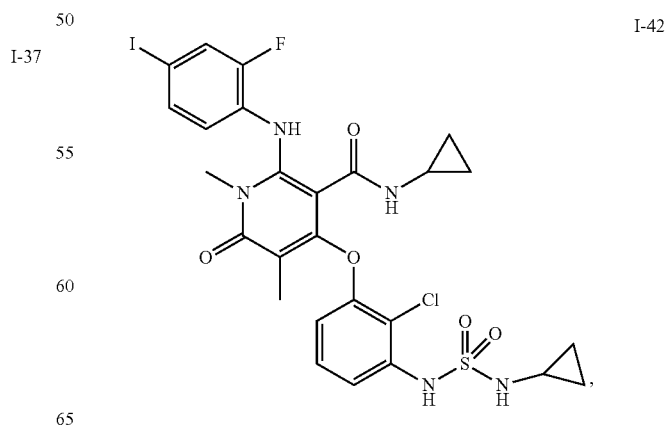

or a pharmaceutically acceptable salt thereof.

18. The pharmaceutical composition of claim 11, wherein the compound is

I-43

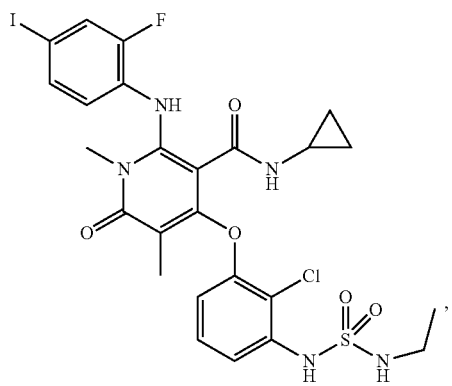

or a pharmaceutically acceptable salt thereof.

19. The pharmaceutical composition of claim 11, wherein the compound is

I-45

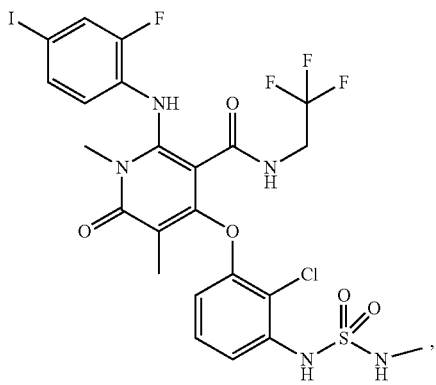

or a pharmaceutically acceptable salt thereof.

20. The pharmaceutical composition of claim 11, wherein the compound is

I-46

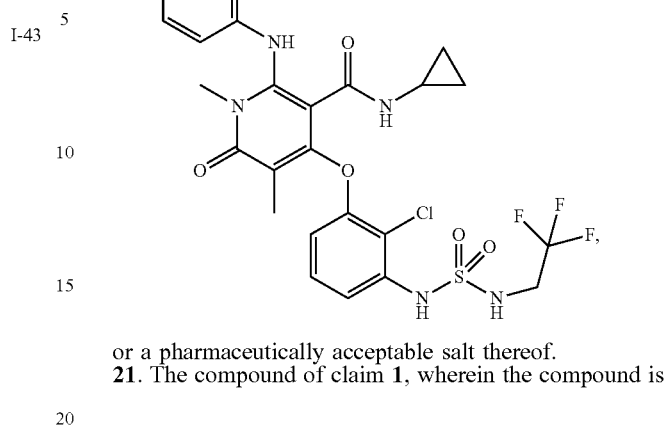

or a pharmaceutically acceptable salt thereof.

21. The compound of claim 1, wherein the compound is

I-112

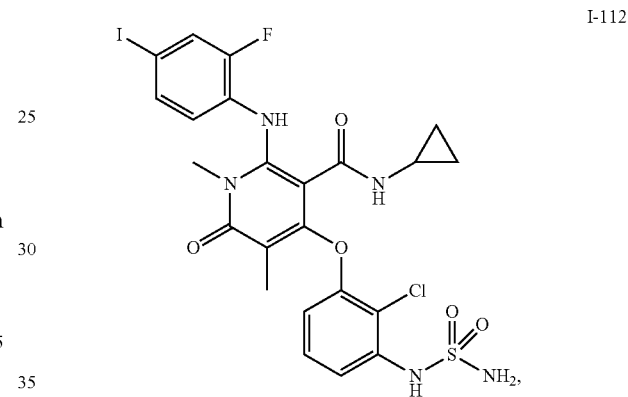

or a pharmaceutically acceptable salt thereof.

22. The pharmaceutical composition of claim 11, wherein the compound is

I-112

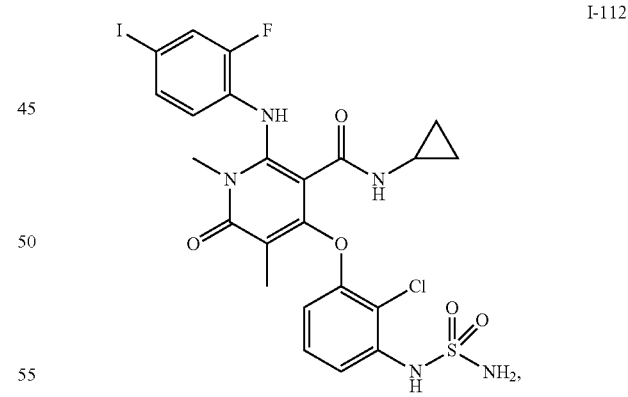

or a pharmaceutically acceptable salt thereof.

* * * * *